US012799482B2

(12) United States Patent
Li et al.

(10) Patent No.: US 12,799,482 B2
(45) Date of Patent: Nov. 17, 2026

(54) ADVANCED GENOME EDITING

(71) Applicant: MBP TITAN, LLC, South San Francisco, CA (US)

(72) Inventors: Xuezi Li, Hayward, CA (US); James Kealey, Sebastopol, CA (US); Kevin Dietzel, Pacifica, CA (US)

(73) Assignee: BIOVERDE TECH LLC, Houston, TX (US)

( * ) Notice: Subject to any disclaimer, the term of this patent is extended or adjusted under 35 U.S.C. 154(b) by 0 days.

(21) Appl. No.: 18/408,520

(22) Filed: Jan. 9, 2024

(65) Prior Publication Data

US 2024/0263171 A1 Aug. 8, 2024

Related U.S. Application Data

(62) Division of application No. 16/755,513, filed as application No. PCT/US2018/055340 on Oct. 11, 2018, now Pat. No. 11,905,513.

(60) Provisional application No. 62/572,012, filed on Oct. 13, 2017.

(51) Int. Cl.

*C12N 15/11* (2006.01)
*C12N 1/20* (2026.01)
*C12N 9/22* (2006.01)

(52) U.S. Cl.

CPC ................ *C12N 15/11* (2013.01); *C12N 1/20* (2013.01); *C12N 9/22* (2013.01); *C12N 2310/20* (2017.05); *C12N 2800/80* (2013.01)

(58) Field of Classification Search

CPC . C12N 15/11; C12N 1/20; C12N 9/22; C12N 2310/20; C12N 2800/80; C12N 15/113; C12N 15/52; C12N 15/63; C12N 15/102; C12N 15/09

See application file for complete search history.

(56) References Cited

U.S. PATENT DOCUMENTS

2016/0317677 A1 11/2016 Bhatia et al.
2017/0152529 A1 6/2017 Coleman et al.
2017/0247710 A1 8/2017 Nagaraju et al.

FOREIGN PATENT DOCUMENTS

WO 2016/205680 A1 12/2016
WO WO 2017-147555 A1 * 8/2017

OTHER PUBLICATIONS

Whisstock et al. Quaterly Reviews of Biophysics, 2003, "Prediction of protein function from protein sequence and structure", 36(3): 307-340. (Year: 2003).*

Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*

Kisselev L., Polypeptide release factors in prokaryotes and eukaryotes: same function, different structure. Structure, 2002, vol. 10: 8-9. (Year: 2002).*

Jiang et al. RNA-guided editing of bacterial genomes using CRIScrisPR-Cas systems. Nature Biotechnology (2013), 31(3): 233-241. (Year: 2013).*

Xu et al. Nucleotide sequence of the mxcQ and mxcE genes, required for methanol dehydrogenase synthesis in Methylobacterium organophilum XX: a two-component regulatory system. Microbiology (1995), 141, 2543-2551. (Year: 1995).*

Hou et al. "Complete genome sequence of the extremely acidophilic methanotroph isolate V4, Methylacidiphilum infernorum, a representative of the bacterial phylum Verrucomicrobia," Biol. Direct, 3(26):1-25 (2008).

"ACD82859: DNA-directed RNA polymerase, beta subunit (Methylacidiphilum infernorum V4)," NCBI GenPept, Accession No. ACD82859, Jan. 31, 2014, pp. 1-2. https://www.ncbi.nlm.nih.gov/protein/ACD82859.1/.

Nguyen et al., Metab Eng (2018), 47:323-333.

Vecherskaya et al., Environmental Microbiology Reports (2009), 1: 442-449.

Clomberg et al., Science (2017), 355:1-10.

Henrad et al., Scientific Reports (2016), 6:21585.

Lee et al., Biofuels Bioproducts & Biorefining (2016), 10: 848-863.

Whisstock et al. Quaterly Reviews of Biophysics (2003), 36:307-340.

Whitkowski et al., Biochemistry (1999), 38:11643-50.

Kisseley et al., Structure (2002), 10:8-9.

* cited by examiner

*Primary Examiner* — Iqbal H Chowdhury

(74) *Attorney, Agent, or Firm* — Gene J. Yao; Barnes & Thornburg LLP

(57) ABSTRACT

Methods of genetically modifying microorganisms using advanced genome editing are disclosed. Methods of modifying the genome of these microorganisms for point mutations, deletions, and DNA insertions are also disclosed. Further, inhibiting expression of genes without manipulating the genome of the microorganism is disclosed. In some cases, the microorganism can be a methylotroph, e.g., a methanotroph.

8 Claims, 6 Drawing Sheets

Specification includes a Sequence Listing.

Cas9 only ~1000 colonies | cas9+gRNA2 10 colonies | cas9+gRNA5 8 colonies | cas9+gRNA2+dsDNA no colonies cPCR verification of ppdK deletion

SL540: 26/36 (72%)

SEQUENCE LISTING

```
Sequence total quantity: 126
SEQ ID NO: 1            moltype = DNA  length = 1713
FEATURE                 Location/Qualifiers
source                  1..1713
                        mol_type = genomic DNA
                        organism = Bacillus subtilis
SEQUENCE: 1
atgaccaagg ccaccaagga acagaaaagc ctggtcaaga accgcggtgc tgaactggtt  60
gtggactgcc tcgtggaaca gggcgtgacc catgtcttcg gcatcccggg cgccaagatc  120
gacgccgtct tcgacgccct gcaggataaa ggtccggaaa tcatcgtggc acgccatgag  180
cagaacgcag ccttcatggc ccaggccgtc ggtcggctga cgggtaagcc cggcgtggtg  240
ctggtcacct ccggtccggg agcctcgaac ctggccacgg gactgctcac cgccaacacc  300
gaaggcgacc cggtggtcgc cctggccggt aatgtcatcc gggcggatcg cctgaagcgc  360
acccatcagt ccctggataa cgcggccctg ttccagccaa tcaccaaata tagtgtcgaa  420
gtgcaggatg tgaagaacat cccggaagcc gtcaccaatg cgttccgaat cgcgtccgcc  480
ggccaagcag gggcagcatt cgtgagcttc ccccaggacg tggtcaatga agtgaccaac  540
accaaaaacg tcagagccgt agccgccccg aagctgggcc ctgcagcaga tgacgccatc  600
tccgctgcca tcgcgaagat ccagaccgca aagctgccgg tcgtgctggt cggaatgaag  660
ggcggacgcc cggaggccat caaggccgtg cgtaaactgc tgaagaaggt gcagctaccg  720
ttcgtggaaa cctaccaggc cgccggcacc ctgagtcggg acttggaaga ccagtatttc  780
ggccgtatcg gcctgttccg caaccagccg ggcgacctgc tcctggaaca agccgatgtg  840
gtgctgacca tcggctacga cccgatcgaa tatgacccga agttctggaa catcaatggc  900
gaccgcacga tcatccatct ggacgaaatc atcgccgaca tcgaccatgc ctatcagccg  960
gacctggaac tgatcggcga catcccgagc accatcaacc acatcgaaca cgatgccgtg  1020
aaggtggaat ttgccgaacg cgaacagaag atcctgtcgg acctgaagca gtatatgcat  1080
gagggcgaac aggtgcctgc cgactggaag tcggacagag cccatccgct ggaaatcgtg  1140
aaggaactgc gtaacgccgt cgacgaccat gtcaccgtca cctgcgatat cggcagccat  1200
gccatttgga tgagccgcta cttccggagc tatgaaccgc tgaccctgat gatctccaac  1260
ggtatgcaga ccctcggcgt cgccctcccg tgggccatcg gcgcaagtct ggtgaagccg  1320
ggcgaaaaag tggtcagcgt gtccggcgac ggcggcttcc tgttctccgc tatggaactg  1380
gaaaccgcgg tccgcctgaa ggccccgatc gtgcatatcg tgtggaacga cagcacctac  1440
gacatggtcg ccttccagca gctgaaaaag tacaaccgca ccagcgccgt ggacttcggc  1500
aatatcgaca tcgtgaagta tgccgaatcc ttcggagcca ccggactgcg cgtggaatcc  1560
ccggaccagc tggcggacgt tctgcgtcag ggcatgaatg ccgaaggtcc cgtgattatc  1620
gatgtgcccg tcgactacag cgacaacatc aacctggcct cggacaaatt gccgaaggag  1680
ttcggcgaac tgatgaaaac aaaagcacta taa                               1713

SEQ ID NO: 2            moltype = DNA  length = 1719
FEATURE                 Location/Qualifiers
source                  1..1719
                        mol_type = genomic DNA
                        organism = Bacillus licheniformis
SEQUENCE: 2
atgaataacg tcgcggccaa gaacgaaacc ctgaccgtcc ggggcgccga actcgtggtg  60
gatagcctga tccagcaggg cgtgacccat gtcttcggca tcccgggcgc caaaatcgac  120
gcggtcttcg acgtgctgaa ggataagggc cccgaactga tcgtctgccg ccatgagcag  180
aacgcggcct tcatggccgc cgccgtcggc cgcctgacgg gcaagccggg cgtctgcctg  240
gtcacctccg gcccgggcgc ctcgaatctc gcgaccggcc tggtcaccgc gaacacggaa  300
ggcgacccgg tggtcgccct ggcgggcgcc gtgaagcggg cggatcggct gaagaagacg  360
caccagtcga tggataacgc cgccctgttc cagcccatca cgaagtacag cgcggaggtg  420
gaagacgcga acaacatccc ggaggccgtg acgaacgcct tccgcgccgc ggcgtccggc  480
caggccggcg cggccttcct cagcttcccc caggatgtca ccgccggccc ggccaccgcc  540
aagccggtca aaaccatgcc cgccccgaag ctgggcgccg cgagcgatga acagatctcc  600
gccgcgatcg cgaagatcca caacgcgaat ctgccggtgg tcctcgtggg catgaagggc  660
ggccggccgg aagccatcga agccgtgcgc cgcctgctcc gcaaggtcaa gctcccgttc  720
gtggaaacct accaggcggc cggcacgctg tcgcacgatc tggaggatca gtacttcggc  780
cggatcggcc tgttccggaa ccagccgggc gacatgctcc tggaaaaggc cgacgtggtc  840
ctgaccgtgg gctacgaccc gatcgagtac gatccggtgt tctggaatgg caaaggcgaa  900
cgctcggtca tccacctcga cgaaatccag gccgatatcg atcacgacta ccagcccgag  960
atcgaactca tcggcgacat cgcggaaacc ctcaatcaca tcgagcatga ctcgctgccg  1020
```

```
gtgtccatcg acgaatcctt cgcgcccgtg ctcgactatc tcaagaaggc gctcgaagaa  1080
cagtcggagc ccccgaagga aacgaagacc gatctggtcc acccgctcca gatcgtgcgc  1140
gacctgcgcg agctgctctc cgatgacatc accgtcacct gcgacatcgg cagccacgcc  1200
atctggatgt cccgctattt ccgcacctat cgcccgcatg gcctcctgat ctccaacggc  1260
atgcagacgc tgggcgtcgc cctgccgtgg gcgatcgccg cgaccctggt gaacccgggc  1320
cagaaggtgg tgtcggtcag cggcgatggc ggcttcctct tctccgcgat ggaactcgaa  1380
accgccgtcc gcctcaaggc gccgatcgtg cacatcgtgt ggaacgactc cacgtacgac  1440
atggtcgcgt tccagcagga aatgaagtac aagcgcacct ccggcgtcga tttcggcggc  1500
atcgacatcg tcaagtatgc ggaatccttc ggcgccaaag gcctccgcgt gaatagcccc  1560
gatgaactgg ccgaggtcct gaaggccggc ctcgacgcgg agggcccggt ggtcatcgac  1620
atccccgtcg actactcgga taacatccac ctggccgacc agcgcttccc gaagaagttc  1680
gaggagcact tcaacaagga agcgtcgaag cagtcctga                        1719

SEQ ID NO: 3            moltype = DNA  length = 1476
FEATURE                 Location/Qualifiers
source                  1..1476
                        mol_type = genomic DNA
                        organism = Escherichia coli
SEQUENCE: 3
atggctaact acttcaacac cctgaacttg cgtcagcagc tggcccagct gggtaagtgc  60
cggttcatgg gccgtgatga gttcgccgat ggcgccagct acctgcaggg caaaaaggtg  120
gtgatcgtgg gctgcggagc ccagggcctg aaccagggcc tgaatatgcg cgatagcggc  180
ctggacatct cctatgctct gcgcaaggaa gcgatcgcgg aaaagcgggc atcctggcgc  240
aaggccaccg aaaacggttt caaagtgggc acctacgaag aactgatccc gcaggccgat  300
ttggtcataa acctgacccc ggacaagcag cattccgatg tggttcgcac cgtccagccg  360
ctgatgaagg acggggcagc cctgggttac tcccacggct tcaacatcgt ggaagtcggc  420
gaacagatcc gcaaggacat caccgtcgtc atggtcgcac cgaagtgtcc gggcaccgaa  480
gtccgggaag aatataagcg cggattcggc gtaccgaccc tgatcgccgt ccatcccgaa  540
aacgacccga agggcgaagg catggccatc gccaaggcct gggctgccgc caccggaggc  600
catcgcgctg gcgtgctgga aagctcgttc gtcgccgaag tgaagagcga cctgatgggc  660
gaacagacca tcctgtgcgg catgctgcag gccggtagcc tgctgtgttt cgacaagctg  720
gtcgaagaag gcaccgaccc tgcgtatgcc gaaaagctga tccagttcgg ctgggaaacc  780
atcaccgaag cgctgaaaca gggcggtatc accctgatga tggaccgcct gtcgaaccct  840
gccaagttac gtgcctatgc cctgagcgaa cagctgaagg aaatcatggc gcctctgttc  900
cagaaacata tggacgatat catcagcggc gagttcagct ccggcatgat ggcggactgg  960
gcgaatgacg acaagaagct gctgacctgg cgggaagaaa ccggcaagac ggccttcgaa  1020
accgcaccgc agtacgaagg caaaatcggc gaacaggagt acttcgacaa aggcgtcctg  1080
atgatcgcga tggtcaaggc gggagtcgaa ctggccttcg aaacaatggt cgatagcggc  1140
atcatcgagg aatccgccta ctacgaaagc ctgcatgaac tcccgctgat cgccaatacc  1200
atagcccgca agcggctgta cgaaatgaac gtcgtgatct ccgacactgc cgaatacggc  1260
aattatctct tctcctatgc ctgcgtgccg ctcctgaagc ccttcatggc cgaactgcag  1320
ccaggcgacc tggggaaggc gatccccgaa ggcgctgtcg acaacggcca gctgcgcgat  1380
gtcaacgaag ccattcgctc ccatgccatc gagcaggtcg gcaagaagct gcgtggctat  1440
atgacggaca tgaagcgcat cgcagtagcc ggataa                           1476

SEQ ID NO: 4            moltype = DNA  length = 1851
FEATURE                 Location/Qualifiers
source                  1..1851
                        mol_type = genomic DNA
                        organism = Escherichia coli
SEQUENCE: 4
atgccgaagt atcggtcagc caccactaca catggccgca acatggcagg cgctcgtgcc  60
ctgtggcgtg ctaccggcat gaccgatgcc gacttcggca agccgatcat cgccgtggtc  120
aactctttca cccagttcgt cccagggcac gttcatctgc gcgacctggg caagctggtg  180
gccgaacaga tcgaggccgc aggtggcgtc gcgaaagagt tcaacaccat cgccgtcgac  240
gatggcatcg ctatgggcca cggtggcatg ctgtatagcc tgccgtcccg cgaactgatc  300
gccgatagcg tcgaatatat ggtgaacgcc cattgcgccg atgctatggt gtgcatcagc  360
aactgcgaca agatcacacc ggggatgctg atggccagcc tgcggctgaa catcccggtg  420
atcttcgtga gcggtggccc gatggaagcc ggcaagacca agctgtcgga tcagatcatc  480
aagctggatc tggtcgacgc catgatccaa ggtgccgatc cgaaggtgag cgactcccag  540
tccgatcagg tggaacggag cgcctgcccg acttgcggct catgcagcgg catgttcacc  600
gccaactcca tgaattgcct gacggaagcc ctgggcctgt cccagcccgg taacgggagc  660
ctgttggcga cccatgccga ccgcaagcag ctgttcctga atgccggcaa gcgcatcgtg  720
gaactgacca agcgctatta tgaacagaac gacgaatccg ccctgccccg taatatcgcc  780
tcaaaagccg ccttcgaaaa cgccatgacc ctggacatcg ctatgggtgg cagcaccaac  840
accgtgctgc acctgctggc tgccgctcag gaagccgaga tcgacttcac catgtccgac  900
atcgacaagc tgagtcggaa ggtgccgcag ctgtgcaagg tggcaccgtc cacccagaag  960
tatcatatgg aagacgtgca tcgcgcaggc ggtgtgatcg gcatcctggg cgaactggat  1020
cgcgctggcc tgctgaatcg cgatgtgaag aacgtcctgg gcctgaccct gccgcagacc  1080
ctggaacagt acgacgttat gctgacccag gatgatgccg tcaagaatat gttccgcgca  1140
ggccctgccg gcattcgcac cacccaagcc ttcagccagg actgccggtg ggataccctg  1200
gatgacgatc gcgccaatgg ctgcatccgt agcctggaac atgcctattc caaggatggc  1260
ggtctggccg ttctgtatgg caacttcgcg gaaaacggct gcatcgtcaa gaccgctggc  1320
gtggatgatt cgatcctgaa gttcaccgga ccggccaaag tctacgaaag ccaggacgat  1380
gccgtcgaag ccatcctggg aggcaaggtc gtcgccggag atgtcgtggt gatccgctat  1440
gaaggcccga aaggcggtcc gggcatgcag gagatgctgt atccgacctc cttcttaaag  1500
agcatgggct tgggcaaagc gtgtgcgctc atcaccgatg gccgcttcag tggcggcacc  1560
agcggcctgt ccatcggcca tgtctcgccg gaagccgcca gtggcggcag catcggcctc  1620
atcgaagacg gcgatctgat cgccatcgat atcccgaatc gtggcatcca gctgcaggtg  1680
```

```
tccgacgccg aactagccgc acggagggaa gcgcaggatg cccgaggcga caaggcctgg  1740
accccgaaga accgtgaacg tcaggtgtcc ttcgcgcttc gcgcctatgc cagcctggcc  1800
accagcgccg ataagggtgc cgtgcgcgac aagagcaaac taggaggata a           1851

SEQ ID NO: 5            moltype = DNA  length = 1689
FEATURE                 Location/Qualifiers
source                  1..1689
                        mol_type = genomic DNA
                        organism = Methylococcus capsulatus
SEQUENCE: 5
atgaccgaca agcacccccg tccccattcg tcccaggtcg tcgacggcat ggagcgggcc  60
ccgagccgcg cgatgctgca cgccgtcggc ttcgccgatg ccgacttcgc caaaccgcag  120
atcggcatcg cttccacctg ggcgatggtg acgccgtgca acatgcacat caacaagctc  180
gccgaggacg cagcacgcgg cgtcgacggc ggcggcggca aggcagtgat cttcaacacc  240
atcaccattt ccgacggcat ctcgatgggc accgaaggaa tgaaatactc cctcgtgtcg  300
cgggaagtca tcgccgactc gatcgaaacc gtggtggcct gtcagggtta tgacggcgtg  360
gtcgccatcg gcggctgcga caagaacatg cccggctgcc tgatcgccct cgcccgcctc  420
aaccgtccgg cggtgttcgt ctatggcggc accatcctgc cgggctgcca cgacggcaag  480
aagctggacg tggtgtcggt gttcgaagcg gtcggcgccc gcgccaacca ccgcatcgac  540
gatgccgaac tgcacgccat cgaatccaat gccatccccg gtccgggctc ctgcggtggc  600
atgtataccg cgaacacgat ggcctccgcc atcgaggcat tagggatgag cctgccgggc  660
agttcggccc aggtggccat ttcccgcgcc aaggaactgg attgcgagcg ggccggcgcc  720
caggtcctca agctcctgga cctggggctc aaaccccgcg acatcatgac caagaaggcg  780
ttcgagaacg ccatcacggt ggtgatcgcc ctgggcggct ccaccaacgc cgtgctgcac  840
ctcctggcca tggccaacgc ctgcggcgtc gacctgaagc tcgacgattt cacccgcatc  900
gggcgcaaag tgccgatgct ggcggatctg aaacccagcg gcagatactc gatggccgaa  960
ctggtggaaa tcggcggcat ccagccgctg atgaagacct tgctggacgc gggactcctg  1020
cacggcgact gcatgaccgt aaccggcaag accctggaag aaaacctggc cgacgcgccc  1080
gactacccgg ccggacaaga catgatccgg tcgctggaca accccatcaa aaaggacagc  1140
catctggtga tcctcaaggg caacctggcg ccggaaggcg cggtcgccaa gatcaccggc  1200
aaggaaggac tgagcttcac cggcaccgcc cgcgtattcg actgcgagga agcggcgctc  1260
acggccatcc tcgacggcac gatcgtgaaa ggcgacgtaa tcgtcatccg ctatgaaggc  1320
cccaagggcg gccccggcat gcgcgagatg ctctcgccga cctcggcggt catgggcaag  1380
ggattgggca aggaggtcgc cctcatcacc gacggccgct ttccggcgg cacccacggc  1440
ttcgtggtcg gccacatcac gccggaagcc tacaccggcg gcccccctggc gatcgtccgg  1500
gacggcgata ccatcaccat cgacgccgaa acccgcgaat tgagcctgca cgtcaccgac  1560
gatgaaatcg gccggcgcct ggcgcagtgg actcaaccgg cgccgcgcta caccaagggc  1620
gtgctggcca aatacgccag gttggtgagc ccggcctcgg aaggcgccgt caccgacgac  1680
ggcctctga                                                          1689

SEQ ID NO: 6            moltype = DNA  length = 1647
FEATURE                 Location/Qualifiers
source                  1..1647
                        mol_type = genomic DNA
                        organism = Carnobacterium divergens
SEQUENCE: 6
atgtataccg tgggcgacta tctcctggag cggctctcgg aactgggcat caaagagatc  60
ttcggcgtgc cgggcgacta caacctgaag ttcctggatc acatcgtgga gcatccgaac  120
ctgaagtgga tcggcaacgc gaatgaactc aacgcggcgt atgccgccga cggctacgcc  180
cgcacgaagg gcgtctccgc gctggtgacc accttcggcg tcggcgagct ctccgccatc  240
aacggcatcg ccggctcgta tgccgagaaa gtcccggtca tccagatcgt gggcagcccc  300
acgatggcgg tgcagaatgc ccataagctg gtgcatcata ccctgggcga tggcaaattc  360
gaccacttcg agaacatgca tgagtccgtc accgaagcca tcggcagcct caccaaggag  420
aacgcggtga ccgagatcga tcgcgtgctg cgggccgccg tgctcaaacg gcgcccggtg  480
tatctgaacc tcccgatcga cgtggccgaa atggtcgtcg aaaaaccgtc gggccccctg  540
ctgcccaagc aggcgagcct gagcgcccgc gaggtcgaac tcgtgcatga gctggagaag  600
gccctgcagc aggcgaagaa cccggtggtc ctggcgggca acgagctggc gtcgttccac  660
ctcgaaacgt acctcgccga cttcatccac aagttcaacc tccccatcac gaccctcccc  720
ttcggcaagg gcgtcttcaa cgaggaagac gagcattatc tgggcgtcta tgcgggctcg  780
ccgaccgaag aaggcctgcg gaagcgcgtc gatacggcgg acctggtcgt ggcgctgggc  840
gcgaagctga cggactccgc cacctccggc ttctcgtacg acttctccga aaaacagctc  900
ttcagcctgg cgtccgacga agtcatcgtc aaagaggaac acctcgaagg catccatctg  960
ccggccgtca tgaaggcgct gacgagcatc gactaccagg gctaccaggg cgacatccag  1020
ccgatggccc ggctgaagag catcaaaccc accaaccagg tgctgaccca gcgccacttc  1080
tgggaggcca tcgaaggctt cctggaaaag ggcgacaccg ccgtcgcgga gcagggcacg  1140
agcttcttcg gcctctcgac cgtgccgctg aagagcgaaa tgtcgttcat cggccagccg  1200
ctgtggggct ccatcggcta tacgttcccg gcgatgctgg gcagccagct cgccaacccg  1260
tccagccggc acctcctgtt catcggcgac ggcagcctgc agctgacgat ccaggagctc  1320
ggcatggccc tccgcgaaaa actcaccccg atcgtgttcg tcatcaacaa taacggctat  1380
acggtcgaac gggaaatcca cggcccgaat gaaatctata acgacatccc gatgtgggac  1440
taccagaaac tcccgctcgt cttcggcggc tccgagcagt cggtcatcac ctataaagtg  1500
acgaccgaac tggaactggc gaacgcgctc aaggcggccc ggctggacaa caaccgcctg  1560
cagtggatcg aagtggtgat ggaccagacc gatgcgccgg agctcctcat gaagctgggc  1620
aagatcttcg cgaagcagaa tagctga                                      1647

SEQ ID NO: 7            moltype = DNA  length = 1650
FEATURE                 Location/Qualifiers
source                  1..1650
                        mol_type = genomic DNA
```

```
                         organism = Methylococcus capsulatus
SEQUENCE: 7
atgggcacgg ttgagcctgg cgctatcgga caacatctgc tcgcctgcct ttaccaggcg  60
ggcgtcgggc acatcttcgg cgttcccggc gattacgtgc tgggcttcta tgatctgatg  120
gccaaaggtc ccgtccggca tatcgggacc acgcgggagg acaccgccgc cttcgccgcc  180
gacggctatg cccgctgccg gggcatgggc gccctggcgg tgacttacgg ggtcggtgcg  240
ctcaacaccg tcaacgccgt cgccggcgcc tatgcggaat cctcgccggt ggtggtcatc  300
agcggtgcgc cgggggtgcg cgagcaaagg gaagacccgt tgatccacca ccgcttcggg  360
ccgttccggt tccagcgcga gatattcgaa cggatcacct gcgccgccgt ggtgctggac  420
gatccggtga tcgccttccg gcaggtggag cgtgcgctcg cagccgcccg tcagcactgc  480
aagccggtgt acatcgagat tcccgccgac cgggtgatgg cgccgggata tccgattcca  540
caggaaaccc cggaaacgcc ttccagcgac gattcggccc tggcggaggc ggtcgccgag  600
gccgcggagc tcctgggccg tgcggtgtcg ccggtgatcc ttgcaggcgt cgagttgcac  660
cggcgagggc tccaggacgc cctcgtcggc ctcgtcgagc aggcccgcct gccggtggcg  720
gcgaccttga ccggcaagtc ggtgttcgcc gagcgccatc ccgcctatct gggggtgtac  780
gagggtgcga tgagcacgga aaacgcccgc tacatggtcg agcagtccga cctcctgctg  840
atgctcgggg tcacgctgaa cgatgtcgac acgggcatct acacggcgcg tctcgatccg  900
cagcgcatcg tccgcgcagc ccagaacgag gtcgtgattc gccatcaccg ctatccccgc  960
gtcctgctcg cggacttcgt cacggccctg gcgcggtccg tcaaggcccg gggcgaggcg  1020
tttccgatgc cggcggggcc ggaaccgtgg gactttcccg cgccggaccg gccgatgacg  1080
atcgcccggc tggtggagcg gctcgaccgc gccctgacct ccgacatgat cgtagtgtgc  1140
gatgtcggcg actgcctgtt cgcagccacc gacctgcgcg tgcacgagcg cagcgaattt  1200
ctggcgtccg ccttctatac ctcgatgggg ttcgcggtgc ccgccgccct cggggcccag  1260
atcgcccgtc cggaccaccg ggcgctgatc ctggtcggcg acggtgcctt ccagatgacc  1320
ggaacggagc tgtcgaccca tgcccgtctc ggcctggcgc ccatcgtggt ggtgctcgac  1380
aatcgcggtt acagcaccga gcgcttcatc ctcgacggag ccttcaacga catcgccgac  1440
tggcgcttcc accggctggg cgaggtgttc ggccccctac agggctacga cgcgcccgac  1500
gaagcggcgt tcgaaaacgc gctcagcgaa gcgctggtca accgaaacat gccgagcctc  1560
atcaacgtcc gtctttcccc cggcgatgcc tcgatagcca tgaagcgtct cgccgggcat  1620
ctgcagtgcc gggtcaaggg cgagggctaa                                 1650

SEQ ID NO: 8             moltype = DNA  length = 1647
FEATURE                  Location/Qualifiers
source                   1..1647
                         mol_type = genomic DNA
                         organism = Methylocaldum szegediense
SEQUENCE: 8
atgggcaccg ccaaggcgga tagcatcggc cagtacctcc tgaaacgcct gtacgaggcc  60
ggcgtgaaac atatcttcgg cgtgcccggc gattacgtgc tgggcttcta cgatctgatg  120
gcgaagagcc cgatccagca cgtcggcacg acccgcgagg acaccgcggc cttcgccgcc  180
gacggctacg cccgctgtcg cggcctcggc gccctggcgg tcacctatgg cgtcggcgcc  240
ctgaacaccg tgaatgccgt cgcgggcgcc tatgccgaat cgagcccggt gatcgtcatc  300
agcggcgccc cgggcgtgcg cgaacagaag gaagacccga tgatccatca tcggttcggc  360
ccgttcacct tccagcggga aatcttcgac cggatcacct gcgccgcggt cacgctggac  420
gatcccatca tcgccttccg ccagatcgac cgggtgatcg cggcggcccg ccactcgtgc  480
aaacccgtgt atatcgaact gccccgcgac ctggtgatgg ccgaaggcca tccggtcccg  540
acggagcccc cggaagagcc cgcctccgat gaggcggccc tgagcgaagc ggtggccgaa  600
accgcggaac tgatgtccaa gtcggtgagc ccccaccgtcc tggcgggcgt cgaactgcac  660
cggcgcggcc tgcaggacgc cctggtggaa ctggtggaac gcgcccggct gccggtggcc  720
gccaccctca ccggcaagag cgtgatcgcc gaacgccacc ccgcctatct gggcgtctac  780
gaaggcgcca tgtcctcgga aaacgcccgc tacatggtgg aacagtccga tctcctgctc  840
atgctgggcg tgacgctgaa cgacatcgac accggcgtct ataccgcccg cctcgacccg  900
catcgcatcg tgcgggcggc ccagaacgag gtggtgatcc gctaccatcg ctatccgcgg  960
gtcaccctgt cggacttcgt cctgagcctg gcccgcaccg tgaaagcgaa gcatgaaacc  1020
ttccccgccc cggtcacgac ccccgaagcc acggagttcc ccatgcccga gcgcccgatg  1080
acgatcgccc gcctcatcga acgcctggac cgcgccctga cccccgacat gatcgtcgtg  1140
agcgatgtgg gcgattgcct gttcgcggcc atcgatctcc gggtctacga gcggagcgag  1200
ttcctctcgt cggccttcta caccacgatg ggcttcgccg tcccggccgc cctgggcgcc  1260
cagatcgcgc ggccggacca ccgggccctg atcctggtgg gcgatggcgc gttccagatg  1320
acgggcaccg agctcagcac gcacatccgc ttcggcctcg cgcccatcgt ggtcgtgttc  1380
aacaactgtg gctattcgac cgaacggtac atcctggacg gcccgttcaa cgacatctcg  1440
tgctggaact tcgaccggct gggcgaactg ttcggcccgc tgaacggcta tgacgcgccg  1500
gacgaggaga gcttcgagaa ggccctcgtc gaggccctgg ccaaccatgc cacgcccagc  1560
atcatcaacg tccacatcag ccgcgacgac agctccagcg cgatgcggcg gctggccgaa  1620
gtcctgaaga gccgcgtccg gggctga                                    1647

SEQ ID NO: 9             moltype = DNA  length = 1653
FEATURE                  Location/Qualifiers
source                   1..1653
                         mol_type = genomic DNA
                         organism = Methylosarcina lacus
SEQUENCE: 9
atgaacaccg ccaagttcga caccatcggc cagtacctgc tcaagcggct gtacgacgcg  60
ggcgtgaaac acatcttcgg cgtgccgggc gattatatcc tgggcttcta tgacctgatg  120
gtgaacagcc cggtccagca catcggcacc acgcgcgagg acaccgcggc cttcgcggcg  180
gacgcctacg cccgctgcct gggcctcggc gcgatggcgg tcacgtacgg cgtgggcgcc  240
ctgaataccg tgaatgccgt cgccggcgcg tatgccgaaa gctcgccggt gatcgtcatc  300
tccggcgccc ccggcatccg cgagcagcgg gaggacccgc tgatccatca tcggttcggc  360
ccgttcacct tccagcggga gatcttcgag cgcatcacct gcgcgaccga agtgctcaac  420
```

```
gacccggtga tcgccttccg ccagatcgat cgcgcgatcg ccaccgcccg gcggctgtgc  480
aagccggtgt acatcgagat cccgcgcgat ctggtgatgg cggaaggcta ccccatgccg  540
gacgaggccc tcgaacccct ggagagcgat gaaaccgccc tgagcgaggc gctggcggaa  600
acgatggaac tgatggcgaa aagcgtctcc ccgatgatca tcgccggcgt cgaactgcat  660
cggcggggcc tgcagagcgc cctcgtcaac ctggtggaac gcgcccatct cccggtggtc  720
gccaccctgt cgggcaaaag cgtcatggcg gaacggcacc cggcctacct gggcatctac  780
gaaggcgcga tgtcctcgga aaatgcccgg tacatggtcg aacagagcga cctcctcctc  840
atgctgggcg tcaccctcaa cgacatcgat accggcatct atacggccaa gctcgacccg  900
catcatatga tccgggcggc ccagaacgag gtggtgatct cctcgcatcg ctacccgcgg  960
gtcaccctct cggacttcct gacggcgctg gtgggcctgg tcaagacccg gagcgaaggc  1020
ttcagctcgc cgccggccgc ctacgaggcc agcgccttcc cggaaccgaa gcggccgatc  1080
accacggcgc ggatgatcgg ccggctgaac caggcgctgt cgccggaaat gatcgtggtg  1140
tgcgacgtgg gcgactgcct cttcgccgcc atcgatctgc aggtgcacga gcagtccgag  1200
ttcctcgcca gctgctacta tgccacgatg ggcttcgccg tgcccgcggc gctcggcgcc  1260
cagatcgcgc ggcccgatca ccggctgctc gtgctggtgg gcgacggcgc cttccagatg  1320
acgggcaccg aactgagcac ccatgcctat ctgggcctca acccgatcgt cgtggtgttc  1380
aacaactccg gctacggcac cgaacgcggc atcctggaag gcccccttcaa cgacatcagc  1440
agctggcggt tcgaccgcct cggcgaagtg ttcggcccgc tgaagggcta tgacgccgcc  1500
accgaggagg ccttcgaagc ggcgctcatc aactccctca acaaccggac gatgccgagc  1560
atcatcaacg tccatctctc cgccgacgac gcctcctccg ccatgaagcg cctcgccgag  1620
cacctgaaga gccgcgtgaa gggcggctcg tga                               1653
```

```
SEQ ID NO: 10          moltype = DNA  length = 1653
FEATURE                Location/Qualifiers
source                 1..1653
                       mol_type = genomic DNA
                       organism = Methylomonas denitrificans
SEQUENCE: 10
atgtcgaccg cgaagttcga caccatcggc cagtatctgc tgaagcggct gtatcaggcc  60
ggcgtcaagg atatcttcgg cgtcccccggc gactacgtgc tgggcttcta tgacctgatg  120
atcaagtcgc aggtgcgcca tatcggcacc acgcgggagg acagcgcggc cttcgcggcc  180
gacggctacg cccggtgtgt gggcatgggc gccctggcgg tgacgtacgg cgtcggcgcc  240
ctgaacacgg tgaacgccat cgccggcgcg tacgccgaat cgtcccccgt cgtcctcatc  300
agcggcgccc cgggcgtgtc cgagcagaag gacgatccgc tgatccatca tcgcttcggc  360
cccttcacgt tccagcgcga aatcttcgaa cggatcagct gtgcctccgt cgtcctgaat  420
gacccggtca tcgcgttccg gcagatcgac catgccatcg aggccgcccg gcgcttctgc  480
aagccggtgt atatcgaact gccgcgggac ctcgtgatgg cggagggcta ccccatgccc  540
accgagacgg tcgaaaagtt cacctccgat gaggccgcgc tgtccgaagc gatcgcggaa  600
accatgaccc tgctcagcaa ggcggtcagc ccgatgatcg tggcgggcgt ggagctgcat  660
cggcgcggcc tgcagggcgc cctggccgac ttcgtggaac ggacctgtct gcccgtggtg  720
gccaccctga cgggcaagtc ggtgatgtcg gagcgccatc ccgcctacct gggcatctac  780
gaaggcgcca tgtcctcgga agcggtgcgc gatcgggtgg agaagagcga tctgctcctg  840
atgctgggcg tgaccctcaa cgaaatcgac accggcatct acacggccaa actgaacagc  900
catagcacga tccgcgccgc gctgaacgag gtcgtgatct ccgcccaccg ctatcccggc  960
atcgcgctgg aagatttcct gggcgccctg gcctcgtcgg tgtccctcag ctcgcgcgag  1020
gtggtcagca gcccgaaacc cccggagtcg atcgccttcc cggaaccgga ccggccgatc  1080
acgacggccc gcctggtcga acggctcaac tccgccctca gcaatgacat gatcgtcgtg  1140
tgtgacgtgg gcgactgcct gttcgcggcc atcgacctcc gcgtgcatga gcagagcgag  1200
ttcctggcct ccgccttcta caccacgatg ggcttcgcgg tgcccgcggc cctcggcgcc  1260
cagatcgccc gccccgaccg gcgggcgctg atcctggtcg gcgacggcgc gttccagatg  1320
accggcaccg aactgtccac gcacgcgcgg ctgggcctga acccgatcgt cgtcgtgttc  1380
aataatggcg gctactcgac cgaacgctgc atcctggaag gcccgttcaa tgatatcaac  1440
ccctggcgct tcgaccgcct gggcgagctg ttcggccccc tggccggcta tgaggccgcc  1500
acggaagccg agttcgagga agccctgctg aacgcgctgg acaaccacgg catgccgtcc  1560
atcatcaatg tgcatctcgc cgccgacgat agctccgagg cgatgaaacg cctggccgag  1620
cacctgcaga gcaaaatcaa gcgggacgcc tga                               1653
```

```
SEQ ID NO: 11          moltype = DNA  length = 1662
FEATURE                Location/Qualifiers
source                 1..1662
                       mol_type = genomic DNA
                       organism = Methylomonas methanica
SEQUENCE: 11
atgaacacgg tcaaactgga aacgatgggc cagtacctgc tgaaccgcct ctatgaggcg  60
ggcgtgaaac atgtcttcgg cgtcccgggc gactatgtcc tgggcttcta cgacctgatg  120
gagaagtccc ccatccagca tatcggcacc acccgcgaag ataccgcggc cttcgccgcc  180
gacggctacg cccgctgccg cggcctgggc gccctggccg tcacgtacgg cgtcggcgcc  240
ctcaacacgg tgaatgcggt ggcgggcgcc tacgcggagt cgtcgcccgt gatcgtcatc  300
agcggcgccc cgggcgtctg tgagcagcgc gatgacccgc tgatccacca ccgcttcggc  360
cccttcacct tccagcgcga gatcttcgaa cggatcacct gcgccaccgc ggtgctgaac  420
gacccggtga tcgcgttccg gcagatcgat cacgccatcg cctccgcccg ccattattgc  480
aagccggtct atatcgaaat cccgcgggac ctcgtgtccg tggaaggcta cccgatgccc  540
gccatcgccg cgatggagcc gtcgggctcc gacaagtccg ccctcagcga ggccgtggcg  600
gaaaccatgt cgctgctgga aaagtccgtg tccccgatgg tcatcgccgg catcgagctc  660
caccgccgcg gcctgcagaa ccgcctcctc gaactgatcg aacgcgcccg cctgcccgtg  720
acggccaccc tcaccggcaa aagcgtgatc gcggagcggc accccgcgta cctgggcatc  780
tatgagggcg cgatgtccag cgaacacgcc cgctatatgg tcgagcagtc cgacctcctc  840
ctcatgctgg gcgtgaccct gaacgaggtc gacacgggca tctacaccgc gaagctggac  900
ccccagcata ccatccgggc ggcgctgaac gaggtggtga tctcggccca ccgctatccg  960
```

```
aatatcgccc tggccgacta tctgaacgcc ctggtggacg cggtgaagcc gtcggaggcg  1020
ggcttctccg ccaaaccggg caaacccgtc gcgcgggcgt tcccggagcc cgaccgcccg  1080
atctcgatca accgcctgat cgaacgcatc aatcaggcgc tggaaccgga gacgatcgtg  1140
gtgtgcgacg tgggcgactg tctcttcgcc gccatcgatc tggaggtcca cgagcagtcg  1200
gagttcctgg cctcgggctt ctataccacg atgggcttcg ccgtgcccgc cgccctgggc  1260
gcccaggtcg cccggcccgg ccaccgcgcc ctgatcctgg tgggcgacgg cgcgttccag  1320
atgaccggca cggaactctc cacccaggcc cggctgggcc tggactcgat cgtgatcgtc  1380
ttcaacaatt cgggctattc cacggagcgg tgcatcctgg agggcccgtt caacgatatc  1440
gcccgctggc gcttcgaccg cctcggcgaa gtcttcggcc cgctgcaggg cttcgacgcg  1500
gcgaccgagg agtccttcga gtcggcgctg atccaggccc tgaacaaccg cagcatgccc  1560
agcatcatca acgtccacct cgcgagcgac gacacgagca gcgcgatgcg gcgcctggcg  1620
gaacacctga agtcgaaggt gcagggcgaa cgcccccgcct ga                    1662
```

```
SEQ ID NO: 12           moltype = DNA  length = 1659
FEATURE                 Location/Qualifiers
source                  1..1659
                        mol_type = genomic DNA
                        organism = Methylohalobius crimeensis
SEQUENCE: 12
atggccacgc gcaactcgac gacctcgatc ggcgagtatc tcctccagcg cctgcacgag  60
gccggcgccc accacatctt cggcgtcccg ggcgattata tcctgaaatt ctatgaacag  120
atctcgcagg gcccggtccg ccacatcggc accacgcgcg aagacaccgc ggcgttcgcg  180
gcggacggct atgcccggtg ccagggcatc ggcgcgatgg ccatcaccta cggcgtgggc  240
gccctcaacg tggtgaatgc cgtcgcgggc gcgtacgccg aaagctcgcc ggtggtcgtg  300
atctcgggcg cccccggcgt gtgggaacag cgcgaggacc cgctgctgca ccaccgcttc  360
ggcccctaca cgttccagcg ggagatcttc gaccggatca cctgtgccac cacggtcctg  420
gacgatccga tcacggcgtt ccgccagatc gatcgcacga tcgccgcggc gcagcgcgaa  480
cataagccgg tctacatcga actgccgcgc gatcgggtca cggtggccgg cgtgccgctc  540
ccggccgtcg cggaggcgac gccccaggaa acgtccgacg ccgccaccct ggacgaggcc  600
gtggccgaaa cgctggccct cctcgcccag gccaagagcc ccgtgctgat cgcgggcgtg  660
gaggtccacc gctgcggcct ccaggatgcg ctcgtcgacc tggtcgtccg cgcgggcctg  720
ccggtcgcgg ccaccctgac gggcaaatcc gtcgtgggcg aacgccaccc ggcgtatatc  780
ggcgtctacg agggcgccgc gtcgtccgaa cacacccgcc agatggtgga acgcgcggac  840
gtgctcatca tgctcggcgt gacgctgaac gacgtggaca ccggcgtcta tacggcgaac  900
ctggaccccc atcgcctggt ccgcgcgtcc cagggcgagg tgaacatccg ctaccatcgg  960
tatccgcgcg tccagctgca ggacttcatc ggcgccctcg cccgccaggt cagcccccgc  1020
cgcgaggccc tgccgtccca gcccttcgtc gatagcggcc ccgccttccc cgtcccgggc  1080
caggcgatga ccacggcgcg gctcatcgcc cgcctgaact gcgccctcac ccccgaaatg  1140
atcgtggtgt ccgatgtggg cgattgcctg ttcgccgcca tcgaactccg ggtctgcgaa  1200
cggagcgagt tcctggcctc cgcctactat acgacgatgg gcttcgcggt gccggccgcc  1260
ctgggcgccc aggtcgcgcg gccggatcgg cgggccctga tcctggtggg cgacggcgcc  1320
ttccagatga cgggcaccga gctgagcacc cacgcccgcc tgaacctggc gccgatcatc  1380
atcgtcttca acaacgccgg ctacagcacg gagcgcaata tcctggaggg cccgttcaat  1440
gacatcgcgg cctggcggtt cgaccgcctc ggcgaagtgt tcggcccccct gcatggctac  1500
gacgccaaga cggaagatgc gttcgagacg gcgctcgccc gcgccctggc cgagacgggc  1560
tgcccgtcgc tcatcaatgt gcatctgtcc ccggacgacg cctcgccggc catgcgccgc  1620
ctgacggagc ggctgtccca tcgcgtgggc aatcagtga                         1659
```

```
SEQ ID NO: 13           moltype = DNA  length = 1635
FEATURE                 Location/Qualifiers
source                  1..1635
                        mol_type = genomic DNA
                        organism = Methylobacter marinus
SEQUENCE: 13
atgagcagca acccgtcgat cggccactac ctgctcacgc ggctgtacga atccggcgtg  60
caccacatct tcggcgtccc gggcgactac atcctccgct tctaccagca gctgagcgag  120
agcccggtgc agcatatcgg caccacgcgc gaagacacgg ccgccttcgc gaccgatgcg  180
tatgcccgct gtcggggcct gggcgcgatg gccgtgacct acggcgtcgg cgccctcaat  240
gtggtcaacg ccgtggcggg cgcccatgcc gagtcgagcc ccatcgtggt catctccggc  300
gcccccggca tcaaggaacg ccgggaacac cccctgctgc atcaccgctt cggcccgttc  360
cgcctgcagc gcgagatctt cgaacggatc acctgcgccg tcgcggtgct ggatgacccc  420
tataccgcct tccggcagat cgaccgggtc ctggcggcgg cgcgggagca ctgcaagccc  480
gtctacatcg agctgccgcg cgatcgcgtg gataccgagg gctatccgat cccgtcggag  540
tccctgccgg cccccgcctc cgacgccgag agcctcaacg aagccgtgga ggaagccctg  600
cagctcctcg atgaggccgc gtcgccggtg ctggtcgccg gcgtggaact gcaccgccgg  660
ggcctccagg atcagctcct ctcgctggtg gataaaaccc atctgccggt cgccgccacg  720
ctcaccggca agtccgtcct gggcgagcgg cacccgtgtt atctgggcat ctacgagggc  780
gcgatgggct ccccccctggc gcgggaccgc gtcgagcagg ccgatttcct gctgatgctg  840
ggcgtcacgc tgaacgatgt ggacctcggc atcttcaccg cccgcctcga cgccaatcgc  900
atcatccggg cctcccagga cgaagtcatc atccaccacc accgctatcc gcaggtcctc  960
ctgcgggact tcgtgtccat gctgaacgaa cggatgaccc cgcgccccca gacgggcccg  1020
gccgtcgccg cgaagccggc cgccttcgat ttcccggtca aggccagccc gatgaagatc  1080
atccggctga tcgcccggct gaatcggttc ctcaccccgg acatggtcgt ggtcagcgac  1140
gtgggcgatt gcctgttcag cgcgatcgac ctgcgggtgc acgaaaacag cgagttcctc  1200
gcctcggcct actacaccag catgggcttc gcggtcccgg ccgcgctggg cgcccagatc  1260
gcccgcccca cccggcgcac gctggtcctc gtgggcgacg gcgcgttcca gatgaccggc  1320
accgagctct cgaccatcgc gcacctcggc ctgaacccga tcgtgatcgt cttcaataac  1380
aagggctact cgaccgaacg ctatatcctg gatggcccgt tcaatgatat cccggcctgg  1440
cagttcgagc gcctgggcga actcttcggc ccgctgaccg gctatgccgc cagcaccgag  1500
```

```
gacgagttcg aagattgtct gaaccaggcc ctggcccagc ggtcgagccc ctccctcatc  1560
aacgtccacc tctccccgga cgatccgagc gccgccatgc ggggcctcgc cgaacatctg  1620
ggcaagcgcg tctga                                                   1635

SEQ ID NO: 14          moltype = DNA  length = 1650
FEATURE                Location/Qualifiers
source                 1..1650
                       mol_type = genomic DNA
                       organism = Methylobacter luteus
SEQUENCE: 14
atggaggtgc atctgatgtc ctccaacccg tccatcggcc attatctgct cgcccgcctg  60
tacgagtccg gcgtgcatca catcttcggc gtccccggcg actacatcct gcgcttctac  120
cagcagctca gcgagtcccc gatccagcac atcggcacca cgcgcgagga caccgccgcc  180
ttcgcgaccg acgcctacgc ccgctgccgg ggcctgggcg cgatggccgt gacctacggc  240
gtgggcgccc tgaacgtcgt gaacggcgtg gccggcgcgt acgcggaatc ctcgccggtc  300
gtggtgatct ccggcgcccc gggcatcaag gaacgccatg aacatccgct gctgcatcat  360
cgcttcggcc cgttccgcct gcagcatgaa atcttcgaac gcatcacctg cgcgacggcg  420
gtcctggacg atccctacat ggcgttccgg cagatcgacc gggtgctggc cgccgcccgc  480
gagcactgca agcccgtgta tatcgagctg ccgcgcgacc gggtggatgt cgaaggctat  540
ccgatgccga gcgagagcat gccggccccg gcctccgacg cggaaagcct gaacgaagcg  600
gtcgaagaaa cgctgcagct gctgggcaag gccgcgtcgc ccgtgctgat cgcgggcgtc  660
gaactgcacc gccgcggcct ccaggacaaa ctgctctccc tggtcgacaa gacccatctc  720
ccggtggccg cctcgctgac cggcaaatcg gtcctgggcg aacgccaccc gtgctatctg  780
ggcatctatg aaggcgcgat gggctcgtcc ctggcccggg actccgtgga gcagtcggac  840
ttcctcctga tgctgggcgt caccatgaac gacatcgatc tgggcatctt caccgcgaag  900
ctggacgcga accgcatcat ccgcgccacg caggatgagg tcatcatcca ccatcatcgc  960
tatccccacg tcctgctgcg ggacttcgtc accgtcctga atgagcgcat cacgccccgc  1020
ccgggcatcc gcccggccgt cgcggcggag ccggccgcct tcgacttccc ggtcaaggac  1080
cagcccatga aaatcctccg gctgatcgaa cggctcaacc gcttcctgac ccccgacatg  1140
gccgtcgtct ccgatgtcgg cgattgcctc ttcgcggcga tcgacctccg ggtgcacgag  1200
aactcggagt tcctggcgtc ggcgtattat accagcatgg gcttcgccgt gcccgcggcg  1260
ctcggcgccc agatcgcgaa cccgacccgc cgcacgctgg tgctggtcgg cgacggcgcc  1320
ttccagatga ccggcaccga actgtccacc atcgcccggt tcggcctgaa cccgatcgtg  1380
atcgtcttca ataactgtgg ctattcgacc gagcggtaca tcctggatgg ccccttcaac  1440
gatatcgcct gctggcagtt cgaacggctg agcgaggtgt tcggcccgct ctcgggctat  1500
tcggcccgga cggaggatga gttcgaaaac tgcctgaccc aggccttcgc ccagcagtcc  1560
tcgccgtccc tcatcaacgt ccacctcccc ccggatgacc cgagcgcggc catgcgcggc  1620
ctcgcggaac acctcggcaa gcgcgtctga                                  1650

SEQ ID NO: 15          moltype = DNA  length = 1629
FEATURE                Location/Qualifiers
source                 1..1629
                       mol_type = genomic DNA
                       organism = Lamprocystis purpurea
SEQUENCE: 15
atgggcgact acctcctgct ccgcctgaag gaagcgggcg tcgaccactg cttcggcgtc  60
cccggcgact acgtcctgcg gttctacgat cggctctgcc ggtcggacat ccggcacatc  120
ggcaccaccc gcgaggacac cgcggccttc gcggccgacg gctacgcccg gtcccgcggc  180
ctgggcgccc tggccgtgac gtatggcgtg ggcgccctca acgtggtcaa cgcggtcgcc  240
ggcgccaacg cggagtcctc cccggtcgtc gtgatctccg gcgccccggg cgtcgcggaa  300
cagcgcgacg atccccagct gcaccatcgg ttcggcccgt tccggttcca gcgcgagatc  360
ttcgaacgca tcacctgcgc gtgtgccgtg ctcgacgacc cgtacaccgc cctgcgcgag  420
atcgaccgca cgctcgacgc ggcgcggcgg tacagccggc ccgtgtatat cgaactcccg  480
cgcgaccggg tcgacacgcc cgccttcccc atcccccacg agccggaaga ggaagccggc  540
agcgacccgg aggccctggc cgaggcggtc gccgaaaccc tggcgctcgt cggccgcgcc  600
caggcccccg tcatcctggc cggcgtggag ctgcaccgcc gcggcctgca ggacctcctg  660
gccggcttcg tgctgaaggc ccacctcccg gtggccgcga cgctgacggg caagtcggtg  720
gtcgccgagc gccagccggg ctacctgggc gtgtacgagg gcgcgatggg cccggaaggc  780
gcccgccgcg tcgtggaaga agccgacctg ctgctcctgc tgggcgtgac cccgaacgac  840
atcgacctgg gcatcaacac cgcccggctg gaccccgccc ggaccgtccg ggccggccag  900
gaagaaatct gggtccatcg gcaccgctac ccgcatgtgc acctgcggga tttcctggcc  960
gcgctgacgg atgccgtggt gccccacccc ggccccctgc cggatgtccc cggcccggtc  1020
ggcgccccgg acttccccca gccgggccag cccatgacga tggcccgcat gatggcccgc  1080
ctgaacgact tcctgacccc cgacatgcag gtggtggccg actccggcga ctgtctgttc  1140
gcgtccgtcg acctgcgcgt ccatgcccgc agcgagttcc tggcctcggc ctattacacg  1200
acgatgggct tcgccgtccc ggccgcgctc ggcgcccagg tcgccaaccc cggccgccgc  1260
ccgctcgtgc tggtgggcga cggcgccttc cagatgaccg gcacggagct gtcgaccgcc  1320
gcccgcctgg gcctcgatcc gatcgtcatc atcggcaata atcgcggcta caccaccgaa  1380
cgcttcatcc tggaaggccc gttcaacgac atcgccgact ggcggttcca tcgcctgggc  1440
gaactgttcg gcccgctgcg gggcttctcg gcccccacgg aagacgcctt cgacgccgcc  1500
ctgggcgccg ccctggcctt ccgggacggc ccctccgtca tcgaggtggc gctgcgcccg  1560
gacgactgct ccgcggccct gacccggctc tccgaacgcc tgcgcgatgt ggtgcagcag  1620
agcgcctga                                                          1629

SEQ ID NO: 16          moltype = DNA  length = 1656
FEATURE                Location/Qualifiers
source                 1..1656
                       mol_type = genomic DNA
                       organism = Andreprevotia chitinilytica
```

```
SEQUENCE: 16
atgcacatgc gggagacgga catggatacg atgggcggct acctgctgca ggccctgcat  60
cgcgagggcg tccggcatgt gttcggcgtg ccgggcgact acatcctgcg ctggtatcag  120
ctgctctcgc agagcaacct gaagcacgtc ggcacctcgc gcgaagactg cgccgcgttc  180
gccgccgacg gctacgcgcg gtgccacggc ctgggcgccc tggccgtcac ctacggcgtc  240
ggcgccctga acgtggtgaa cgcggtggcc ggcgcgaacg cggagtccag ccccgtggtg  300
gtcatcagcg gcgccccggg cgtcgcggaa cagcgccaga acccgctgct ccaccaccgc  360
ttcggcccgt tctgcttcca gcgcgaaatc ttcgaacgca tgacgtgcta cgcggcggcg  420
ctcgacgatc ccctcctggc gcggcgccag atcgaccgcg ccctggagct ggcccagctc  480
catcacaagc cggtctacct cgaactgccg cgggatctcg tggatgcgga actgccgccg  540
gccctctcgc cgcccacctc ctcggcgccc atctcggatt gggacgcgct cgaagaagcg  600
gtcgcggaaa ccctcagcct cctggcgaag gcgaaaagcg ccgcggtcct cgccggctcg  660
gagctgcacc gctaccagct gcaggacgag ctgacgcagc tcgtggaacg gggcgccctc  720
cccgtggccg ccaccctgac cggcaagtcc gtgatcgccg agcgccaccc ggcctacatg  780
ggcatctacg aaggcgcgat gggcggcgcc cgcacgcggg aactgatcga gcgggcggac  840
gtgctgctgc tgctgggcgc caccctcaat gatgtggatc tgggcatctt caccgccaag  900
ctggatgtcc agcacatggt gcaggcgacc gccgatggcg tccagatcca ccaccaccgc  960
tacaccggcg tcccccctcgg cgactatgtg cgggccctga cggcgggcat cgaacgctcg  1020
ggccgctccc tcccggtggt ggaacccccc ctggcggcca tcggcttccc gatcacctcg  1080
cagcccatga ccgtggcccg cctgatcggc cgcctcaatg ataccctgcc gcaggacatg  1140
atcgtcgtct gtgacaccgg cgactgcctc ttcgcctccc tggagctccg cgtccatgcc  1200
cgcaccgcct tcctggcctc ggcgttctac acgacgatgg gcttcgccgt gcccgcctcg  1260
ctgggcgccc agctcggctc gggccggcgc cccctggtgc tggtgggcga tggcgccttc  1320
cagatgacgg gcaccgagct ggccaccgcc gcgtggaagg gcctgaaccc catcgtcatc  1380
gtcttcaaca acgccggcta ctccaccgag cgcttcatcc tggacggccc cttcaacgac  1440
atcccgtcgt ggcagttcca tcgcctgggc gaactgttcg gcccgctggc cggcttcgat  1500
gtccacgacg aagagtcgtt cgactccgcc tggcgctcgg ccctcgccca gaccgatcgc  1560
ccgtcgctgc tgaacgtgca tctggccccc gacgacccct cgcccgcgat gcggcggctg  1620
ggcgaacatc tgggcaagcg ggtgcgggcg ggctga                            1656

SEQ ID NO: 17          moltype = DNA  length = 1647
FEATURE                Location/Qualifiers
source                 1..1647
                       mol_type = genomic DNA
                       organism = Lactococcus lactis
SEQUENCE: 17
atgtacaccg taggagacta cctacttgac agactccatg agctgggcat agaggaaatc  60
ttcggagtcc cgggtgatta caacctgcag ttcctggacc agatcatcag ccacaaggac  120
atgaagtggg tgggcaacgc gaacgaactg aacgcgagct atatggcgga cggttatgcc  180
cgcaccaaga aggcagccgc gttcctcacc actttcggcg tgggcgaact cagcgccgtg  240
aacggcttgg caggcagcta tgcggaaaac ctgccggtgg tggaaatcgt cggctccccg  300
acctcgaagg tgcagaacga gggcaagttc gtgcatcata ccctggcgga cggggacttc  360
aagcatttca tgaagatgca cgaacccgtc accgctgccc gcacgctgct gaccgcggaa  420
aacgcgaccg tggagatcga ccgggtcctc tccgccctgc tgaaggaacg gaagcccgtg  480
tacatcaatc tacccgtcga cgtagcagcc gccaaggccg aaaagccctc gctcccgctg  540
aagaaggaga actcgacgag caacacgagt gaccaggaaa tcctgaacaa gatccaggag  600
tcgttaaaga acgcgaagaa gccgatcgtc atcaccggcc atgagatcat cagcttcggc  660
cttgagaaga ccgtgacaca gttcatctcc aagaccaagc tgcccatcac caccctcaac  720
ttcggcaagt ccagcgtgga cgaagccctg ccgagcttcc tgggcatcta caacggcacc  780
ctgtcggaac ccaacctgaa ggagttcgtc gaaagcgcgg acttcatcct gatgctgggc  840
gtgaagctga ccgactcctc gacgggagcc ttcacccatc acctgaacga aaacaagatg  900
atctccctca acatcgatga aggcaagatc ttcaacgagc gcatccaaaa cttcgacttc  960
gaaagcctga tctcctcgct gctggacctg tccgagatcg agtacaaggg caagtacatc  1020
gacaagaagc aggaagactt cgtgccgtcg aacgcgctgc tgtcgcagga ccgcctgtgg  1080
caggcggtcg aaaacctgac gcagtcaaac gaaaccatcg tcgccgaaca gggaacctcg  1140
ttcttcggtg cctcaagtat cttcctgaag tccaagtccc acttcatcgg ccagcccctg  1200
tggggctcga tcggctatac cttcccggca gcgctaggct cccagatcgc ggacaaggaa  1260
tcgcggcacc tgctcttcat cggcgacggc tccctgcagc tgaccgtcca ggagctgggc  1320
ctcgccatcc gggaaaagat caacccgatc tgcttcatca ttaacaacga cggctacacc  1380
gtggagcgcg agattcatgg cccgaaccag agctacaacg acatccccat gtggaactac  1440
tctaagctgc cggaatcgtt tggcgccacg gaggaccggg tggtcagcaa gatcgtccgg  1500
acggagaacg agttcgtctc ggtgatgaag gaagcgcagg cggaccccaa ccggatgtat  1560
tggatcgagc tcatcttggc caaggagggc gctccgaagg tcctgaagaa gatgggcaag  1620
ctcttcgccg aacagaacaa gtcgtaa                                      1647

SEQ ID NO: 18          moltype = DNA  length = 1713
FEATURE                Location/Qualifiers
source                 1..1713
                       mol_type = genomic DNA
                       organism = Lactococcus lactis
SEQUENCE: 18
atgggctcgt cccatcatca tcaccaccat tccagcggcc tggtcccgcg cggcagccac  60
atggcctcga tgtacaccgt gggcgattac ctgctggacc ggctccacga actgggcatc  120
gaagagatct tcggcgtccc gggcgactat aacctccagt tcctggatca gatcatctcc  180
cgcgaggaca tgaaatggat cggcaatgcg aacgagctga acgcctccta tatggccgac  240
ggctatgccc gcaccaaaaa agccgccgcc ttcctgacca cgttcggcgt gggcgaactg  300
tcggccatca acggcctggc cggctcctac gccgagaacc tgcccgtggt ggaaatcgtg  360
ggctcgccga cctcgaaggt ccagaacgac ggcaagttcg tgcaccacac gctcgcggac  420
ggcgacttca agcacttcat gaagatgcac gagccggtca ccgccgcccg caccctgctg  480
```

```
acggccgaga acgcgaccta tgaaatcgac cgggtgctct cccagctcct gaaggagcgg  540
aagccggtgt acatcaacct ccccgtcgat gtggccgccg ccaaggccga gaaacccgcg  600
ctgagcctgg agaaggagtc ctccacgacc aacaccaccg aacaggtgat cctcagcaag  660
atcgaagaat ccctcaagaa cgcccagaaa cccgtggtga tcgcgggcca tgaggtgatc  720
tcgttcggcc tggagaaaac cgtcacccag ttcgtgagcg aaaccaagct ccccatcacc  780
accctcaact tcggcaagtc ggccgtggac gagtccctgc cgtccttcct gggcatctat  840
aatggcaaac tgtcggaaat cagcctgaaa aatttcgtcg aaagcgccga cttcatcctc  900
atgctgggcg tgaagctgac cgactcctcg accggcgcct tcacccacca cctcgatgaa  960
aacaagatga tctccctgaa catcgacgaa ggcatcatct tcaacaaggt ggtcgaagac  1020
ttcgacttcc gggccgtcgt gtcgagcctg tccgaactga aaggcatcga atatgaaggc  1080
cagtacatcg acaagcagta tgaagagttc atcccgtcgt cggcgccgct cagccaggat  1140
cgcctctggc aggccgtgga aagcctgacc cagtccaacg aaacgatcgt cgccgaacag  1200
ggcacctcgt tcttcggcgc cagcacgatc ttcctgaagt ccaactcccg gttcatcggc  1260
cagccgctgt ggggctcgat cggctacacg ttcccggccg cgctgggcag ccagatcgcc  1320
gacaaggaat cccgccacct cctgttcatc ggcgacggct ccctccagct gaccgtgcag  1380
gagctgggcc tgtcgatccg cgaaaagctg aatccgatct gcttcatcat caacaacgac  1440
ggctacacgg tcgaacggga gatccacggc ccgacgcagt cctacaacga catcccccatg  1500
tggaactaca gcaaactccc ggaaaccttc ggcgccaccg aagaccgcgt cgtctcgaag  1560
atcgtgcgga ccgaaaacga gttcgtgtcc gtgatgaaag aggcgcaggc ggatgtgaac  1620
cggatgtact ggatcgaact ggtcctggag aaagaggacg ccccgaagct cctgaagaag  1680
atgggcaagc tcttcgccga gcagaacaaa tga                              1713
```

```
SEQ ID NO: 19          moltype = DNA  length = 1650
FEATURE                Location/Qualifiers
source                 1..1650
                       mol_type = genomic DNA
                       organism = Streptococcus didelphis
SEQUENCE: 19
atgtataccg tcggcgatta tctgctggat cggctcaagg aaatcggcat cgaccatatc  60
ttcggcgtcc cgggcgacta caacctccag ttcctggatc agatcaccgc ccgcgacgac  120
ctcaaatggg tgggcaacgc caacgaactc aacgcgagct acatgtccga cggctatgcc  180
cgcaccaaga aggccgccgc cttcgtcacc accttcggcg tgggcgaact gtcggcgatc  240
aacggcctgg ccggctcgtt cgcggaaaac gtccccgtga tcgagatcgt cggctcgccg  300
acgaccaagg tgcaggaagc cggcaaactg gtgcaccata cgctcggcga cggcaacttc  360
aatcacttcc aggagatgca caaatcggtc accgtggccc aggtcaaagt cagcgccgaa  420
catgcccaga ccgacatcga ccaggtgctc ctgtccctgc tgaaggagcg gaagccggtg  480
tatatcaacc tgcccatcga tgtggcccag atgcccgccc agaagccgga atcggccctc  540
ctggtcgaga aggtcatctc cgagcaggac aagatcatcc tgcaggcgat cgagaaaggc  600
ctgaagaccg ccaagcagcc cctcatcatg gtcggccatg aagtcgccag cttcggcctg  660
gaagccacca tcaacaactt catcaaaaag aagaagtacc ccgtgacctc gctcagcctg  720
ggcaaaggca tcgtcaacga gtcgccggaa accttcctgg gcatctactc cggcgccctg  780
tccccgcagg ccctgaaaga ctacgtcgat caggcggact tcatcctcac cctcggcgtc  840
aagctgaccg actccgtgac gggcggcttc agccagggct tcgatgcgaa gcaggtgctg  900
agcctggccg ccaaccaggc gtcgctcttc ggcgaaaact accagggcta tcacttctcc  960
gacgtgatcc gcgaaatcga aaatctggac atccccagct attcgggctc ctatatcgcc  1020
aagaccaagg tcgccgattt cgaagcggag aagggccagg tcctgtccca gaagcgcttc  1080
tggcaggcga tggaatcgtt cgtccaggcc ggcgacacca tcttcgccga gcagggcacc  1140
tcgtacttcg gcgcgagcca gctcaacctg aaagagaacg tggcctacca gggccagccg  1200
ctctggggca gcatcggcta taccttcccg gccgtcttcg gcagccagct cgcgaacccc  1260
gattcgcggc atatcctgtt cgtcggcgac ggcagcctgc agctgaccgt ccaggacatc  1320
ggcctggcgc tgcgcgagca gctgaacacg atcgtgttcg tcatcaacaa cgacggctat  1380
accgtggagc gcaagatcca cggcccggaa gaggtctata atgacatccc gcagtggcag  1440
tacagccagc tccccgcctc cttcggcggc aacgactcgc aggtcctggc ccggaaagtg  1500
agcaccgaag aggagctggt cgaaatcctg gaaaaggcgc gggccgacgt gtcccggatg  1560
tattggatcg agctcatgct ccccaaaatg gacgcgccgg agtatctgga aaagctgggc  1620
aagctgttcg cccagcagaa taaagcctga                                  1650
```

```
SEQ ID NO: 20          moltype = DNA  length = 1647
FEATURE                Location/Qualifiers
source                 1..1647
                       mol_type = genomic DNA
                       organism = Enterococcus caccae
SEQUENCE: 20
atgtacaccg tcgccgatta cctgctggat cgcctgaagg agctgggcat cgatgagctg  60
ttcggcgtgc cgggcgacta caacctgcag ttcctcgacc acatcaccgc ccgccaggac  120
ctggagtgga tcggcaacgc caacgaactg aacgccgcgt atatggccga cggctacgcc  180
cggaccaagg gcatctcggc gttcgtgacc accttcggcg tgggcgagct gtccgccatc  240
aatggcctcg ccggcagctt cgcggagaac gtcccggtcg tcgagatcgt gggctccccg  300
accaccacgg tccagaacga caagaagctg gtgcatcaca cgctgggcga cggcaatttc  360
ctgcatttcg agaagatgca tgaagaggtc accgccgcca tcgcgcacct caccgccgaa  420
aacgcgctga ccgaaatcga ccgggtgctc atcatcgcca tgatcgagaa gcgcccggtc  480
tatatcaacc tcccgatcga catcgccgag ttcaaagcca ccccgccgct cagcccccctg  540
agccggtcgg ccgaaaagct gacggatgtc gaaatcgcca tcctcgacaa ggtggaaaag  600
gcgctgtcgc aggcgaagaa ccccgtcgtg atcgccggcc acgaaatcct cagctaccat  660
atcgaacatc agctggacga gttcatccag aagttcaacc tcccgatcac cacgctgccc  720
ctgggcaaac gcgcgttcaa tgaggaagac ccgcactatc tcggcaccta cagcggctcc  780
accaccgagg agccgctgaa gacccgcgtg gataccgcgg atctggtcct gctgctgggc  840
gcgaagctga cggactcggc cacctcgggc ttctccttcg gcttcaccga ccagcagatc  900
atcagcatcg gctccacgga ggtcctcttc tacggcgaaa ccttcaaagc cgtgcagctc  960
```

```
gaccgcttcg tctcggcgct caccaccctg agcttctccc ggtacgaaga tgaaatccag  1020
ccggtgaccc ggatcagcaa ccaggcgatc aaggacgaga agctgtcgca gaagcagttc  1080
tgggagatgg tcgagacgtt cctgatcccg ggcgacaccg tgatcggcga gcagggcacc  1140
tcgttcttcg gcctgaccaa cgtcgccctg aagcggaata tgcacttcat cggccagccg  1200
ctgtggggca gcatcggcta tacgttcccg tcggccctcg gctcgcagat cgccaacaag  1260
gaaagccggc atctgctgtt catcggcgat ggctccctcc agctgaccgt gcaggaactg  1320
ggcaccgccc tgcgcgagaa gctgacgccg atcgtcttcg tcatcaacaa caatggctat  1380
accgtggaac gggagatcca cggcgccacc gagcagtaca acgacatccc catgtgggat  1440
tatcagaacc tgccgctcgt gttcggcggc aacaaccaga ccgtcgccac ctacaaggtc  1500
accaccgcga tcgaactgga tgaggtcatg aaaaccgccc gcaaggacac caagcgcctg  1560
cagtggatcg aagtggtcat ggcgcaggat gacgcgccgg aactgctcaa gaaactcgcc  1620
aaaatcttcg ccaaacagaa cagctga                                     1647
```

```
SEQ ID NO: 21          moltype = DNA  length = 1647
FEATURE                Location/Qualifiers
source                 1..1647
                       mol_type = genomic DNA
                       organism = Enterococcus haemoperoxidus
SEQUENCE: 21
atgtacacca tcagcgacta cctcctggac cggctgaagg aactcggcat cgacgaagtc  60
ttcggcgtcc cgggcgacta caacctccag ttcctcgatc atatcaccgc ccgcgaagac  120
ctgaaatgga tcggcaacgc gaatgaactc aatgccgcct acatggcgga cggctatgcc  180
cgcaccaagg gcatcagcgc cttcgtgacc accttcggcg tcggcgaact gagcgcggtg  240
aacggcctgg ccggctcgta cgccgagaac gtgccggtgg tcgagatcat cggcagcccc  300
accaccaccg tgcagaacaa caagaaactg gtccaccaca cgctgggcga tggcgacttc  360
ctgcggttcg aaaagatgca cgaggaagtc accgccgcga tcgcccatct gaccatcgag  420
aatgccacga gcgaaatcga ccgcgtcctg acgatcgcca tgaccgagaa gcgccccgtg  480
tatatcaacc tgccgatcga tatcgcggaa accaagacga acaagccgaa caaaccgctg  540
cagaagatga ccgagcggct cacggaagcc gaagcgacca tcctgtcgaa ggtcgagaag  600
gccctccagc aggcggagaa cccggtcatc atcgccggcc atgagatcct gtcctaccac  660
atcgagcacc agctgaatga gttcatccag aagttcaatc tccccatcac cacgctgccg  720
ctgggcaagg gcgccttcga cgaggaagac tcgcactaca tgggcacgta ttccggctcc  780
cccacggaag agcccctgaa gagccgcgtg gataacgccg atctggtcct gctgctcggc  840
gccaagctga ccgattccgc gacctccggc ttctcgttcg gcttcaccga caagcagatc  900
atcagcatcg gcgcgaccga agtcctgttc tacggcgaga aacacgaggc catccagctc  960
gatcgcttcg tgtccgccct gtccacgctc tccttctccc gcttcaccgg cgatctgctc  1020
ccggtgaaac ggatcagcaa ggtcgagttc aaggacgagc agctcaccca gaagcgcttc  1080
tggaagatgg tcgaaacgtt cctgctccag ggcgacaccg tcgtgggcga acagggcacc  1140
agcttcttcg gcctgaccaa tgtgcccctg aagaaggata tgcacttcat cggccagccg  1200
ctctggggca gcatcggcta taccttcccc agcaccctgg gctcgcagat cgccaacaag  1260
gactcccgcc acctgctgtt catcggcgat ggctcgctgc agctgaccgt gcaggagctc  1320
ggcacggcca tccgggagaa gctcacgccg atcgtcttcg tcatcaacaa caacggctac  1380
accgtggaac gcgaaatcca cggcgccacc gagcagtaca acgacatccc gatgtgggac  1440
taccagaacc tcccccctggt cttcggcggc acgagccaga ccgtggcgac gtataaagcc  1500
acgaccgaag cggagctggc cgaggtcatg aagtccgccc ggaaggatac ggagcggctg  1560
cagtggatcg aggtggtgat ggaccaggaa gacgcgcccc tgctgctgca gaagctggcc  1620
aagatcttcg ccaagcagaa ctcgtga                                     1647
```

```
SEQ ID NO: 22          moltype = DNA  length = 1647
FEATURE                Location/Qualifiers
source                 1..1647
                       mol_type = genomic DNA
                       organism = Enterococcus moraviensis
SEQUENCE: 22
atgtacacgg tggcggacta tctgctggac cggctgaaag agctgggcat cgacgaagtg  60
ttcggcgtgc ccggcgacta caacctgcag ttcctcgacc acatcacggc ccggaaggac  120
ctcgaatgga tcggcaatgc caacgaactg aacgccgcct acatggccga cggctacgcc  180
cgcaccaagg gcatctccgc gctggtcacc accttcggcg tcggcgaact gtcggccatc  240
aatggcctgg ccggctcgta cgcggaaagc atcccggtga tcgaaatcgt gggctccccg  300
acgacgacgg tgcagcagaa caagaagctc gtgcatcata cgctgggcga cggcgatttc  360
ctgcggttcg agcgcatcca cgaggaggtg tcggcggcca tcgcgcacct gtccaccgag  420
aacgccccct ccgagatcga ccgcgtgctg acggtggcca tgaccgaaaa gcgcccggtc  480
tatatcaacc tcccgatcga tatcgcggag atgaaagcgt cggcccccac cacgcccctg  540
aaccacacca cggatcagct gacgaccgtc gagacggcca tcctcaccaa ggtcgaggat  600
gcgctgaagc agtccaagaa tcccgtcgtc atcgccggcc acgagatcct gagctaccac  660
atcgaaaatc agctggaaca gttcatccag aagttcaacc tgccgatcac cgtgctcccg  720
ttcggcaagg gcgccttcaa cgaagaggac gcgcattacc tgggcaccta tacgggcagc  780
acgaccgacg agtccatgaa gaatcgcgtc gaccatgcgg acctggtcct gctgctcggc  840
gccaagctca ccgactcggc cacctcgggc ttcagcttcg gcttcacgga gaagcagatg  900
atctcgatcg gctcgaccga agtgctgttc tatggcgaga agcaggagac ggtgcagctc  960
gaccgcttcg tgagcgccct gtcgaccctg tccttctccc gcttcaccga cgagatgccg  1020
agcgtgaaac gcctggccac cccgaaggtg cgcgatgaga agctgaccca gaagcagttc  1080
tggcagatgg tcgagagctt cctgctccag ggcgacaccg tcgtgggcga gcagggcacg  1140
agcttcttcg gcctgacgaa tgtgccccctg aaaaaggaca tgcacttcat cggccagccg  1200
ctgtggggca gcatcggcta tacgttcccc agcgccctgg gcagccagat cgccaacaaa  1260
gagtcccgcc acctgctgtt catcggcgac ggctcgctcc agctgacggt ccaggagctg  1320
ggcaccgcga tccgcgaaaa gctgaccccc atcgtgttcg tcatcaacaa caacggctat  1380
accgtggaac gcgagatcca cggcgcgacc gagcagtaca acgacatccc catgtgggac  1440
taccagaaac tgccgttcgt gttcggcggc accgatcaga cggtggccac ctataaggtg  1500
```

tccaccgaaa tcgaactcga taacgcgatg acccgggccc ggacggacgt ggaccgcctc 1560
cagtggatcg aagtcgtgat ggaccagaac gacgccccgg tcctgctgaa gaagctcgcc 1620
aagatcttcg cgaaacagaa ctcctga 1647

SEQ ID NO: 23 moltype = DNA length = 1647
FEATURE Location/Qualifiers
source 1..1647
mol_type = genomic DNA
organism = Carnobacterium maltaromaticum
SEQUENCE: 23
atgtataccg tgggcaacta cctgctggac cgcctcaccg aactgggcat ccgggatatc 60
ttcggcgtcc cgggcgatta taacctcaag ttcctggacc atgtcatgac ccataaggaa 120
ctgaattgga tcggcaacgc caacgagctg aatgcggcct atgccgccga cggctacgcg 180
cggaccaagg gcatcgcggc cctggtcacc accttcggcg tgggcgaact gagcgcggcc 240
aatggcaccg cgggctccta tgccgaaaag gtgcccgtgg tgcagatcgt gggcacgccc 300
acgacggcgg tgcagaactc ccacaaactg gtgcaccata ccctgggcga cggccgcttc 360
gatcacttcg aaaagatgca gaccgagatc aatggcgcca tcgcgcatct gaccgcggac 420
aacgccctgg cggagatcga tcgcgtgctg cggatcgccg tgaccgaacg gtgcccggtc 480
tatatcaacc tggccatcga tgtcgcggag gtggtggccg aaaaaccgct gaagcccctg 540
atggaggaat cgaagaaagt cgaggaggag acggccctcg tcctcaacaa gatcgaaaag 600
gcgctccagg actccaaaaa cccggtggtc ctgatcggca acgagatcgc cagcttccat 660
ctggaatcgg cgctggccga tttcgtcaag aagttcaacc tcccggtcac ggtgctgccc 720
ttcggcaagg gcggcttcga cgaggaggat gcgcacttca tcggcgtcta taccggcgcc 780
ccgaccgccg aaagcatcaa ggagcgggtg gaaaaggccg acctcatcct catcatcggc 840
gcgaagctga ccgatagcgc caccgcgggc ttctcctacg acttcgagga ccgccaggtc 900
atcagcgtcg gcagcgacga agtgtccttc tatggcgaga tcatgaaacc cgtggcgttc 960
gcccagttcg tgaacggcct gaactccctg aattacctgg gctacaccgg cgaaatcaag 1020
caggtggagc gggtggcgga catcgaggcg aaggcgtcga atctcaccca gaacaacttc 1080
tggaagttcg tggaaaagta cctgtcgaac ggcgacaccc tggtggccga gcagggcacc 1140
agcttcttcg gcgcctcgct cgtgccgctg aaatcgaaga tgaagttcat cggccagccg 1200
ctgtggggca gcatcggcta tacgttcccc gccatgctgg gcagccagat cgcgaatccc 1260
gcgagccggc atctgctctt catcggcgac ggctccctgc agctgaccat ccaggagctc 1320
ggcatgacct tccgggagaa actgaccccg atcgtgttcg tcatcaacaa cgatggctac 1380
accgtcgagc gggaaatcca cggcccgaac gagctctaca acgatatccc gatgtgggat 1440
tatcagaacc tcccgtacgt gttcggcggc aacaagggca acgtcgccac ctataaggtc 1500
accaccgagg aagaactggt ggccgccatg tcccaggccc ggcaggacac cacccggctg 1560
cagtggatcg aggtcgtgat gggcaaacag gattcgccgg acctcctggt ccagctgggc 1620
aaggtgttcg ccaagcagaa cagctga 1647

SEQ ID NO: 24 moltype = DNA length = 1647
FEATURE Location/Qualifiers
source 1..1647
mol_type = genomic DNA
organism = Brochothrix thermosphacta
SEQUENCE: 24
atgtatacga tcggcgacta cctcctcgac cggctgaacg agctgggcgt ggaagacatc 60
ttcggcgtgc cgggcgacta caacctgacg ttcctcgatc atatcaccgc gcatccgcag 120
ctctcctggg tcggcaatgc caacgaactc aacgccgcct acgccgccga tggctatgcg 180
cggacgaaag gcttcgccgc gctggtgacg accttcggcg tcggcgagct gtcggccatc 240
aacggcctcg ccggctcctt cgccgaacgg gtgccggtca tcgagatcgt cggcagcccg 300
gtcagcaccg tgcagaccga caagaagctg gtgcaccaca ccctgggcga cggcgacttc 360
ctgcacttcg agaagatgca tgacgccgtc acggtggcct cggcgcacct cacgatccag 420
aacgccacca gcgaaatcga ccgggtcctg acgaccgccc tctcgctgcg gcgccccggc 480
tatatcaacc tgcccatcga cgtggcggcg gccccggccg aaaaagccca gaaaaagctc 540
cagctgaaag tgaccagccc gatcgacagc acgctgctgg aaaagatcca gacggccttc 600
tcctcggcca agcagcccgt cttcatcacg ggccatgaaa tccagtccta ccacctggag 660
gataccgtgg cgaagatcgc cgcgcacacg accgtgccgg tcgcggccct ctcgctgggc 720
aagagctcca tcgatgaaac ccatccccag ttcgtcggca tctactccgg cgccctgacg 780
gcggagcccc tgaaaaccta cgtcgataac gccgatctgg tgatcctgct cggcgcccag 840
ctgaccgaca cggccacctc gggcttcagc cagtccttct cggccagcaa aatcatcgcc 900
atccacccgg aaacgaccac cgtgttcggc caggattacc cgtcgaacga tttcaaggaa 960
ctgatcgagg ccctcacgac catcgattac cgcatggaaa cctccgcggc cctgaagacg 1020
atgccgtcca ccaaggagtt catcgccacc gacacgctgc tcacccagaa tcgcttctgg 1080
gaagccatcg aaaccaactt caagcagaac gataccatcg tggcggaaca gggcacgtcg 1140
ttcttcggca tcaccaatac ccagttcaag aaagatatgc gcctgatcgg ccagcccctg 1200
tggggctcga tcggctatac gttccccgcc gccctgggct cgcagctggc cgcccgctcc 1260
aagcggcatc tgctcttcat cggcgatggc tcgctgcagc tgaccatcca ggaactgggc 1320
atggcgctcc gcgccaaact cacccccctg atcttcgtca tcaacaacaa cggctacacc 1380
gtggaacgcg agatccacgg cccgaacgaa cggtataatg acatcccgac ctgggactat 1440
gcgcagctgc cgaccgtgtt cggcggcacg gaccagaacg tggccacgta taaggtgacg 1500
accgaaaccg aactggcgga ggcgctcgtc accgccaagg cggacaccac ccgcctgcag 1560
tggatcgagg tggtgatgga ccagacggac gccccggaac tgctgaaaga gatgggccgc 1620
atcttcgcca agcagaacac ccattga 1647

SEQ ID NO: 25 moltype = DNA length = 1647
FEATURE Location/Qualifiers
source 1..1647
mol_type = genomic DNA
organism = Carnobacterium gallinarum

```
SEQUENCE: 25
atgtacacgg tcgccgatta cctgctcgat cggctgaagg aactgggcat caatgacatc  60
ttcggcgtcc cgggcgatta taacctcaag ttcctggacc acatcacggc ccgcgacgac  120
ctgaaatgga tcggcaacgc gaacgagctg aacgcggcgt atatggccga tggctacgcc  180
cgcaccaaag gcatggccgc gctggtcacg accttcggcg tcggcgaact ctcggccatg  240
aacggcatcg gcggctcgtt cgccgagaaa gtcccggtca tcgagatcgt gggctccccc  300
accaccgccg tccagaatgc ccagaaactg gtccatcata cgctgggcga cggccgcttc  360
aaccatttcg agaagatgca tgaggcgatc accgtgggca tcggctcgct gaccaaggag  420
aatgccatca ccgaaatcga tcgcatcctg ggcctggcgt ccgagaagcg gcagcccggc  480
tacctgaacc tgccgatcga tgtggccgaa atggaagtgg agaaaccgaa caagccgctc  540
ttcgatacca aggtcatgga aatcaaaatg gaacaggagc tcatcaagag catcgagaaa  600
gtgctcaact cggtcaagca tccggtcatc atcgccggca acgagatcgc cagcttccat  660
ctggaggcca agctggccga gttcatcgag aagttcaatc tccccgtcac cacgctgccg  720
ttcggcaagg gcgtcttcaa cgaagaagat aagcattatc tgggcgtgta tacgggcacc  780
cccacgacgg aacccctgaa gtcctacgtc gaccaggcgg atctggtcct cctgctgggc  840
gccaagctga ccgactccgc caccagcggc ttcagccagg gcttcaccga gaagcagatg  900
atctcgctgg cctcggacga ggtcatcttc cagggcgagc acctcgccgg catccagctc  960
cccaccgtcc tggatgagct gctgatgatc aactatccgg gctaccacgg cgagatccag  1020
ccgatgtcgc ggctggcgga agtgaagtcg tcctccagcc tcgtcaccca ggcgtacttc  1080
tgggaggccg tcgagtcgta cctggaagaa ggcgatacgc tcgtcgccga acagggcacc  1140
agcttcttcg gcgcctccac cgtccccatg aagaagggca tgagcttcat cggccagccg  1200
ctgtggggct ccatcggcta cacgttcccg gccatgctcg gctcgcagat cgccaagaag  1260
ggctcgcgcc atctgctgtt catcggcgac ggctcgctcc agctgaccgt ccaggaactg  1320
ggcatgacgc tccgggaaaa gctggcgccg atcgtgttca tcatcaacaa taacggctac  1380
accgtggaac gggaaatcca cggccccgaa gaaatctata acgacatccc gatgtgggac  1440
taccagaagc tcccgtccgt cttcggcggc accgccgaaa acgtggtgac ctataaggtc  1500
cagaccgagg cggagctggc caccgccatg cgcaaggccc gcctggactc gaagcggctg  1560
cagtggatcg aagtggtgat gaaccagaag gacgccccgg acctcctggt gcagatgggc  1620
aagatcttcg ccaagcagaa tagctga                                    1647

SEQ ID NO: 26          moltype = DNA  length = 1647
FEATURE                Location/Qualifiers
source                 1..1647
                       mol_type = genomic DNA
                       organism = Carnobacterium divergens
SEQUENCE: 26
atgtataccg tgggcgacta tctcctggag cggctctcgg aactgggcat caaagagatc  60
ttcggcgtgc cgggcgacta caacctgaag ttcctggatc acatcgtgga gcatccgaac  120
ctgaagtgga tcggcaacgc gaatgaactc aacgcggcgt atgccgccga cggctacgcc  180
cgcacgaagg gcgtctccgc gctggtgacc accttcggcg tcggcgagct ctccgccatc  240
aacggcatcg ccggctcgta tgccgagaaa gtcccggtca tccagatcgt gggcagcccc  300
acgatggcgg tgcagaatgc ccataagctg gtgcatcata ccctgggcga tggcaaattc  360
gaccacttcg agaacatgca tgagtccgtc accgaagcca tcggcagcct caccaaggag  420
aacgcggtga ccgagatcga tcgcgtgctg cgggccgccg tgctcaaacg gcgcccggtg  480
tatctgaacc tcccgatcga cgtggccgaa atggtcgtcg aaaaaccgtc gggccccctg  540
ctgcccaagc aggcgagcct gagcgcccgc gaggtcgaac tcgtgcatga gctggagaag  600
gccctgcagc aggcgaagaa cccggtggtc ctggcgggca acgagctggc gtcgttccac  660
ctcgaaacgt acctcgccga cttcatccac aagttcaacc tccccatcac gaccctcccc  720
ttcggcaagg gcgtcttcaa cgaggaagac gagcattatc tgggcgtcta tgcgggctcg  780
ccgaccgaag aaggcctgcg gaagcgcgtc gatacggcgg acctggtcgt ggcgctgggc  840
gcgaagctga cggactccgc cacctccggc ttctcgtacg acttctccga aaaacagctc  900
ttcagcctgg cgtccgacga agtcatcgtc aaagaggaac acctcgaagg catccatctg  960
ccggccgtca tgaaggcgct gacgagcatc gactaccagg gctaccaggg cgacatccag  1020
ccgatggccc ggctgaagag catcaaaccc accaaccagg tgctgaccca gcgccacttc  1080
tgggaggcca tcgaaggctt cctggaaaag ggcgacaccg ccgtcgcgga gcagggcacg  1140
agcttcttcg gcctctcgac cgtgccgctg aagagcgaaa tgtcgttcat cggccagccg  1200
ctgtggggct ccatcggcta tacgttcccg gcgatgctgg gcagccagct cgccaacccg  1260
tccagccggc acctcctgtt catcggcgac ggcagcctgc agctgacgat ccaggagctc  1320
ggcatggccc tccgcgaaaa actcaccccg atcgtgttcg tcatcaacaa taacggctat  1380
acggtcgaac gggaaatcca cggcccgaat gaaatctata acgacatccc gatgtgggac  1440
taccagaaac tcccgctcgt cttcggcggc tccgagcagt cggtcatcac ctataaagtg  1500
acgaccgaac tggaactggc gaacgcgctc aaggcggccc ggctggacaa caaccgcctg  1560
cagtggatcg aagtggtgat ggaccagacc gatgcgccgg agctcctcat gaagctgggc  1620
aagatcttcg cgaagcagaa tagctga                                    1647

SEQ ID NO: 27          moltype = DNA  length = 1104
FEATURE                Location/Qualifiers
source                 1..1104
                       mol_type = genomic DNA
                       organism = Helicobacter bizzozeronii
SEQUENCE: 27
atgcagacga cgatcggcca gtatctcctg gaccggctga agtcctacgg cgtgcagcat  60
ctcttcggcg tgcccggcga ctataacctg gccttcctcg acctgatcga agacgatccg  120
cacatccagt gggtcggcaa ctgcaacgaa ctgaatgcgt cctacgccgc cgacggctac  180
gcgcggctca agagcatggg cgccctcctg acgaccttcg gcgtcggcga gctgagcgcc  240
atcaacggca tcgccggctc gtacgcggaa tccgtgccgg tcgtgaagat cgtcggcatg  300
ccctcccgcg gcgtggtcca ttcccgcaag ctggtgcacc acaccctggg cgacggcgag  360
ttcctcaagt tctacaacat gtatgccgaa gtgagcgtcg cccagacgat cctcaacaaa  420
cagaacgccc agagcgaaat cgaccgcgtc ctgggcgaat gcttcctgca taaaaagccg  480
```

```
gtctacatcg gcctcccggt ggacgtgacg cacatcccga tcgaaacgta cgcccccctcc  540
cccctggtgg ccaagagcga cccgaaaatc ctcaacgcct tcctgaagga cgcccaggag  600
ctgctgtcga agagcaaatc ccaggtggtc atggcggatt atgaagtgaa ccgctaccag  660
ttcaaccagg agctgacgcg cttcatcgaa gccgtgaacc tgcccatcgt gtcgctggcg  720
atgggcaagg gcgtcttcga tgaaacgcac ccgaacttca tcggcgtgta taacggcatc  780
ctctcggacg cccgggtgag ctcgctgatg aagcacgccg actgcgcgat cctggtgggc  840
gtgaagctga cggactcgct gacggccggc ttccactata tccgcgaaca tcacctgtcc  900
atccagatcc acccccttcta ctcccagatc ggcgaaaaga cgtacgacga tatcctcatg  960
caggacgtgc tgaaagcgct cgcccagctg aagttccagg cctcgttccc gaaggagacg  1020
caccccaaaa cgccgcacct gaacggcaag ctgacccagg acaagttctt caagatcgac  1080
tcgcgcatcc tgaccccccc gtga                                         1104

SEQ ID NO: 28          moltype = DNA  length = 822
FEATURE                Location/Qualifiers
source                 1..822
                       mol_type = genomic DNA
                       organism = Staphylococcus aureus
SEQUENCE: 28
atgaaacagc gcatcggcgc ctacctgatc gatgccatcc accgcgccgg cgtggacaag  60
atcttcggcg tcccgggcga tttcaacctc gccttcctgg acgatatcat cagcaacccg  120
aacgtggatt gggtcggcaa caccaacgag ctgaacgcct cgtatgcggc cgatggctat  180
gcccgcctca acggcctggc ggccctggtc accaccttcg gcgtgggcga actgtcggcg  240
gtgaatggca tcgcgggcag ctatgccgag cgcatcccgg tgatcgccat caccggcgcc  300
cccacccgcg ccgtcgagca ggccggcaag tatgtgcatc atagcctggg cgaaggcacg  360
ttcgatgact accggaagat gttcgcccat atcaccgtgg cccagggcta catcacgccc  420
gagaatgcga cgaccgaaat cccccgcctc atcaacacgg ccatcgccga gcgccgcccg  480
gtgcatctcc acctgcccat cgatgtggcg atctcggaga tcgagatccc caccccgttc  540
gaggtgacgg cggcgaaaga cacggacgcc tcgacctata tcgagctgct ggccagcaaa  600
ctgcaccaga gcaagcagcc catcatcatc acgggccatg agatcaactc cttccatctg  660
caccaggaac tggaagattt cgtcaatcag acccagatcc ccgtggcgca gctctcgctg  720
ggcaaaggcg ccttcaacga ggaaaacccg tactatatgg gcatctacga tggcaagctg  780
cccaaaatca agtatgcgat catgtggacc acggcgatct ga                     822

SEQ ID NO: 29          moltype = DNA  length = 1665
FEATURE                Location/Qualifiers
source                 1..1665
                       mol_type = genomic DNA
                       organism = Fictibacillus macauensis
SEQUENCE: 29
atgaacaacc attataccgt cggcacctat ctgctgcatc gcctgtccga gctgggcgtc  60
cgccatatgt tcggcgtgcc cggcgactat aatctgacgt tcctggacga tgtcatcgac  120
ttcgaaggca tggaatggat cggcaactgt aacgagctca acgccgccta cgcggccgac  180
ggctatgccc gcatcaacgg catggccgcc ctggtgacca ccttcggcgt cggcgagctg  240
tcggccatca acggcatcgc cggctcgtac gccgaaaaag tgccggtcgt caaaatcacg  300
ggcatgccca ccaccaacgt gatgaaccag aatctgtacg tccatcacac gctgggcgac  360
ggcaacttcc agcacttcgg caacatgttc caggaggtca ccgccgcgca gacgatgctg  420
acccaggaaa acgcggcgca ggagatcgat cgcgtgctgc tcgcctgctg gcacgaaaag  480
cgcccggtgc acatcaacct cccgatcgat gtctacaaca agccggtcaa cccccccgag  540
cattcgctcc tggaacgggg catctcgtcg aacgcgaccg cgctcgaaca gatgctgacc  600
accgtgatcc cgacgatcaa ggaggccacc tcgcccgtga tcctggcgga ttatgaggtg  660
tatcgctacc aggcccagga agccctgatg ctgctggcgg aaaagaccgg cttcccggtg  720
gccaccctga gcatgggcaa gggcgtgttc aacgaaaccc atccccagtt catcggcgtg  780
tacaacggcg acctgtcgtc cgactacgtg aagaatatgg tcgaccatgc cgactgtatc  840
ctctccatcg gcgtcaagct gaccgacagc atcacgggcg gcttcagcca tgagttcacc  900
gaggagcagg tcatcgacat ctccccgtat agcgtgagca aaaaagccct caaatgggcg  960
cccatcacga tgctggatgc gctgggcgcc atcacggatg ccctggagca gaagccgacc  1020
cccgccacca ccgcgcggct cgccgcctac tcgaacgaga gctccttcac cgcgacgaac  1080
acgacgctga cccaggagcg cttcttcgac caggtgtccc acttcctcca ggagggcgac  1140
gtgatcctgg cggaacaggg caccagcttc ttcggcgcgg ccacgatgcc gctcccgaag  1200
ggcgccacgt tcatcggcca gccgctgtgg ggcagcatcg gctacaccct gccggccctg  1260
ctgggcagcc agctggccga cgaatcccgc cgcaatctcc tgctcatcgg cgatggctcg  1320
ttccagctca ccgcccagga gctgtcgacg atgctgcgcc agcggatcgc gccgatcatc  1380
ttcctcatca acaacgacgg ctacaccgtg gaacgggcga tccacggcga gaatcaggtg  1440
tataacgaca tccagatgtg ggactattcg aagctgccgg cggtcttcgg cgcggcggac  1500
gccagcgtca cctacaaggt ccggaccgaa gaggagctgg aggcggccct gcatagcgcc  1560
cagaactcgt cccagctggt cttcatcgaa gtgatgatgg agaagaatga cacccccgaa  1620
ctgctgacgg ccctgagcaa gcgcttcgcg aatcagaaca actga                  1665

SEQ ID NO: 30          moltype = DNA  length = 1083
FEATURE                Location/Qualifiers
source                 1..1083
                       mol_type = genomic DNA
                       organism = Saccharomyces cerevisiae
SEQUENCE: 30
atgagctatc ccgagaagtt cgaggggatc gccatccaga gccacgagga ctggaagaac  60
ccgaaaaaga ccaagtatga tccgaagccc ttctacgatc acgacatcga catcaagatc  120
gaggcctgcg gcgtctgcgg cagcgatatc cattgtgcgg ctggccactg gggcaacatg  180
aagatgccgt tggtcgtcgg ccacgagatc gtgggcaagg tcgtgaagtt aggcccgaaa  240
agcaacagcg gcttgaaggt gggccagcgc gtgggtgtgg gtgcgcaggt cttcagctgt  300
```

```
ctggagtgcg accgttgcaa gaacgacaac gaaccgtact gcaccaagtt cgtcaccacc  360
tactcgcagc cctacgagga cggctacgtc tcgcagggcg gttacgccaa ctatgtccga  420
gtccacgaac acttcgtggt gcccatcccg gaaaatatcc ccagccatct ggcggctccc  480
ctgctgtgcg gtggcttgac cgtctacagc cccctcgtcc gcaatggctg cggtcccggc  540
aagaaggtgg gtatcgtggg cctcggcggt ataggctcta tgggcacgct gatctcgaaa  600
gcgatgggcg cagaaacgta cgtgatctcg cgttcctcgc gcaagcgcga ggatgcgatg  660
aagatgggtg cggaccacta catcgccacg ctggaggagg gtgactgggg tgagaagtac  720
ttcgacacgt tcgacctcat cgtggtgtgc gcgagttccc tgacggacat cgacttcaat  780
atcatgccca aggcgatgaa ggtcggaggg cgcatcgtct ccatctcgat cccggagcag  840
cacgaaatgc tgtcgctgaa gccctacggc ctgaaagccg tctccattag ctactcggcg  900
ctcggtagta tcaaggagct caaccagctg ttgaagttgg tttccgaaaa ggacatcaag  960
atctgggtgg aaacgctccc ggtgggcgaa gccggtgtgc acgaggcctt tgagcggatg  1020
gagaaggggg atgtccgtta tcggtttaca ctcgtcggct acgataaaga gttctcggat  1080
taa                                                               1083
```

```
SEQ ID NO: 31          moltype = DNA  length = 1164
FEATURE                Location/Qualifiers
source                 1..1164
                       mol_type = genomic DNA
                       organism = Escherichia coli
SEQUENCE: 31
atgaacaact ttaatctgca caccccaacc cgcattctgt ttggtaaagg cgcaatcgct  60
ggtttacgcg aacaaattcc tcacgatgct cgcgtattga ttacctacgg cggcggcagc  120
gtgaaaaaaa ccggcgttct cgatcaagtt ctggatgccc tgaaaggcat ggacgtgctg  180
gaatttggcg gtattgagcc aaacccggct tatgaaacgc tgatgaacgc cgtgaaactg  240
gttcgcgaac agaaagtgac tttcctgctg gcggttggcg gcggttctgt actggacggc  300
accaaattta tcgccgcagc ggctaactat ccggaaaata tcgatccgtg gcacattctg  360
caaacgggcg gtaaagagat taaaagcgcc atcccgatgg gctgtgtgct gacgctgcca  420
gcaaccggtt cagaatccaa cgcaggcgcg gtgatctccc gtaaaaccac aggcgacaag  480
caggcgttcc attctgccca tgttcagccg gtatttgccg tgctcgatcc ggtttatacc  540
tacaccctgc cgccgcgtca ggtggctaac ggcgtagtgg acgcctttgt acacaccgtg  600
gaacagtatg ttaccaaacc ggttgatgcc aaaattcagg accgtttcgc agaaggcatt  660
ttgctgacgc taatcgaaga tggtccgaaa gccctgaaag agccagaaaa ctacgatgtg  720
cgcgccaacg tcatgtgggc ggcgactcag gcgctgaacg gtttgattgg cgctggcgta  780
ccgcaggact gggcaacgca tatgctgggc cacgaactga ctgcgatgca cggtctggat  840
cacgcgcaaa cactggctat cgtcctgcct gcactgtgga atgaaaaacg cgataccaag  900
cgcgctaagc tgctgcaata tgctgaacgc gtctggaaca tcactgaagg ttccgatgat  960
gagcgtattg acgccgcgat tgccgcaacc cgcaatttct ttgagcaatt aggcgtgccg  1020
acccacctct ccgactacgg tctggacggc agctccatcc cggctttgct gaaaaaactg  1080
gaagagcacg gcatgaccca actgggcgaa aatcatgaca ttacgttgga tgtcagccgc  1140
cgtatatacg aagccgcccg ctaa                                        1164
```

```
SEQ ID NO: 32          moltype = DNA  length = 1149
FEATURE                Location/Qualifiers
source                 1..1149
                       mol_type = genomic DNA
                       organism = Escherichia coli
SEQUENCE: 32
atggcgaatc ggatgatcct caatgaaacg gcctggttcg gccgcggcgc ggtcggcgcc  60
ctcaccgatg aggtcaagcg gcggggctac cagaaggccc tgatcgtcac ggataaaacc  120
ctggtgcagt gcggcgtcgt cgccaaggtg accgacaaga tggatgcggc cggcctggcc  180
tgggcgatct acgacggcgt ggtgcccaac cccaccatca ccgtggtgaa ggaaggcctg  240
ggcgtgttcc agaactcggg cgcggattat ctcatcgcga tcggcggcgg cagcccccag  300
gacacctgca aggccatcgg catcatctcg aacaaccccg agttcgcgga cgtgcgctcc  360
ctggagggcc tgtcgccgac gaacaagccc tccgtcccga tcctcgccat cccgacgacg  420
gccggcaccg cggccgaggt gaccatcaat tacgtcatca ccgacgagga aaagcggcgc  480
aagttcgtgt gtgtggaccc ccatgacatc ccccaggtcg ccttcatcga cgccgacatg  540
atggatggca tgcccccgc cctcaaggcc gcgacgggcg tggacgcgct gacgcatgcc  600
atcgaaggct acatcacccg gggcgcctgg gccctgacgg atgccctgca tatcaaggcc  660
atcgaaatca tcgccggcgc cctgcgcggc tccgtggccg gcgacaagga tgcgggcgag  720
gagatggcgc tgggccagta cgtggccggc atgggcttct ccaatgtggg cctgggcctg  780
gtgcatggca tggcccatcc gctcggcgcc ttctacaaca cgccgcatgg cgtcgcgaac  840
gcgatcctcc tgccgcatgt catgcgctac aatgcggact tcacgggcga gaaataccgc  900
gatatcgccc gggtcatggg cgtgaaggtc gagggcatgt cgctggaaga ggcgcggaac  960
gccgcggtcg aagccgtctt cgccctgaac cgggatgtgg gcatcccgcc gcacctgcgc  1020
gatgtcggcg tccgcaagga agacatcccc gcgctggcgc aggccgccct ggacgatgtg  1080
tgcaccggcg gcaacccccg cgaggcgacg ctggaagaca tcgtcgaact ctaccatacc  1140
gcgtggtga                                                         1149
```

```
SEQ ID NO: 33          moltype = DNA  length = 1170
FEATURE                Location/Qualifiers
source                 1..1170
                       mol_type = genomic DNA
                       organism = Clostridium acetobutylicum
SEQUENCE: 33
atgctctcgt tcgactacag catccccacc aaggtcttct tcggcaaagg caagatcgac  60
gtgatcggcg aagagatcaa aaagtacggc tcccgcgtgc tgatcgtcta cggcggcggc  120
tcgatcaaac gcaacggcat ctatgaccgg gccacggcga tcctgaagga aaacaacatc  180
gccttctacg agctgtccgg cgtggagccc aacccgcgga tcaccacggt caagaagggc  240
```

```
atcgaaatct gtcgcgaaaa caacgtcgac ctggtgctgg ccatcggcgg cggcagcgcg  300
atcgattgct ccaaggtgat cgccgccggc gtctattatg acggcgacac ctgggacatg  360
gtcaaagacc ccagcaagat caccaaagtg ctgccgatcg cctccatcct caccctgagc  420
gcgacgggca gcgaaatgga tcagatcgcc gtgatctcga acatggagac gaacgaaaag  480
ctcggcgtgg gccacgacga tatgcggccg aagttctcgg tcctcgatcc gacgtatacc  540
ttcacggtgc cgaagaacca gaccgccgcc ggcacggcgg acatcatgtc gcataccttc  600
gaatcgtatt tcagcggcgt cgaaggcgcg tatgtccagg acggcatcgc ggaagccatc  660
ctccgcacct gcatcaagta tggcaagatc gcgatggaaa agaccgacga ctacgaggcc  720
cgcgcgaatc tgatgtgggc ctcgtccctg gccatcaatg gcctgctgag cctcggcaag  780
gatcggaaat ggtcgtgcca cccgatggag cacgagctga gcgcctatta cgacatcacc  840
cacggcgtgg gcctggccat cctgaccccc aactggatgg aatatatcct gaacgacgac  900
acgctgcata aattcgtgtc gtacggcatc aacgtctggg gcatcgataa gaacaaggac  960
aactacgaga tcgcccgcga agccatcaaa aatacgcggg agtacttcaa cagcctgggc  1020
atcccgtcga agctgcgcga ggtcggcatc ggcaaagata aactggagct gatggccaag  1080
caggcggtgc gcaactcggg cggcacgatc ggcagcctcc gccccatcaa cgcggaggat  1140
gtgctggaga tcttcaagaa gagctattga                                    1170

SEQ ID NO: 34          moltype = DNA  length = 1173
FEATURE                Location/Qualifiers
source                 1..1173
                       mol_type = genomic DNA
                       organism = Clostridium acetobutylicum
SEQUENCE: 34
atggtcgatt tcgagtattc gatcccgacg cggatcttct tcggcaagga caaaatcaac  60
gtcctgggcc gcgaactcaa gaaatacggc agcaaagtgc tgatcgtcta cggcggcggc  120
tcgatcaagc ggaacggcat ctacgataag gccgtgtcga tcctggaaaa gaatagcatc  180
aagttctatg aactggcggg cgtcgaaccg aacccccgcg tgaccaccgt cgagaagggc  240
gtcaagatct gccgggaaaa cggcgtggaa gtcgtgctgg cgatcggcgg cggctccgcg  300
atcgactgcg ccaaggtgat cgcggcggcc tgcgagtacg acggcaatcc ctgggacatc  360
gtcctggacg gctccaagat caagcgcgtc ctcccgatcg ccagcatcct gaccatcgcc  420
gcgacgggct cggaaatgga cacctgggcc gtcatcaaca atatggatac caacgaaaag  480
ctcatcgcgg cccacccgga catggccccg aagttctcga tcctcgatcc cacctacacc  540
tacaccgtcc cgacgaacca gaccgcggcc ggcaccgccg atatcatgtc ccatatcttc  600
gaggtgtatt tctccaacac caagacggcg tacctccagg accgcatggc ggaggcgctc  660
ctccggacct gcatcaagta cggcggcatc gccctggaga agccggacga ctatgaggcc  720
cgcgccaacc tcatgtgggc gtcctccctg gcgatcaatg gcctgctgac gtacggcaaa  780
gacacgaact ggtccgtgca tctcatggag cacgagctgt cggcctatta tgatatcacc  840
cacggcgtgg gcctcgcgat cctcacgccc aactggatgg aatacatcct caacaatgat  900
acggtgtaca agttcgtcga gtacggcgtc aatgtctggg gcatcgataa ggaaaaaaat  960
cactatgaca tcgcgcatca ggcgatccag aagacgcgcg actacttcgt caacgtgctc  1020
ggcctgccct cccgcctccg cgacgtgggc atcgaagagg aaaagctgga tatcatggcc  1080
aaggagagcg tgaagctgac cggcggcacc atcggcaacc tgcgccccgt gaacgcctcc  1140
gaggtcctcc agatcttcaa aaagtcggtg tga                                 1173

SEQ ID NO: 35          moltype = DNA  length = 1011
FEATURE                Location/Qualifiers
source                 1..1011
                       mol_type = genomic DNA
                       organism = Escherichia coli
SEQUENCE: 35
atgaaggccg cggtcgtgac caaggaccat cacgtcgatg tcacgtacaa gacgctgcgc  60
tccctgaagc atggcgaagc gctgctgaag atggagtgct gtggcgtctg ccacacggac  120
ctgcatgtga aaaacggcga cttcggcgac aagaccggcg tcatcctcgg ccacgaaggc  180
atcggcgtcg tggccgaggt gggccccggc gtcacgtccc tcaagccggg cgatcgggcc  240
tcggtggcgt ggttctatga gggctgcggc cactgcgaat attgcaactc gggcaacgaa  300
accctgtgtc ggtcggtgaa aaatgcgggc tactccgtcg acggcggcat ggcggaagaa  360
tgtatcgtgg tggccgacta cgccgtgaag gtcccggatg gcctggacag cgccgccgcc  420
tcgtcgatca cctgcgccgg cgtcaccacc tataaggcgg tgaaactgag caaaatccgc  480
ccgggccagt ggatcgccat ctacggcctg ggcggcctgg gcaacctggc cctgcagtac  540
gccaagaatg tcttcaacgc gaaggtcatc gccatcgatg tcaatgatga acagctgaag  600
ctggccacgg agatgggcgc ggacctggcg atcaacagcc acaccgaaga cgcggccaag  660
atcgtccagg agaagaccgg cggcgcccat gccgccgtgg tgaccgccgt ggccaaagcc  720
gccttcaatt ccgccgtcga cgccgtccgg gccggcggcc gggtcgtcgc ggtgggcctg  780
ccgccggagt cgatgtccct cgacatcccg cgcctggtgc tggatggcat cgaggtggtg  840
ggctccctgg tcggcacccg ccaggacctg accgaagcct tccagttcgc cgccgaaggc  900
aaggtcgtgc ccaaggtcgc cctgcggccc ctcgccgaca tcaacaccat cttcacggag  960
atggaggaag gcaagatccg gggccgcatg gtcatcgatt tccgccactg a             1011

SEQ ID NO: 36          moltype = DNA  length = 1020
FEATURE                Location/Qualifiers
source                 1..1020
                       mol_type = genomic DNA
                       organism = Escherichia coli
SEQUENCE: 36
atgtccatga tcaaaagcta cgccgcgaaa gaggcgggcg gcgagctgga ggtgtatgag  60
tatgacccgg gcgagctgcg gccccaggac gtggaagtgc aggtcgacta ctgcggcatc  120
tgccattcgg acctctcgat gatcgataac gagtggggct tcagccagta ccccctggtg  180
gccggccacg aggtgatcgg ccgcgtggtc gccctgggct cggccgcgca ggataaaggc  240
ctgcaggtcg gccagcgcgt cggcatcggc tggacggccc gcagctgcgg ccattgcgat  300
```

```
gcctgcatca gcggcaatca gatcaattgc gaacagggcg cggtcccgac catcatgaac  360
cggggcggct tcgccgaaaa gctgcgggcc gattggcagt gggtgatccc gctgccggag  420
aacatcgata tcgagtcggc cggccccctg ctgtgcggcg gcatcaccgt cttcaagccg  480
ctcctgatgc atcatatcac ggcgaccagc cgggtcggcg tgatcggcat cggcggcctc  540
ggccacatcg cgatcaaact gctgcacgcg atgggctgcg aggtcaccgc gttctcctcg  600
aaccccgcca aggagcagga agtgctggcg atgggcgccg ataaagtcgt gaactcgcgc  660
gacccccagg ccctcaaagc cctggccggc cagttcgatc tcatcatcaa cacggtgaac  720
gtgtcgctgg actggcagcc ctacttcgaa gccctgacct atggcggcaa cttccatacc  780
gtcggcgccg tgctgacccc gctgtccgtc ccggccttca ccctgatcgc cggcgaccgc  840
agcgtgtccg gcagcgccac cggcacgccg tatgagctgc gcaagctgat gcgcttcgcc  900
gcccgcagca aggtcgcccc gaccaccgag ctgttcccca tgtccaagat caatgacgcg  960
atccagcatg tccgggacgg caaggcccgc tatcgcgtcg tcctcaaggc ggacttctga  1020
```

```
SEQ ID NO: 37          moltype = DNA  length = 1149
FEATURE                Location/Qualifiers
source                 1..1149
                       mol_type = genomic DNA
                       organism = Escherichia coli
SEQUENCE: 37
atggcgaatc ggatgatcct caatgaaacg gcctggttcg gccgcggcgc ggtcggcgcc  60
ctcaccgatg aggtcaagcg gcggggctac cagaaggccc tgatcgtcac ggataaaacc  120
ctggtgcagt gcggcgtcgt cgccaaggtg accgacaaga tggatgcggc cggcctggcc  180
tgggcgatct acgacggcgt ggtgcccaac cccaccatca ccgtggtgaa ggaaggcctg  240
ggcgtgttcc agaactcggg cgcggattat ctcatcgcga tcggcggcgg cagcccccag  300
gacacctgca aggccatcgg catcatctcg aacaaccccg agttcgcgga cgtgcgctcc  360
ctggagggcc tgtcgccgac gaacaagccc tccgtcccga tcctcgccat cccgacgacg  420
gccggcaccg cggccgaggt gaccatcaat tacgtcatca ccgacgagga aaagcggcgc  480
aagttcgtgt gtgtggaccc ccatgacatc cccaggtcg ccttcatcga cgccgacatg  540
atggatggca tgccccccgc cctcaaggcc gcgacgggcg tggacgcgct gacgcatgcc  600
atcgaaggct acatcacccg gggcgcctgg gccctgacgg atgccctgca tatcaaggcc  660
atcgaaatca tcgccggcgc cctgcgcggc tccgtggccg gcgacaagga tgcgggcgag  720
gagatggcgc tgggccagta cgtggccggc atgggcttct ccaatgtggg cctgggcctg  780
gtgcatggca tggcccatcc gctcggcgcc ttctacaaca cgccgcatgg cgtcgcgaac  840
gcgatcctcc tgccgcatgt catgcgctac aatgcggact tcacgggcga gaaataccgc  900
gatatcgccc gggtcatggg cgtgaaggtc gagggcatgt cgctggaaga ggcgcggaac  960
gccgcggtcg aagccgtctt cgccctgaac cgggatgtgg gcatcccgcc gcacctgcgc  1020
gatgtcggcg tccgcaagga agacatcccc gcgctggcgc aggccgccct ggacgatgtg  1080
tgcaccggcg gcaacccccg cgaggcgacg ctggaagaca tcgtcgaact ctaccatacc  1140
gcgtggtga                                                         1149
```

```
SEQ ID NO: 38          moltype = DNA  length = 1020
FEATURE                Location/Qualifiers
source                 1..1020
                       mol_type = genomic DNA
                       organism = Escherichia coli
SEQUENCE: 38
atgtccatga tcaaaagcta tgccgcgaag gaagccggcg gcgagctgga ggtctacgag  60
tacgaccccg gcgaactccg cccgcaggac gtggaggtgc aggtggatta ctgcggcatc  120
tgccacagcg acctgtcgat gatcgacaac gagtggggct tcagccagta cccgctggtg  180
gccggccatg aagtgatcgg ccgcgtcgtc gcgctgggct ccgccgccca ggataaaggc  240
ctgcaggtcg gccagcgcgt gggcatcggc tggaccgccc ggtcgtgcgg ccactgcgac  300
gcctgcatct cgggcaacca gatcaattgc gagcagggcg ccgtccccac catcatgaac  360
cgcggcggct tcgcggagaa gctccgcgcg gactggcagt gggtgatccc gctgccggaa  420
aatatcgata tcgaatccgc cggccccctg ctgtgcggcg gcatcaccgt cttcaagccg  480
ctcctgatgc atcatatcac cgccacctcc cgcgtcggcg tcatcggcat cggcggcctc  540
ggccacatcg ccatcaaact cctgcatgcg atgggctgtg aagtgaccgc cttcagcagc  600
aaccccgcga aagagcagga agtgctcgcg atgggcgcgg acaaggtcgt gaacagccgc  660
gatccccagg ccctcaaagc gctggccggc cagttcgatc tcatcatcaa caccgtcaac  720
gtctcgctcg actggcagcc gtacttcgaa gcgctgacgt acggcggcaa cttccacacc  780
gtgggcgcgg tcctgacgcc cctgtcggtg ccggcgttca ccctgatcgc cggcgatcgg  840
agcgtgtcgg gctccgccac cggcaccccg tatgagctgc ggaagctgat gcggttcgcg  900
gcccgcagca aggtcgcccc gacgaccgag ctgttcccca tgagcaagat caacgacgcc  960
atccagcatg tgcgcgatgg caaagcccgg tatcgcgtgg tcctgaaagc ggatttctga  1020
```

```
SEQ ID NO: 39          moltype = DNA  length = 1164
FEATURE                Location/Qualifiers
source                 1..1164
                       mol_type = genomic DNA
                       organism = Escherichia coli
SEQUENCE: 39
atgaacaatt tcaacctcca caccccgacc cgcatcctct tcggcaaggg cgccatcgcc  60
ggcctgcgcg agcagatccc gcacgacgcc cgcgtcctca tcacctatgg cggcggctcc  120
gtcaaaaaga ccggcgtgct cgatcaggtc ctggacgccc tgaagggcat ggacgtgctg  180
gagttcggcg gcatcgagcc gaacccggcc tacgagacgc tgatgaatgc ggtgaagctg  240
gtgcgcgagc agaaggtcac gttcctgctc gcggtcggcg gcggctcggt gctggacggc  300
accaagttca tcgccgccgc ggcgaattat cccgagaaca tcgatccctg gcacatcctg  360
cagacgggcg gcaaggagat caagtcggcc atcccgatgg gctgcgtcct gaccctcccc  420
gccaccggct cggagagcaa cgccggcgcc gtgatctcgc gcaaaaccac cggcgacaaa  480
caggcgttcc actccgccca tgtgcagccg gtcttcgcgg tgctggaccc cgtctacacg  540
```

```
tacaccctcc cgccgcggca ggtcgccaac ggcgtggtcg atgccttcgt gcatacggtg  600
gagcagtacg tcaccaagcc ggtggatgcc aagatccagg accgcttcgc ggagggcatc  660
ctgctgacgc tgatcgagga cggcccgaaa gccctcaagg aaccggaaaa ctacgatgtg  720
cgggcgaacg tcatgtgggc cgcgacccag gccctgaacg gcctgatcgg cgccggcgtg  780
ccccaggatt gggcgacgca catgctgggc cacgaactca ccgcgatgca cggcctcgac  840
cacgcccaga cgctcgccat cgtcctgccg gccctgtgga atgagaagcg ggacaccaag  900
cgggcgaagc tcctgcagta tgccgaacgg gtgtggaaca tcaccgaagg ctcggacgat  960
gaacgcatcg atgccgccat cgcggccacg cggaacttct tcgagcagct gggcgtcccg  1020
acccatctct ccgactacgg cctggatggc tcctccatcc ccgcgctgct gaaaaaactg  1080
gaagaacacg gcatgaccca gctgggcgaa aaccacgaca tcaccctgga tgtctcgcgc  1140
cgcatctacg aagccgcccg gtga                                        1164

SEQ ID NO: 40          moltype = DNA  length = 1011
FEATURE                Location/Qualifiers
source                 1..1011
                       mol_type = genomic DNA
                       organism = Geobacillus stearothermophilus
SEQUENCE: 40
atgcgggcgg ccgtggtgac caaggaccac aaggtcagca tcgaagataa gaaactgcgg  60
gccctgaaac ccggcgaggc gctggtgcag accgaatatt gtggcgtgtg tcatacggat  120
ctccatgtca aaaacgccga tttcggcgat gtgaccggcg tgacgctcgg ccatgagggc  180
atcggcaagg tgatcgaagt cgccgaagac gtggaaagcc tcaagatcgg cgatcgcgtg  240
tccatcgcct ggatgttcga gtcgtgtggc cgctgcgagt attgcacgac cggccgggaa  300
accctgtgtc ggagcgtcaa gaatgccggc tacaccgtgg acggcgcgat ggccgaacag  360
gtcatcgtga cggccgacta tgcggtcaag gtcccggaaa agctggaccc ggccgcggcg  420
tcgtcgatca cctgcgcggg cgtcaccacc tataaggccg tcaaggtgag caatgtcaaa  480
ccgggccagt ggctgggcgt cttcggcatc ggcggcctgg gcaacctggc cctgcagtac  540
gcgaagaatg tcatgggcgc caaaatcgtg gccttcgata tcaacgatga caagctggcg  600
ttcgccaaag aactcggcgc ggatgcgatc atcaactcga aggacgtgga cccggtggcc  660
gaggtgatga aactgacgga caacaagggc ctggacgcga cggtcgtcac cagcgtcgcg  720
aagaccccct tcaatcaggc ggtcgacgtg gtcaaggcgg gcgcccgcgt ggtggccgtg  780
ggcctgccgg tcgacaaaat gaacctggat atcccgcgcc tcgtgctgga cggcatcgag  840
gtggtgggca gcctggtcgg cacccgccag gacctgcggg aggccttcga gttcgcggcc  900
gagaataaag tgacgcccaa ggtccagctc cggaagctcg aagaaatcaa cgatatcttc  960
gaggagatgg aaaacggcac gatcaccggc cggatggtca tcaagttctg a          1011

SEQ ID NO: 41          moltype = DNA  length = 1020
FEATURE                Location/Qualifiers
source                 1..1020
                       mol_type = genomic DNA
                       organism = Geobacillus stearothermophilus
SEQUENCE: 41
atgaaggcgg ccgtcgtgaa cgagttcaag aaggcgctgg aaatcaagga ggtcgagcgg  60
cccaaactcg aagagggcga ggtcctggtg aagatcgagg cctgcggcgt gtgccatacc  120
gacctgcacg ccgcccacgg cgactggccg atcaagccga aactgcccct gatcccgggc  180
cacgagggcg tgggcatcgt cgtggaagtg gcgaagggcg tgaaaagcat caaagtgggc  240
gatcgcgtcg gcatcccgtg gctgtacagc gcgtgcggcg agtgcgagta ctgcctgacg  300
ggccaggaaa cgctctgccc gcatcagctg aatggcggct attccgtgga cggcggctat  360
gccgagtatt gcaaagcccc ggccgactat gtcgccaaga tcccggacaa tctggacccc  420
gtcgaggtcg cccccatcct gtgcgccggc gtgaccacct ataaggcgct gaaagtctcg  480
ggcgcccggc cgggcgagtg ggtcgcgatc tacggcatcg gcggcctggg ccacatcgcc  540
ctgcagtacg ccaaggcgat gggcctgaac gtggtcgcgg tcgacatctc cgacgagaaa  600
tcgaagctgg cgaaagatct cggcgcggac atcgccatca atggcctgaa ggaagacccg  660
gtcaaggcga tccatgacca ggtcggcggc gtccatgccg ccatctccgt cgcggtgaat  720
aagaaagcct tcgagcaggc ctatcagtcc gtcaagcgcg gcggcaccct ggtcgtggtg  780
ggcctcccga atgcggacct gccgatcccc atcttcgata cggtgctcaa cggcgtgtcg  840
gtgaagggca gcatcgtcgg cacccgcaag gacatgcagg aagccctgga tttcgccgcg  900
cggggcaagg tccgccccat cgtggaaacg gccgagctgg aggaaatcaa cgaagtgttc  960
gagcgcatgg aaaaaggcaa aatcaacggc cgcatcgtcc tgaagctgaa ggaggattga  1020

SEQ ID NO: 42          moltype = DNA  length = 1041
FEATURE                Location/Qualifiers
source                 1..1041
                       mol_type = genomic DNA
                       organism = Geobacillus themoglucosidas
SEQUENCE: 42
atgaaagccc tgacctatct gggcccgggc aaaaaagaac tgatggaaaa accgaagccg  60
aagatcgaaa aagagacgga tgccatcgtc aagatgatca aaaccaccat ctgcggcacc  120
gacctccata tcctgtcggg cgacgtgccc accgtggaag agggccgcat cctgggccac  180
gagggcgtcg gcatcatcga ggaagtgggc tccgccgtca agaacttcaa gaaaggcgac  240
cgggtgctga tctcgtgcat caccagctgt ggcaagtgcg agaattgcaa gaagggcctg  300
tacgcccact gcgaggacgg cggctggatc ctgggccatc tgatcgacgg cacccaggcc  360
gagtacgtgc gcatccccca tgcggacaac agcctgtacc cgatccccga gggcgtcgac  420
gaggaagccc tggtcatgct gtcggatatc ctgcccaccg gcttcgagat cggcgtgctg  480
aacggcaagg tccagcccgg ccagaccgtg gcgatcatcg gcgccggccc ggtgggcatg  540
gccgcgctgc tgaccgccca gttctacagc ccggccgaga tcatcatggt ggacctggac  600
gataaccgcc tcgaagtggc gaagaagttc ggcgcgaccc aggtcgtcaa cagcgcggat  660
ggcaaggcgg tggagaagat catggaactc accggcggca agggcgtgga cgtggcgatg  720
gaagccgtcg gcatcccggc caccttcgat atctgccagg agatcgtgaa gccgggcggc  780
```

```
tacatcgcca acatcggcgt gcatggcaag tccgtggagt tccatatcga aaaactgtgg  840
atccgcaaca tcaccctgac gacgggcctg gtgaacacca cgagcacgcc catgctgctg  900
aagacggtgc agtcgaagaa gctcaagccc gaacagctca tcacccaccg cttcgccttc  960
agcgatatca tgaaagcgta cgaagtcttc ggcaacgccg ccaaggagaa ggcgctgaaa  1020
gtcatcatca gcaattcgtg a                                            1041

SEQ ID NO: 43          moltype = DNA  length = 1023
FEATURE                Location/Qualifiers
source                 1..1023
                       mol_type = genomic DNA
                       organism = Geobacillus themoglucosidas
SEQUENCE: 43
atgaaagccg cggtggtcaa tgagttcaag cagaaactcg aaatcaagga agtcgaaaag  60
ccgaagctca actacggcga agtgctggtg aaaatcgagg cctgcggcgt ctgccacacc  120
gacctccatg cggcccacgg cgactggccc gtcaagccga agctgcccct gatcccgggc  180
catgagggcg tgggcatcgt cgtggaagtc gcggagggcg tcaagagcgt caaggtcggc  240
gaccgggtgg gcatcccctg gctgtattcc gcctgcggcg aatgcgaata ctgcctgagc  300
ggccaggaaa ccctgtgccc ccaccagctg aacggcggct atagcgcgga tggcggctat  360
gccgagtact gtaaagcccc cgccaactac gtggcgaaga tcccggaaca tctggacccc  420
gtggaagtgg cgcccatcct ctgcgcgggc gtgaccacct ataaagccct caaggtgtcc  480
aacgccaaac ccggcgagtg ggtcgccatc tacggcatcg gcggcctcgg ccatatcgcg  540
ctgcagtacg ccaaggcgat gggcctcaac gtcatcgccg tggatatcag cgacgagaaa  600
atcgaactgg cgaaacagct cggcgcggac atcgcgatca acggcctgaa agaagatccg  660
gtggaagcca tccagcagaa cgtcggcggc gcccacgccg cgatcagcgt cgccgtgacc  720
aagaaggcgt tcgaacaggc ctatcagagc gtccggcggg gcggctgcct ggtcgtggtc  780
ggcctgccca acgaggacct gcccatcccg atcttcaaca ccgtcctgaa tggcatcacc  840
gtcaagggct ccatcgtggg cacgcggaag gatatgcagg aagcgctgga tttcgcggcg  900
cggggcaagg tgcggccgat cgtcgagacg gccccgctgg agaagatcaa tgaggtcttc  960
gaacgcatgg agaagggcaa gatcaatggc cgcgtcgtgc tcaccatcgg cgtcaaccgc  1020
tga                                                                1023

SEQ ID NO: 44          moltype = DNA  length = 1023
FEATURE                Location/Qualifiers
source                 1..1023
                       mol_type = genomic DNA
                       organism = Lactococcus lactis
SEQUENCE: 44
atgaaggcgg ccgtcgtgcg gcacaacccg gacggctatg ccgatctggt ggagaaggag  60
ctccgcgcga tcaagccgaa cgaggccctc ctggacatgg agtactgcgg cgtgtgccac  120
accgacctgc acgtcgccgc cggcgatttc ggcaacaaag ccggcaccgt cctgggccat  180
gagggcatcg gcatcgtgaa ggaaatcggc accgatgtgt cgtccctcca ggtgggcgac  240
cgggtcagcg tcgcctggtt cttcgaaggc tgcggccact gcgagtactg cgtgtccggc  300
aacgagacgt tctgccggga agtcaagagc gcgggctaca gcgtcgatgg cggcatggcc  360
gaggaagcca tcgtcgtcgc cgactacgcc gtgaaggtcc cggatggcct cgatcccatc  420
gaggccagca gcatcacctg cgcgggcgtg accacctaca aggccatcaa ggtgtccggc  480
gtcaaaccgg gcgattggca ggtgatcttc ggcgccggcg gcctgggcaa cctcgcgatc  540
cagtacgcca aaaacgtctt cggcgcgaag gtcatcgcgg tggacatcaa ccaggacaag  600
ctgaacctcg cgaagaagat cggcgccgat gtcaccatca actcgggcga tgtcaacccg  660
gtcgacgaga tcaagaaaat caccggcggc ctgggcgccc agtcggccat cgtgtgcgcg  720
gtcgcccgca tcgcgttcga acaggcggtg gccagcctca aaccgatggg caaaatggtg  780
gcggtggccg tcccgaacac cgagatgacc ctgagcgtgc cgaccgtggt cttcgacggc  840
gtcgaggtcg cgggctcgct cgtcggcacc cggctggacc tcgccgaggc cttccagttc  900
ggcgcggagg gcaaagtcaa gccgatcgtc gcgacccgga agctggagga gatcaatgac  960
atcatcgatg agatgaaggc cggcaagatc gaaggccgga tggtcatcga tttcaccaag  1020
tga                                                                1023

SEQ ID NO: 45          moltype = DNA  length = 1023
FEATURE                Location/Qualifiers
source                 1..1023
                       mol_type = genomic DNA
                       organism = Lactococcus lactis
SEQUENCE: 45
atgaaggcgg cggtcgtgcg ccataacccg gacggctacg ccgacctggt ggaaaaggag  60
ctgcgggcca tcaagccgaa cgaggcgctg ctcgacatgg agtactgcgg cgtctgccat  120
acggacctcc acgtcgccgc cggcgactac ggcaacaagg cgggcacggt gctgggccat  180
gagggcatcg gcatcgtgaa ggaaatcggc accgacgtgt cctccctgca ggtcggcgac  240
cgggtcagcg tcgcctggtt cttcgagggc tgtggccact gcgagtattg tgtcagcggc  300
aatgaaacgt tctgtcgcga agtcaaaaac gccggctact cggtcgatgg cggcatggcg  360
gaagaagcca tcgtggtcgc ggactatgcc gtgaaggtgc cggacggcct ggaccccatc  420
gaagcgtcct cgatcacctg cgcgggcgtc acgacctaca aggcgatcaa agtgtcgggc  480
gtcaagccgg gcgactggca ggtgatcttc ggcgcgggcg gcctcggcaa cctcgccatc  540
cagtacgcca agaacgtctt cggcgccaaa gtgatcgccg tcgacatcaa tcaggacaaa  600
ctgaatctgg cgaaaaagat cggcgccgat gtcatcatca acagcggcga tgtgaacccg  660
gtggacgaga tcaaaaagat cacgggcggc ctcggcgccc agagcgcgat cgtgtgcgcc  720
gtggcccgca tcgccttcga acaggccgtc gcgtccctga agccgatggg caagatggtc  780
gccgtcgccc tcccgaacac ggaaatgacg ctgtccgtcc cgaccgtggt cttcgacggc  840
gtggaagtgg ccggctcgct ggtcggcacc cggctggacc tcgccgaggc cttccagttc  900
ggcgcggaag gcaaggtcaa gccgatcgtg gccacgcgca agctcgaaga gatcaatgat  960
atcatcgatg agatgaaggc gggcaagatc gaaggccgca tggtcatcga tttcaccaag  1020
```

```
tga                                                                    1023

SEQ ID NO: 46          moltype = DNA  length = 1206
FEATURE                Location/Qualifiers
source                 1..1206
                       mol_type = genomic DNA
                       organism = Oenococcus oeni
SEQUENCE: 46
atgcgcggca gccatcatca ccatcaccac ggcagcgccg aacgggccta cgatttcctg  60
atgccctccg tcaacttctt cggcccgggc gtgatctcca agatcggcga acgggcgaaa  120
atgctcggca tgaagaagcc ggtgatcgtc accgataagt tcctggagaa tctgaaaaat  180
ggcgccgtgg cccagaccct ggccagcctc aagaagagcg gcgtcgatta cgtcgtgtat  240
aacggcgtgg agcccaaccc caaaatccac aacatcaagg aggtgaaaac cctgtacgaa  300
aaggaagacg ccgacagcat catcaccgtg ggcggcggct cggcccacga tacgggcaag  360
ggcgccggca tcatcatgac gaacggcgat gacatcacca agctggccgg catcgaaacc  420
ctgaagaatc ccctccccccc cctgatcgcc gtgaatacca ccgcgggcac cggctcggaa  480
ctcacgcggc acgccgtcat cacgaacgag gaaacccatc tgaagttcgt cgtggtgtcc  540
tggcgcaaca tcccgctggt cagcttcaat gaccccaccc tgatgctgga catccccaag  600
ggcctcaccg cggccacggg catggacgcc ttcgtccagg cggtcgaacc gtacgtgagc  660
gtggatcaca atcccatcac cgactcccag tgtatccagg ccatcaagct gatcgaatcg  720
tcgctgcggg aggccgtggc gaacggccat aacctgcagg cccgcaccaa aatggtggaa  780
gccgaaatgc tcgcgggcat ggcgttcaat aacgccaacc tgggctacgt ccacgcgatg  840
gcccatcagc tgggcggcca gtacgacgcc ccgcatggcg tctgctgcgc cctgctcctg  900
ccgtatgcgg aggagtacaa cctgatcgcc gacccggaac gcttcgcgga actggcccgc  960
atcatgggcg agaacaccga cggcctctcg acccgcgacg cggccgaact gtccatcaag  1020
gcgatgaaac agctgtcgga ggacgtgggc atcccgcact cgatcaagga catcggcgcc  1080
aagccggagg acttcgacct gatggccgaa aatgcgctga aggacggcaa tgccttctcc  1140
aacccgcgca aaggcaccaa ggaggatatc gtcaagatct tccaggaggc ctatgacgcc  1200
aaatga                                                                 1206

SEQ ID NO: 47          moltype = DNA  length = 1002
FEATURE                Location/Qualifiers
source                 1..1002
                       mol_type = genomic DNA
                       organism = Pectobacterium atrosepticum
SEQUENCE: 47
atgctgaatt tcaccctcca taccccgacg aagatcctgt tcggcgaggg ccagatcgcg  60
gagctgggca aggagatccc ggccgacgcc cgcatcctca tcacctacgg cggcggctcg  120
gtcaaacaca acggcgtgct ggatcaggtg taccgggcgc tggaaggccg gaacgtgcgg  180
gagttctccg gcatcgagcc caacccgacc tacgaaacgc tcatgaaggc cgtggaggtg  240
gtccgggcgg aaaagatcga tttcctgctc gccgtgggcg gcggcagcgt cgtcgacggc  300
accaagttca tcgccgcggc ggccgactac caggccgcgc aggacccgtg gcacatcctc  360
cagaccggcg gcgccgaaat cgaccggggc gtggccctcg ccgcggtgct gaccctgccc  420
gccacgggca gcgaatccaa taacggcgcc gtcatcaccc gcaaaagcac caatgacaag  480
ctcgcgttcc ggtccccgca tacgcagccc ctcttcgccg tcctcgaccc ggtggtcacg  540
tacaccctgc cggcccggca gatcgcgaat ggcgtcgtcg acgccttcgt ccacaccgtc  600
gagcagtacc tgacctactc cgtcgacgcg aaagtccagg atcgcttcgc cgagggcctg  660
ctgctcaccc tggtcgaaga gggcccccgg gccctggccg aacccgaaaa ctacaaagtg  720
cgggcgaatg tcatgtggag cgccacgatg gcgctgaacg gcctcatcgg cgccggcgtc  780
ccccaggatt ggtcgaccca catgctgggc cacgaactca cggccctgca cggcctcgac  840
cacgcgcaga cgctggccat cgtcctgccg gccatgctgg cggcccggaa atcccagaaa  900
cgggataaac tcctgcagta cgccgagcgc gtctggaacc tccgcgacgg ctcggaagat  960
cagcggatcg acggcgccat cgccgccacg cgcgatttct ga                          1002

SEQ ID NO: 48          moltype = DNA  length = 1056
FEATURE                Location/Qualifiers
source                 1..1056
                       mol_type = genomic DNA
                       organism = Psychrobacter cryohalolentis
SEQUENCE: 48
atggccaata ccaaggccta cgccgccacg gcgccggatt cgggcctggc cccgtacgcg  60
atcgaccggc gggaactgcg ggccgatgac gtggcgatcg aaatcgacta ctgtggcgtg  120
tgccatagcg atctccatac cgtggaaaac gactggggcg gctcgaagta cccggtgatc  180
ccgggccatg agatcgtcgg ccgggtgacg gcggtgggcc ccgaggtcag ccatttcaag  240
gccggcgacc tcgtgggcgt gggctgcatg gtggattcgt gtcgctcgtg cagcgcctgc  300
gacagcggcc tcgaacagta ttgcatcgag ggcagcacga tgacctacgg cagcctggac  360
cgccacgatg gctccgtcac ccacggcggc tacagcgaac gcatcgtcgt ctcggaacgg  420
ttcgtcgtgc gggtgcccga aaaactggac ccggcctcgg ccgcccccgat cctgtgcgcc  480
ggcatcacga cgtacagccc gctgaagcac ttcaaggtgg gcaagggcca taaagtcggc  540
gtcctgggca tgggcggcct gggccatatg ggcgtgaagt tcgccaaggc cctgggcgcc  600
gaggtgacga tcttcacccg gtccgaggcg aaagtggccg aagcgaagaa acagggcgcc  660
gaccatgtca tcatctcgac cgataaggag cagatgaagg ccgccgccga cagcttcgat  720
ttcctcctcg acaccatccc ggtggcgcac gacctgaatc cgtatctgaa gtgtctgaaa  780
tacgatggca cccacatcct cgtgggcctg ctgacccccca tcgaaccggc gctgcaggcc  840
ggcctcctgg tcaccaagcg gcgcgtcgtg gcgggcagcc tgatcggcgg catgcccgag  900
acgcaggaag tcctggactt ctgcgccgaa catgacatca cctgtgatat cgagatgctc  960
gacatccgca acatcaacga agcgtacgtc cgcatgaaaa agggcgatgt caagtaccgc  1020
ttcgtgatcg atatgaagac gctgaaggaa ggctga                                 1056
```

```
SEQ ID NO: 49          moltype = DNA  length = 1713
FEATURE                Location/Qualifiers
source                 1..1713
                       mol_type = genomic DNA
                       organism = Bacillus subtilis
SEQUENCE: 49
atgaccaagg ccaccaagga acagaaaagc ctggtcaaga accgcggtgc tgaactggtt  60
gtggactgcc tcgtggaaca gggcgtgacc catgtcttcg gcatcccggg cgccaagatc  120
gacgccgtct tcgacgccct gcaggataaa ggtccggaaa tcatcgtggc acgccatgag  180
cagaacgcag ccttcatggc ccaggccgtc ggtcggctga cgggtaagcc cggcgtggtg  240
ctggtcacct ccggtccggg agcctcgaac ctggccacgg gactgctcac cgccaacacc  300
gaaggcgacc cggtggtcgc cctggccggt aatgtcatcc gggcggatcg cctgaagcgc  360
acccatcagt ccctggataa cgcggccctg ttccagccaa tcaccaaata tagtgtcgaa  420
gtgcaggatg tgaagaacat cccggaagcc gtcaccaatg cgttccgaat cgcgtccgcc  480
ggccaagcag gggcagcatt cgtgagcttc ccccaggacg tggtcaatga agtgaccaac  540
accaaaaacg tcagagccgt agccgccccg aagctgggcc ctgcagcaga tgacgccatc  600
tccgctgcca tcgcgaagat ccagaccgca aagctgccgg tcgtgctggt cggaatgaag  660
ggcggacgcc cggaggccat caaggccgtg cgtaaactgc tgaagaaggt gcagctaccg  720
ttcgtggaaa cctaccaggc cgccggcacc ctgagtcggg acttggaaga ccagtatttc  780
ggccgtatcg gcctgttccg caaccagccg ggcgacctgc tcctggaaca agccgatgtg  840
gtgctgacca tcggctacga cccgatcgaa tatgacccga agttctggaa catcaatggc  900
gaccgcacga tcatccatct ggacgaaatc atcgccgaca tcgaccatgc ctatcagccg  960
gacctggaac tgatcggcga catcccgagc accatcaacc acatcgaaca cgatgccgtg  1020
aaggtggaat ttgccgaacg cgaacagaag atcctgtcgg acctgaagca gtatatgcat  1080
gagggcgaac aggtgcctgc cgactggaag tcggacagag cccatccgct ggaaatcgtg  1140
aaggaactgc gtaacgccgt cgacgaccat gtcaccgtca cctgcgatat cggcagccat  1200
gccatttgga tgagccgcta cttccggagc tatgaaccgc tgaccctgat gatctccaac  1260
ggtatgcaga ccctcggcgt cgccctcccg tgggccatcg gcgcaagtct ggtgaagccg  1320
ggcgaaaaag tggtcagcgt gtccggcgac ggcggcttcc tgttctccgc tatggaactg  1380
gaaaccgcgg tccgcctgaa ggccccgatc gtgcatatcg tgtggaacga cagcacctac  1440
gacatggtcg ccttccagca gctgaaaaag tacaaccgca ccagcgccgt ggacttcggc  1500
aatatcgaca tcgtgaagta tgccgaatcc ttcggagcca ccggactgcg cgtggaatcc  1560
ccggaccagc tggcggacgt tctgcgtcag ggcatgaatg ccgaaggtcc cgtgattatc  1620
gatgtgcccg tcgactacag cgacaacatc aacctggcct cggacaaatt gccgaaggag  1680
ttcggcgaac tgatgaaaac aaaagcacta taa                               1713

SEQ ID NO: 50          moltype = DNA  length = 1671
FEATURE                Location/Qualifiers
source                 1..1671
                       mol_type = genomic DNA
                       organism = Clostridium autoethanogenum
SEQUENCE: 50
atgaatcggg atatcaagaa agaggtgcag ctcaacacgg cccagatgct ggtcaagtgt  60
ctggaagccg agggcgtcaa gtatatcttc ggcatcccgg gcgaggagaa tctcgaaatc  120
atgaacgcca tctcggattc cacgatcgag ttcatcacca cccgccatga acagggcgcg  180
gccttcatgg ccgacgtgta cggccggctg accggcaagg cgggcgtgtg tctgagcacc  240
ctcggccccg gcgcgaccaa cctggtcacc ggcgtggccg acgccgactc cgacggcgcc  300
cccgtggtcg cgatcaccgg ccaggtgggc acggagcgga tgcacatcac ctcccatcag  360
ttcctcgacc tctgcaagat gttcgagccg atcaccaagc ggagcaagca gatcgtccgc  420
ccggacacgg tgtcggagat catccgcctg gtgttcaagt acgccgaaag cgaaaagccc  480
ggcgcctgtc atatcgacct gccggtcaac atcgccaaga tgcccgtcgg cgccctggag  540
aagccgctgg agaaaaaaat cccgccgaag gaacacgcgg acctgtccac catcgaggaa  600
gcggcgtccg agatcttcaa ggccaaaaac cccatcatcc tggccggcag cggcgccatc  660
cgcggcaaca gcagcaaggc ggtcaccgag ttcgccacca agctgaagat ccccgtcatc  720
aacacgatga tggccaaggg catcatcccg atggacaaca agtatagcat gtggaccatc  780
ggcatccccc agaaggacta tgtgaacaag atcatcgaag aggccgacct ggtcatcacc  840
atcggctacg acatcgtgga atatgccccg tcgaaatgga acatcaacgg cgacatcaag  900
atcgtccata tcgacgcccg cccctcgcac atcaacaaac tctaccagcc catcgtggag  960
gtggtcggcg acatcagcga cgcgctgtat aacatcctgc gccgcaccag ctcgaaagac  1020
gagccggtca aggcgctgga gatcaagtcg gaaatgctgg cggagcacga gtcctacgcg  1080
aacgacaatg cgttcccgat gaagccgcag cgcatcctca acgatgtgcg caaagtcatg  1140
ggcccgcacg acatcgtgat ctccgatgtg ggcgcccata aaatgtggat cgcccgccac  1200
tataactgct acgagccgaa tacctgcatc atctcgaacg gcttcgccac gatgggcatc  1260
ggcgtcccgg gcgcgatcgc cgccaaactc atcaacccgg ataagaaggt cctggccatc  1320
gtcggcgacg gcggcttcat gatgaataac caggaactgg agacggcgct gcgcatcaaa  1380
acgcccatcg tggtcctcat cttcaacgac tccaattacg gcctcatcaa gtggaagcag  1440
gaggagcatt atggcaaatc gtgctatgtg gacttcacca acccggactt cgtgaagctg  1500
gccgagagca tgtacgccaa aggctatcgc gtggagaaag ccgaggatct gatcccgacc  1560
ctcgaagagg ccttcaagca gaatgtcccg gcggtcatcg actgccaggt ggactatggc  1620
gagaatatca agctcaccaa gcacctcaag gaggtctatg aaaacatgtg a           1671

SEQ ID NO: 51          moltype = DNA  length = 1719
FEATURE                Location/Qualifiers
source                 1..1719
                       mol_type = genomic DNA
                       organism = Bacillus licheniformis
SEQUENCE: 51
atgaataacg tcgcggccaa gaacgaaacc ctgaccgtcc ggggcgccga actcgtggtg  60
gatagcctga tccagcaggg cgtgacccat gtcttcggca tcccgggcgc caaaatcgac  120
```

```
gcggtcttcg acgtgctgaa ggataagggc cccgaactga tcgtctgccg ccatgagcag  180
aacgcggcct tcatggccgc cgccgtcggc cgcctgacgg gcaagccggg cgtctgcctg  240
gtcacctccg gcccgggcgc ctcgaatctc gcgaccggcc tggtcaccgc gaacacggaa  300
ggcgacccgg tggtcgccct ggcgggcgcc gtgaagcggg cggatcggct gaagaagacg  360
caccagtcga tggataacgc cgccctgttc cagcccatca cgaagtacag cgcggaggtg  420
gaagacgcga acaacatccc ggaggccgtg acgaacgcct tccgcgccgc ggcgtccggc  480
caggccggcg cggccttcct cagcttcccc caggatgtca ccgccggccc ggccaccgcc  540
aagccggtca aaaccatgcc cgcccccgaag ctgggcgccg cgagcgatga acagatctcc  600
gccgcgatcg cgaagatcca caacgcgaat ctgccggtgg tcctcgtggg catgaagggc  660
ggccggccgg aagccatcga agccgtgcgc cgcctgctcc gcaaggtcaa gctcccgttc  720
gtggaaacct accaggcggc cggcacgctg tcgcacgatc tggaggatca gtacttcggc  780
cggatcggcc tgttccggaa ccagccgggc gacatgctcc tggaaaaggc cgacgtggtc  840
ctgaccgtgg gctacgaccc gatcgagtac gatccggtgt tctggaatgg caaaggcgaa  900
cgctcggtca tccacctcga cgaaatccag gccgatatcg atcacgacta ccagcccgag  960
atcgaactca tcggcgacat cgcggaaacc ctcaatcaca tcgagcatga ctcgctgccg  1020
gtgtccatcg acgaatcctt cgcgcccgtg ctcgactatc tcaagaaggc gctcgaagaa  1080
cagtcggagc ccccgaagga aacgaagacc gatctggtcc acccgctcca gatcgtgcgc  1140
gacctgcgcg agctgctctc cgatgacatc accgtcacct gcgacatcgg cagccacgcc  1200
atctggatgt cccgctattt ccgcacctat cgcccgcatg gcctcctgat ctccaacggc  1260
atgcagacgc tgggcgtcgc cctgccgtgg gcgatcgccg cgaccctggt gaacccgggc  1320
cagaaggtgg tgtcggtcag cggcgatggc ggcttcctct tctccgcgat ggaactcgaa  1380
accgccgtcc gcctcaaggc gccgatcgtg cacatcgtgt ggaacgactc cacgtacgac  1440
atggtcgcgt tccagcagga aatgaagtac aagcgcacct ccggcgtcga tttcggcggc  1500
atcgacatcg tcaagtatgc ggaatccttc ggcgccaaag gcctccgcgt gaatagcccc  1560
gatgaactgg ccgaggtcct gaaggccggc ctcgacgcgg agggcccggt ggtcatcgac  1620
atccccgtcg actactcgga taacatccac ctggccgacc agcgcttccc gaagaagttc  1680
gaggagcact tcaacaagga agcgtcgaag cagtcctga                         1719
```

```
SEQ ID NO: 52          moltype = DNA  length = 720
FEATURE                Location/Qualifiers
source                 1..720
                       mol_type = genomic DNA
                       organism = Clostridium autoethanogenum
SEQUENCE: 52
atggatgatg aggtgaaagt cccgaaccac atctaccaga tgtcgaccat caatgccctg  60
gtcagcggcc tctacgacgg ctgtgtgtcg ctctcgaagc tcctgaaaaa gggcaatttc  120
ggcatcggca cgttcaaggg cctggatggc gagctgaccc tcctgaacgg cacgttctat  180
cgcaccaaac cggatggctc cgtgtacgtg tgcagcaaga acgtgagcgt cccctttcgcg  240
gtcgtcaccg agctggagaa ctacaatacc tataacatcc agaatcgcac ctcctatgag  300
gacatccgca aggagctgga ctcgttcatc gagtcgaaga acatcttcta tgccttctat  360
atggaaggca aattcaacta cgtcaaaacc cgcaccgtcg tgaagcagaa catgccgtac  420
aagccgatgg ccgaggtggt caaagaccag ccgatgttcg aatacaacgg cgtcgatggc  480
tacgtcgtcg gcttccggtg cccggattat gtggaaggcc tcaatgtgcc cggctaccat  540
ttccacttca tcaacaagga caaaaagttc ggcggccaca tctccgagtt ctcgatcgag  600
aacgccaaag tctacgtcca gaactgctcc tgtttccgca tggagctccc gaagaatgag  660
agcttctaca acatggaggt ccaggaccgc aacgacgaaa tcacgtccgt ggagaaatga  720
```

```
SEQ ID NO: 53          moltype = DNA  length = 780
FEATURE                Location/Qualifiers
source                 1..780
                       mol_type = genomic DNA
                       organism = Klebsiella pneumoniae
SEQUENCE: 53
atgaaccact cggccgaatg cacctgcgaa gagagcctct gcgaaaccct ccgggccttc  60
tcggcccagc acccggagag cgtcctgtac cagacgagcc tgatgtcggc gctgctgtcg  120
ggcgtgtatg aaggctcgac gaccatcgcc gacctgctga agcatggcga cttcggcctg  180
ggcaccttca atgaactgga cggcgagctc atcgccttca gctcgcaggt gtatcagctc  240
cgggccgatg gctccgcccg gaaggcccag cccgaacaga agacccccgtt cgccgtgatg  300
acctggttcc agccgcagta tcggaagacc ttcgaccacc ccgtgagccg ccagcagctc  360
cacgaggtga tcgaccagca gatcccgagc gacaacctct tctgcgccct gcgcatcgac  420
ggccatttcc gccacgcgca tacccgcacc gtcccgcggc agaccccgcc ctaccgcgcc  480
atgaccgatg tcctggatga ccagccggtc ttccggttca accagcgcga gggcgtcctg  540
gtcggcttcc gcaccccgca gcacatgcag ggcatcaacg tcgcgggcta tcatgaacac  600
ttcatcaccg atgatcgcaa gggcggcggc cacctcctcg actaccagct ggaccacggc  660
gtcctgacct tcggcgaaat ccataagctg atgatcgacc tccccgccga cagcgccttc  720
ctgcaggcga atctgcatcc ggacaacctc gatgccgcca tccgctccgt cgagtcgtga  780
```

```
SEQ ID NO: 54          moltype = DNA  length = 1074
FEATURE                Location/Qualifiers
source                 1..1074
                       mol_type = genomic DNA
                       organism = Clostridium autoethanogenum
SEQUENCE: 54
atgaaggccg tcctgtggta cgacaaaaag gatgtccgcg tggaagaaat cgaggaaccg  60
aaggtgaaag aaaacgccgt gaagatcaaa gtcaagtggt gcggcatctg cggctcggac  120
ctgcatgagt atctcggcgg cccgatcttc atcccggtcg gcacccccca cccgctgtcg  180
aagagcaccg cgcccgtcgt gctgggccac gagttctcgg gcgaagtggt ggagatcggc  240
agcaaagtga ccaagttcaa ggcgggcgac cgcgtcatcg tggaaccgat cgtcgcctgc  300
ggcaaatgcc cggcctgcct ggaaggcaag tacaatctgt gcgaggcgct gggcttccac  360
```

```
ggcctgtgcg gcagcggcgg cggcttcgcc gagtacacgg tgttcccgga agatttcgtg  420
cacaagatcc ccgacacgat ggattatgaa caggccgcgc tggtggagcc gatggcggtc  480
gcgctgcact ccctgcgggt gggcaacttc accacgggca acaccgccct ggtcctgggc  540
gcgggcccga tcggcctggc caccatccag tgcctcaaag cgtcgggcgc ccggatcgtc  600
atcgtcttcc agcgcaaatc ggtgcggcag gaatacgcca agaagttcgg cgcggacgtg  660
gtcctcgacc cgaatgaggt ggacgtgatc gaggaaatca aaaagctgac cggcggcgtg  720
ggcgtggaca cgagcttcga aaccaccggc gccaacgtcg gcatcaacac cgcgatccag  780
gcgctgaaat atgagggcac cgccgtcatc acctccgtct gggagaagaa cgccgagatc  840
aatccgaacg acctggtctt caccgaaaag aaggtcgtcg gcaccctcgc gtaccggcac  900
gagttcccgt cgaccatcgc cctgatgaac gacggccgca tcaagaccga tggctatatc  960
accaagcgga tcgccctgga agacatcgtc aaggagggct tcgaaaccct gaccggcccg  1020
gagaagaaaa agcacgtcaa aatcatcgtc acgcccgata aaagcctcct gtga        1074
```

```
SEQ ID NO: 55           moltype = DNA  length = 1053
FEATURE                 Location/Qualifiers
source                  1..1053
                        mol_type = genomic DNA
                        organism = Bacillus subtilis
SEQUENCE: 55
atgaaagccc tgctgtggca taaccagcgc gacgtgcggg tggaagaggt cccggagccc  60
gccgtccgca gcggcgcggt gaaaatcaaa gtgaaatggt gcggcatctg tggcaccgac  120
ctgcatgaat atctggccgg ccccatcttc atcccgacgg aggaacatcc gctgacgcac  180
gtcaaggccc cggtcatcct cggccatgag ttcagcggcg aggtggtgga gatcggcgaa  240
ggcgtcacca atcacaaagt cggcgatcgc gtggtcgtcg aaccgatcta ctcgtgcggc  300
aagtgtgagg cgtgcaagca cggccactat aatgtctgcg agcagctggt gttccacggc  360
ctgggcggcg acggcggcgg cttctcggag tacaccgtgg tgccggcgga tatggtccac  420
cacatcccgg atgaaatgac ctacgagcag ggcgccctgg tcgagccggc cgccgtggcg  480
gtgcacgcgg tgcgccagag caaactcaag gagggcgaag ccgtggccgt cttcggctgc  540
ggcccgatcg gcctgctggt catccaggcg gccaaagcgg cgggcgcgac cccgtcatc  600
gcggtcgagc tgtcgaagga acgccaggag ctcgccaagc tggcgggcgc ggattatgtc  660
ctgaaccccg ccgaacagga cgtggtggcg gaaatccgga acctgaccaa cggcctgggc  720
gtcaacgtct ccttcgaggt caccggcgtg gaagtcgtcc tgcggcaggc gatcgaatcg  780
acctcgttcg agggccagac ggtcatcgtg tcggtctggg agaaggacgc caccatcacg  840
cccaataatc tggtcctgaa agagaaggaa gtggtcggca tcctcggcta ccggcatatc  900
ttcccgtccg tcatcaagct gatctcgtcg ggccagatcc aggccgagaa actcatcacc  960
aagaagatca cggtggacca ggtggtcgaa gaaggcttcg aagcgctggt caaggataag  1020
aagcaggtga agatcctcgt gtcgccgaag tga                               1053
```

```
SEQ ID NO: 56           moltype = DNA  length = 1053
FEATURE                 Location/Qualifiers
source                  1..1053
                        mol_type = genomic DNA
                        organism = Paenibacillus polymyxa
SEQUENCE: 56
atgcaggcgc tgcgctggca cggcatcaag gacctgcggc tggagaacat cgagcagccc  60
gccgccctcc cgggcaaggt gaagatcaag gtggaatggt gcggcatctg cggcagcgac  120
ctgcatgaat atgtcgccgg cccgatcttc atccccgaaa acgcgcagca tccgctcacg  180
ggcgagaagt cgcccatcgt gatgggccat gagttctccg gccagttctt cgacttcggc  240
gaaggcgtga cgaaaatcca ggtgggcgac cgcgaagtgg tggagccggt cttcgcgtgt  300
ggcgaatgcg atgcgtgccg gcagggcaaa tataacctgt gcgataagat gggcttcctg  360
ggcctggccg gcggcggcgg cggcttctcg gaatatgtcg ccgcggatga gcatatggtg  420
cacaaaatcc ccgagtccgt gtccttcgaa cagggcgccc tggtcgagcc gtccgccgtc  480
gccctctacg cggtccgcca gatccagctg aaggtcgatg acaaggcggt ggtcttcggc  540
gccggcccca tcggcctgct cgtcatcgaa gcgctgaacg ccagcggcgc gagcgaaatc  600
tatgcggaag agctcagcga agagcgcacc gccaaagccg aagacctggg cgccatcgtg  660
ctcgacccca acacgtacga tgtcgtcgag gaactccata agcgcacgaa tggcggcgtc  720
tacgtcccct atgaggtcac ggaagtcccg cccgtgctga cccaggccat cgagtccgcc  780
aagatctccg gcgaaatcat gatcgtcatc atcttcgaaa aggaggccct catcaagccg  840
aacaacatcg tcatgaatga acggaacctg acgggcctga tctgctacga cgatgtgttc  900
ccggccctga tctccctcat ggagaatggc tacttccccg ccgacaagct ggtcatcaaa  960
cggatcaagc tggtggatgt catcgaagcg gccttcgagt cgctcctgat cgaggagtac  1020
caggtgacca tcctcgtgtc gccgcacgcc tga                               1053
```

```
SEQ ID NO: 57           moltype = DNA  length = 3696
FEATURE                 Location/Qualifiers
source                  1..3696
                        mol_type = genomic DNA
                        organism = Mycobacterium bovis
SEQUENCE: 57
atggccaata tctcgtcccc gttcggccag aacgagtggc tcgtggaggc catgtatcgg  60
aagttccggg acgacccgtc cagcgtcgac ccgtcctggc acgagttcct cgtggactac  120
tcccccgagc cgaccagcca gccggcggcc gagccgaccc gggtcacgtc gccgctcgtc  180
gccgaacggg ccgccgccgc cgccccccag gcgcccccca agccggccga cacggccgcc  240
gccggcaacg gcgtggtggc ggccctggcc gccaagaccg ccgtgccgcc cccggccgaa  300
ggcgacgaag tcgccgtcct ccggggcgcg gcggcggcgg tcgtgaagaa catgagcgcg  360
tccctggagg tgccgaccgc cacgtcggtc cgggccgtcc ccgcgaaact cctcatcgac  420
aaccgcatcg tcatcaataa ccagctgaag cggacgcggg gcggcaagat ctcgttcacg  480
cacctcctcg gctacgcgct cgtgcaggcc gtcaagaagt tcccgaacat gaaccggcac  540
tacacggaag tggacggcaa acccacggcc gtcacccccg cccatacgaa cctcggcctg  600
```

```
gccatcgacc tgcagggcaa ggacggcaag cggtcgctgg tggtcgccgg catcaagcgc  660
tgcgagacga tgcgcttcgc gcagttcgtc acggcctatg aagacatcgt ccgccgggcc  720
cgggacggca agctcaccac ggaagatttc gcgggcgtca ccatctcgct caccaatccc  780
ggcacgatcg gcaccgtcca tagcgtgccg cgcctgatgc ccggccaggg cgcgatcatc  840
ggcgtcggcg cgatggaata ccccgccgag ttccagggcg cgtccgagga gcggatcgcg  900
gaactgggca tcggcaagct catcaccctc accagcacgt atgaccaccg catcatccag  960
ggcgccgagt cgggcgactt cctccggacg atccatgagc tgctgctgag cgacggcttc  1020
tgggatgagg tgttccggga actgtccatc ccgtatctgc cggtccggtg gagcacggac  1080
aaccccgata gcatcgtgga caaaaacgcc cgcgtgatga acctcatcgc cgcctaccgc  1140
aaccgcggcc acctgatggc cgacaccgat ccgctgcggc tcgacaaagc ccgcttccgg  1200
agccatcccg acctggaagt cctgacccac ggcctcaccc tgtgggatct ggatcgggtc  1260
ttcaaggtcg acggcttcgc cggcgcccag tacaagaagc tgcgcgatgt gctcggcctg  1320
ctgcgggacg cctattgccg ccacatcggc gtggagtacg cgcacatcct cgacccggaa  1380
cagaaagaat ggctggaaca gcgcgtcgaa accaagcatg tgaagcccac ggtggcgcag  1440
cagaagtaca tcctgtcgaa gctgaatgcg gccgaagcct tcgaaacctt cctgcagacc  1500
aagtacgtcg gccagaagcg cttctccctg gaaggcgccg agtccgtcat cccgatgatg  1560
gatgccgcga tcgaccagtg cgccgaacac ggcctggacg aagtcgtgat cggcatgccc  1620
catcgcggcc ggctcaacgt cctcgcgaac atcgtcggca agccgtactc gcagatcttc  1680
acggagttcg aaggcaacct gaacccctcc caggcccacg gcagcggcga cgtgaaatat  1740
cacctgggcg ccaccggcct gtatctgcag atgttcggcg acaacgacat ccaggtcagc  1800
ctgaccgcca accctcgca tctggaagcc gtcgaccccg tcctggaagg cctggtccgc  1860
gcgaagcagg acctcctgga ccacggcagc atcgatagcg acggccagcg ggccttctcc  1920
gtggtgcccc tcatgctgca cggcgacgcc gccttcgccg gccagggcgt ggtcgccgag  1980
acgctcaacc tggcgaacct gcccggctac cgcgtcggcg gcacgatcca catcatcgtc  2040
aacaatcaga tcggcttcac caccgccccc gagtactccc gcagctcgga atactgcacc  2100
gatgtggcga aaatgatcgg cgccccgatc ttccatgtca atggcgatga tccggaagcg  2160
tgcgtgtggg tggcccgcct ggcggtggat ttccgccagc ggttcaagaa ggatgtggtg  2220
atcgacatgc tgtgctaccg ccgccggggc cataatgaag gcgacgatcc ctccatgacc  2280
aacccctaca tgtacgatgt cgtggacacg aagcgcggcg cccgcaagtc ctataccgag  2340
gccctcatcg gccggggcga tatcagcatg aaagaagccg aggatgcgct ccgcgactat  2400
cagggccagc tggaacgggt gttcaacgag gtgcgggaac tcgaaaaaca cggcgtccag  2460
ccgtccgaga gcgtggagtc cgatcagatg atcccggcgg gcctcgccac ggcggtcgat  2520
aagtccctgc tggcccggat cggcgatgcc ttcctggccc tccccaatgg cttcacggcg  2580
cacccgcggg tgcagccggt gctcgaaaaa cgccgggaaa tggcctacga aggcaagatc  2640
gactgggcct tcggcgagct gctggcgctg ggctccctgg tggccgaagg caaactggtg  2700
cgcctgtccg gccaggactc gcgccgcggc accttctccc agcgccactc ggtcctgatc  2760
gatcgccata ccggcgagga gttcaccccg ctccagctcc tggccacgaa ctccgacggc  2820
tcgcccaccg gcggcaagtt cctggtgtat gacagccccc tgagcgagta tgcggcggtc  2880
ggcttcgagt acggctacac cgtcggcaat cccgacgccg tcgtcctgtg ggaagcgcag  2940
ttcggcgact tcgtcaatgg cgcccagtcg atcatcgacg agttcatctc gtcgggcgag  3000
gccaaatggg gccagctctc gaacgtcgtg ctgctgctcc cgcacggcca cgaaggccag  3060
ggcccggatc acacctccgc ccggatcgaa cggttcctgc agctctgggc cgagggctcc  3120
atgacgatcg ccatgcccag caccccgtcc aactatttcc acctcctgcg gcgccatgcg  3180
ctcgacggca tccagcggcc cctgatcgtc ttcacgccga agagcatgct gcgccataag  3240
gccgccgtct cggagatcaa ggacttcacc gagatcaaat tccggtcggt gctggaagaa  3300
ccgacctatg aagatggcat cggcgaccgc aataaggtgt cgcgcatcct gctgacctcg  3360
ggcaagctgt actacgagct ggccgcccgc aaggccaaag acaaccggaa cgacctggcc  3420
atcgtccggc tggagcagct ggcgcccctc ccgcgccggc gcctgcgcga aaccctggat  3480
cgctatgaga acgtcaagga gttcttctgg gtgcaggagg aacccgcgaa tcagggcgcc  3540
tggccccgct tcggcctgga gctgccggag ctgctccccg acaagctggc cggcatcaag  3600
cggatcagcc gccgcgcgat gtcggccccg agctcgggct ccagcaaggt ccatgcggtc  3660
gagcagcagg agatcctgga tgaagcgttc ggctga                            3696
```

```
SEQ ID NO: 58           moltype = DNA  length = 3696
FEATURE                 Location/Qualifiers
source                  1..3696
                        mol_type = genomic DNA
                        organism = Mycobacterium tuberculosis
SEQUENCE: 58
atggccaaca tcagcagccc cttcggccag aatgaatggc tcgtggagga gatgtaccgg  60
aagttccggg atgatcccag ctcggtcgat ccgtcgtggc acgagttcct ggtcgactat  120
agccccgaac ccacctccca gccggcggcc gagcccacgc gggtgacctc cccgctggtc  180
gcggaacgcg ccgcggcggc ggccccccag gccccgccga aacccgccga tacggccgcc  240
gcgggcaacg gcgtcgtcgc ggccctggcc gcgaagaccg ccgtgccccc ccccgccgag  300
ggcgacgagg tggcggtgct ccggggcgcc gccgcggccg tggtcaagaa catgagcgcc  360
tccctcgaag tgccgaccgc caccagcgtc cgggcggtgc cggccaagct gctgatcgat  420
aatcggatcg tcatcaacaa tcagctgaaa cggacccgcg gcggcaagat cagcttcacc  480
catctgctcg gctatgcgct ggtccaggcc gtgaagaagt tccccaacat gaatcgccac  540
tataccgaag tcgacggcaa acccaccgcc gtgaccccgg cgcacacgaa cctcggcctg  600
gcgatcgacc tgcagggcaa ggacggcaag cggagcctcg tggtggccgg catcaaacgg  660
tgcgagacga tgcggttcgc gcagttcgtg acggcctatg aggatatcgt gcgccgcgcc  720
cgggacggca aactgaccac cgaagacttc gccggcgtca cgatctcgct gaccaacccg  780
ggcaccatcg gcacggtcca ttcggtcccg cgcctcatgc cgggccaggg cgccatcatc  840
ggcgtgggcg cgatggaata tcccgccgag ttccagggcg cctccgagga gcggatcgcc  900
gagctgggca tcggcaaact catcacgctg acctccacgt atgaccaccg catcatccag  960
ggcgcggaaa gcggcgactt cctccggacg atccatgagc tgctgctctc cgacggcttc  1020
tgggatgaag tgttccgcga gctgtcgatc ccctatctcc cggtgcgctg gagcaccgac  1080
aacccggact cgatcgtgga caaaaacgcc cgcgtcatga atctgatcgc cgcgtaccgc  1140
aatcggggcc acctcatggc ggacacggac cccctgcggc tcgataaggc ccggttccgc  1200
```

```
tcccaccccg acctcgaagt cctgacccac ggcctgaccc tgtgggacct ggatcgcgtc  1260
ttcaaggtcg atggcttcgc cggcgcccag tataagaagc tgcgcgatgt gctgggcctg  1320
ctccgcgatg cctattgccg gcatatcggc gtggagtacg cccacatcct ggaccccgag  1380
cagaaagaat ggctggaaca gcgcgtcgaa acgaagcacg tcaagcccac cgtcgcgcag  1440
cagaaataca tcctcagcaa actcaacgcc gccgaagcgt tcgaaacgtt cctccagacg  1500
aagtacgtgg gccagaaacg cttcagcctg gaaggcgcgg agagcgtcat ccccatgatg  1560
gacgccgcca tcgaccagtg cgccgaacac ggcctggatg aagtggtcat cggcatgccg  1620
caccgcggcc ggctcaacgt cctggccaat atcgtgggca agccctacag ccagatcttc  1680
accgagttcg aaggcaacct gaacccgtcg caggcgcacg gctcgggcga tgtcaagtac  1740
catctcggcg ccacgggcct gtatctgcag atgttcggcg acaacgacat ccaggtgtcc  1800
ctgacggcga accccagcca cctggaggcg gtcgatcccg tcctggaagg cctggtgcgg  1860
gccaagcagg atctcctcga ccacggctcg atcgactccg atggccagcg ggcgttcagc  1920
gtggtgcccc tcatgctgca tggcgacgcg gcgttcgcgg gccagggcgt ggtggcggaa  1980
accctcaacc tcgcgaacct cccgggctat cgggtgggcg gcaccatcca tatcatcgtg  2040
aacaaccaga tcggcttcac cacggcgccg gaatattccc ggagctcgga atattgcacg  2100
gacgtggcca agatgatcgg cgccccgatc ttccacgtca atggcgatga cccggaggcc  2160
tgtgtgtggg tcgcccggct ggccgtcgat ttccgccagc gcttcaaaaa agatgtggtc  2220
atcgacatgc tctgctaccg ccgccggggc cataatgagg gcgacgaccc ctccatgacg  2280
aacccgtacg tctacgacgt ggtcgacacc aagcgcggcg cccgcaagtc ctatacggag  2340
gcgctcatcg gccgcggcga catctcgatg aaggaagcgg aagacgcgct ccgcgactac  2400
cagggccagc tggagcgcgt cttcaacgaa gtgcgggaac tcgaaaagca tggcgtgcag  2460
ccctccgaat cggtggagag cgatcagatg atcccggccg gcctggccac cgccgtcgat  2520
aaaagcctgc tcgcccgcat cggcgacgcc ttcctggccc tgccgaacgg cttcacggcc  2580
catccccgcg tccagccggt gctggagaaa cgccgcgaaa tggcctacga gggcaagatc  2640
gattgggcct tcggcgagct gctggcgctc ggcagcctgg tggccgaagg caagctcgtg  2700
cggctctccg gccaggactc gcggcgcggc acgttctcgc agcgccattc cgtgctgatc  2760
gaccggcaca ccggcgaaga gttcaccccc ctccagctgc tggccaccaa ttcggacggc  2820
agcccgacgg gcggcaagtt cctggtctat gactccccgc tgagcgagta tgccgccgtc  2880
ggcttcgagt atggctacac cgtcggcaat ccggacgcgg tcgtgctgtg ggaagcgcag  2940
ttcggcgact tcgtgaacgg cgcccagtcg atcatcgatg agttcatctc gtcgggcgaa  3000
gccaagtggg gccagctcag caacgtggtg ctcctgctcc cgcacggcca cgagggccag  3060
ggcccggatc atacgagcgc ccgcatcgag cggttcctgc agctgtgggc cgagggctcc  3120
atgacgatcg cgatgccctc gacgccgtcc aactacttcc acctgctgcg ccggcacgcg  3180
ctggacggca tccagcgccc gctgatcgtc ttcaccccca agagcatgct ccggcacaaa  3240
gccgccgtgt ccgagatcaa ggacttcacg gagatcaaat tccggagcgt gctggaggag  3300
cccacgtacg aggacggcat cggcgaccgc aacaaggtgt cccgcatcct cctgacgagc  3360
ggcaagctgt actacgagct cgccgcccgc aaggccaagg ataaccggaa cgacctggcc  3420
atcgtgcgcc tcgaacagct ggccccgctg ccgcgccgcc ggctgcggga aaccctggac  3480
cgctacgaga acgtcaaaga gttcttctgg gtccaggaag aaccggccaa ccagggcgcg  3540
tggccgcgct tcggcctgga actgcccgag ctcctgccgg acaagctggc cggcatcaag  3600
cgcatctcgc ggcgggcgat gagcgccccg tcgagcggct cctccaaggt gcatgccgtg  3660
gagcagcagg aaatcctgga cgaggcgttc ggctga                            3696
```

```
SEQ ID NO: 59           moltype = DNA  length = 3738
FEATURE                 Location/Qualifiers
source                  1..3738
                        mol_type = genomic DNA
                        organism = Corynebacterium terpenotabidum
SEQUENCE: 59
atgaactcga ccaacttcgg cagcaatggc tggctggtcg accagatgca ccagcagttc  60
aaggaagatc cgcagtcggt cgacaaggaa tggcgcgact tcttcaccgc cggctcggcg  120
tccggcccgg atgccccgga aacgaccgcc ccgacgacca ccgccgccac gaccacgacc  180
gcgaccacga gcgcggcccc cgccaccgcg cagaccagcg gcgtggccgt cccgtccacc  240
gcgggcacca cccaccgggc ctcggcgcc gcgaccgtgg cctcgaacgt ggccctgagc  300
gcgaacccga tccccgaacg ggtcgccccc ccggccccga aggacgcggc cgagccgctg  360
accccgggcg aggccgccct gaaaggcgcc cagcgggcga tcgccaaaaa catggacgcc  420
agcctggata tccccaccgc gacgacggtc cgcgacatgc cggccaaact catgttcgaa  480
aaccgggcca tgatcaacaa ccatctgcgc agccagggcc ggggcaagat ctcgttcacc  540
cacatcctgg gctgggcgat ggtcaacgcc gtgaaagccc accccaccat gaataacaat  600
tacaaggtca tcgacggcaa gccgtcggtc gtgacccccg aacatatcaa tctcggcctc  660
gccatcgatc tggtcagcaa aaacggctcg cggaacctgg tcgtggccgc catccgcgcg  720
tgcgaaacct tcgacttcga gggcttcgtg gacgcctacg aggacatcgt ggtccgcgcc  780
cggaagggca aactgacgat ggacgacttc agcggcgtca ccatccagct gaccaacccg  840
ggcggcatcg gcacccgcca ctccgtcccg cgcctgacgc acggccaggg cgcgatcatc  900
ggcgtgggcg cgatggacta cccggcggag ttcgccggcg cctcggaaga ccgcctcgcg  960
gacctgggcg tgggcaaact ggtgaccatc acgagcacgt atgaccaccg gatcatccag  1020
ggcgccgagt cgggcgagtt cctgcgcgac atgagccgcc agctcatcga cgatggcttc  1080
tgggacggca tctacgccag cctgaaagtc ccgtatgcgc ccgtgcggtg gtcgcaggac  1140
gtgcccaaca ccggcgtcga caagagcacc cgcgtcatgc agctcatcga ggcgtaccgc  1200
tcccgcggcc acctgatcgc cgacatcgac ccgctgcatt ggacccagcc cggcctgccg  1260
gtgccggacc atagcgacct ggacatcgaa tcccacggcc tgaccctgtg ggacttcgac  1320
cggcgcttcc acgtcggcgg cttcgccggc cgcgaatcga tgaccctgcg ggaagtgctg  1380
gccacgctgc ggaaggcgta tacgctgaag gtcggctccg aatataccca tatcctcgac  1440
aaggacgaac gcctctggct ccaggagcac atcgaggccg gccagcagaa gctcagcaac  1500
cccgaacaga agtatctgct gcagacgctg aactccgccg aggcgttcga aaacttcctg  1560
cagaccaaat atatcggcca gaagcgcttc agcctggaag gcgccgaagc cctgatcccg  1620
ctgctcgatg ccgccgcgga tcaggccgcc gaacagggcc tcgaagaggt ggtgatcggc  1680
atgccgcatc gcggccggct gaatgtcctc gcgaacatcg tcggcaaacc gtacagcacc  1740
atcttcggcg agttcgaggg caacatcgag ccggccgccg cgggcggctc cggcgatgtc  1800
```

```
aaataccatc tgggcgccga gggcgtgtat acgcagatgt tcggcgacaa cgacatcaag  1860
gtgacgctga ccgccaaccc ctcccacctg gaagcggtca atcccgtcat ggagggcctc  1920
gcgcgggcgc atcaggatat ctcgccccgg gcggaggatc ggccgatcat gccgatcctg  1980
atgcacggcg acgccgcctt caccggcctg ggcatcgtcc cggaaacgat caacatggcc  2040
cagctgcggg gctactccgt gggcggcacg gtgcatgtgg tggtcaacaa ccagatcggc  2100
ttcaccacga cgccggatcg cggccggtcc acgcactacg cgacggacat cgcgaagggc  2160
ttcgattgcc ccgtcttcca cgtcaacggc gacgatccgg aggccgtcgt ctgggtcgcc  2220
cggctcgccg tggaataccg gcgccgcttc ggcaaagacg tgttcatcga cctggtgtgt  2280
tatcggcgcc gcggccataa tgaagccgat gaccccagca tgacccagcc cgaactgtac  2340
agcatcatcg agagccggcc gacggtccgg agcctgtatc atgacacgct ggtcggccgg  2400
ggcgacatca cggcggaaga cgcccagcgg gccgccgacg acttccacgg ccagctggaa  2460
agcgtcttca accaggtcaa ggaaggcgtg aagggcgtga ccccggcggc ccagaccggc  2520
atcgccggcg gccaggacct gtccaccggc ctcgacacca gcatcaccgc ggatgtgatc  2580
gccgagatcg gcgattccta taccgtggat gcccccgaag acttcaatgt ccaccagcgc  2640
gtgaagcccg tggtcaaacg gcggcaccag atgtcgcgcc agggcaagat cgattgggcg  2700
ttcggcgaac tcctcgcgtt cggctcgctg gcccgggaag gccggctggt ccggctcgcc  2760
ggcgaggact cgcagcgggg caccttcacc cagcggcacg ccatcctgtt cgacagcacc  2820
accaacaagc ccttcagccc cctggaaatg gtcgcgcgga actccggcaa cggcggctcg  2880
ttccgggcct tcaattcccc gctgacggaa tatgcgggca tgggcttcga gtatggctac  2940
tcggtgggca acctggatgc cgtggtggcc tgggaggcgc agttcggcga cttcgcggac  3000
ggcgcccaga cgatcatcga cgagtacatc tcctccggcg aggccaaatg gggccagctg  3060
tcgagcgtga tcctgctgct cccgcacggc tacgagggcc agggcccgga ccactcctcc  3120
gcccgcatcg aacgctacct gcagatggcc gccgaaggct cgatgaccat cgcgcagccg  3180
tcgacgcccg ccaaccactt ccacctgctc cgccgccacg ccctgggcac catgcggcgc  3240
ccgctggtcg tcttcacccc gaagtccatg ctgcgcaaca aggcggccgt ctcctcggtc  3300
gaagacttca cggaagtcac caagttccgg agcgtcctgg atgacccccg gttcgcggat  3360
ggcaccgccg accggagcgg cgtcaagacg gtgctgatgt gttccggcaa gatctactat  3420
gatctggaga agaagcgggc ggaagacggc cgcgacgata tcgccatcgt ccgcgtcgaa  3480
atgctgcatc ccatcccgca taaccgcatc cgcgaaacgg tcgtggaggg ctaccccggc  3540
gcggaggtgc gctgggtgca ggacgagccc gccaaccagg gcgcctggcc gttcctggcc  3600
ctcaacctcc ccgagcgcat ccccggcttc accatgaagc gcgtcagccg ccgggcccag  3660
agcagcaccg ccacgggcgt ggccaaggtc caccatctgg agcaggagac gctgctgacc  3720
gaagccttcg ccacctga                                                3738

SEQ ID NO: 60          moltype = DNA  length = 3777
FEATURE                Location/Qualifiers
source                 1..3777
                       mol_type = genomic DNA
                       organism = Rhodococcus jostii
SEQUENCE: 60
atgagctcgt cctcgacctc ccagttcggc cagaaccagt ggctcgtgga tgaaatgtac  60
cagcgcttcc aggatgatcc gtcgtccgtg gacgcctcct ggcatgagtt cctgacggac  120
tatagccccg acgccgccgc caaggcgggc gcggcgaacg gccacggcac caacggcacc  180
accacggcgg cgccggcggc ggcgccgtcc gccaaagccg cgaccccccc ggtccccgag  240
agcgagacgg ccccgaaacc ccagaccaag acggcgaacg gcgcggcgcc gaaagccgcg  300
cccaacggcg cggcgccgaa ggccgcggcc cccaagaccg aggcccccaa gaaggccgcc  360
cccgcgaagg aaacggccgc gacggacgcg aaagcctcgg ccccggcccc cgccgtggag  420
gaatccaagg tgctgcgggg cgccgccgcc gccgtcgcca agaatatgtc cgcgtcgctc  480
gccatcccga ccgccacctc cgtccgggcc atcccggcga agctgatgtt cgacaaccgc  540
atcgtcatca acaaccacct ggcgcggacc cggggcggca agatctcgtt cacccatctg  600
ctgggctacg cgatcgtgca ggccgtgaaa gcgttcccca acatgaaccg ccacttcgcg  660
gagatcgatg gcaagcccaa tgcggtgacc cccgcccata ccaatctggg cctcgcgatc  720
gatctgccgg gcaaagatgg cagccgctcg ctggtcgtcg cggccatcaa gaacaccgat  780
acgcacaatt tcacccagtt ctatagcgcc tacgaggata tcgtgcgccg ggcgcgggac  840
ggcaaactga ccgccgaaga cttcagcggc gtcacgatct cgctgaccaa cccgggcggc  900
atcggcaccg tccattccgt cccgcgcctg atgaacggcc agggcgccat catcggcgcg  960
ggcgcgatgg agtacccggc cgagttccag ggcgcctcgg acgagcggct ggccgaaatc  1020
ggcgtcggca agctgatgac cctcacgagc acctacgatc atcggatcat ccagggcgcc  1080
gaatccggcg acttcctccg gacgatccat aatctgctca tcagcgacga gttctacgac  1140
gaaatcttcc atgccctgca tatcccctat gaacccgtcc ggtggcgcaa agacgtgccc  1200
gaaggcgccg tggataagaa cacccgggtc ctggagctca tcgccgccta ccggaaccgc  1260
ggccacctga tggcggacac cgacccgctg cagttcgtga aggacaagtt ccggtcgcac  1320
ccggacctcg acgtgcgcac ccatgatctg acgctctggg acctggatcg ggagttcaaa  1380
gtgggcggct tccacggcca ggagaagatg aagctgcgcg atgtcctgtc ggtgctgcgc  1440
gatgcgtatt gtcgccatgt cggcgtggag tatacccaca tcctggagcc ggagcagcag  1500
cagtggctgc aggatcgcgt cgaggcccac cacgtcaaac cgacggtcgc ccagcagaag  1560
tatatcctgt ccaaactgaa cgccgccgag gccttcgaga cgttcctgca gacgaagtat  1620
gtcggccaga aacgcttctc gctggagggc gcggagagcg tgatccccat gatggacgcc  1680
gtcatcgacc aggccgccga gcatcagctg gacgaggtgg tgatcggcat gccgcatcgg  1740
ggccgcctga atgtcctggc gaacatcgtg ggcaagccgt attccaagat cttcaccgag  1800
ttcgagggca acatgaaccc ggcggcggcc cacggcagcg gcgacgtgaa gtatcacctg  1860
ggcgccgaag gcacgtatat ccagatgttc ggcgataacg acatcaccgt ctcgctcacc  1920
gcgaacccga gccatctgga agccgtggac ccggtgctgg agggcctggt ccgggccaag  1980
caggacatcc tcgacaaggg cgaagacggc ttcacggtgc tccccctcat gctccacggc  2040
gacgcggcct tcgccggcca gggcgtggtc gccgagacgc tcaacctcgc cctgctgcgc  2100
ggctaccgga ccggcggcac cgtgcacatc gtggtgaaca accaggtcgg cttcacgacc  2160
gcccccgagt atagccgctc cagcgagtac tgcacggatg tggcgaagat gatcggcgcc  2220
cccatcttcc acgtcaacgg cgatgacccc gaggcgtgcg tgtgggtggc ccagctggcg  2280
gtggacttcc gcgagaagtt ccagaaggac gtggtcatcg acatgatctg ttatcggcgg  2340
```

```
cggggccata atgagggcga cgatccgagc atgacccagc ccgcgatgta cgacgtgatc  2400
gacacgaaac gctccgtccg caaatcctat accgagtcgc tgatcggccg cggcgacatc  2460
tcgctgaagg aagcggagga cgccctgcgc gactatcagg gccagctgga acgggtcttc  2520
aatgaggtgc gcgagctgga gaagtacacg cccgaaccga gcgagagcgt cgagctggac  2580
caggtcctgc ccacgaagct gaaaacctcc gtcgatgaat cggtgctgga gcgcatcggc  2640
gatgccttcg tgaacgtccc ggagggcttc acggtccatc cgcgggtgaa gccggtgatc  2700
gaaaagcgcc gcgagatgag ccgcgaaggc aagatcgact gggccttcgc cgagctgctg  2760
gccttcggct ccctggtgga tcagggcaag atggtgcgcc tctccggcca ggacagcaag  2820
cgcggcacgt tcacccagcg ccactcggtc ctcatcgacc gcaaaaccgg cgccgaatat  2880
accccctcc agaacctggg cagcgaaaac ccgggcaagt tcctggtcta cgattccgcg  2940
ctgagcgagt tcgcggcggt cggcttcgag tacggctata gcgtcggcaa ccccgacgcg  3000
ctggtgctgt gggaagccca gttcggcgat ttcgtgaatg gcgcccagag catcatcgac  3060
gagttcatct cgtcgggcga agccaaatgg ggccagctga gcgacgtggt cctgctgctg  3120
ccccacggcc acgaaggcca gggcccggac catacgtccg gccgcatcga acggttcctc  3180
cagctgtgtg ccgaaggctc catgaccgtg gcggtcccca gcacgccggc ctcgtacttc  3240
cacctgctgc gccggcatag cctcgacggc atccgccggc cgctcgtcgt gttcaccccc  3300
aaaagcatgc tgcgcaacaa agccgccgtg agcgacgtgg aagacttcac gaccggcaag  3360
ttccggagcg tcttcgagga gcccacctac gagacgggcg atgccgagcg ggacaaggtg  3420
cgccgggtcc tcctggtgtc gggcaagctg tactgggagc tgctggccaa gaagcagaag  3480
gataaccgcg aggacatcgc catcgtgcgc atcgaacagc tgtaccccgt cccctcgcgg  3540
cggctccgcg agacgctgga ccgctacccc aacgccaccg agttccgctg ggtgcaggag  3600
gagcccgcca accagggcgc ctggcccttc ttcggcctcg cgctgcccga actgctgccc  3660
gacaaactgt cgggcatcaa gcgcatcagc cgccggtcca tgtcggcccc gtcctccggc  3720
tcgtccaagg tgcacgcggt cgaacagcag gaaatcatcg acgaggcctt cggctga     3777

SEQ ID NO: 61          moltype = DNA  length = 1116
FEATURE                Location/Qualifiers
source                 1..1116
                       mol_type = genomic DNA
                       organism = Porphyromonas gingivalis
SEQUENCE: 61
atgcagctgt tcaaactcaa aagcgtgacg caccacttcg atacgttcgc ggagttcgcc  60
aaggagttct gcctcggcga gcgggacctg gtcatcacca atgagttcat ctacgagccc  120
tatatgaagg cgtgccagct cccgtgccac ttcgtcatgc aggaaaagta cggccagggc  180
gaaccgtcgg atgagatgat gaacaacatc ctggcggata tccggaacat ccagttcgac  240
cgggtcatcg gcatcggcgg cggcaccgtc atcgacatct ccaaactgtt cgtcctgaaa  300
ggcctcaacg acgtgctgga cgccttcgac cgcaaaatcc cgctcatcaa ggagaaggag  360
ctcatcatcg tgcccacgac ctgcggcacc ggctcggaag tgaccaacat ctcgatcgcc  420
gagatcaagt cgcgccacac caagatgggc ctggcggatg acgcgatcgt ggccgaccat  480
gccatcatca tccccgagct gctgaagagc ctgccgttcc acttctatgc gtgctccgcc  540
atcgatgccc tgatccacgc catcgagagc tacgtctcgc cgaaggcctc cccgtacagc  600
cggctgttca gcgaggcggc ctgggacatc atcctggaag tcttcaagaa gatcgccgag  660
cacggccccg aatatcggtt cgaaaagctc ggcgagatga tcatggccag caattacgcc  720
ggcatcgcct tcggcaacgc cggcgtcggc gccgtccacg ccctgtcgta cccgctgggc  780
ggcaattatc atgtgccgca tggcgaagcg aattaccagt tcttcaccga ggtgttcaag  840
gtctatcaga agaaaaaccc gttcggctac atcgtcgagc tgaactggaa gctgtcgaag  900
atcctgaact gccagccgga gtatgtgtat cccaagctgg atgaactcct gggctgcctg  960
ctgaccaaaa agccgctgca tgaatatggc atgaaggacg aagaggtgcg gggcttcgcc  1020
gaatcggtgc tgaagaccca gcagcgcctg ctcgccaaca actacgtgga gctgaccgtc  1080
gacgaaatcg aaggcatcta ccgccggctg tactga                           1116

SEQ ID NO: 62          moltype = DNA  length = 1116
FEATURE                Location/Qualifiers
source                 1..1116
                       mol_type = genomic DNA
                       organism = Clostridium kluyveri
SEQUENCE: 62
atgaagctcc tgaagctggc cccggatgtg tacaaattcg ataccgccga ggagttcatg  60
aagtatttca aggtcggcaa gggcgacttc atcctgacga acgagttcct ctataaaccc  120
ttcctggaaa agttcaatga tggcgccgac gccgtgttcc aggaaaagta cggcctgggc  180
gagccgtccg acgaaatgat caacaacatc atcaaggata tcggcgacaa acagtacaat  240
cggatcatcg cggtgggcgg cggcagcgtc atcgatatcg ccaaaatcct gtcgctgaaa  300
tacacggacg attccctgga cctgttcgaa ggcaaggtcc cgctggtgaa gaataaagag  360
ctcatcatcg tcccgaccac ctgcggcacc ggctcggaag tgacgaatgt ctcggtcgcc  420
gaactgaagc ggcgccatac gaagaaaggc atcgcctccg acgaactcta tgcgacgtac  480
gcggtcctgg tgcccgagtt catcaaaggc ctgccctata agttcttcgt gacgagctcc  540
gtcgacgccc tcatccatgc gaccgaggcc tacgtgtcgc cgaacgccaa cccctacacc  600
gacatgttct cggtcaaggc gatggaactg atcctgaacg gctacatgca gatggtggag  660
aagggcaacg attatcgcgt ggaaatcatc gaggatttcg tgatcggctc caactacgcg  720
ggcatcgcgt tcggcaacgc gggcgtcggc gcggtccatg ccctcagcta ccccatcggc  780
ggcaactacc atgtcccgca tggcgaagcc aactacctct tcttcacgga gatcttcaag  840
acctactacg agaagaaccc gaatggcaag atcaaggacg tgaataagct cctggcgggc  900
atcctcaagt gcgatgagtc cgaggcgtac gattcgctct cgcagctgct ggacaaactg  960
ctctcgcgca agccgctgcg cgagtacggc atgaaggagg aagagatcga aaccttcgcc  1020
gacagcgtga tcgaaggcca gcagcggctg ctggtcaaca actacgagcc cttcagccgc  1080
gaggatatcg tcaacaccta caaaaagctc tactga                           1116

SEQ ID NO: 63          moltype = DNA  length = 1296
FEATURE                Location/Qualifiers
```

```
source                 1..1296
                       mol_type = genomic DNA
                       organism = Porphyromonas gingivalis
SEQUENCE: 63
atgaaggacg tgctggccga gtacgcctcg cgcatcgtct cggcggaaga agcggtcaag  60
cacatcaaga acggcgagcg cgtcgcgctc tcgcatgccg ccggcgtccc gcagtcctgc  120
gtcgatgccc tggtccagca ggccgatctc ttccagaatg tcgaaatcta ccatatgctc  180
tgcctgggcg agggcaagta catggccccc gagatggcgc cgcatttccg ccatatcacg  240
aatttcgtcg gcggcaactc gcggaaagcc gtggaggaga accgggccga cttcatcccc  300
gtgttcttct acgaggtccc cagcatgatc cgcaaagata tcctccacat cgacgtggcg  360
atcgtgcagc tgagcatgcc ggatgagaac ggctactgca gcttcggcgt gagctgtgac  420
tacagcaagc cggccgccga atccgcccac ctcgtcatcg gcgagatcaa ccggcagatg  480
ccgtacgtcc acggcgacaa cctgatccac atcagcaagc tggactacat cgtcatggcc  540
gactatccga tctatagcct ggcgaaaccc aagatcggcg aggtcgagga ggccatcggc  600
cggaactgcg ccgagctgat cgaagacggc gccaccctcc agctgggcat cggcgccatc  660
ccggacgccg ccctgctctt cctgaaagac aagaaagacc tgggcatcca caccgaaatg  720
ttcagcgacg gcgtcgtcga actggtccgg agcggcgtca tcaccggcaa gaaaaaaacc  780
ctgcacccgg gcaaaatggt cgcgacgttc ctgatgggct ccgaagatgt ctatcatttc  840
atcgacaaga accccgacgt ggagctctac ccggtggact atgtgaacga cccgcgcgtc  900
atcgcccaga acgacaacat ggtcagcatc aactcctgta tcgagatcga cctcatgggc  960
caggtcgtga gcgaatgtat cggctccaag cagttctcgg gcacgggcgg ccaggtggac  1020
tacgtccgcg gcgcggcgtg gtcgaagaac ggcaagtcga tcatggccat cccctccacc  1080
gccaagaacg gcaccgcctc gcgcatcgtg ccgatcatcg cggagggcgc cgcggtgacg  1140
accctgcgga acgaagtgga ttacgtggtc acggagtatg gcatcgccca gctgaagggc  1200
aagtcgctcc gccagcgggc ggaagcgctg atcgcgatcg cgcacccgga cttccgggag  1260
gagctgacca aacacctgcg gaaacggttc ggctga                            1296

SEQ ID NO: 64          moltype = DNA  length = 1296
FEATURE                Location/Qualifiers
source                 1..1296
                       mol_type = genomic DNA
                       organism = Porphyromonas gingivalis
SEQUENCE: 64
atgcagtggc aggaactcta ccggcagcgc gtgtgctccg cggatgaagc cgtcgtggat  60
agcctgaagc ccggcaccaa ggtggtcttc ggccatgccg ccgccgcgcc cgtgcggttc  120
tcgcaggcca tgtatcgcca gcgcgaaaag ctcgaaaaca tcaccgtgtt ccatatgctc  180
tatttcggcg atgcccccca cctggccccc gaaatgcgct cccatgtcca cccgacgctc  240
aacttcctgg aaggcaatag ccgcccccgcg tcgcgggatc ggcgcgtgga tttcatcccc  300
tgccacttcc acgaagtgcc cgagctgttc cgccagggct tcttcccccct cgacgtggcg  360
gtggtgcagg tgtcgacccc gaacgaggag ggctattgta gcttcggcgt ctcgtgtgac  420
tatacgaagg ccgcggccga atgtgccccg gtcgtggtgg ccgaggtgaa caagcagatg  480
ccgttcatcg gcggcgagaa cctgatccat atctccaagc tgacccatat catcgaagtg  540
gatgagccga tcgccgaggt gctgcccccc gcgatcagcg acctggagct gcgcatcggc  600
cagaactgcg cgtccctcat caaggacggc gatacgctcc agctgggcat cggcggcatc  660
ccggacgcgg tgctgcgggc cctggaaggc cataaagacc tcggcatcca cacggagatg  720
ttcaccgacg gcgtgatgcg gatgatccgg aagggcatca tcaacggcaa gaaaaagacc  780
ctgcacccgg aaaaagtggt gaccagcctg atcttcggca gcaaagaact gtacgacttc  840
gtcaacaaca acccggtgat cgagtgctat ccggtcgatt atatcaacaa tccggatgtc  900
atcggcaaga acgaccgcat ggtgagcatc aactcctgcc tggaaatgga cctgatgggc  960
caggccgcga gcgaaagcat cggctacgaa cagttctccg gctcgggcgg ccaggtggat  1020
ttcctgcggg gcgcgaagcg gtccaaaggc ggcatcagca tcatggcctt cccctccacg  1080
gccaagaagg gcacggagtc ccgcatcgtg cccatcctga aggagggcgc gtgcgtcacg  1140
accggccgca atgaggtgga ttacgtcgtc accgagtacg gcgtcgcccg cctccggggc  1200
gccaccctcc ggcagcgggc cgaggccctg acggccatcg cccatcccga cttccgcccc  1260
gccctggagg aagagatccg ccggcgcttc gagtga                            1296

SEQ ID NO: 65          moltype = DNA  length = 1317
FEATURE                Location/Qualifiers
source                 1..1317
                       mol_type = genomic DNA
                       organism = Clostridium aminobutyricum
SEQUENCE: 65
atggattgga aaaagatcta cgaagatcgc acctgcaccg ccgatgaagc cgtcaagtcc  60
atcaagtccg gcgaccgcgt cctgttcgcc cactgtgtcg ccgaaccccc ggtgctggtc  120
gaagcgatgg tggccaacgc cgcggcgtac aagaacgtca ccgtgagcca tatggtgacc  180
ctgggcaagg gcgaatatag caagcccgag tacaaggaga acttcacgtt cgagggctgg  240
ttcacctccc cgtcgacgcg gggctcgatc gcggagggcc acggccagtt cgtgcccgtg  300
ttcttccatg aggtgccgtc cctgatccgc aaggatatct tccacgtcga cgtgttcatg  360
gtcatggtgt ccccgcccga tcataacggc ttctgctgtg tcggcgtcag cagcgactac  420
acgatgcagg ccatcaagtc ggccaagatc gtgctggcgg aagtcaacga ccaggtgccc  480
gtggtgtatg gcgatacgtt cgtgcatgtc tcgaacatcg ataagttcgt ggaaacctcg  540
catccgctcc cggaaatcgg cctgccgaaa atcggcgagg tggaagcggc catcggcaaa  600
cactgtgcct ccctgatcga agacggctcg acgctgcagc tgggcatcgg cgccatcccc  660
gacgccgtgc tcagccagct gaaagacaag aagcacctgg gcatccactc ggagatgatc  720
tccgacggcg tcgtggacct gtatgaggcg ggcgtgatcg actgctccca gaagtcgatc  780
gacaagggca aaatggcgat caccttcctg atgggcacca agcgcctgta cgacttcgcg  840
gcgaacaatc cgaaggtgga gctgaaaacg gtggactaca tcaaccatcc gtcggtggtg  900
gcccagtgct ccaagatggt gtgcatcaac gcctgcctgc aggtggattt catgggccag  960
atcgtgagcg acagcatcgg caccaagcgc ttctcgggcg tgggcggcca ggtcgacttc  1020
```

```
gtgcggggcg cctccatgag catcgacggc aagggcaagg cgatcatcgc catgccgtcg  1080
gtcgccaaga agaaggacgg cagcatgatc tcgaaaatcg tccccttcat cgatcacggc  1140
gccgccgtga ccacctcgcg gaacgacgcc gattatgtgg tcacggagta cggcatcgcc  1200
gagatgaaag gcaagtccct ccaggaccgg gcccgggcgc tcatcaacat cgcgcacccg  1260
gatttcaagg atgagctgaa ggcggagttc gagaagcggt tcaacgcggc gttctga     1317

SEQ ID NO: 66          moltype = DNA  length = 2577
FEATURE                Location/Qualifiers
source                 1..2577
                       mol_type = genomic DNA
                       organism = Clostridium aminobutyricum
SEQUENCE: 66
atgaaggtga ccaaccagaa agaactgaag cagaaactga acgaactgcg ggaggcgcag  60
aaaaagttcg ccacctatac ccaggagcag gtggacaaaa tcttcaagca gtgtgcgatc  120
gccgccgcca aagaacggat caacctggcg aaactcgccg tcgaagaaac cggcatcggc  180
ctcgtggagg acaagatcat caaaaatcac ttcgccgccg aatatatcta taacaaatac  240
aagaacgaga agacctgcgg catcatcgac catgacgact cgctgggcat caccaaagtc  300
gccgagccca tcggcatcgt ggccgcgatc gtgcccacca ccaacccgac gagcaccgcc  360
atcttcaagt cgctgatctc cctgaagacg cgcaatgcga tcttcttcag cccccatccg  420
cgggccaaaa agtcgacgat cgcggcggcc aaactgatcc tggacgccgc ggtcaaggcc  480
ggcgccccga aaaatatcat cggctggatc gacgaaccgt ccatcgagct gtcccaggac  540
ctcatgtccg aagccgacat catcctggcg accggcggcc cgagcatggt gaaggccgcc  600
tattccagcg gcaaaccggc catcggcgtc ggcgccggca acacccccgc gatcatcgac  660
gagtccgccg acatcgacat ggccgtctcc tcgatcatcc tgagcaagac ctacgataac  720
ggcgtcatct gcgcgtcgga acagagcatc ctggtcatga actccatcta tgaaaaggtc  780
aaggaagagt tcgtgaagcg cggctcgtat atcctgaacc agaatgaaat cgcgaagatc  840
aaggagacga tgttcaagaa cggcgccatc aacgccgaca tcgtcggcaa gagcgcctat  900
atcatcgcga agatggccgg catcgaagtg ccgcagacca ccaagatcct gatcggcgaa  960
gtccagtccg tcgaaaagtc cgaactgttc tcccacgaaa agctgagccc ggtgctcgcc  1020
atgtacaaag tcaaagactt cgacgaggcc ctcaaaaagg cgcagcggct catcgaactg  1080
ggcggcagcg gccatacctc gtcgctgtac atcgatagcc agaacaacaa ggacaaagtc  1140
aaagagttcg gcctggcgat gaagacgagc cgcaccttca tcaacatgcc gagcagccag  1200
ggcgcgtccg gcgacctgta caacttcgcc atcgcccccga gcttcacgct cggctgcggc  1260
acctggggcg gcaattcggt gtcgcagaac gtggaaccga aacatctgct gaacatcaaa  1320
tccgtcgcgg agcgccgcga aaatatgctc tggttcaagg tcccgcagaa gatctatttc  1380
aaatatggct gcctgcgctt cgccctcaaa gaactgaaag acatgaataa gaaacgcgcc  1440
ttcatcgtca ccgataaaga tctgttcaag ctgggctacg tgaacaaaat cacgaaggtc  1500
ctggatgaga tcgatatcaa gtacagcatc ttcaccgaca tcaagtccga tcccaccatc  1560
gactccgtca agaagggcgc caaagagatg ctcaacttcg aaccggacac catcatcagc  1620
atcggcggcg gctcgccgat ggacgcggcc aaggtcatgc atctgctcta tgaatatccg  1680
gaggccgaga tcgaaaacct ggccatcaac ttcatggaca tccggaaacg catctgcaac  1740
ttcccgaagc tcggcacgaa agccatcagc gtggccatcc ccacgaccgc gggcaccggc  1800
tcggaagcca cgccgttcgc ggtcatcacg aatgacgaaa ccggcatgaa ataccccctg  1860
acctcctacg agctcacccc caatatggcc atcatcgaca cggagctcat gctcaacatg  1920
ccgcggaagc tcaccgccgc caccggcatc gatgccctgg tgcacgccat cgaagcctac  1980
gtgagcgtga tggcgaccga ctataccgat gagctggccc tccgggccat caagatgatc  2040
ttcaagtatc tgccgcgggc ctacaaaaac ggcacgaatg acatcgaggc ccgcgaaaag  2100
atggcgcatg cgagcaacat cgcgggcatg gccttcgcga acgccttcct gggcgtgtgc  2160
catagcatgg cgcacaaact gggcgcgatg catcacgtcc cgcatggcat cgcctgtgcc  2220
gtcctgatcg aggaggtcat caagtacaac gccacggatt gtccgaccaa acagaccgcc  2280
ttcccgcagt acaagtcccc gaacgcgaag cggaaatacg cggagatcgc ggagtacctg  2340
aatctgaaag gcaccagcga caccgaaaaa gtcacggccc tcatcgaagc catctcgaaa  2400
ctgaaaatcg atctgagcat cccccagaac atctccgcgg ccggcatcaa taagaaggat  2460
ttctataaca cgctggacaa gatgagcgag ctggcgttcg atgaccagtg cacgaccgcc  2520
aacccccggt atccgctgat ctccgaactc aaggacatct acatcaagtc cttctga     2577

SEQ ID NO: 67          moltype = DNA  length = 2676
FEATURE                Location/Qualifiers
source                 1..2676
                       mol_type = genomic DNA
                       organism = Escherichia coli
SEQUENCE: 67
atggcggtga cgaacgtcgc cgaactgaac gccctcgtcg aacgggtgaa aaaggcgcag  60
cgggagtacg cctcgttcac gcaggagcag gtggataaaa tcttccgcgc cgccgccctg  120
gccgcggccg acgcccgcat cccgctcgcc aaaatggcgg tggccgagtc cggcatgggc  180
atcgtggagg acaaggtcat caagaaccat ttcgcctccg agtacatcta caacgcctac  240
aaggacgaga agacctgcgg cgtcctgtcg gaggacgata ccttcggcac catcacgatc  300
gccgagccca tcggcatcat ctgcggcatc gtcccgacca ccaatcccac ctccaccgcc  360
atcttcaaaa gcctcatctc cctgaaaacc cgcaatgcga tcatcttcag cccccatccc  420
cgcgccaaag acgccacgaa caaggcggcc gacatcgtcc tccaggccgc catcgcggcc  480
ggcgccccca aagacctgat cggctggatc gaccagccgt cggtggagct gtccaacgcc  540
ctcatgcatc acccggacat caatctcatc ctggccacgg gcggcccggg catggtgaag  600
gccgcctact ccagcggcaa gccggcgatc ggcgtgggcg cgggcaacac gcccgtggtc  660
atcgacgaaa cggccgatat caaacgcgcc gtcgcctccg tgctcatgag caagaccttc  720
gacaacggcg tgatctgcgc gtcggaacag tcggtcgtgg tcgtcgactc cgtgtacgac  780
gcggtgcgcg agcgcttcgc cacgcatggc ggctacctgc tgcagggcaa ggagctgaaa  840
gccgtgcagg acgtgatcct caaaaacggc gccctgaacg ccgccatcgt cggccagccc  900
gcgtataaga tcgcggagct ggccggcttc tcggtcccgg agaacacgaa gatcctgatc  960
ggcgaggtca cggtcgtcga cgagagcgaa cccttcgccc acgagaagct gtccccgacc  1020
```

```
ctggcgatgt accgggcgaa agacttcgaa gacgcggtcg agaaggccga gaaactggtg  1080
gcgatgggcg gcatcggcca tacgagctgt ctgtacaccg accaggacaa tcagcccgcc  1140
cgcgtgtcct acttcggcca gaaaatgaag accgcccgca tcctcatcaa tacgcccgcg  1200
agccagggcg gcatcggcga tctctacaat ttcaagctcg cgccgtcgct gaccctcggc  1260
tgcggctcct ggggcggcaa ctccatctcc gagaacgtgg gcccgaaaca cctcatcaac  1320
aagaagaccg tggccaagcg ggcggagaac atgctgtggc ataagctgcc caagtcgatc  1380
tacttccgcc ggggctcgct gcccatcgcg ctggacgaag tcatcacgga cggccacaag  1440
cgggcgctga tcgtgacgga ccgcttcctg ttcaataacg gctacgccga ccagatcacc  1500
tccgtcctga aggccgcggg cgtcgaaacg gaagtcttct tcgaagtcga agccgacccg  1560
accctctcca tcgtccggaa gggcgccgag ctggccaatt ccttcaagcc ggatgtcatc  1620
atcgcgctgg gcggcggctc gccgatggac gccgccaaaa tcatgtgggt gatgtacgag  1680
caccccgaaa cgcacttcga agaactggcg ctgcgcttca tggatatccg caagcggatc  1740
tacaaattcc cgaaaatggg cgtgaaagcg aagatgatcg cggtgacgac caccagcggc  1800
acgggctccg aggtgacgcc gttcgcggtc gtcaccgatg atgccaccgg ccagaaatac  1860
cccctggccg actacgccct gacccccgac atggccatcg tggacgccaa tctcgtgatg  1920
gacatgccga agagcctctg cgccttcggc ggcctggatg ccgtgacgca tgcgatggag  1980
gcgtatgtca gcgtgctggc gtccgagttc tcggacggcc aggcgctgca ggccctgaag  2040
ctgctgaagg agtacctgcc ggcctcctac cacgagggct ccaaaaaccc ggtggcccgg  2100
gagcgggtcc actcggcggc caccatcgcg ggcatcgcct tcgcgaacgc cttcctcggc  2160
gtgtgccatt cgatggccca caagctgggc tcccagttcc atatccccca cggcctggcg  2220
aacgcgctgc tgatctgtaa cgtcatccgg tacaacgcga acgataaccc gaccaaacag  2280
accgccttct cccagtatga ccgcccccag gcccggcgcc gctatgcgga aatcgccgac  2340
catctcggcc tgtcggcccc gggcgaccgc accgccgcca agatcgagaa gctgctggcc  2400
tggctcgaaa cgctgaaggc cgaactgggc atcccgaagt cgatccgcga agccggcgtc  2460
caggaagcgg acttcctggc gaatgtggat aaactgagcg aggacgcctt cgatgaccag  2520
tgcacgggcg ccaacccgcg ctacccgctc atcagcgagc tgaaacagat cctgctcgac  2580
acctattatg gccgcgatta cgtcgagggc gaaaccgccg cgaagaagga ggccgccccg  2640
gccaaagccg aaaagaaggc caagaaaagc gcctga                            2676
```

```
SEQ ID NO: 68          moltype = DNA  length = 1164
FEATURE                Location/Qualifiers
source                 1..1164
                       mol_type = genomic DNA
                       organism = Escherichia coli
SEQUENCE: 68
atgaacaact ttaatctgca caccccaacc cgcattctgt ttggtaaagg cgcaatcgct  60
ggtttacgcg aacaaattcc tcacgatgct cgcgtattga ttacctacgg cggcggcagc  120
gtgaaaaaaa ccggcgttct cgatcaagtt ctggatgccc tgaaaggcat ggacgtgctg  180
gaatttggcg gtattgagcc aaacccggct tatgaaacgc tgatgaacgc cgtgaaactg  240
gttcgcgaac agaaagtgac tttcctgctg gcggttggcg gcggttctgt actggacggc  300
accaaattta tcgccgcagc ggctaactat ccggaaaata tcgatccgtg gcacattctg  360
caaacgggcg gtaaagagat taaaagcgcc atcccgatgg gctgtgtgct gacgctgcca  420
gcaaccggtt cagaatccaa cgcaggcgcg gtgatctccc gtaaaaccac aggcgacaag  480
caggcgttcc attctgccca tgttcagccg gtatttgccg tgctcgatcc ggtttatacc  540
tacaccctgc cgccgcgtca ggtggctaac ggcgtagtgg acgcctttgt acacaccgtg  600
gaacagtatg ttaccaaacc ggttgatgcc aaaattcagg accgtttcgc agaaggcatt  660
ttgctgacgc taatcgaaga tggtccgaaa gccctgaaag agccagaaaa ctacgatgtg  720
cgcgccaacg tcatgtgggc ggcgactcag gcgctgaacg gtttgattgg cgctggcgta  780
ccgcaggact gggcaacgca tatgctgggc cacgaactga ctgcgatgca cggtctggat  840
cacgcgcaaa cactggctat cgtcctgcct gcactgtgga atgaaaaacg cgataccaag  900
cgcgctaagc tgctgcaata tgctgaacgc gtctggaaca tcactgaagg ttccgatgat  960
gagcgtattg acgccgcgat tgccgcaacc cgcaatttct ttgagcaatt aggcgtgccg  1020
acccacctct ccgactacgg tctggacggc agctccatcc cggctttgct gaaaaaactg  1080
gaagagcacg gcatgaccca actgggcgaa aatcatgaca ttacgttgga tgtcagccgc  1140
cgtatatacg aagccgcccg ctaa                                        1164
```

```
SEQ ID NO: 69          moltype = DNA  length = 1149
FEATURE                Location/Qualifiers
source                 1..1149
                       mol_type = genomic DNA
                       organism = Escherichia coli
SEQUENCE: 69
atggcgaatc ggatgatcct caatgaaacg gcctggttcg gccgcggcgc ggtcggcgcc  60
ctcaccgatg aggtcaagcg gcggggctac cagaaggccc tgatcgtcac ggataaaacc  120
ctggtgcagt gcggcgtcgt cgccaaggtg accgacaaga tggatgcggc cggcctggcc  180
tgggcgatct acgacggcgt ggtgcccaac cccaccatca ccgtggtgaa ggaaggcctg  240
ggcgtgttcc agaactcggg cgcggattat ctcatcgcga tcggcggcgg cagcccccag  300
gacacctgca aggccatcgg catcatctcg aacaaccccg agttcgcgga cgtgcgctcc  360
ctggagggcc tgtcgccgac gaacaagccc tccgtcccga tcctcgccat cccgacgacg  420
gccggcaccg cggccgaggt gaccatcaat tacgtcatca ccgacgagga aaagcggcgc  480
aagttcgtgt gtgtggaccc ccatgacatc ccccaggtcg ccttcatcga cgccgacatg  540
atggatggca tgcccccgc cctcaaggcc gcgacgggcg tggacgcgct gacgcatgcc  600
atcgaaggct acatcacccg gggcgcctgg gccctgacgg atgccctgca tatcaaggcc  660
atcgaaatca tcgccggcgc cctgcgcggc tccgtggccg gcgacaagga tgcgggcgag  720
gagatggcgc tgggccagta cgtggccggc atgggcttct ccaatgtggg cctgggcctg  780
gtgcatggca tggcccatcc gctcggcgcc ttctacaaca cgccgcatgg cgtcgcgaac  840
gcgatcctcc tgccgcatgt catgcgctac aatgcggact tcacgggcga gaaataccgc  900
gatatcgccc gggtcatggg cgtgaaggtc gagggcatgt cgctggaaga ggcgcggaac  960
gccgcggtcg aagccgtctt cgccctgaac cgggatgtgg gcatcccgcc gcacctgcgc  1020
```

```
gatgtcggcg tccgcaagga agacatcccc gcgctggcgc aggccgccct ggacgatgtg  1080
tgcaccggcg gcaacccccg cgaggcgacg ctggaagaca tcgtcgaact ctaccatacc  1140
gcgtggtga                                                          1149

SEQ ID NO: 70          moltype = DNA  length = 1407
FEATURE                Location/Qualifiers
source                 1..1407
                       mol_type = genomic DNA
                       organism = Clostridium beijerinckii
SEQUENCE: 70
atgaacaagg acacgctgat ccccaccacg aaagacctca aggtgaagac caacggcgag  60
aacatcaacc tgaaaaacta caaggacaac agcagctgct tcggcgtgtt cgaaaacgtc  120
gaaaacgcca tcagctcggc ggtgcatgcc cagaaaatcc tcagcctgca ctatacgaag  180
gaacagcgcg aaaagatcat caccgaaatc cgcaaggccg cgctccagaa caaagaggtg  240
ctggccacga tgatcctgga ggaaacccat atgggccgct acgaagataa aatcctgaag  300
cacgagctgg tggcgaaata cacgcccggc accgaagacc tgacgaccac cgcctggagc  360
ggcgataacg gcctgacggt ggtggagatg tcgccgtatg gcgtgatcgg cgcgatcacc  420
ccgtccacca acccgaccga aacggtcatc tgtaactcga tcggcatgat cgcggccggc  480
aacgcggtcg tgttcaatgg ccacccgtgc gccaagaagt gcgtcgcctt cgccgtcgag  540
atgatcaaca aggccatcat ctcctgcggc ggcccggaga acctcgtgac gacgatcaaa  600
aacccgacga tggagtccct ggatgccatc atcaagcacc cgtccatcaa gctgctctgc  660
ggcaccggcg gcccgggcat ggtcaaaacg ctgctgaact ccggcaaaaa agccatcggc  720
gcgggcgcgg gcaacccccc cgtcatcgtg gatgacaccg ccgacatcga gaaagccggc  780
cggtcgatca tcgaaggctg ctccttcgac aataacctcc cgtgcatcgc cgagaaagag  840
gtcttcgtct tcgagaacgt cgcggacgat ctgatctcca acatgctgaa gaacaacgcc  900
gtcatcatca acgaagacca ggtgtccaag ctgatcgacc tcgtgctgca gaagaacaat  960
gaaacccagg agtacttcat caacaagaag tgggtcggca aggacgcgaa gctgttcctg  1020
gacgaaatcg atgtggagtc cccgagcaat gtgaagtgca tcatctgcga ggtcaacgcg  1080
aaccacccct tcgtcatgac cgagctcatg atgccgatcc tgccgatcgt gcgggtgaag  1140
gatatcgacg aagccatcaa gtacgcgaaa atcgcggaac agaatcggaa gcattcggcc  1200
tatatctaca gcaagaacat cgataacctc aaccgcttcg aacgggagat cgacaccacc  1260
atcttcgtca agaacgccaa atccttcgcc ggcgtgggct atgaggcgga aggcttcacc  1320
accttcacga tcgccggctc caccggcgag ggcatcacct ccgcccggaa cttcacccgc  1380
cagcgccgct gcgtgctggc gggctga                                      1407

SEQ ID NO: 71          moltype = DNA  length = 1083
FEATURE                Location/Qualifiers
source                 1..1083
                       mol_type = genomic DNA
                       organism = Saccharomyces cerevisiae
SEQUENCE: 71
atgagctatc ccgagaagtt cgaggggatc gccatccaga gccacgagga ctggaagaac  60
ccgaaaaaga ccaagtatga tccgaagccc ttctacgatc acgacatcga catcaagatc  120
gaggcctgcg gcgtctgcgg cagcgatatc cattgtgcgg ctggccactg ggcaacatg   180
aagatgccgt tggtcgtcgg ccacgagatc gtgggcaagg tcgtgaagtt aggcccgaaa  240
agcaacagcg gcttgaaggt gggccagcgc gtgggtgtgg gtgcgcaggt cttcagctgt  300
ctggagtgcg accgttgcaa gaacgacaac gaaccgtact gcaccaagtt cgtcaccacc  360
tactcgcagc cctacgagga cggctacgtc tcgcagggcg gttacgccaa ctatgtccga  420
gtccacgaac acttcgtggt gcccatcccg gaaaatatcc ccagccatct ggcggctccc  480
ctgctgtgcg gtggcttgac cgtctacagc cccctcgtcc gcaatggctg cggtcccggc  540
aagaaggtgg gtatcgtggg cctcggcggt ataggctcta tgggcacgct gatctcgaaa  600
gcgatgggcg cagaaacgta cgtgatctcg cgttcctcgc gcaagcgcga ggatgcgatg  660
aagatgggtg cggaccacta catcgccacg ctggaggagg gtgactgggg tgagaagtac  720
ttcgacacgt tcgacctcat cgtggtgtgc gcgagttccc tgacggacat cgacttcaat  780
atcatgccca aggcgatgaa ggtcggaggg cgcatcgtct ccatctcgat cccggagcag  840
cacgaaatgc tgtcgctgaa gccctacggc ctgaaagccg tctccattag ctactcggcg  900
ctcggtagta tcaaggagct caaccagctg ttgaagttgg tttccgaaaa ggacatcaag  960
atctgggtgg aaacgctccc ggtgggcgaa gccggtgtgc acgaggcctt tgagcggatg  1020
gagaaggggg atgtccgtta tcggtttaca ctcgtcggct acgataaaga gttctcggat  1080
taa                                                                1083

SEQ ID NO: 72          moltype = DNA  length = 1023
FEATURE                Location/Qualifiers
source                 1..1023
                       mol_type = genomic DNA
                       organism = Acinetobacter baylyi
SEQUENCE: 72
atgacgacca acgtcatcca tgcctatgcg gccatgcagg ccggcgaggc gctggtgccg  60
tatagcttcg acgcgggcga gctccagccg catcaggtcg aggtgaaggt ggaatactgc  120
ggcctgtgtc attccgatgt gtcggtcctg aataacgaat ggcactcctc cgtctatccg  180
gtggtcgccg gccacgaggt catcggcacg atcacccagc tgggcagcga agccaagggc  240
ctgaagatcg gccagcgcgt cggcatcggc tggacggccg agagctgcca ggcctgcgat  300
cagtgcatct ccggccagca ggtgctgtgc accggcgaga acaccgccac catcatcggc  360
catgccggcg gcttcgcgga taaagtgcgg gccggctggc agtgggtgat cccgctcccg  420
gatgagctcg atcccacgag cgccggcccg ctgctgtgtg gcggcatcac cgtgttcgac  480
ccgatcctga agcaccagat ccaggccatc caccatgtcg ccgtgatcgg catcggcggc  540
ctgggccaca tggcgatcaa gctgctcaag gcctggggct gtgaaatcac cgccttcagc  600
agcaatccca acaagaccga cgaactgaag gcgatgggcg ccgaccatgt ggtcaactcc  660
cgcgatgacg cggaaatcaa gagccagcag ggcaagttcg acctgctgct gtcgacggtg  720
```

```
aatgtccccc tcaactggaa cgcctacctg aataccctgg ccccgaacgg cacgttccac  780
ttcctgggcg tcgtcatgga gccgatcccg gtgccggtgg gcgccctcct gggcggcgcg  840
aaaagcctga ccgcctcgcc cacgggcagc cccgccgccc tccgcaagct gctggagttc  900
gccgcccgca agaacatcgc gccccagatc gaaatgtatc ccatgagcga gctgaacgaa  960
gccatcgagc gcctgcatag cggccaggcc cgctatcgga tcgtgctcaa agcggacttc  1020
tga                                                               1023

SEQ ID NO: 73           moltype = DNA  length = 1020
FEATURE                 Location/Qualifiers
source                  1..1020
                        mol_type = genomic DNA
                        organism = Escherichia coli
SEQUENCE: 73
atgtccatga tcaaaagcta cgccgcgaaa gaggcgggcg gcgagctgga ggtgtatgag  60
tatgacccgg gcgagctgcg gccccaggac gtggaagtgc aggtcgacta ctgcggcatc  120
tgccattcgg acctctcgat gatcgataac gagtggggct tcagccagta ccccctggtg  180
gccggccacg aggtgatcgg ccgcgtggtc gccctgggct cggccgcgca ggataaaggc  240
ctgcaggtcg gccagcgcgt cggcatcggc tggacggccc gcagctgcgg ccattgcgat  300
gcctgcatca gcggcaatca gatcaattgc gaacagggcg cggtcccgac catcatgaac  360
cggggcggct tcgccgaaaa gctgcgggcc gattggcagt gggtgatccc gctgccggag  420
aacatcgata tcgagtcggc cggccccctg ctgtgcggcg gcatcaccgt cttcaagccg  480
ctcctgatgc atcatatcac ggcgaccagc cgggtcggcg tgatcggcat cggcggcctc  540
ggccacatcg cgatcaaact gctgcacgcg atgggctgcg aggtcaccgc gttctcctcg  600
aaccccgcca aggagcagga agtgctggcg atgggcgccg ataaagtcgt gaactcgcgc  660
gacccccagg ccctcaaagc cctggccggc cagttcgatc tcatcatcaa cacggtgaac  720
gtgtcgctgg actggcagcc ctacttcgaa gccctgacct atggcggcaa cttccatacc  780
gtcggcgccg tgctgacccc gctgtccgtc ccggccttca ccctgatcgc cggcgaccgc  840
agcgtgtccg gcagcgccac cggcacgccg tatgagctgc gcaagctgat gcgcttcgcc  900
gcccgcagca aggtcgcccc gaccaccgag ctgttcccca tgtccaagat caatgacgcg  960
atccagcatg tccgggacgg caaggcccgc tatcgcgtcg tcctcaaggc ggacttctga  1020

SEQ ID NO: 74           moltype = DNA  length = 1167
FEATURE                 Location/Qualifiers
source                  1..1167
                        mol_type = genomic DNA
                        organism = Escherichia coli
SEQUENCE: 74
atgaacctgc atgaatatca ggccaagcag ctgttcgcgc ggtatggcct cccggcgccg  60
gtcggctacg cctgtacgac cccgcgggaa gcggaggagg ccgcctccaa gatcggcgcc  120
ggcccgtggg tggtcaaatg ccaggtgcat gcgggcggcc ggggcaaggc gggcggcgtg  180
aaggtcgtca actccaagga ggacatccgc gccttcgccg agaactggct gggcaagcgg  240
ctggtgacct atcagacgga cgccaatggc cagcccgtca atcagatcct ggtcgaggcg  300
gccacggaca tcgcgaaaga actgtacctc ggcgccgtcg tggaccggag cagccggcgg  360
gtggtgttca tggcgtccac cgagggcggc gtggaaatcg aaaaagtggc cgaggaaacc  420
ccgcacctga tccataaagt cgcgctggac ccgctgaccg gccccatgcc gtatcagggc  480
cgggaactcg cgttcaagct cggcctggag ggcaagctgg tgcagcagtt cacgaaaatc  540
ttcatgggcc tggcgaccat cttcctggag cgcgacctgg ccctgatcga aatcaacccg  600
ctggtcatca cgaagcaggg cgacctgatc tgcctggacg gcaagctcgg cgccgacggc  660
aacgccctgt tccgccagcc ggacctgcgg gaaatgcgcg atcagtcgca ggaggacccc  720
cgggaggccc aggcggccca gtgggagctg aattatgtgg cgctcgatgg caatatcggc  780
tgcatggtca atggcgcggg cctggcgatg ggcacgatgg acatcgtgaa gctgcatggc  840
ggcgagcccg ccaacttcct ggacgtgggc ggcggcgcga ccaaagagcg ggtgacggaa  900
gcgttcaaga tcatcctgag cgacgataaa gtcaaggccg tgctggtcaa catcttcggc  960
ggcatcgtcc gctgcgacct gatcgccgac ggcatcatcg gcgcggtggc ggaggtcggc  1020
gtcaatgtgc cggtcgtggt ccgcctggag ggcaacaacg ccgaactggg cgccaagaag  1080
ctggccgatt ccggcctgaa catcatcgcg gcgaagggcc tgaccgatgc cgcgcagcag  1140
gtcgtggccg ccgtcgaggg caagtga                                     1167

SEQ ID NO: 75           moltype = DNA  length = 870
FEATURE                 Location/Qualifiers
source                  1..870
                        mol_type = genomic DNA
                        organism = Escherichia coli
SEQUENCE: 75
atgtccatcc tcatcgacaa gaacaccaag gtgatctgcc agggcttcac cggctcccag  60
ggcaccttcc acagcgagca ggcgatcgcc tacggcacca agatggtggg cggcgtcacc  120
cccggcaagg gcggcaccac ccatctcggc ctcccggtgt tcaatacggt gcgggaagcc  180
gtggcggcca ccggcgcgac cgccagcgtc atctatgtgc ccgcgccgtt ctgcaaggac  240
tccatcctgg aagccatcga cgccggcatc aagctcatca tcaccatcac cgagggcatc  300
cccaccctcg acatgctgac ggtgaaagtc aagctggacg aggcgggcgt ccggatgatc  360
ggccccaact gcccgggcgt catcaccccc ggcgagtgca aatcggcat ccagccgggc  420
cacatccaca aaccgggcaa ggtgggcatc gtctcgcgct ccggcaccct cacctatgaa  480
gccgtcaagc agaccaccga ctatggcttc ggccagtcga cctgcgtcgg catcggcggc  540
gaccccatcc cgggctcgaa cttcatcgac atcctggaga tgttcgagaa agacccccag  600
accgaggcca tcgtgatgat cggcgagatc ggcggctcgg cggaggagga ggcggcggcg  660
tacatcaaag agcatgtgac caagccggtc gtgggctata tcgcgggcgt gacggcgccc  720
aagggcaagc gcatgggcca tgcgggcgcc atcatcgcgg gcggcaaagg caccgcggat  780
gagaagttcg ccgccctgga ggccgccggc gtcaagaccg tccgcagcct cgccgatatc  840
ggcgaagccc tgaagaccgt gctcaagtga                                  870
```

```
SEQ ID NO: 76          moltype = DNA  length = 1362
FEATURE                Location/Qualifiers
source                 1..1362
                       mol_type = genomic DNA
                       organism = Clostridium kluyveri
SEQUENCE: 76
atgtcgaatg aagtctcgat caaggaactg atcgaaaagg cgaaggtggc ccagaagaaa  60
ctggaagcct actcgcagga gcaggtggat gtcctggtca aggccctggg caaggtcgtg  120
tatgataacg cggagatgtt cgccaaagaa gcggtggaag aaacggaaat gggcgtgtac  180
gaggacaagg tggcgaagtg ccacctgaaa tccggcgcca tctggaacca tatcaaggac  240
aagaaaaccg tgggcatcat caaggaagag ccggagcggg ccctggtcta cgtcgccaag  300
cccaagggcg tggtggccgc caccacgccc atcaccaacc ccgtcgtcac gccgatgtgt  360
aatgcgatgg ccgcgatcaa gggccgcaat acgatcatcg tggcccccgca ccccaaagcg  420
aaaaaggtgt ccgcccacac cgtcgagctg atgaacgccg agctgaagaa gctgggcgcc  480
ccggagaaca tcatccagat cgtggaagcg ccctcgcggg aggcggcgaa ggaactcatg  540
gagagcgccg acgtggtcat cgccaccggc ggcgcgggcc gggtgaaggc cgcctactcg  600
tccggccgcc ccgcgtacgg cgtcggcccg ggcaactcgc aggtcatcgt cgacaagggc  660
tatgactaca acaaggccgc gcaggacatc atcaccggcc gcaagtatga caacggcatc  720
atctgctcct ccgagcagag cgtgatcgcg cccgccgaag actatgacaa ggtgatcgcc  780
gccttcgtcg agaatggcgc gttctacgtg gaggatgaag aaaccgtgga aaagttccgc  840
tccaccctgt tcaaagacgg caagatcaat tccaagatca tcggcaagag cgtccagatc  900
atcgccgacc tggcgggcgt caaggtcccc gagggcacga aggtcatcgt gctgaagggc  960
aagggcgcgg gcgagaagga tgtcctgtgc aaggaaaaga tgtgcccggt gctggtggcc  1020
ctgaagtacg acaccttcga agaggccgtc gaaatcgcga tggccaacta tatgtatgaa  1080
ggcgccggcc acaccgccgg catccattcg gacaacgacg agaacatccg ctacgcgggc  1140
accgtgctcc ccatcagccg cctcgtggtg aaccagccgg ccaccaccgc cggcggcagc  1200
ttcaataacg gcttcaaccc caccaccacc ctgggctgcg gcagctgggg ccgcaacagc  1260
atctcggaaa acctcacgta cgaacatctc atcaacgtct cccgcatcgg ctatttcaac  1320
aaggaagcga aggtgccctc ctatgaagag atctggggct ga                     1362

SEQ ID NO: 77          moltype = DNA  length = 1356
FEATURE                Location/Qualifiers
source                 1..1356
                       mol_type = genomic DNA
                       organism = Porphyromonas gingivalis
SEQUENCE: 77
atggagatca aggaaatggt gtccctggcc cgcaaggccc agaaggagta ccaggccacc  60
cataatcagg aagccgtgga caacatctgc cgcgccgcgg cgaaagtcat ctacgaaaat  120
gccgccatcc tcgcccgcga ggcggtcgat gaaaccggca tgggcgtgta cgaacacaag  180
gtggccaaga atcagggcaa aagcaagggc gtgtggtaca acctgcataa caagaaaagc  240
atcggcatcc tgaacatcga cgagcgcacc ggcatgatcg agatcgccaa gcccatcggc  300
gtcgtcggcg cggtcacgcc gaccaccaat cccatcgtca ccccgatgtc caacatcatc  360
ttcgcgctga aaacctgcaa cgcgatcatc atcgcccccc acccgcgcag caaaaaatgc  420
tcggcccacg ccgtgcggct catcaaggaa gccatcgcgc cgttcaacgt gccggagggc  480
atggtgcaga tcatcgaaga gccgtcgatc gagaagaccc aggaactgat gggcgccgtc  540
gacgtggtgg tggccaccgg cggcatgggc atggtgaagt cggcgtatag ctcgggcaag  600
ccgagcttcg gcgtgggcgc cggcaacgtg caggtcatcg tcgattcgaa catcgatttc  660
gaagccgccg cggaaaagat catcacgggc cgcgcgttcg ataacggcat catctgctcc  720
ggcgaacaga gcatcatcta caacgaggcg gataaggagg ccgtcttcac ggccttccgg  780
aaccacggcg cgtacttctg cgatgaagcc gaaggcgatc gcgcccgggc ggcgatcttc  840
gaaaacggcg ccatcgccaa agacgtggtg ggccagagcg tggcgttcat cgccaagaaa  900
gcgaacatca atatccccga aggcacgcgc atcctggtgg tggaagcccg cggcgtcggc  960
gcggaagatg tgatctgcaa ggaaaagatg tgccccgtga tgtgcgccct gtcctacaaa  1020
cacttcgaag agggcgtcga gatcgcccgc accaacctcg cgaacgaggg caacggccac  1080
acctgcgcca tccattcgaa taatcaggcc cacatcatcc tggccggcag cgagctcacc  1140
gtcagccgca tcgtggtcaa cgcgccctcc gccaccaccg ccggcggcca tatccagaac  1200
ggcctggccg tgacgaacac cctgggctgc ggctcgtggg gcaacaacag catctcggaa  1260
aacttcacct ataagcatct gctcaatatc agccgcatcg ccccgctgaa cagcagcatc  1320
catatcccgg acgacaaaga gatctgggaa ctctga                           1356

SEQ ID NO: 78          moltype = DNA  length = 287
FEATURE                Location/Qualifiers
misc_feature           1..287
                       note = Variant of mxaF promoter
source                 1..287
                       mol_type = other DNA
                       organism = synthetic construct
SEQUENCE: 78
gaggttcagg cgaaaccgca gactcaaggg cgcttgctcc cgggaaagat cgtattagtt  60
tgcctcgatc ggcggtcctt gtgacaggga gatattcccg acggatccgg ggcattcgag  120
cggaaccgcc cgccgtggga gtttttccag cgagcattcg agagtttttc aaggcggctt  180
cgaggggtta ttccgtaacg ccgccgacat gatctgtccc ggaatctccg ccgctgttcg  240
tagagcgccg atgcagggtc ggcatcaatc attcttggag gagacac                287

SEQ ID NO: 79          moltype = DNA  length = 4107
FEATURE                Location/Qualifiers
misc_feature           1..4107
                       note = Cas9 sequence used in Expression Vector
```

```
source                  1..4107
                        mol_type = other DNA
                        organism = synthetic construct
SEQUENCE: 79
atggacaaga agtattcgat cggcctggac atcggcacca acagcgtcgg ctgggcggtc  60
atcacggatg agtacaaggt gccgtcgaag aagttcaagg tgctgggcaa taccgaccgc  120
catagcatca agaagaatct catcggcgca ctgctgttcg actccggcga aaccgccgaa  180
gcgacccgcc tcaagcgcac ggcccggcgg cgctatacgc gccggaagaa ccgcatctgc  240
tacctccagg aaatcttctc caacgagatg gccaaggtgg atgactcctt cttccatcgc  300
ctggaagaat ccttcctggt cgaagaagat aagaaacatg agcgccaccc catcttcggc  360
aatatcgtgg acgaggtggc gtatcacgag aaataccccga ccatctatca cctgcggaaa  420
aagctggtgg actcgacgga caaagccgac ctgcgcctca tctatctggc cctggcccac  480
atgatcaagt tccggggcca tttcctgatc gaaggcgacc tgaaccccga taacagcgac  540
gtggacaagc tcttcatcca gctcgtccag acctataacc agctgttcga ggagaacccc  600
atcaacgcct cgggcgtgga cgccaaggcc atcctgagcg cacggctctc caagtcgcgc  660
cgcctggaaa acctgatcgc gcagctgccg ggcgaaaaga aaaacggcct gttcggcaac  720
ctgatcgccc tgtccctcgg cctcaccccg aacttcaagt ccaacttcga cctggccgag  780
gacgcgaagc tccagctgtc gaaagacacc tacgatgacg acctggacaa cctcctggcg  840
cagatcggcg accagtacgc cgacctcttc ctcgcggcca agaatctgtc ggacgccatc  900
ctgctgtcgg atatcctgcg ggtgaatacg gagatcacga aggccccccct ctcggcctcg  960
atgatcaagc gctacgacga gcaccatcag gacctgacgc tgctcaaggc cctcgtccgg  1020
cagcagctgc cggagaagta taaagagatc ttcttcgacc agtccaagaa cggctacgcg  1080
ggctacatcg acggcggcgc gtcgcaggag gagttctata aattcatcaa gccgatcctg  1140
gagaaaatgg acggcaccga agaactcctc gtcaagctga accgggagga tctgctccgc  1200
aagcagcgca ccttcgacaa tggctccatc ccgcaccaga tccatctcgg cgagctgcac  1260
gccatcctgc gccgccagga ggacttctac cccttcctca aagacaaccg ggagaaaatc  1320
gagaagatcc tgacgttccg catcccctac tacgtgggcc ccctcgcccg cggcaactcg  1380
cggttcgcgt ggatgacccg gaagagcgag gagacgatca ccccgtggaa tttcgaggag  1440
gtcgtcgata aaggcgcgtc ggcgcagtcg ttcatcgagc gcatgaccaa cttcgataaa  1500
aatctgccga acgaaaaagt cctgcccaag catagcctgc tgtacgagta cttcacggtc  1560
tacaacgagc tgacgaaagt gaaatatgtc acggagggca tgcgcaaacc ggccttcctg  1620
tccggcgagc agaaaaaggc catcgtggat ctgctgttca agacgaaccg gaaggtcacc  1680
gtgaaacagc tgaaggaaga ttacttcaag aaaatcgagt gcttcgattc cgtcgaaatc  1740
agcggcgtgg aggaccgctt caatgcctcg ctgggcacct atcacgatct cctcaagatc  1800
atcaaggaca aggacttcct ggacaacgaa gagaacgagg acatcctgga agacatcgtc  1860
ctcaccctga ccctgttcga ggaccgcgaa atgatcgaag agcgcctgaa gacctacgcc  1920
cacctgttcg acgacaaggt catgaagcag ctcaagcgcc gccggtacac cggctggggc  1980
cgcctgtccc ggaagctgat caacggcatc cgcgataagc agagcggcaa gacgatcctg  2040
gacttcctca agagcgacgg cttcgccaat cggaatttca tgcagctcat ccacgacgat  2100
agcctgacct tcaaagagga tatccagaag gcgcaggtgt ccggccaggg cgacagcctg  2160
cacgaacata tcgccaacct ggcgggctcc cccgcgatca agaaaggcat cctccagacg  2220
gtcaaagtcg tggacgagct ggtcaaggtg atgggccgcc acaaaccgga gaatatcgtc  2280
atcgagatgg cacgcgagaa ccagaccacg cagaagggcc agaagaacag ccgggaacgc  2340
atgaaacgga tcgaagaggg catcaaggaa ctgggctcgc agatcctgaa ggagcacccc  2400
gtcgaaaaca cgcagctcca gaacgagaag ctgtatctgt actatctcca gaacggccgg  2460
gacatgtatg tcgatcagga actggatatc aaccgcctct ccgattacga tgtggaccac  2520
atcgtgccgc agagcttcct gaaagacgac tcgatcgaca acaaggtcct gacccggtcg  2580
gacaagaacc gcggcaagtc ggataacgtg ccgtcggaag aagtcgtgaa aaagatgaag  2640
aactactggc ggcagctcct gaacgcgaag ctcatcacgc agcgcaagtt cgacaatctg  2700
accaaggccg agcgcggcgg cctctcggaa ctcgacaagg cgggcttcat caaacggcag  2760
ctcgtcgaga cgcgccagat caccaaacac gtggcccaga tcctggacag ccggatgaac  2820
accaaatacg acgaaaacga caagctgatc cgcgaagtca aggtcatcac gctgaagagc  2880
aagctggtgt cggatttccg caaggatttc cagttctaca aggtgcgcga gatcaacaat  2940
taccatcacg cgcacgatgc ctatctcaat gcggtcgtgg gcaccgccct gatcaaaaag  3000
tacccgaaac tggagtccga gttcgtctac ggcgactata aggtctatga tgtccgcaag  3060
atgatcgcca aatcggagca ggagatcggc aaggcgaccg cgaaatattt cttctactcg  3120
aacatcatga atttcttcaa gaccgagatc acgctggcga acggcgaaat ccgcaagcgg  3180
cccctgatcg aaaccaatgg cgagaccggc gagatcgtgt gggacaaagg ccgggatttc  3240
gccaccgtcc gcaaggtcct ctcgatgccg caggtgaaca tcgtcaagaa gacggaggtc  3300
cagaccggcg gcttcagcaa agaaagcatc ctccccaagc ggaatagcga caaactgatc  3360
gcccggaaga aggactggga cccgaagaag tatggcggct tcgatagccc caccgtcgcc  3420
tattccgtcc tggtggtggc gaaggtggag aaaggcaaaa gcaagaaact gaagagcgtg  3480
aaggagctgc tgggcatcac catcatggaa cgcagcagct tcgagaagaa cccgatcgac  3540
ttcctggaag ccaaaggcta taaggaagtg aagaaggacc tcatcatcaa actcccgaag  3600
tattcgctgt tcgagctgga aaatggccgc aaacggatgc tcgcctccgc gggcgaactc  3660
cagaagggca acgaactggc gctgccgtcc aaatacgtca acttcctcta tctggccagc  3720
cattacgaaa agctgaaggg ctcgcccgaa gataacgagc agaaacagct gttcgtcgag  3780
cagcacaagc actacctcga cgagatcatc gagcagatca gcgagttctc caagcgggtg  3840
atcctcgcgg acgccaacct ggacaaggtg ctgtcggcgt acaacaaaca tcgggataag  3900
ccgatccgcg agcaggccga aaatatcatc cacctgttca ccctgacgaa cctcggcgcc  3960
cccgccgcct tcaagtattt cgataccacc atcgaccgga agcgctatac ctccaccaaa  4020
gaggtcctgg atgccaccct catccaccag tccatcacgg gcctgtacga gacccgcatc  4080
gacctgtcgc agctgggcgg cgactaa                                      4107

SEQ ID NO: 80           moltype = DNA  length = 35
FEATURE                 Location/Qualifiers
misc_feature            1..35
                        note = J23111 Promoter-gRNA sequence
source                  1..35
```

```
                         mol_type = other DNA
                         organism = synthetic construct
SEQUENCE: 80
ttgacggcta gctcagtcct aggtatagtg ctagc                          35

SEQ ID NO: 81            moltype = DNA  length = 83
FEATURE                  Location/Qualifiers
misc_feature             1..83
                         note = Cas9 handle and terminator region
source                   1..83
                         mol_type = other DNA
                         organism = synthetic construct
SEQUENCE: 81
gttttagagc tagaaatagc aagttaaaat aaggctagtc cgttatcaac ttgaaaaagt  60
ggcaccgagt cggtgctttt ttt                                       83

SEQ ID NO: 82            moltype = DNA  length = 20
FEATURE                  Location/Qualifiers
misc_feature             1..20
                         note = pSL148 - Targeting Sequence
source                   1..20
                         mol_type = other DNA
                         organism = synthetic construct
SEQUENCE: 82
gctcgaagcc cattaccacg                                           20

SEQ ID NO: 83            moltype = DNA  length = 138
FEATURE                  Location/Qualifiers
misc_feature             1..138
                         note = pSL148 - Full sgRNA sequence
source                   1..138
                         mol_type = other DNA
                         organism = synthetic construct
SEQUENCE: 83
ttgacggcta gctcagtcct aggtatagtg ctagcgctcg aagcccatta ccacggtttt  60
agagctagaa atagcaagtt aaaataaggc tagtccgtta tcaacttgaa aaagtggcac  120
cgagtcggtg cttttttt                                             138

SEQ ID NO: 84            moltype = DNA  length = 201
FEATURE                  Location/Qualifiers
misc_feature             1..201
                         note = pSL148 - Donor Sequence
source                   1..201
                         mol_type = other DNA
                         organism = synthetic construct
SEQUENCE: 84
gttcgacgcc gaattcgaag ccatcaagca ccaggccggg gtcgccgccg acatcggcct  60
gagcgccgtc catctcgccg acatcggcga acgtttcctc gccgtcgtac gccgccatac  120
cggcaagcct ttccccgagg acgtctacga gcagctcgag atcgcgatcc gggcggtatt  180
cgactcctgg atgggaaacg c                                         201

SEQ ID NO: 85            moltype = DNA  length = 20
FEATURE                  Location/Qualifiers
misc_feature             1..20
                         note = pSL150 - Targeting Sequence
source                   1..20
                         mol_type = other DNA
                         organism = synthetic construct
SEQUENCE: 85
tcaaccacga tacactccag                                           20

SEQ ID NO: 86            moltype = DNA  length = 138
FEATURE                  Location/Qualifiers
misc_feature             1..138
                         note = pSL150 - Full sgRNA sequence
source                   1..138
                         mol_type = other DNA
                         organism = synthetic construct
SEQUENCE: 86
ttgacggcta gctcagtcct aggtatagtg ctagctcaac cacgatacac tccaggtttt  60
agagctagaa atagcaagtt aaaataaggc tagtccgtta tcaacttgaa aaagtggcac  120
cgagtcggtg cttttttt                                             138

SEQ ID NO: 87            moltype = DNA  length = 199
FEATURE                  Location/Qualifiers
misc_feature             1..199
                         note = pSL150 - Donor Sequence
source                   1..199
                         mol_type = other DNA
```

```
                       organism = synthetic construct
SEQUENCE: 87
gtgaccgagc ctatctggaa ttgctcaagg ccctggccca gttgcgcctg ctggaacggc  60
tgaatgctcg aaaaatgggc cggaaccggc tctgatcctg cagtgacaag cggcgaacgc  120
gacagttcga ggagaccatc atgacgatga aaaagcgtgt ctacgccttc tccgaaggcg  180
acggcaagaa caaacgcct                                               199

SEQ ID NO: 88          moltype = DNA  length = 20
FEATURE                Location/Qualifiers
misc_feature           1..20
                       note = pSL128 - Targeting Sequence
source                 1..20
                       mol_type = other DNA
                       organism = synthetic construct
SEQUENCE: 88
ggaccagaac aatccgttgt                                              20

SEQ ID NO: 89          moltype = DNA  length = 138
FEATURE                Location/Qualifiers
misc_feature           1..138
                       note = pSL128 - Full sgRNA sequence
source                 1..138
                       mol_type = other DNA
                       organism = synthetic construct
SEQUENCE: 89
ttgacggcta gctcagtcct aggtatagtg ctagcggacc agaacaatcc gttgtgtttt  60
agagctagaa atagcaagtt aaaataaggc tagtccgtta tcaacttgaa aaagtggcac  120
cgagtcggtg ctttttttt                                               138

SEQ ID NO: 90          moltype = DNA  length = 1044
FEATURE                Location/Qualifiers
misc_feature           1..1044
                       note = pSL128 - Donor Sequence
source                 1..1044
                       mol_type = other DNA
                       organism = synthetic construct
SEQUENCE: 90
taccatgcgc atcgatctga ccgagacgca gctggatgcc ctggtggaaa tctaccggat  60
gatgcggccg ggcgaaccgc cgaccaagga ggccgcccag accctgttcg aaaatctgtt  120
tttctcggcc gaacgctatg atctgtcggc tgtcggccgg atgaagttca accggcgcct  180
ggggcggacc gatcctaccg gccccggcgt gctggaaaac gatgacatca tcgcggtgct  240
gaaggaactg atcaacatcc gtaacggggg gggcacggtc gacgacatcg accatctggg  300
taaccgccgc gtccggtccg tgggggagat ggtggagaat cagttcaggc tcgggctggt  360
ccgggtcgaa cgggccgtga aggagcgtct gtcgctgccc gacgccgatg gtctgatgcc  420
acaggagatc atcaacgcca aaccggtggc cgcttccatc aaggaattct tcggttcgag  480
ccagctttcg cggttcatgg accagaataa cccattatct gaggtcactc acaagcgccg  540
tgtctcggct ctggggccgg gggggctggc gcgtgagcgc gccggcttcg aagtgcgcga  600
cgtgcatacc acccactacg gccgtgtctg tccgatcgaa acgcccgaag gtccgaacat  660
cggcctgatc aactcgctcg cggtctactc gcgcaccaac gaatacggct ttctggagac  720
gccgtatcga aaggtgatcg acggccgggt gaccgatcag atcgagtacc tgtcggctat  780
cgaggagggc cagtactaca ttgctcaggc cagcgcctcg gtcgatgaaa acggcatgct  840
caaggatgaa ctggtgtcgt gtcgccacaa ggatgaattc accctggcgt cgcgggaaaa  900
catcaactac atggatgtgt cgtccaaaca gatcgtgtcg gtcgcggcct cgctgatccc  960
cttcctcgaa cacgatgatg ccaaccgcgc cctgatgggc tcgaacatgc agcggcaggc  1020
cgtcccgacg ctgcgtacgg agaa                                         1044

SEQ ID NO: 91          moltype = DNA  length = 20
FEATURE                Location/Qualifiers
misc_feature           1..20
                       note = gap gRNA5 - Targeting Sequence
source                 1..20
                       mol_type = other DNA
                       organism = synthetic construct
SEQUENCE: 91
cgtcgtgcat gagtgcaccg                                              20

SEQ ID NO: 92          moltype = DNA  length = 138
FEATURE                Location/Qualifiers
misc_feature           1..138
                       note = gap gRNA5 - Full sgRNA sequence
source                 1..138
                       mol_type = other DNA
                       organism = synthetic construct
SEQUENCE: 92
ttgacggcta gctcagtcct aggtatagtg ctagccgtcg tgcatgagtg caccggtttt  60
agagctagaa atagcaagtt aaaataaggc tagtccgtta tcaacttgaa aaagtggcac  120
cgagtcggtg ctttttttt                                               138

SEQ ID NO: 93          moltype = DNA  length = 1307
```

```
FEATURE                 Location/Qualifiers
misc_feature            1..1307
                        note = gap gRNA5 - Donor Sequence
source                  1..1307
                        mol_type = other DNA
                        organism = synthetic construct
SEQUENCE: 93
ccgggacgga acgcttgcca ggccatctgg atgtggcggg gaccggcgcc gtcgacgaac  60
acgatctcga ggtcgtcggc caccgccaga tagagcatgt tgcgaatggg gacgaacagt  120
gggtcggggc gccggcggcc gagcagtacc cggctgaggt tgtaggttgc ggcgccgagc  180
aggcgtgcct cgcgtcggag ttcgcgcgaa cgatggaagg tttcctgcat gtggatggcg  240
tcgcttgctg ggtcccggtt taagctatca gccttggtgc gcgaagggca agaactggac  300
gctcggcgcg gcgctttgct atattggcca cgctttgtat tgacagattc cccggagaat  360
gcccgattct ccctcgccga aggcccgcag gcgtccggcc gggacggcct cgactgctct  420
ccccacccca ctccgccggt cgccaagggt gcgagggctc tcgcgcatga ccccatcctc  480
actttatttc agcatttctg gagcagggca atgacgatta agattgcaat caatggatat  540
gggcgcatcg gccgcaacat cctgcgggcg atttacgaaa ccgggcgcaa ggatgtggag  600
atcgtcgcca tcaatgacct gggggatgcc cagatcaacg cccatctcac ccgccatgac  660
accgtgcacg ggccgttccg ggggaccgtg gaggtcggcg agggcgaaat catcgtcaac  720
ggcgaccgca tcagggtttt ttccgagaag gatccttcca agctgccctg gggggctttg  780
ggcgtggacg tcgtgcatga gtgatagcac ctgttccgca ccaaggccaa atgccagccg  840
catctcgatg ccggcgccaa gaaggtgatc atttcggccc cggccgacaa gaacgagtgc  900
gacgcgacca tcgtctacgg ggtcaatgag catacgctga aagccgccca caccgtcatc  960
tcgaatgcat cctgcaccac caactgcctg gcgccgctgg tcaagccgct gctgggaaaa  1020
atcgggatcg tgtccggcct catgaccacc gtgcattcct acaccaacga ccaggtgctc  1080
accgacgttt atcacaagga tctgtaccgg gcacgggcgg cggcgctgaa catgatcccg  1140
accaagaccg gcgcggcgca ggccgtgggg ctggtgctgc cggagctgga cggcaaactg  1200
tccggtttcg ccatccgggt gccgaccgcc aatgtatcgg tcgtggacct gaccttcatc  1260
gcggcccggg aaaccgacaa ggacgagatc aacgccatcc tcaaggc              1307

SEQ ID NO: 94           moltype = DNA  length = 20
FEATURE                 Location/Qualifiers
misc_feature            1..20
                        note = pIK11 - Targeting Sequence
source                  1..20
                        mol_type = other DNA
                        organism = synthetic construct
SEQUENCE: 94
cccatcacct atcagcacaa                                            20

SEQ ID NO: 95           moltype = DNA  length = 138
FEATURE                 Location/Qualifiers
misc_feature            1..138
                        note = pIK11 - Full sgRNA sequence
source                  1..138
                        mol_type = other DNA
                        organism = synthetic construct
SEQUENCE: 95
ttgacggcta gctcagtcct aggtatagtg ctagccccat cacctatcag cacaagtttt  60
agagctagaa atagcaagtt aaaataaggc tagtccgtta tcaacttgaa aaagtggcac  120
cgagtcggtg cttttttt                                              138

SEQ ID NO: 96           moltype = DNA  length = 1149
FEATURE                 Location/Qualifiers
misc_feature            1..1149
                        note = pIK11 - Donor Sequence
source                  1..1149
                        mol_type = other DNA
                        organism = synthetic construct
SEQUENCE: 96
aagatcgatg acaccgtcaa ctgggtgaaa aaggtcgatc tgaagaccgg cctgccgatc  60
cgcgatccgg agtacagcac ccgcatggac cacaatgcca aaggcatctg tccctcggcc  120
atgggctatc acaaccaggg catcgagtcc tacgatccgg acaagaagct gttcttcatg  180
ggcgtgaacc acatctgcat ggactgggag ccgttcatgc tgccctaccg cgccggccag  240
ttctttgtgg gggcgaccct caacatgtat ccgggaccca aggggatgct gggtcaggtc  300
aaggcgatga acgcggtcac cggcaagatg gaatgggaag tgccggagaa gtttgcggtc  360
tggggtggca ccttggcgac cgccggcgac ctcgtgttct acggtaccct cgacggcttc  420
atcaaggccc gcgacacccg taccggcgag ctgaagtggc agttccagtt gccctccggc  480
gtgatcggcc atcccatcac gtaccaacat aacggcaagc aatacattgc catctactcc  540
ggcgtcggcg gctggccagg agtagggctg gtattcgacc tgaaggaccc gaccgcaggt  600
ctgggagctg tgggtgcgtt cagggaactg gcgcattaca cccagatggg tggatcggtg  660
ttcgtgttct cgctttgagt cgaaggggtg gaggcgctcc tgggggagcg cccctatccc  720
atgctgtcga aaggatgaat catgcgaatg aaccgtattg cagccgcggg gttggccgcc  780
tccctcgcgg tcgtgggatg cgtgcaggca gcgacgagcg tcgaaccgct caaggtctgc  840
tccgcggaaa acgagatgcc gtattcggac aaggccggag agggtttcga aaataagttg  900
gctgagctcc ttggaaaggg attgggacgg ccagtcgaga acgtgtggtg gaccgatgcc  960
cgctatttcg tccgggatta tctggacagg ggtttgtgcg atgtggtcat cggcgtcgat  1020
accggcgacc cgcggatgct caccagcagt ccttattacc ggtccggcta cgtattcgtc  1080
taccgcaagg acacgggact gagcatccaa gattggaaca gcgcggcact gaagaccgtg  1140
```

```
aagcggatc                                                         1149

SEQ ID NO: 97          moltype = DNA  length = 20
FEATURE                Location/Qualifiers
misc_feature           1..20
                       note = pSL178 - Targeting Sequence
source                 1..20
                       mol_type = other DNA
                       organism = synthetic construct
SEQUENCE: 97
tcaaccacga tacactccag                                             20

SEQ ID NO: 98          moltype = DNA  length = 138
FEATURE                Location/Qualifiers
misc_feature           1..138
                       note = pSL178 - Full sgRNA sequence
source                 1..138
                       mol_type = other DNA
                       organism = synthetic construct
SEQUENCE: 98
ttgacggcta gctcagtcct aggtatagtg ctagctcaac cacgatacac tccaggtttt  60
agagctagaa atagcaagtt aaaataaggc tagtccgtta tcaacttgaa aaagtggcac  120
cgagtcggtg ctttttt                                                138

SEQ ID NO: 99          moltype = DNA  length = 322
FEATURE                Location/Qualifiers
misc_feature           1..322
                       note = pSL178 - Donor Sequence
source                 1..322
                       mol_type = other DNA
                       organism = synthetic construct
SEQUENCE: 99
gtgttccctg gaacacgcca tcaatttcga tctcgtgctc aacaccgacc atctgccagc  60
cggtaacgct ctgccgaccg tactcatggc ggtacggcag ttcggcttcg aaatcttcga  120
tctcggtcag cgggaagcct cgtgagcccg gcggtgggac agaccgcatc ccgtctgcta  180
acggtcgaga tcgtcgacgt ctgccgggag atattttccg ggcgttgtag ccgggtggtc  240
gcgccagcgg cagacggtga ggtcggcgtt ctgccccgtc atacgccgtt cctgacccgg  300
ctccggcccg gcgagataag gc                                          322

SEQ ID NO: 100         moltype = DNA  length = 20
FEATURE                Location/Qualifiers
misc_feature           1..20
                       note = pSL179 - Targeting Sequence
source                 1..20
                       mol_type = other DNA
                       organism = synthetic construct
SEQUENCE: 100
tcaaccacga tacactccag                                             20

SEQ ID NO: 101         moltype = DNA  length = 138
FEATURE                Location/Qualifiers
misc_feature           1..138
                       note = pSL179 - Full sgRNA sequence
source                 1..138
                       mol_type = other DNA
                       organism = synthetic construct
SEQUENCE: 101
ttgacggcta gctcagtcct aggtatagtg ctagctcaac cacgatacac tccaggtttt  60
agagctagaa atagcaagtt aaaataaggc tagtccgtta tcaacttgaa aaagtggcac  120
cgagtcggtg ctttttt                                                138

SEQ ID NO: 102         moltype = DNA  length = 2028
FEATURE                Location/Qualifiers
misc_feature           1..2028
                       note = pSL179 - Donor sequence
source                 1..2028
                       mol_type = other DNA
                       organism = synthetic construct
SEQUENCE: 102
gtgttccctg gaacacgcca tcaatttcga tctcgtgctc aacaccgacc atctgccagc  60
cggtaacgct ctgccgaccg tactcatggc ggtacggcag ttcggcttcg aaatcttcga  120
tctcggtcag cgggaagcct cgtgagcccg gcggtgggac agaccgcatc ccgtctgcta  180
acggtcgaga tcgtcgacgt ctgccgggag atattttccg ggcgttgtag ccgggtggtc  240
gcgccagcgg cagacggtga ggtcggcgtt ctgccccgtc atacgccgtt cctgacccgg  300
ctccggcccg gcgagataag gctcaggacc gaggcaggcg aagaccagta tttctacctc  360
tccgggggct acatggaggt gcagcgctgg gaggtcagca tcctggccga ccaggtgctc  420
cgctcccaag agatcgaccg ggaagcggcc ctggcggcca agcgcaacgc agagcggatg  480
ctccgcgaga accggattcc cggcgagcgt gaccgagcct atctggaatt gctcaaggcc  540
ctggcccagt tgcgcctgct ggaacggctg aatgctcgaa aaatgggccg gaaccggctc  600
```

```
tgatcctgca gtgacaagcg gcgaacgcga cagttcgagg agaccatcat gacgatgaaa  660
aagcgtgtct acgccttctc cgaaggcgac ggcaagaaca aacgcctgct cggcggcaag  720
ggcgccaacc tctgcgaaat gacgcagatc gggctcaacg tgccgccggg tttcgttatt  780
accacggaag cctgcctcga atacctggca gacaagaagc tgccggccgg cttgatggac  840
gaagtccggg agcacatggc ccggctcgaa cgggctaccg gcaagcgctt cggcgatccc  900
gccaatccac tcttggtttc ggtgcgttcc ggttcggccc tgtccatgcc gggcatgatg  960
gataccattc tcaacctcgg cctcaaccac gatacactct ttcctcgccg tcgtacgccg  1020
ccataccggc aagcctttcc ccgaggacgt ctacgagcag ctcgagatcg cgatccgggc  1080
ggtattcgac tcctggatgg gaaagcgcgc ggtggattac cgccgcgaat tccacatcac  1140
gcccgaccag gccaacggca cggcggtgaa cgtggtgacc atggtgttcg gcaacatggg  1200
cgacgactcc gccaccggtg tcggcttcac ccgcaatccg ggtaccggtg agaacgagat  1260
gttcggcgag tatctggtca acgcccaggg tgaggatgtg gtagccggaa tccgcacgcc  1320
caagcccgtg cacgagatgg caaccgaaat gccggcgctt tacgcccaac tggtggaact  1380
gcgcgacaag ctcgaagccc attaccacga ggtgcaggac ttcgagtaca ccatcgagaa  1440
gggggtcttg tactgtctgc agacgcgcaa cggcaagatg aacgcccagg cgatggtgcg  1500
cacctcggtc gagatgtgcc gggaaggact gatcacgcgg gatcaggccc tcttgcgggt  1560
caaccccgcc catctggaac agttactcca tccctgcctc gacacctcgc acaaccccac  1620
gccgctggcg caggggctgc ctgcctcgcc cggcgccgcc agcggccgtt gcgtgttcga  1680
tgcggatcag gccgaactgt tgggacgggc cggtgaaaag gtcatcctgg tgcgtgagga  1740
gaccaagccg gaagacatcc acggcttctt cgcggcccag ggaatcctca ccagtcgcgg  1800
cggcaagacc tcgcatgccg ccgtggtcgc ccgcggcatg ggcaaggcct gcgtggccgg  1860
ggccgaaggc atcagggtgg acagccgggc gcggctggca acggtgggag aggtcacgtt  1920
gcacgaaggt gacatcatca ccatcgacgg cagcaccggc cgtgtctatc tcggcgcgat  1980
cccgacgatc gcgccgacct tctccgaaca cctcaggaca ctgctgtc             2028

SEQ ID NO: 103         moltype = DNA  length = 20
FEATURE                Location/Qualifiers
misc_feature           1..20
                       note = pSL162 - Targeting Sequence
source                 1..20
                       mol_type = other DNA
                       organism = synthetic construct
SEQUENCE: 103
tcaaccacga tacactccag                                            20

SEQ ID NO: 104         moltype = DNA  length = 138
FEATURE                Location/Qualifiers
misc_feature           1..138
                       note = pSL162 - Full sgRNA sequence
source                 1..138
                       mol_type = other DNA
                       organism = synthetic construct
SEQUENCE: 104
ttgacggcta gctcagtcct aggtatagtg ctagctcaac cacgatacac tccaggtttt  60
agagctagaa atagcaagtt aaaataaggc tagtccgtta tcaacttgaa aaagtggcac  120
cgagtcggtg ctttttt                                               138

SEQ ID NO: 105         moltype = DNA  length = 199
FEATURE                Location/Qualifiers
misc_feature           1..199
                       note = pSL162 - Donor Sequence
source                 1..199
                       mol_type = other DNA
                       organism = synthetic construct
SEQUENCE: 105
gtgaccgagc ctatctggaa ttgctcaagg ccctggccca gttgcgcctg ctggaacggc  60
tgaatgctcg aaaaatgggc cggaaccggc tctgatcctg cagtgacaag cggcgaacgc  120
gacagttcga ggagaccatc atgacgatga aaaagcgtgt ctacgccttc tccgaaggcg  180
acggcaagaa caaacgcct                                             199

SEQ ID NO: 106         moltype = DNA  length = 20
FEATURE                Location/Qualifiers
misc_feature           1..20
                       note = pSL154 - Targeting Sequence
source                 1..20
                       mol_type = other DNA
                       organism = synthetic construct
SEQUENCE: 106
tcaaccacga tacactccag                                            20

SEQ ID NO: 107         moltype = DNA  length = 138
FEATURE                Location/Qualifiers
misc_feature           1..138
                       note = pSL154 - Full sgRNA sequence
source                 1..138
                       mol_type = other DNA
                       organism = synthetic construct
SEQUENCE: 107
ttgacggcta gctcagtcct aggtatagtg ctagctcaac cacgatacac tccaggtttt  60
```

```
agagctagaa atagcaagtt aaaataaggc tagtccgtta tcaacttgaa aaagtggcac  120
cgagtcggtg ctttttt                                                 138

SEQ ID NO: 108          moltype = DNA  length = 1075
FEATURE                 Location/Qualifiers
misc_feature            1..1075
                        note = pSL154 - Donor Sequence
source                  1..1075
                        mol_type = other DNA
                        organism = synthetic construct
SEQUENCE: 108
gtgaccgagc ctatctggaa ttgctcaagg ccctggccca gttgcgcctg ctggaacggc  60
tgaatgctcg aaaaatgggc cggaaccggc tctgatcctg cagtgacaag cggcgaacgc  120
gacagttcga ggagaccatc atgacgatga aaaagcgtgt ctacgccttc tccgaaggcg  180
acggcaagaa caaacgcctg ctcggcggca agggcgccaa cctctgcgaa atgacgcaga  240
tcgggctcaa cgtgccgccg ggtttcgtta ttaccacgga agcctgcctc gaatacctgg  300
cagacaagaa gctgccggcc ggcttgatgg acgaagtccg ggagcacatg gcccggctcg  360
aacgggctac cggcaagcgc ttcggcgatc ccgccaatcc actcttggtt tcggtgcgtt  420
ccggttcggc cctgtccatg ccgggcatga tggataccat tctcaacctc ggcctcaacc  480
acgatacact ctaagtgcca gggcgtgccc ttgggctccc cgggcgcggg gttgatccgg  540
cagaccggca acgagcgctt cggtcacgat gcctaccggc ggttcatcca gttgttcggc  600
aaggttgccc tcggtgttcc cgacgagctg ttcgacgccg aattcgaagc catcaagcac  660
caggccgggg tcgccgccga catcggcctg agcgccgtcc atctcgccga catcggcgaa  720
cgtttcctcg ccgtcgtacg ccgccatacc ggcaagcctt tccccgagga cgtctacgag  780
cagctcgaga tcgcgatccg ggcggtattc gactcctgga tgggaaagcg cgcggtggat  840
taccgccgcg aattccacat cacgcccgac caggccaacg gcacggcggt gaacgtggtg  900
accatggtgt tcggcaacat gggcgacgac tccgccaccg gtgtcggctt cacccgcaat  960
ccgggtaccg gtgagaacga gatgttcggc gagtatctgg tcaacgccca gggtgaggat  1020
gtggtagccg gaatccgcac gcccaagccc gtgcacgaga tggcaaccga aatgc       1075

SEQ ID NO: 109          moltype = DNA  length = 20
FEATURE                 Location/Qualifiers
misc_feature            1..20
                        note = pSL175 - Targeting Sequence
source                  1..20
                        mol_type = other DNA
                        organism = synthetic construct
SEQUENCE: 109
tactacggag caagttcccg                                              20

SEQ ID NO: 110          moltype = DNA  length = 138
FEATURE                 Location/Qualifiers
misc_feature            1..138
                        note = pSL175 - Full sgRNA sequence
source                  1..138
                        mol_type = other DNA
                        organism = synthetic construct
SEQUENCE: 110
ttgacggcta gctcagtcct aggtatagtg ctagctacta cggagcaagt tcccggtttt  60
agagctagaa atagcaagtt aaaataaggc tagtccgtta tcaacttgaa aaagtggcac  120
cgagtcggtg ctttttt                                                 138

SEQ ID NO: 111          moltype = DNA  length = 1045
FEATURE                 Location/Qualifiers
misc_feature            1..1045
                        note = pSL175 - Donor Sequence
source                  1..1045
                        mol_type = other DNA
                        organism = synthetic construct
SEQUENCE: 111
gccaggacag aaatgcctcg acttcgctgc tgcccaaggt tgccgggtga cgcacaccgt  60
ggaaacggat gaaggcacga acccagttga cataagcctg ttcggttcgt aaactgtaat  120
gcaagtagcg tatgcgctca cgcaactggt ccagaacctt gaccgaacgc agcggtggta  180
acggcgcagt ggcggttttc atggcttgtt atgactgttt ttttgtacag tctatgcctc  240
gggcatccaa gcagcaagcg cgttacgccg tgggtcgatg tttgatgtta tggagcagca  300
acgatgttac gcagcagcaa cgatgttacg cagcagggca gtcgccctaa aacaaagtta  360
ggtggctcaa gtatgggcat cattcgcaca tgtaggctcg gccctgacca agtcaaatcc  420
atgcgggctg ctcttgatct tttcggtcgt gagttcggag acgtagccac ctactcccaa  480
catcagccgg actccgatta gctcccccaa ctgagagaac tcaaaggtta ccccagttgg  540
ggcgggtaac ttgctccgta gtaagacatt catcgcgctt gctgccttcg accaagaagc  600
ggttgttggc gctctcgcgg cttacgttct gcccaggttt gagcagccgc gtagtgagat  660
ctatatctat gatctcgcag tctccggcga gcaccggagg cagggcattg ccaccgcgct  720
catcaatctc ctcaagcatg aggccaacgc gcttggtgct tatgtgatct acgtgcaagc  780
agattacggt gacgatcccg cagtggctct ctatacaaag ttgggcatac gggaagaagt  840
gatgcacttt gatatcgacc caagtaccgc cacctaacaa ttcgttcaag ccgagatcgg  900
cttcataact tcgtatagca tacattatac gaagttattg gcagagcatt acgctgactt  960
gaccagaggc tgcatttcca ccgctgattg cgattcggaa ggtgcaggcc ggagggtccg  1020
gaccgccgct ccacccgttg ttttc                                        1045
```

```
SEQ ID NO: 112          moltype = DNA  length = 20
FEATURE                 Location/Qualifiers
misc_feature            1..20
                        note = pSL163 - Targeting Sequence
source                  1..20
                        mol_type = other DNA
                        organism = synthetic construct
SEQUENCE: 112
tcaaccacga tacactccag                                              20

SEQ ID NO: 113          moltype = DNA  length = 138
FEATURE                 Location/Qualifiers
misc_feature            1..138
                        note = pSL163 - Full sgRNA sequence
source                  1..138
                        mol_type = other DNA
                        organism = synthetic construct
SEQUENCE: 113
ttgacggcta gctcagtcct aggtatagtg ctagctcaac cacgatacac tccaggtttt  60
agagctagaa atagcaagtt aaaataaggc tagtccgtta tcaacttgaa aaagtggcac  120
cgagtcggtg cttttttt                                                138

SEQ ID NO: 114          moltype = DNA  length = 1785
FEATURE                 Location/Qualifiers
misc_feature            1..1785
                        note = pSL163 - Donor Sequence
source                  1..1785
                        mol_type = other DNA
                        organism = synthetic construct
SEQUENCE: 114
gtgaccgagc ctatctggaa ttgctcaagg ccctggccca gttgcgcctg ctggaacggc  60
tgaatgctcg aaaaatgggc cggaaccggc tctgatcctg cagtgacaag cggcgaacgc  120
gacagttcga ggagaccatc atgacgatga aaaagcgtgt ctacgccttc tccgaaggcg  180
acggcaagaa caaacgcctg ctcggcggca agggcgccaa cctctgcgaa atgacgcaga  240
tcgggctcaa cgtgccgccg ggtttcgtta ttaccacgga agcctgcctc gaatacctgg  300
cagacaagaa gctgccggcc ggcttgatgg acgaagtccg ggagcacatg gcccggctcg  360
aacgggctac cggcaagcgc ttcggcgatc ccgccaatcc actcttggtt tcggtgcgtt  420
ccggttcggc cctgtccatg ccgggcatga tggataccat tctcaacctc ggcctcaacc  480
acgatacact ctaattgacg gctagctcag tcctaggtat agtgctagca aaaagctcaa  540
cgagaggaag ttccatggcc atcatcaagg agttcatgcg cttcaaggtg cacatggagg  600
gctccgtgaa cggccacgag ttcgagatcg agggcgaggg cgagggccgc ccctacgagg  660
gcacccagac cgccaagctg aaggtgacca agggtggccc cctgcccttc gcctgggaca  720
tcctgtcccc tcagttcatg tacggctcca aggcctacgt gaagcacccc gccgacatcc  780
ccgactactt gaagctgtcc ttccccgagg gcttcaagtg ggagcgcgtg atgaacttcg  840
aggacggcgg cgtggtgacc gtgacccagg actcctccct ccaggacggc gagttcatct  900
acaaggtgaa gctgcgcggc accaacttcc cctccgacgg ccccgtaatg cagaagaaga  960
ccatgggctg ggaggcctcc tccgagcgga tgtaccccga ggacggcgcc ctgaagggcg  1020
agatcaagca gaggctgaag ctgaaggacg gcggccacta cgacgctgag gtcaagacca  1080
cctacaaggc caagaagccc gtgcagctgc ccggcgccta caacgtcaac atcaagttgg  1140
acatcacctc ccacaacgag gactacacca tcgtggaaca gtacgaacgc gccgagggcc  1200
gccactccac cggcggcatg gacgagctgt acaagtaagg gttgatccgg cagaccggca  1260
acgagcgctt cggtcacgat gcctaccggc ggttcatcca gttgttcggc aaggttgccc  1320
tcggtgttcc cgacgagctg ttcgacgccg aattcgaagc catcaagcac caggccgggg  1380
tcgccgccga catcggcctg agcgccgtcc atctcgccga catcggcgaa cgtttcctcg  1440
ccgtcgtacg ccgccatacc ggcaagcctt tccccgagga cgtctacgag cagctcgaga  1500
tcgcgatccg ggcggtattc gactcctgga tgggaaagcg cgcggtggat taccgccgcg  1560
aattccacat cacgcccgac caggccaacg gcacggcggt gaacgtggtg accatggtgt  1620
tcggcaacat gggcgacgac tccgccaccg gtgtcggctt cacccgcaat ccgggtaccg  1680
gtgagaacga gatgttcggc gagtatctgg tcaacgccca gggtgaggat gtggtagccg  1740
gaatccgcac gcccaagccc gtgcacgaga tggcaaccga aatgc                  1785

SEQ ID NO: 115          moltype = DNA  length = 20
FEATURE                 Location/Qualifiers
misc_feature            1..20
                        note = pSL165 - Targeting Sequence
source                  1..20
                        mol_type = other DNA
                        organism = synthetic construct
SEQUENCE: 115
tcaaccacga tacactccag                                              20

SEQ ID NO: 116          moltype = DNA  length = 138
FEATURE                 Location/Qualifiers
misc_feature            1..138
                        note = pSL165 - Full sgRNA sequence
source                  1..138
                        mol_type = other DNA
                        organism = synthetic construct
SEQUENCE: 116
```

```
ttgacggcta gctcagtcct aggtatagtg ctagctcaac cacgatacac tccaggtttt  60
agagctagaa atagcaagtt aaaataaggc tagtccgtta tcaacttgaa aaagtggcac  120
cgagtcggtg ctttttt                                                 138

SEQ ID NO: 117          moltype = DNA  length = 2184
FEATURE                 Location/Qualifiers
misc_feature            1..2184
                        note = pSL165 - Donor sequence
source                  1..2184
                        mol_type = other DNA
                        organism = synthetic construct
SEQUENCE: 117
gtgaccgagc ctatctggaa ttgctcaagg ccctggccca gttgcgcctg ctggaacggc  60
tgaatgctcg aaaaatgggc cggaaccggc tctgatcctg cagtgacaag cggcgaacgc  120
gacagttcga ggagaccatc atgacgatga aaaagcgtgt ctacgccttc tccgaaggcg  180
acggcaagaa caaacgcctg ctcggcggca agggcgccaa cctctgcgaa atgacgcaga  240
tcgggctcaa cgtgccgccg ggtttcgtta ttaccacgga agcctgcctc gaatacctgg  300
cagacaagaa gctgccggcc ggcttgatgg acgaagtccg ggagcacatg gcccggctcg  360
aacgggctac cggcaagcgc ttcggcgatc ccgccaatcc actcttggtt tcggtgcgtt  420
ccggttcggc cctgtccatg ccgggcatga tggataccat tctcaacctc ggcctcaacc  480
acgatacact ctaattgacg gctagctcag tcctaggtat agtgctagca aaaagctcaa  540
cgagaggaag ttccatgagc tatcccgaga agttcgaggg gatcgccatc cagagccacg  600
aggactggaa gaacccgaaa aagaccaagt atgatccgaa gcccttctac gatcacgaca  660
tcgacatcaa gatcgaggcc tgcggcgtct gcggcagcga tatccattgt gcggctggcc  720
actggggcaa catgaagatg ccgttggtcg tcggccacga gatcgtgggc aaggtcgtga  780
agttaggccc gaaaagcaac agcggcttga aggtgggcca gcgcgtgggt gtgggtgcgc  840
aggtcttcag ctgtctggag tgcgaccgtt gcaagaacga caacgaaccg tactgcacca  900
agttcgtcac cacctactcg cagccctacg aggacggcta cgtctcgcag ggcggttacg  960
ccaactatgt ccgagtccac gaacacttcg tggtgcccat cccggaaaat atccccagcc  1020
atctggcggc tcccctgctg tgcggtggct tgaccgtcta cagcccccctc gtccgcaatg  1080
gctgcggtcc cggcaagaag gtgggtatcg tgggcctcgg cggtataggc tctatgggca  1140
cgctgatctc gaaagcgatg ggcgcagaaa cgtacgtgat ctcgcgttcc tcgcgcaagc  1200
gcgaggatgc gatgaagatg ggtgcggacc actacatcgc cacgctggag gagggtgact  1260
ggggtgagaa gtacttcgac acgttcgacc tcatcgtggt gtgcgcgagt tccctgacgg  1320
acatcgactt caatatcatg cccaaggcga tgaaggtcgg agggcgcatc gtctccatct  1380
cgatcccgga gcagcacgaa atgctgtcgc tgaagcccta cggcctgaaa gccgtctcca  1440
ttagctactc ggcgctcggt agtatcaagg agctcaacca gctgttgaag ttggtttccg  1500
aaaaggacat caagatctgg gtggaaacgc tcccggtggg cgaagccggt gtgcacgagg  1560
cctttgagcg gatggagaag ggggatgtcc gttatcggtt tacactcgtc ggctacgata  1620
aagagttctc ggattaaggg ttgatccggc agaccggcaa cgagcgcttc ggtcacgatg  1680
cctaccggcg gttcatccag ttgttcggca aggttgccct cggtgttccc gacgagctgt  1740
tcgacgccga attcgaagcc atcaagcacc aggccggggt cgccgccgac atcggcctga  1800
gcgccgtcca tctcgccgac atcggcgaac gtttcctcgc cgtcgtacgc cgccataccg  1860
gcaagccttt ccccgaggac gtctacgagc agctcgagat cgcgatccgg gcggtattcg  1920
actcctggat gggaaagcgc gcggtggatt accgccgcga attccacatc acgcccgacc  1980
aggccaacgg cacggcggtg aacgtggtga ccatggtgtt cggcaacatg ggcgacgact  2040
ccgccaccgg tgtcggcttc acccgcaatc cgggtaccgg tgagaacgag atgttcggcg  2100
agtatctggt caacgcccag ggtgaggatg tggtagccgg aatccgcacg cccaagcccg  2160
tgcacgagat ggcaaccgaa atgc                                         2184

SEQ ID NO: 118          moltype = DNA  length = 4107
FEATURE                 Location/Qualifiers
misc_feature            1..4107
                        note = dCas9
source                  1..4107
                        mol_type = other DNA
                        organism = synthetic construct
SEQUENCE: 118
atggacaaga agtattcgat cggcctggcc atcggcacca acagcgtcgg ctgggcggtc  60
atcacggatg agtacaaggt gccgtcgaag aagttcaagg tgctgggcaa taccgaccgc  120
catagcatca agaagaatct catcggcgca ctgctgttcg actccggcga aaccgccgaa  180
gcgacccgcc tcaagcgcac ggcccggcgg cgctatacgc gccggaagaa ccgcatctgc  240
tacctccagg aaatcttctc caacgagatg gccaaggtgg atgactcctt cttccatcgc  300
ctggaagaat ccttcctggt cgaagaagat aagaaacatg agcgccaccc catcttcggc  360
aatatcgtgg acgaggtggc gtatcacgag aaataccccga ccatctatca cctgcggaaa  420
aagctggtgg actcgacgga caaagccgac ctgcgcctca tctatctggc cctggcccac  480
atgatcaagt tccggggcca tttcctgatc gaaggcgacc tgaaccccga taacagcgac  540
gtggacaagc tcttcatcca gctcgtccag acctataacc agctgttcga ggagaacccc  600
atcaacgcct cgggcgtgga cgccaaggcc atcctgagcg cacggctctc caagtcgcgc  660
cgcctggaaa acctgatcgc gcagctgccg ggcgaaaaga aaaacggcct gttcggcaac  720
ctgatcgccc tgtccctcgg cctcaccccg aacttcaagt ccaacttcga cctggccgag  780
gacgcgaagc tccagctgtc gaaagacacc tacgatgacg acctggacaa cctcctggcg  840
cagatcggcg accagtacgc cgacctcttc ctcgcggcca agaatctgtc ggacgccatc  900
ctgctgtcgg atatcctgcg ggtgaatacg gagatcacga aggccccccct ctcggcctcg  960
atgatcaagc gctacgacga gcaccatcag gacctgacgc tgctcaaggc cctcgtccgg  1020
cagcagctgc cggagaagta taaagagatc ttcttcgacc agtccaagaa cggctacgcg  1080
ggctacatcg acggcggcgc gtcgcaggag gagttctata aattcatcaa gccgatcctg  1140
gagaaaatgg acggcaccga agaactcctc gtcaagctga accgggagga tctgctccgc  1200
aagcagcgca ccttcgacaa tggctccatc ccgcaccaga tccatctcgg cgagctgcac  1260
```

```
gccatcctgc gccgccagga ggacttctac cccttcctca aagacaaccg ggagaaaatc  1320
gagaagatcc tgacgttccg catcccctac tacgtgggcc ccctcgcccg cggcaactcg  1380
cggttcgcgt ggatgacccg gaagagcgag gagacgatca ccccgtggaa tttcgaggag  1440
gtcgtcgata aaggcgcgtc ggcgcagtcg ttcatcgagc gcatgaccaa cttcgataaa  1500
aatctgccga acgaaaaagt cctgcccaag catagcctgc tgtacgagta cttcacggtc  1560
tacaacgagc tgacgaaagt gaaatatgtc acggagggca tgcgcaaacc ggccttcctg  1620
tccggcgagc agaaaaaggc catcgtggat ctgctgttca agacgaaccg gaaggtcacc  1680
gtgaaacagc tgaaggaaga ttacttcaag aaaatcgagt gcttcgattc cgtcgaaatc  1740
agcggcgtgg aggaccgctt caatgcctcg ctgggcacct atcacgatct cctcaagatc  1800
atcaaggaca aggacttcct ggacaacgaa gagaacgagg acatcctgga agacatcgtc  1860
ctcaccctga ccctgttcga ggaccgcgaa atgatcgaag agcgcctgaa gacctacgcc  1920
cacctgttcg acgacaaggt catgaagcag ctcaagcgcc gccggtacac cggctggggc  1980
cgcctgtccc ggaagctgat caacggcatc cgcgataagc agagcggcaa gacgatcctg  2040
gacttcctca agagcgacgg cttcgccaat cggaatttca tgcagctcat ccacgacgat  2100
agcctgacct tcaaagagga tatccagaag gcgcaggtgt ccggccaggg cgacagcctg  2160
cacgaacata tcgccaacct ggcgggctcc cccgcgatca agaaaggcat cctccagacg  2220
gtcaaagtcg tggacgagct ggtcaaggtg atgggccgcc acaaaccgga gaatatcgtc  2280
atcgagatgg cacgcgagaa ccagaccacg cagaagggcc agaagaacag ccgggaacgc  2340
atgaaacgga tcgaagaggg catcaaggaa ctgggctcgc agatcctgaa ggagcacccc  2400
gtcgaaaaca cgcagctcca gaacgagaag ctgtatctgt actatctcca gaacggccgg  2460
gacatgtatg tcgatcagga actggatatc aaccgcctct ccgattacga tgtggacgcc  2520
atcgtgccgc agagcttcct gaaagacgac tcgatcgaca acaaggtcct gacccggtcg  2580
gacaagaacc gcggcaagtc ggataacgtg ccgtcggaag aagtcgtgaa aaagatgaag  2640
aactactggc ggcagctcct gaacgcgaag ctcatcacgc agcgcaagtt cgacaatctg  2700
accaaggccg agcgcggcgg cctctcggaa ctcgacaagg cgggcttcat caaacggcag  2760
ctcgtcgaga cgcgccagat caccaaacac gtggcccaga tcctggacag ccggatgaac  2820
accaaatacg acgaaaacga caagctgatc cgcgaagtca aggtcatcac gctgaagagc  2880
aagctggtgt cggatttccg caaggatttc cagttctaca aggtgcgcga gatcaacaat  2940
taccatcacg cgcacgatgc ctatctcaat gcggtcgtgg gcaccgccct gatcaaaaag  3000
tacccgaaac tggagtccga gttcgtctac ggcgactata aggtctatga tgtccgcaag  3060
atgatcgcca aatcggagca ggagatcggc aaggcgaccg cgaaatattt cttctactcg  3120
aacatcatga atttcttcaa gaccgagatc acgctggcga acggcgaaat ccgcaagcgg  3180
cccctgatcg aaaccaatgg cgagaccggc gagatcgtgt gggacaaagg ccgggatttc  3240
gccaccgtcc gcaaggtcct ctcgatgccg caggtgaaca tcgtcaagaa gacggaggtc  3300
cagaccggcg gcttcagcaa agaaagcatc ctccccaagc ggaatagcga caaactgatc  3360
gcccggaaga aggactggga cccgaagaag tatggcggct tcgatagccc caccgtcgcc  3420
tattccgtcc tggtggtggc gaaggtggag aaaggcaaaa gcaagaaact gaagagcgtg  3480
aaggagctgc tgggcatcac catcatggaa cgcagcagct tcgagaagaa cccgatcgac  3540
ttcctggaag ccaaaggcta taaggaagtg aagaaggacc tcatcatcaa actcccgaag  3600
tattcgctgt tcgagctgga aaatggccgc aaacggatgc tcgcctccgc gggcgaactc  3660
cagaagggca acgaactggc gctgccgtcc aaatacgtca acttcctcta tctggccagc  3720
cattacgaaa agctgaaggg ctcgcccgaa gataacgagc agaaacagct gttcgtcgag  3780
cagcacaagc actacctcga cgagatcatc gagcagatca gcgagttctc caagcgggtg  3840
atcctcgcgg acgccaacct ggacaaggtg ctgtcggcgt acaacaaaca tcgggataag  3900
ccgatccgcg agcaggccga aaatatcatc cacctgttca ccctgacgaa cctcggcgcc  3960
cccgccgcct tcaagtattt cgataccacc atcgaccgga agcgctatac ctccaccaaa  4020
gaggtcctgg atgccaccct catccaccag tccatcacgg gcctgtacga gacccgcatc  4080
gacctgtcgc agctgggcgg cgactaa                                      4107
```

```
SEQ ID NO: 119          moltype = DNA  length = 20
FEATURE                 Location/Qualifiers
misc_feature            1..20
                        note = oriV_dcas9_gRNA3 - Targeting Sequence
source                  1..20
                        mol_type = other DNA
                        organism = synthetic construct
SEQUENCE: 119
ataatgtgtg gaattgtgag                                              20

SEQ ID NO: 120          moltype = DNA  length = 138
FEATURE                 Location/Qualifiers
misc_feature            1..138
                        note = oriV_dcas9_gRNA3 - Full sgRNA sequence
source                  1..138
                        mol_type = other DNA
                        organism = synthetic construct
SEQUENCE: 120
tttatagcta gctcagccct tggtacaatg ctagcataat gtgtggaatt gtgaggtttt  60
agagctagaa atagcaagtt aaaataaggc tagtccgtta tcaacttgaa aaagtggcac  120
cgagtcggtg ctttttttt                                                138

SEQ ID NO: 121          moltype = DNA  length = 72
FEATURE                 Location/Qualifiers
misc_feature            1..72
                        note = Ptrc_laxZ - Promoter
source                  1..72
                        mol_type = other DNA
                        organism = synthetic construct
SEQUENCE: 121
```

```
ttgacaatta atcatccggc tcgtataatg tgtggaattg tgagcggata acaattaacg  60
agaggaagtt cc                                                      72

SEQ ID NO: 122          moltype = DNA  length = 3075
FEATURE                 Location/Qualifiers
misc_feature            1..3075
                        note = Ptrc_laxZ - LacZ sequence used in Vector
source                  1..3075
                        mol_type = other DNA
                        organism = synthetic construct
SEQUENCE: 122
atgaccatga ttacggattc actggccgtc gttttacaac gtcgtgactg ggaaaaccct  60
ggcgttaccc aacttaatcg ccttgcagca catccccctt tcgccagctg gcgtaatagc  120
gaagaggccc gcaccgatcg cccttcccaa cagttgcgca gcctgaatgg cgaatggcgc  180
tttgcctggt ttccggcacc agaagcggtg ccggaaagct ggctggagtg cgatcttcct  240
gaggccgata ctgtcgtcgt cccctcaaac tggcagatgc acggttacga tgcgcccatc  300
tacaccaacg tgacctatcc cattacggtc aatccgccgt ttgttcccac ggagaatccg  360
acgggttgtt actcgctcac atttaatgtt gatgaaagct ggctacagga aggccagacg  420
cgaattattt ttgatggcgt taactcggcg tttcatctgt ggtgcaacgg gcgctgggtc  480
ggttacggcc aggacagtcg tttgccgtct gaatttgacc tgagcgcatt tttacgcgcc  540
ggagaaaacc gcctcgcggt gatggtgctg cgctggagtg acggcagtta tctggaagat  600
caggatatgt ggcggatgag cggcattttc cgtgacgtct cgttgctgca taaaccgact  660
acacaaatca gcgatttcca tgttgccact cgctttaatg atgatttcag ccgcgctgta  720
ctggaggctg aagttcagat gtgcggcgag ttgcgtgact acctacgggt aacagtttct  780
ttatggcagg gtgaaacgca ggtcgccagc ggcaccgcgc ctttcggcgg tgaaattatc  840
gatgagcgtg gtggttatgc cgatcgcgtc acactacgtc tgaacgtcga aaacccgaaa  900
ctgtggagcg ccgaaatccc gaatctctat cgtgcggtgg ttgaactgca caccgccgac  960
ggcacgctga ttgaagcaga agcctgcgat gtcggtttcc gcgaggtgcg gattgaaaat  1020
ggtctgctgc tgctgaacgg caagccgttg ctgattcgag gcgttaaccg tcacgagcat  1080
catcctctgc atggtcaggt catggatgag cagacgatgg tgcaggatat cctgctgatg  1140
aagcagaaca actttaacgc cgtgcgctgt tcgcattatc cgaaccatcc gctgtggtac  1200
acgctgtgcg accgctacgg cctgtatgtg gtggatgaag ccaatattga aacccacggc  1260
atggtgccaa tgaatcgtct gaccgatgat ccgcgctggc taccggcgat gagcgaacgc  1320
gtaacgcgaa tggtgcagcg cgatcgtaat cacccgagtg tgatcatctg gtcgctgggg  1380
aatgaatcag gccacggcgc taatcacgac gcgctgtatc gctggatcaa atctgtcgat  1440
ccttcccgcc cggtgcagta tgaaggcggc ggagccgaca ccacggccac cgatattatt  1500
tgcccgatgt acgcccgcgt ggatgaagac cagcccttcc cggctgtgcc gaaatggtcc  1560
atcaaaaaat ggctttcgct acctggagag acgcgcccgc tgatcctttg cgaatacgcc  1620
cacgcgatgg gtaacagtct tggcggtttc gctaaatact ggcaggcgtt tcgtcagtat  1680
ccccgtttac agggcggctt cgtctgggac tgggtggatc agtcgctgat taaatatgat  1740
gaaaacggca acccgtggtc ggcttacggc ggtgattttg gcgatacgcc gaacgatcgc  1800
cagttctgta tgaacggtct ggtctttgcc gaccgcacgc cgcatccagc gctgacggaa  1860
gcaaaacacc agcagcagtt tttccagttc cgtttatccg ggcaaaccat cgaagtgacc  1920
agcgaatacc tgttccgtca tagcgataac gagctcctgc actggatggt ggcgctggat  1980
ggtaagccgc tggcaagcgg tgaagtgcct ctggatgtcg ctccacaagg taaacagttg  2040
attgaactgc ctgaactacc gcagccggag agcgccgggc aactctggct cacagtacgc  2100
gtagtgcaac cgaacgcgac cgcatggtca gaagccgggc acatcagcgc ctggcagcag  2160
tggcgtctgg cggaaaacct cagtgtgacg ctccccgccg cgtcccacgc catcccgcat  2220
ctgaccacca gcgaaatgga tttttgcatc gagctgggta ataagcgttg gcaatttaac  2280
cgccagtcag gctttctttc acagatgtgg attggcgata aaaaacaact gctgacgccg  2340
ctgcgcgatc agttcacccg tgcaccgctg gataacgaca ttggcgtaag tgaagcgacc  2400
cgcattgacc ctaacgcctg ggtcgaacgc tggaaggcgg cgggccatta ccaggccgaa  2460
gcagcgttgt tgcagtgcac ggcagataca cttgctgatg cggtgctgat tacgaccgct  2520
cacgcgtggc agcatcaggg gaaaacctta tttatcagcc ggaaaaccta ccggattgat  2580
ggtagtggtc aaatggcgat taccgttgat gttgaagtgg cgagcgatac accgcatccg  2640
gcgcggattg gcctgaactg ccagctggcg caggtagcag agcgggtaaa ctggctcgga  2700
ttagggccgc aagaaaacta tcccgaccgc cttactgccg cctgttttga ccgctgggat  2760
ctgccattgt cagacatgta taccccgtac gtcttcccga gcgaaaacgg tctgcgctgc  2820
gggacgcgcg aattgaatta tggcccacac cagtggcgcg gcgacttcca gttcaacatc  2880
agccgctaca gtcaacagca actgatggaa accagccatc gccatctgct gcacgcggaa  2940
gaaggcacat ggctgaatat cgacggtttc catatgggga ttggtggcga cgactcctgg  3000
agcccgtcag tatcggcgga attccagctg agcgccggtc gctaccatta ccagttggtc  3060
tggtgtcaaa aataa                                                   3075

SEQ ID NO: 123          moltype = DNA  length = 4077
FEATURE                 Location/Qualifiers
source                  1..4077
                        mol_type = genomic DNA
                        organism = Methylococcus capsulatus
SEQUENCE: 123
atggcttact cgtttaccga gaaaaaacga attcgcaaga gtttcggaaa gcgtcaggac  60
gtgctggagg tcccctatct tctggcgaca caggttgact cgtaccggcg gtttttgcaa  120
ctcgacaagc agcccgccgc ccggagcgac gaaggtctgc atgcggcgtt gaagtcggtt  180
ttcccgatca agagccattc cggcaacatc gtactcgaat atgtgagtta ccggctgggc  240
gacccggtgt tcgacgtcaa ggaatgccag cagcgtggaa ccacctacgc cgccccgctg  300
cgcgtgctcg tccgtctggt ggtctacgac aaggatgcgc cggtgggcgc caaggtcgtc  360
agagacatca aggagcagga gatctacatg ggcgaaattc cgctcatgac cgacaacggc  420
acgttcgtca tcaacggtac cgagcgggtg atcgtttccc aactgcaccg ttcgcccggc  480
gtatttttcg accatgatcg gggaaagacc cattcttcgg gaaagctgct gttcaatgcc  540
```

```
agaatcatcc cctaccgcgg gtcctggctg gacttcgaat tcgaccacaa ggactgcgtt  600
tacgtccgta tcgacaggcg tcgcaagctg cccgccacgg tgttgctgcg agccctgggc  660
tatgacaacg agcagatcat cgccgagttt ttcgacacca accgtttcct gctctcatcc  720
gccggcattc agctggaact gatacccgag cggctgcgcg gcgatatcgc cagcttcgac  780
attcggcttg gcgatcagat cgtggtcgag aaggaccacc ggatcacggc gcgtcacatc  840
cggatgctgc aaaaggagaa cgtgaacctc ctcgacgtcc ccaaggacta cctgtacggc  900
aagattcttg cccacaacgt cgtggatact tcgacgggcg aactgatcgc caaggtgaat  960
caggagatca cggaggatgt ctatgcgcgt ctcgtggctg cggccatccc cgagatccgt  1020
acgctctatg tgaacgatct cgaccgcggt ccgtacattt ccaataccat gcgcatcgat  1080
ctgaccgaga cgcagctgga tgccctggtg gaaatctacc ggatgatgcg gccgggcgaa  1140
ccgccgacca aggaggccgc ccagaccctg ttcgaaaatc tgtttttctc ggccgaacgc  1200
tatgatctgt cggctgtcgg ccggatgaag ttcaaccggc gcctggggcg gaccgatcct  1260
accggccccg gcgtgctgga aaacgatgac atcatcgcgg tgctgaagga actgatcaac  1320
atccgtaacg gggggggcac ggtcgacgac atcgaccatc tgggtaaccg ccgcgtccgg  1380
tccgtggggg agatggtgga gaatcagttc aggctcgggc tggtccgggt cgaacgggcc  1440
gtgaaggagc gtctgtcgct gcccgacgcc gatggtctga tgccacagga gatcatcaac  1500
gccaaaccgg tggccgcttc catcaaggaa ttcttcggtt cgagccagct ttcgcagttc  1560
atggaccaga acaatccgtt gtcggaggtc actcacaagc gccgtgtctc ggctctgggg  1620
ccgggggggc tggcgcgtga gcgcgccggc ttcgaagtgc gcgacgtgca taccacccac  1680
tacggccgtg tctgtccgat cgaaacgccc gaaggtccga acatcggcct gatcaactcg  1740
ctcgcggtct actcgcgcac caacgaatac ggctttctgg agacgccgta tcgaaaggtg  1800
atcgacggcc gggtgaccga tcagatcgag tacctgtcgg ctatcgagga gggccagtac  1860
tacattgctc aggccagcgc ctcggtcgat gaaaacggca tgctcaagga tgaactggtg  1920
tcgtgtcgcc acaaggatga attcaccctg gcgtcgcggg aaaacatcaa ctacatggat  1980
gtgtcgtcca aacagatcgt gtcggtcgcg gcctcgctga tccccttcct cgaacacgat  2040
gatgccaacc gcgccctgat gggctcgaac atgcagcggc aggccgtccc gacgctgcgt  2100
acggagaagc ctctggtggg cacgggcatg gaacgcatcg tcgcccgcga ttccggcgtg  2160
gcggtcgtcg ccaagcgcgg tggcacggtc gagttcgtgg acgccagccg catcgtggtc  2220
cgggtgaacg acgaggagac cgaggcgggg gttccgggtg tggatatcta caacctgacc  2280
aaatacaccc gttccaacca gaacacctgt attaaccaga ggccgttggt taagccgggc  2340
gacgtcgtgg cccgcaacga cgtgctggcg gatggtcctt cgaccgacat gggcgaactg  2400
gcgctgggcc agaatctgct ggtcgcgttc atgccctgga acggttacaa cttcgaagac  2460
tcgatcctga tttcggaacg cgtggtgcag gacgaccgtt tcacgaccat ccacatcgag  2520
gagaagacct gcgtcgctcg agacaccaaa ctggggcccg aggaaatcac cgccgacatt  2580
ccgaacgttg gggaggccgc gctgtccaag ctggacgagt cgggtatcgt ctacatcggc  2640
gccgaggtca aggccggcga catcctggtg ggcaaggtga cgcccaaggg cgaaacccag  2700
ctcaccccgg aggagaagct gctgcgagcg atcttcggtg agaaggcctc ggatgtgaag  2760
gacacttcgc tgcgcgtgcc ttcgggtatg gacggcacgg tcatagacgt gcaggtcttc  2820
acccgcgacg gcgtgaagaa ggatgaacgc gcccgtcaga tcgaggaagc cgagattgag  2880
agggttcgca aggatctgaa cgatcagctc cgtatcatcg agaaggactt ttaccagcgg  2940
gccgagcaga tggttctggg caaggtcgcc gacatggggc cgggcggtct gaagcgcggc  3000
gccaccatca cccgggaata cctggattcg atcaagcccg cccagtggct ggagatccgg  3060
ttgcaggacg aagacgtcaa tcttcagatc gaagcgatcg ccgagcagat cgcccagcag  3120
cgcgaggaaa tcgcgaagcg gctcgaagag aagcgccgca agatcaccat gggtgacgac  3180
ctcgctccgg gtgtgctcaa gatggtaaag gtgtacctgg ccgtcaagcg ccgtattcag  3240
ccgggcgaca agatggccgg ccgccacggg aacaaaggtg tgatttcccg catcgtaccg  3300
gtggaagaca tgccgtattc ggctgacggt acgccggtcg acatcgtgtt gaacccactg  3360
ggcgtgcctt cgcgcatgaa cgtaggccag gtgctcgaga cccatctcgg ctgggcggcc  3420
aagggtgtgg gcctgaagat cggcggatg ctggaggcca aggccaagat cgaggagatc  3480
cggtctttcc tcactcaggt gtacaacgtg agtggccgcc aggaggacat cgccagtctg  3540
agcgacgccg aggtgctgga gctcgccggt aatctgcagg acggcgtgcc gatggcgact  3600
cccgtgttcg atggagccac cgaggaagac atcaaggcca tgctgcggct ggccgatctt  3660
cccgaaagcg gccaggcaac tttgttcgac ggacgtaccg gcgacgtgtt cgaccgtccg  3720
gtgaccgtcg gttacatgta catgctcaaa ctcaatcatc tggtcgacga caagatgcac  3780
gcacggtcca ccggtccgta cagtctggtg acccagcagc cgctgggcgg caaggcgcaa  3840
ttcggtggac agcgtttcgg cgaaatggag gtgtgggcgt tggaggccta cggtgccgcc  3900
tatactctgc aggagatgct gacggtgaaa tctgacgacg tgaacggcag gaccaagatg  3960
tacaagaaca tcgtcgacgg tgatcaccgt atggaagccg ccatgcccga gtcgttcaac  4020
gtcctgatca aagagatccg ctcgctcgga atcaacatcg agctcgagca ggactga     4077
```

```
SEQ ID NO: 124         moltype = DNA  length = 20
FEATURE                Location/Qualifiers
misc_feature           1..20
                       note = RPOB gRNA targeting sequence
source                 1..20
                       mol_type = other DNA
                       organism = synthetic construct
SEQUENCE: 124
ggaccagaac aatccgttgt                                            20
```

```
SEQ ID NO: 125         moltype = DNA  length = 103
FEATURE                Location/Qualifiers
misc_feature           1..103
                       note = RPOB gRNA with Handle and Terminator
source                 1..103
                       mol_type = other DNA
                       organism = synthetic construct
SEQUENCE: 125
ggaccagaac aatccgttgt gttttagagc tagaaatagc aagttaaaat aaggctagtc  60
```

```
cgttatcaac ttgaaaaagt ggcaccgagt cggtgctttt ttt                   103

SEQ ID NO: 126          moltype = DNA  length = 1044
FEATURE                 Location/Qualifiers
misc_feature            1..1044
                        note = RpoB Donor DNA
source                  1..1044
                        mol_type = other DNA
                        organism = synthetic construct
SEQUENCE: 126
taccatgcgc atcgatctga ccgagacgca gctggatgcc ctggtggaaa tctaccggat  60
gatgcggccg ggcgaaccgc cgaccaagga ggccgcccag accctgttcg aaaatctgtt  120
tttctcggcc gaacgctatg atctgtcggc tgtcggccgg atgaagttca accggcgcct  180
ggggcggacc gatcctaccg gccccggcgt gctggaaaac gatgacatca tcgcggtgct  240
gaaggaactg atcaacatcc gtaacggggg gggcacggtc gacgacatcg accatctggg  300
taaccgccgc gtccggtccg tgggggagat ggtggagaat cagttcaggc tcgggctggt  360
ccgggtcgaa cgggccgtga aggagcgtct gtcgctgccc gacgccgatg gtctgatgcc  420
acaggagatc atcaacgcca aaccggtggc cgcttccatc aaggaattct tcggttcgag  480
ccagctttcg cggttcatgg accagaataa cccattatct gaggtcactc acaagcgccg  540
tgtctcggct ctggggccgg gggggctggc gcgtgagcgc gccggcttcg aagtgcgcga  600
cgtgcatacc acccactacg gccgtgtctg tccgatcgaa acgcccgaag gtccgaacat  660
cggcctgatc aactcgctcg cggtctactc gcgcaccaac gaatacggct ttctggagac  720
gccgtatcga aaggtgatcg acggccgggt gaccgatcag atcgagtacc tgtcggctat  780
cgaggagggc cagtactaca ttgctcaggc cagcgcctcg gtcgatgaaa acggcatgct  840
caaggatgaa ctggtgtcgt gtcgccacaa ggatgaattc accctggcgt cgcgggaaaa  900
catcaactac atggatgtgt cgtccaaaca gatcgtgtcg gtcgcggcct cgctgatccc  960
cttcctcgaa cacgatgatg ccaaccgcgc cctgatgggc tcgaacatgc agcggcaggc  1020
cgtcccgacg ctgcgtacgg agaa                                        1044
```

ADVANCED GENOME EDITING

SEQUENCE LISTING

This application contains a Sequence Listing, which has been submitted electronically in XML format and is hereby incorporated by reference in its entirety. The XML copy was created on Jan. 9, 2024, is named 75594-404221.xml and is 275,599 bytes in size.

BACKGROUND OF THE INVENTION

Genomic editing is the key to molecular biology. Genome editing uses specific nucleases to create site-specific double-strand breaks (DSBs) at desired locations within the genome of a cell in order to insert, delete, or replace one or more nucleotides. The DSBs are then repaired, which result in the desired modifications.

Currently there are four families of engineered nucleases that are used for genome edits, including meganucleases, zinc finger nucleases (ZFN), transcription activator-like effector-based nucleases (TALEN), and clustered regularly interspaced short palindromic repeats (CRISPR)-Cas systems.

In general, the meganucleases method of gene editing is the least efficient of the methods mentioned above. Due to the nature of its DNA-binding element and the cleaving element, it is limited to recognizing one potential target every 1,000 nucleotides. Boglioli, E., Richard, M., "Rewriting the book of life: a new era in precision genome editing". Boston Consulting Group, September 2015. ZFN was developed to overcome the limitations of meganucleases. The number of possible targets ZFN can recognize was increased to one in every 140 nucleotides. Boglioli, E., 2015. However, both methods are unpredictable due to the ability of their DNA-binding elements affecting each other. As a result, high degrees of expertise and lengthy and costly validation processes are required.

TALE nucleases are the most precise and specific method and yield a higher efficiency than the previous two methods using meganucleases and ZFN. TALEN achieves higher efficiency because the DNA-binding element contains an array of TALE subunits, each of them having the capability of recognizing a specific DNA nucleotide chain independent from others, resulting in a higher number of target sites with high precision. New TALEN take about one week and a few hundred dollars to create, with specific expertise in molecular biology and protein engineering. Boglioli, E., 2015.

CRISPR nucleases are slightly less precise compared to TALENs. However, the CRISPR method has been shown to be the quickest and cheapest method. CRISPR also requires the least amount of expertise in molecular biology as the design lays in the guide RNA instead of the proteins. One major advantage that CRISPR has over the ZFN and TALEN methods is that it can be directed to target different DNA sequences using its ~80 nt CRISPR single guide ribonucleic acids (sgRNAs), while both ZFN and TALEN methods required construction and testing of the proteins created for targeting each DNA sequence. Barrangou. R., and Doudna, J. A., "Applications of CRISPR technologies in research and beyond". *Nature Biotechnology.* 34:933-941, 2016.

The subject matter of the present invention relates to microorganisms, such as methanotrophs, and methods to genomically edit their DNA.

INCORPORATION BY REFERENCE

All publications, patents, and patent applications cited herein are hereby incorporated by reference in their entireties to the same extent as if each individual publication, patent, or patent application was specifically and individually indicated to be incorporated by reference in its entirety. In the event of a conflict between a term herein and a term in an incorporated reference, the term herein controls.

SUMMARY

Disclosed herein is a method of genetic engineering comprising: (a) contacting a microorganism capable of converting a $C_1$ carbon to a multicarbon product with a polynucleotide encoding for a Cas enzyme and a guide ribonucleic acid (gRNA); and (b) growing the microorganism until genetic modification occurs.

In some cases, the microorganism capable of converting a $C_1$ carbon to a multicarbon product is a methylotroph. For example, the methylotroph can be a methanotroph. If the microorganism is a methanotroph, it can be from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis*, or Methyloacidophilum. Particular methanotrophs that can be used are methanotrophs from the genus *Methylococcus*, such as *Methylococcus capsulatus.*

In some cases, the $C_1$ carbon is carbon monoxide (CO), carbon dioxide ($CO_2$), methane ($CH_4$), or any combination thereof. For example, the $C_1$ carbon used can be $CH_4$.

In some cases, the Cas enzyme is Cas1, Cas1B, Cas2, Cas3, Cas4, Cas5, Cas5d, Cas5t, Cas5h, Cas5a, Cas6, Cas7, Cas8, Cas9, Cas10, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Csd1, Csd2, Cst1, Cst2, Csh1, Csh2, Csa1, Csa2, Csa3, Csa4, Csa5, C2c1, C2c2, C2c3, Cpf1, CARF, DinG, homologues thereof, or modified versions thereof. For example, the Cas enzyme use can be Cas9.

In some cases, the polynucleotide encoding for a gRNA used can be at least partially homologous to a promoter, intron, or coding sequence of an RNA polymerase beta-subunit (rpoB) gene or a gene within the 2,3-butanediol (2,3-BDO), 1,4-butanediol (1,4-BDO), isobutyraldehyde, or isobutanol pathway. For example, the polynucleotide encoding for a gRNA can be at least partially homologous to a promoter, intron, or coding sequence of rpoB. Additionally, the polynucleotide encoding for a gRNA can be directed to a promoter, intron, or coding sequence of gene within the 2,3-BDO pathway. If targeting the promoter, intron, or coding sequence of a gene within the 2,3-BDO pathway, the promoter, intron or coding sequence can be from the genes encoding an acetoin reductase, alpha-acetolactate decarboxylase, or acetolactate synthase.

In some cases the polynucleotide encoding for a gRNA can be directed to a promoter, intron, or coding sequence of a gene within the 1,4-BDO pathway. If targeting the promoter, intron, or coding sequence of a gene within the 1,4-BDO pathway, the promoter, intron or coding sequence can be from the genes encoding a pyruvate dehydrogenase (aceEF), citrate synthase (gltA), aconitate hydratase 1 (acnA), isocitrate dehydrogenase (icdA), citrate synthase (gltA), succinyl-CoA synthetase (SucC), CoA-dependent succinate semialdehyde dehydrogenase (SucD). 4-hyrobutyrate dehydrogenase (4hbD), 4-hydroxybutyryl-CoA transferase (Cat2), aldehyde dehydrogenase (Ald), alcohol dehydrogenase (Adh), or α-ketoglutarate decarboxylase (kgd).

In some cases, the polynucleotide encoding for a gRNA can be directed to a promoter, intron, or coding sequence of a gene within the isobutyraldehyde pathway. If targeting the promoter, intron, or coding sequence of a gene within the isobutyraldehyde pathway, the promoter, intron or coding sequence can be from the genes encoding an acetolactate synthase (AlsS), ketol-acid reductoisomerase (IlvC), dihydroxy-acid dehydratase (IlvD), and 2-keto acid decarboxylase (KDC).

In some cases, the polynucleotide encoding for a gRNA can be directed to a promoter, intron, or coding sequence of a gene within the isobutanol pathway. If targeting the promoter, intron, or coding sequence of a gene within the isobutanol pathway, the promoter, intron or coding sequence can be from the genes encoding an AlsS, IlvC, IlvD, KDC, or Adh.

In some cases, the microorganism used has a lower transformation efficiency compared to an *E. coli* bacterium. The transformation efficiency of the microorganism is increased prior to trying to transform the microorganism with any nucleic acids.

In some cases, the polynucleotide encoding for the gRNA can be transformed prior to the polynucleotide encoding for a Cas enzyme. Additionally, the method can further comprise contacting the microorganism with a donor polynucleotide. In some cases, the microorganism is contacted with the donor polynucleotide prior to being contacted with a polynucleotide encoding for a Cas enzyme. In some cases, the microorganism is contacted concurrently with the donor polynucleotide and the polynucleotide encoding for a gRNA. In some cases, the donor polynucleotide and the polynucleotide encoding for a gRNA are on a single plasmid. The donor polynucleotides used in the methods can be less than 1000 bases. For example, the donor polynucleotide can be less than 600 bases. In some cases, the donor polynucleotide can be less than 100 bases.

In some cases, the polynucleotide encoding for a Cas enzyme can be within a plasmid. The plasmid in some cases does not comprise a strong promoter. In some cases, the plasmid can comprise a mutated promoter. In some cases, the promoter can be a pMxaF promoter.

Also disclosed is a genetically modified microorganism capable of converting a $C_1$ carbon to a multicarbon product comprising a nucleic acid encoding a heterologous Cas enzyme. The genetically modified microorganism can be a methylotroph, such as a methanotroph or any of the genus and/or species described throughout. The $C_1$ carbon is carbon monoxide (CO), carbon dioxide ($CO_2$), methane ($CH_4$), any combination thereof, or any $C_1$ described throughout.

In some cases, the genetically modified microorganism comprises a heterologous Cas enzyme. Any of the Cas enzymes described throughout can be used. The Cas enzymes can be expressed in a plasmid. The plasmids can also include a stronger, mutated, and/or pMxaF promoter.

In some cases, the genetically modified microorganism can further comprise a polynucleotide encoding for a gRNA. In some cases, the genetically modified microorganism can comprise a polynucleotide encoding for a gRNA that is at least partially homologous to a portion of a promoter, intron, or coding sequence of an rpoB gene or a gene within the 2,3-BDO, 1,4-BDO, isobutyraldehyde, or isobutanol pathway. For example, the polynucleotide encoding for a gRNA can be at least partially homologous to a promoter, intron, or coding sequence of rpoB.

In some cases, the genetically modified microorganism can have a lower transformation efficiency compared to an *E. coli* bacteria. However, before transformation with nucleic acids, the transformation efficiency of the microorganism can be increased.

In some cases, the microorganism can comprise a point mutation compared to a wild-type microorganism of the same species. For example, the point mutation can be within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the microorganism can comprise a deletion of one or more nucleotides compared to a wild-type microorganism of the same species. For example, the deletion of one or more nucleotides can be within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the microorganism can comprise an addition of one or more nucleotides compared to a wild-type microorganism of the same species. For example, the addition of one or more nucleotides can be within a promoter, intron, or coding sequence of an rpoB gene or a gene within the 2,3-butanediol (2,3-BDO), 1,4-butanediol (1,4-BDO), isobutyraldehyde, or isobutanol pathway.

Also disclosed herein is a method of replacing a single nucleotide within the genome of a microorganism that is capable of converting a $C_1$ carbon to a multicarbon product comprising: (a) contacting the microorganism with a polynucleotide encoding for i) a Cas enzyme and ii) a polynucleotide encoding for a gRNA; and (b) growing the microorganism until a single nucleotide is replaced within the genome of the microorganism.

In some cases, the microorganism can be a methylotroph, such as a methanotroph or any microorganism described throughout. In some cases, the $C_1$ carbon can be any $C_1$ carbon described throughout. In some cases, the Cas enzyme can be any described throughout, such as a Cas9 enzyme. The Cas enzymes can be expressed in a plasmid. The plasmids can also include a stronger, mutated, and/or pMxaF promoter. In some cases, the polynucleotide encoding for a gRNA is at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the polynucleotide encoding for a gRNA is transformed prior to the polynucleotide encoding for a Cas enzyme. In some instances, the method can further comprise contacting the microorganism with a donor polynucleotide. For example, the microorganism can be contacted with the donor polynucleotide prior to being contacted with a polynucleotide encoding for a Cas enzyme. In some cases, the microorganism can be contacted concurrently with the donor polynucleotide and polynucleotide encoding for a gRNA. In some cases, the donor polynucleotide and polynucleotide encoding for a gRNA are contained on a single plasmid. In some cases, the donor polynucleotide can be less than 1000 bases. For example, the donor polynucleotide can be less than 600 bases. In some cases, the donor polynucleotide is can be less than 100 bases.

In some cases, the replacement of a single nucleotide can result in a different nucleotide. In some cases, the replacement occurs at a single nucleotide within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, as a result of the single nucleotide replacement, the expression of one or more genes can be changed. Additionally, in some cases, the replacement can change the activity of one or more enzymes.

Also disclosed herein is a method of removing one or more nucleotides from the genome of a genetically modified microorganism that is capable of converting a $C_1$ carbon to a multicarbon product comprising: (a) contacting the microorganism with a polynucleotide encoding for i) a Cas enzyme and ii) a polynucleotide encoding for a gRNA; and (b) growing the microorganism until one or more nucleotides within the genome of the microorganism is removed.

In some cases, the microorganism can be a methylotroph, such as a methanotroph or any microorganism described throughout. In some cases, the $C_1$ carbon can be any $C_1$ carbon described throughout. In some cases, the Cas enzyme can be any described throughout, such as a Cas9 enzyme. The Cas enzymes can be expressed in a plasmid. The plasmids can also include a stronger, mutated, and/or pMxaF promoter. In some cases, the polynucleotide encoding for a gRNA is at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, two or more nucleotides are removed from the targeted nucleic acid. For example, the removal of two or more nucleotides can occur within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the polynucleotide encoding for a gRNA is transformed prior to the polynucleotide encoding for a Cas enzyme. In some instances, the method can further comprise contacting the microorganism with a donor polynucleotide. For example, the microorganism can be contacted with the donor polynucleotide prior to being contacted with a polynucleotide encoding for a Cas enzyme. In some cases, the microorganism can be contacted concurrently with the donor polynucleotide and polynucleotide encoding for a gRNA. In some cases, the donor polynucleotide and polynucleotide encoding for a gRNA are contained on a single plasmid. In some cases, the donor polynucleotide can be less than 1500 bases. In some cases, the donor polynucleotide can be less than 1000 bases. For example, the donor polynucleotide can be less than 600 bases. In some cases, the donor polynucleotide is can be less than 100 bases.

In some cases, the removal of one or more nucleotides can change the expression of one or more genes. In some cases, the removal of one or more nucleotides can change the activity of one or more enzymes.

Disclosed herein is a method of adding one or more nucleotides to the genome of a microorganism capable of converting a $C_1$ carbon to a multicarbon product comprising: (a) contacting the microorganism with a polynucleotide encoding for i) a Cas enzyme and ii) a polynucleotide encoding for a gRNA; and (b) growing the microorganism until one or more nucleotides is added to the genome of the microorganism.

In some cases, the microorganism can be a methylotroph, such as a methanotroph or any microorganism described throughout. In some cases, the $C_1$ carbon can be any $C_1$ carbon described throughout. In some cases, the Cas enzyme can be any described throughout, such as a Cas9 enzyme. The Cas enzymes can be expressed in a plasmid. The plasmids can also include a stronger, mutated, and/or pMxaF promoter. In some cases, the polynucleotide encoding for a gRNA is at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, two or more nucleotides can be added to a target nucleic acid. For example, the addition of one or more nucleotides can occur within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the polynucleotide encoding for a gRNA is transformed prior to the polynucleotide encoding for a Cas enzyme. In some instances, the method can further comprise contacting the microorganism with a donor polynucleotide. For example, the microorganism can be contacted with the donor polynucleotide prior to being contacted with a polynucleotide encoding for a Cas enzyme. In some cases, the microorganism can be contacted concurrently with the donor polynucleotide and polynucleotide encoding for a gRNA. In some cases, the donor polynucleotide and polynucleotide encoding for a gRNA are contained on a single plasmid. In some cases, the donor polynucleotide can be less than 1500 bases. In some cases, the donor polynucleotide can be less than 1000 bases. For example, the donor polynucleotide can be less than 600 bases. In some cases, the donor polynucleotide is can be less than 100 bases.

In some cases, the addition of one or more nucleotides can change the expression of one or more genes. In some cases, the addition of one or more nucleotides can change the activity of one or more enzymes.

Also disclosed herein is a method of inhibiting expression of a gene within a methylotroph comprising contacting the methylotroph with a polynucleotide encoding for i) a modified Cas enzyme and ii) a polynucleotide encoding for a gRNA, where the modified Cas enzyme does not cleave nucleic acids.

In some cases, the microorganism can be a methylotroph, such as a methanotroph or any microorganism described throughout. In some cases, the modified Cas enzyme can be any described throughout, such as a modified Cas9 enzyme. In some cases, the Cas enzyme can be expressed within a plasmid. In some cases, the polynucleotide encoding for a gRNA is at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the inhibition of gene expression is greater than 10% compared to a wild-type microorganism of the same species. For example, the inhibition of gene expression is greater than 50% compared to a wild-type microorganism of the same species.

Also disclosed herein is a vector comprising a polynucleotide encoding for a Cas9 enzyme, where the Cas9 enzyme is capable of being expressed in a methylotroph, such as a methanotroph (e.g., a methanotroph from the genus *Methylococcus*).

Further disclosed herein is a method of screening for genome editing in a methylotroph comprising contacting the methylotroph with a first polynucleotide encoding for a gRNA, and subsequently with a second polynucleotide encoding a Cas9 enzyme, where the first polynucleotide encoding for a gRNA is at least partially complementary to a polynucleotide that is within a promoter, intron, or coding sequence of an rpoB gene. In some cases, the methylotroph can be a methanotroph, for example from the genus *Methylococcus*.

In some cases, the Cas enzyme can be any Cas enzyme disclosure throughout, such as a Cas9 enzyme. In some cases, the Cas enzyme can be expressed within a plasmid.

The method used herein can produce colonies when plated. These can be referred to as colony forming units (CFU). In some cases, the method described herein can produce CFU that are decreased by at least 1.1 fold. In some cases, the CFU can be decreased by at least 2 fold. In some cases, the CFU can be decreased by at least 3 fold. In some cases, the CFU can be decreased by at least 4 fold.

DETAILED DESCRIPTION OF THE INVENTION

Figure 1:
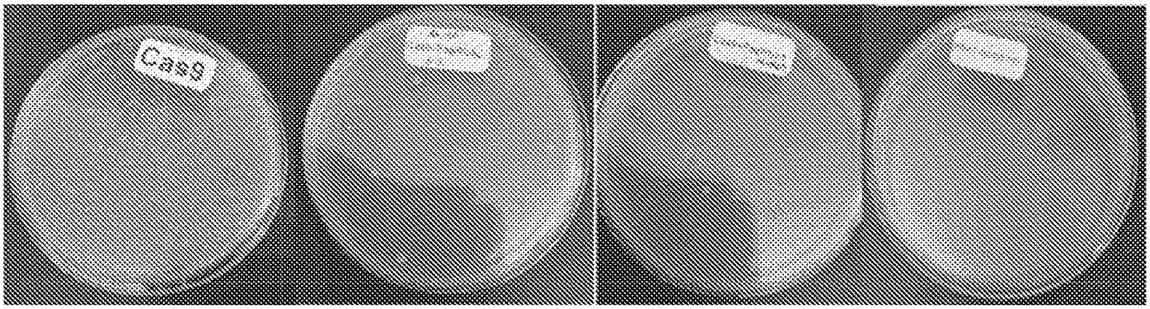
FIG. 1 depicts plates of *Methylococcus capsulatus* colonies. *Methylococcus capsulatus* were transformed with a plasmid expressing: 1) Cas9 only; 2) Cas9+gRNA2; 3) Cas9+gRNA5; or 4) Cas9+gRNA2+double stranded DNA (dsDNA). *Methylococcus capsulatus* that were transformed with all three (i.e., group 4) did not produce any colonies, indicating a lack of gene editing. The other groups, which are negative controls, grew colonies indicating an off target effect.

As summarized above, aspects of the invention include genetically modified microorganisms that are produced using advanced genomic editing tools. The genetically modified microorganisms include methylotrophs, such as methanotrophs, which are capable of using a $C_1$ carbon source, such as methane, as the primary carbon source for the organism. Additionally, as summarized above, advanced genome editing tools can be used to inhibit the expression of a gene.

Advanced genome editing can be used in many ways to alter the genome of a microorganism. For example, advanced genome editing can be used to generate a point mutation at any sequence within the genome. Additionally, advanced genome editing can be used to add one or more nucleotides to any sequence within a genome.

The precision, accuracy, and efficacy of the advanced genome editing is very high compared to that of traditional methods of genetic engineering.

Before the present invention is described in greater detail, it is to be understood that this invention is not limited to particular cases described, as such can, of course, vary. It is also to be understood that the terminology used herein is for the purpose of describing particular cases only, and is not intended to be limiting, since the scope of the present invention will be limited only by the appended claims.

I. Definitions

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value. In some cases, the numerical disclosed throughout can be "about" that numerical value even without specifically mentioning the term "about."

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The phrases "recombinant host cell," "genetically engineered host cell," "engineered host cell," "genetically modified host cell," and their grammatical equivalents as used herein may be used interchangeably and can refer to host cells that have been genetically modified to: (a) express one or more exogenous polynucleic acids; (b) over-express one or more endogenous and/or one or more exogenous polynucleic acids, such as those included in a vector, or which have an alteration in expression of an endogenous gene; or (c) knock-out or down-regulate an endogenous gene. In addition, certain genes may be physically removed from the genome (e.g., knock-outs) or they may be engineered to have reduced, altered or enhanced activity. The phrases "recombinant host cell," "genetically engineered host cell," "engineered host cell," and "genetically modified host cell" refer not only to the particular subject host cell, but to the progeny or potential progeny of such a cell. Because certain modifications may occur in succeeding generations due to either mutation or environmental influences, such progeny may not, in fact, be identical to the parent cell, but are still included within the scope of the term(s) as used herein.

The terms "engineer," "genetically engineer," "modify," "genetically modify," and their grammatical equivalents as used herein can refer to any manipulation of a microorganism that results in a detectable change in the microorganism, where the manipulation includes, but is not limited to, introducing non-native metabolic functionality via heterologous (exogenous) polynucleic acids or removing native-functionality via polynucleic acid deletions, mutations or knock-outs. The term "metabolically engineered" generally involves rational pathway design and assembly of biosynthetic genes (or open reading frames), genes associated with operons, and control elements of such polynucleic acids, for the production of a desired metabolite. "Metabolically engineered" may further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway.

As used herein, the terms "genetic modification," "genetically modified" and their grammatical equivalents can refer to any modification of a polynucleic acid and/or polypeptide that results in an altered nucleic acid or polypeptide (i.e., relative to the wild-type nucleic acid or polypeptide sequence). Genetic modification includes, for example, point mutations, substitutions, deletions, or insertions of single or multiple residues in a polynucleic acid (or the encoded polypeptide), which includes alterations arising within a protein-encoding region of a gene as well as alterations in regions outside of a protein-encoding sequence, such as, but not limited to, regulatory or promoter sequences. A genetic modification may be an alteration of any type. For instance, the modification may be a deletion, insertion, mutation, rearrangement, or any combination thereof. In certain cases, a portion of a genetically modified microorganism's genome may be replaced with one or more heterologous (exogenous) polynucleic acids. In some cases, the modification is naturally-occurring. In other cases, the modification is the result of artificial selection pressure. In still other cases, the modification is the result of genetic engineering. One form of genetic modification is disruption, such as by knockout. As used herein, the term "introducing," as used in phrases such as "introducing into the host cell" at least one polynucleic acid includes methods known in the art for introducing polynucleic acids into a cell, including, but not limited to transformation (e.g., calcium chloride, electroporation), transduction, transfection, conjugation and the like.

The term "genetic modification" or "genetically modified" and their grammatical equivalents as used herein can refer to one or more alterations of a nucleic acid, e.g., the nucleic acid within a microorganism's genome. For example, genetic modification can refer to alterations, additions, and/or deletion of nucleic acid (e.g., whole genes or fragments of genes).

The term "disrupting" and its grammatical equivalents as used herein can refer to a process of altering a gene, e.g., by deletion, insertion, mutation, rearrangement, or any combination thereof. For example, a gene can be disrupted by knockout. Disrupting a gene can be partially reducing or completely suppressing expression (e.g., mRNA and/or protein expression) of the gene. Disrupting can also include inhibitory technology, such as shRNA, siRNA, microRNA, dominant negative, or any other means to inhibit functionality or expression of a gene or protein.

The term "gene editing" and its grammatical equivalents as used herein can refer to genetic engineering in which one or more nucleotides are inserted, replaced, or removed from a genome. For example, gene editing can be performed using a nuclease (e.g., a natural-existing nuclease or an artificially engineered nuclease).

As used herein, the term "endogenous," and its grammatical equivalents when used in reference to polynucleic acids (and the polypeptides encoded therein), can refer to polynucleic acids and polypeptides that are expressed in the organism in which they originated (i.e., they are innate to the organism). In contrast, the terms "heterologous" and "exogenous" are used interchangeably, and as defined herein with reference to polynucleic acids (and the polypeptides encoded therein), indicates polynucleic acids and polypeptides that are expressed in an organism other than the organism from which they (i.e., the polynucleic acid or polypeptide sequences) originated or where derived.

As used herein, the term "homolog" and its grammatical equivalents, as used with respect to an original protein, polypeptide, gene, or polynucleic acid (or ORF encoding the same) of a first family or species, can refer to distinct proteins, genes, or polynucleic acids of a second family or species that correspond (structurally, functionally, and/or genomically) to the original protein, gene, or polynucleic acid of the first family or species. Most often, "homologs" will have functional, structural or genomic similarities. Techniques are known by which homologs of a protein, gene or polynucleic acid can readily be cloned using genetic probes and PCR. Identity of cloned sequences as "homologs" can be confirmed using functional assays and/or by genomic mapping of the genes.

As used herein, the term "strong promoter" and its grammatical equivalents as used herein can refer to a promoter that has the ability to increase the transcription at a high level. For example, pMxaF, J2311, J12100, and J23102 each can be considered a strong promoter. As used herein, the term "weak promoter" and its grammatical equivalents as used herein can refer to a promoter that has the ability to increase the transcription, but at a low level. For example, pBAD, J23110, lacO, J23116, J23106, J23105, J23108, J23107, J23115, and J23114 can each be considered a weak promoter. Additionally, the term "medium strength promoter" and its grammatical equivalents, as used herein can refer to a promoter that has the ability to increase the transcription at a level that is less than what is considered high but higher than what is considered low. For example, J23118, J23104, J23101, J23119, and uMCA3034, can each be considered a medium strength promoter. In some cases, medium strength promoters can be used in lieu of strong or weak promoters.

The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C."

As used herein, the term "substantially similar" and its grammatical equivalents, when used in reference to the similarity between a sequence and a reference sequence, means that the sequences are at least 50% (but not 100%) identical. In some cases, the sequences are 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.9%, 99.99%, 99.999%, or 99.9999% identical. In some cases, the term substantially similar refers to a sequence that is at least 50% identical. In some instances, the term substantially similar refers to a sequence that is 55% identical. In some instances, the term substantially similar refers to a sequence that is 60% identical. In some instances, the term substantially similar refers to a sequence that is 65% identical. In some instances, the term substantially similar refers to a sequence that is 70% identical. In some instances, the term substantially similar refers to a sequence that is 75% identical. In some instances, the term substantially similar refers to a sequence that is 80% identical. In some instances, the term substantially similar refers to a sequence that is 81% identical. In some instances, the term substantially similar refers to a sequence that is 82% identical. In other instances, the term substantially similar refers to a sequence that is 83% identical. In other instances, the term substantially similar refers to a sequence that is 84% identical. In some instances, the term substantially similar refers to a sequence that is 85% identical. In some instances, the term substantially similar refers to a sequence that is 86% identical. In other instances, the term substantially similar refers to a sequence that is 87% identical. In other instances, the term substantially similar refers to a sequence that is 88% identical. In other instances, the term substantially similar refers to a sequence that is 89% identical. In some instances, the term substantially similar refers to a sequence that is 90% identical. In some instances, the term substantially similar refers to a sequence that is 91% identical. In some instances, the term substantially similar refers to a sequence that is 92% identical. In some instances, the term substantially similar refers to a sequence that is 93% identical. In some instances, the term substantially similar refers to a sequence that is 94% identical. In some instances, the term substantially similar refers to a sequence that is 95% identical. In some instances, the term substantially similar refers to a sequence that is 96% identical. In some instances, the term substantially similar refers to a sequence that is 97% identical. In some instances, the term substantially similar refers to a sequence that is 98% identical. In some instances, the term substantially similar refers to a sequence that is 99% identical. In some instances, the term substantially similar refers to a sequence that is 99.9% identical. In some instances, the term substantially similar refers to a sequence that is 99.99% identical. In some instances, the term substantially similar refers to a sequence that is 99.999% identical. In some instances, the term substantially similar refers to a sequence that is 99.9999% identical. To determine the percentage of identity between two sequences, the two sequences are aligned, using, for example, the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids/nucleotides is determined between the two sequences. Methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990:215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919) using a gap opening penalty of 10 and a gap extension penalty of 0.1, so that the highest order match obtained between two sequences where at least 50% of the total length of one of the two sequences is involved in the alignment.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

As will be apparent to those of skill in the art upon reading this disclosure, each of the individual cases described and illustrated herein has discrete components and features which may be readily separated from or combined with the features of any of the other several cases without departing from the scope or spirit of the present invention. Any recited method can be carried out in the order of events recited or in any other order which is logically possible.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

II. Genetically Modified Microorganisms and Methods of Making the Same

The present disclosure is directed, in part, to genetically modified microorganisms that have been modified using advanced genome editing techniques.

Microorganisms

In some cases, the microorganisms can use $C_1$ carbon substrates, such as CO, $CO_2$, and $CH_4$, to synthesize a desired end product. This, however, does not mean that these microorganisms use solely $C_1$ carbons. Some of the microorganisms can be made to utilize additional carbon substrates, including carbon substrates that the microorganism naturally uses. For example, if the microorganism naturally uses sugar for carbon substrates, this microorganism can be made to utilize a different carbon source such as a $C_1$ carbon.

The microorganisms can be a prokaryote or a eukaryote. In some cases, for example, the microorganisms can be bacteria, yeast, or algae.

Microorganisms that can convert $C_1$ carbon substrates into desired products include those capable of using natural gas as a carbon substrate. For example, the microorganism can use methane contained within the natural gas as a carbon source to make such desired products. Such microorganisms can include methanotrophs. Methanotrophs that can be particularly useful include those from the genera *Methylobacter, Methylomicrobium, Methylomonas, Methylocaldum, Methylococcus, Methylosoma. Methylosarcina, Methylothermus, Methylohalobius, Methylogaea, Methylovulum, Crenothrix, Clonothrix, Methylosphaera, Methylocapsa, Methylocella, Methylosinus, Methylocystis*, Methyloacidophilum, or any combinations thereof. In some cases, the methanotroph is from the genus *Methylococcus*. In one instance, the methanotroph can be a methanotroph from the species *Methylococcus capsulatus*. In some cases, the methanotroph can be an obligate methanotroph. In other cases, the methanotroph can be a facultative methanotroph.

Some microorganisms are capable of using $CO_2$ as a substrate. Such microorganisms include methanogens. Microorganisms that are capable of using $CO_2$ as a substrate can contain chlorophyll. Examples thereof include algae and cyanobacteria.

Some microorganisms are capable of using CO as a substrate. Examples include anaerobic microorganisms such as *Clostridium*. These microorganism can be genetically modified so as to make substantial amounts of 2,3-BDO In some cases, the microorganism used in the methods described throughout can be one that does not naturally express any Cas enzymes. In this case, any Cas enzymes that are present within the microorganism are heterologous to that microorganism.

In some cases, the heterologous Cas enzyme that is present within the microorganism can be expressed within a plasmid. The plasmids expressing the heterologous Cas enzyme can comprise a promoter, including but not limited to such promoters as a pMxaF or pBAD promoter. In some cases however, the plasmid does not comprise a strong promoter, for example a weak promoter. In some cases, the plasmid can comprise a mutated promoter. For example, the promoter can be a mutated promoter, such as a mutated pMxaF promoter. In some cases, the mutation contained in the promoter can make the promoter weaker.

Nucleic Acids Encoding for Enzymes

Certain enzymes can be used to generate useful chemical products. Some useful chemical products can include, but are not limited to, isobutanol, isobutyraldehyde, 2,3-butanediol (2,3-BDO), and 1,4-butanediol (1,4-BDO). In some cases, certain proteins, such as RNA polymerase beta-subunits (EC:2.7.7.6) (encoded by such genes as rpoB or rpoB2) can confer to a microorganism resistance to some antibiotics, such as rifampin. In some cases, the polynucleotide of the promoters or introns of these enzymes can be altered by using the techniques described throughout.

Isobutanol

In some cases, polynucleotides encoding for enzymes of the isobutanol pathway can be used. For example, the microorganism can contain (either endogenously or heterologous) one or more polynucleotides encoding for an acetolactate synthase (AlsS); ketol-acid reductoisomerase (KARI); dihydroxy-acid dehydratase (DHAD); 2-keto acid decarboxylase (KDC); and alcohol dehydrogenase (ADH). One or more of the polynucleotides can be native to the microorganism. In some cases, one or more of the polynucleotides can be heterologous to the microorganism.

In some cases, the acetolactate synthase (AlsS) can be encoded by a polynucleotide that is substantially similar to a gram positive bacterium AlsS gene. In some cases, the AlsS can be encoded by a polynucleotide that is substantially similar to SEQ ID NO: 1. In some other cases, the AlsS can be encoded by a polynucleotide that is substantially similar to SEQ ID NO: 2.

In some cases, the ketol-acid reductoisomerase can be encoded by a polynucleotide that is substantially similar to a gram negative bacterium ketol-acid reductoisomerase gene. In some cases, the ketol-acid reductoisomerase can be encoded by a polynucleotide that is substantially similar to SEQ ID NO: 3.

In some cases, the dihydroxy-acid dehydratase can be encoded by a polynucleotide that is substantially similar to a gram negative bacterium dihydroxy-acid dehydratase gene. In some cases, the dihydroxy-acid dehydratase can be encoded by a polynucleotide that is substantially similar to SEQ ID NO: 4. In some cases, the dihydroxy-acid dehydratase can be encoded by a polynucleotide that is substantially similar to SEQ ID NO: 5.

In some cases, the 2-keto acid decarboxylase (KDC) can be encoded by a polynucleotide that is substantially similar to a gram positive bacterium KDC gene. In some cases, the KDC can be encoded by a polynucleotide that is substantially similar to any one of SEQ ID NOs: 6 to 29.

In some cases, the alcohol dehydrogenase (ADH) can be encoded by a polynucleotide that is substantially similar to a gram positive or gram negative bacterium ADH gene. In some cases, the ADH can be encoded by a polynucleotide that is substantially similar to any one of SEQ ID NOS: 30 to 48.

In some cases, the promoters and/or the introns of the isobutanol pathway genes can be altered using the advance genome editing tools described herein. This alteration may enhance the expression of the genes that are controlled by the promoters and/or introns. In some cases, the alternation may inhibit the expression of the genes that are controlled by the promoters and/or introns.

In some cases, the codons can be optimized based on the microorganism in which the genes will be provided or the enzymes will be expressed.

Isobutyraldehyde

In some instances, polynucleotides encoding enzymes of the isobutyraldehyde pathway can be used. For example, the microorganism can contain (either endogenously or heterologous) one or more polynucleotides encoding for an acetolactate synthase (AlsS); ketol-acid reductoisomerase; dihydroxy-acid dehydratase; and 2-keto acid decarboxylase (KDC). One or more of the polynucleotides can be native to the microorganism. In some cases, one or more of the polynucleotides can be heterologous to the microorganism.

In some cases, the acetolactate synthase (AlsS) can be encoded by a polynucleotide that is substantially similar to a gram positive bacterium AlsS gene. In some cases, the AlsS can be encoded by a polynucleotide that is substantially similar to SEQ ID NO: 1. In some other cases, the AlsS can be encoded by a polynucleotide that is substantially similar to SEQ ID NO: 2.

In some cases, the ketol-acid reductoisomerase can be encoded by a polynucleotide that is substantially similar to a gram negative bacterium ketol-acid reductoisomerase gene. In some cases, the ketol-acid reductoisomerase can be encoded by a polynucleotide that is substantially similar to SEQ ID NO: 3.

In some cases, the dihydroxy-acid dehydratase can be encoded by a polynucleotide that is substantially similar to a gram negative bacterium dihydroxy-acid dehydratase gene. In some cases, the dihydroxy-acid dehydratase can be encoded by a polynucleotide that is substantially similar to SEQ ID NO: 4. In some cases, the dihydroxy-acid dehydratase can be encoded by a polynucleotide that is substantially similar to SEQ ID NO: 5.

In some cases, the 2-keto acid decarboxylase (KDC) can be encoded by a polynucleotide that is substantially similar to a gram positive bacterium KDC gene. In some cases, the KDC can be encoded by a polynucleotide that is substantially similar to any one of SEQ ID NOs: 6 to 29.

In some cases, the promoters and/or the introns of the isobutyraldehyde pathway genes can be altered using the advance genome editing tools described herein. This alteration may enhance the expression of the genes that are controlled by the promoters and/or introns. In some cases, the alternation may inhibit the expression of the genes that are controlled by the promoters and/or introns.

In some cases, the codons can be optimized based on the microorganism in which the genes will be provided or the enzymes will be expressed.

2,3-BDO

In some instances, polynucleotides encoding enzymes of the 2,3-BDO pathway can be used. For example, the microorganism can contain (either endogenously or heterologous) one or more polynucleotides encoding for an acetolactate synthase (AlsS), alpha-acetolactate decarboxylase (budA), and/or acetoin reductase. One or more of the polynucleotides can be native to the microorganism. In some cases, one or more of the polynucleotides can be heterologous to the microorganism.

In some cases, the acetolactate synthase can be encoded by a polynucleotide that is substantially similar to any one of SEQ ID NOs: 49 to 51.

In some cases, the alpha-acetolactate decarboxylase can be encoded by a polynucleotide that is substantially similar to SEQ ID NO: 52 or 53.

In some cases, the acetoin reductase can be encoded by a polynucleotide that is substantially similar to any one of SEQ ID NOs: 54 to 56. In some cases, the acetoin reductase can be NADPH-dependent. In some cases, the acetoin reductase can be NADH-dependent.

In some cases, the promoters and/or the introns of the 2,3-BDO pathway genes can be altered using the advance genome editing tools described herein.

In some cases, the codons can be optimized based on the microorganism in which the genes will be provided or the enzymes will be expressed.

1,4-BDO

In some instances, polynucleotides encoding enzymes of the 1,4-BDO pathway can be used. For example, the microorganism can contain (either endogenously or heterologous) one or more polynucleotides encoding for a pyruvate dehydrogenase (aceEF), citrate synthase (gltA), aconitate hydratase 1 (acnA), isocitrate dehydrogenase (icdA), α-ketoglutarate decarboxylase (kgd), succinyl-CoA synthetase (sucC), CoA-dependent succinate semialdehyde dehydrogenase (sucD), 4-hyrobutyrate dehydrogenase (4hbD), 4-hydroxybutyryl-CoA transferase (cat2), aldehyde dehydrogenase (ald), and/or alcohol dehydrogenase (adh).

In some cases, the α-ketoglutarate decarboxylase (kgd) can be encoded by a polynucleotide that is substantially similar to any one of SEQ ID NOs: 57 to 60.

In some cases, the 4-hydroxybutyrate dehydrogenase (4hbD) can be encoded by a polynucleotide that is substantially similar to SEQ ID NO. 61 or 62.

In some cases, the 4-hydroxybutyrate CoA transferase (Cat2) can be encoded by a polynucleotide that is substantially similar to any one of SEQ ID NOs: 63 to 65.

In some cases, the aldehyde dehydrogenase gene and/or alcohol dehydrogenase can be encoded by a polynucleotide that is substantially similar to any one of SEQ ID NOs: 66 to 73.

In some cases, the succinyl CoA synthease beta subunit (sucC) can be encoded by a polynucleotide that is substantially similar to SEQ ID NO: 74.

In some cases, the succinyl CoA synthease alpha subunit (sucD) can be encoded by a polynucleotide that is substantially similar to any one of SEQ ID NOs: 75 to 77.

In some cases, the promoters and/or the introns of the 1,4-BDO pathway genes can be altered using the advance genome editing tools described herein.

In some cases, the codons can be optimized based on the microorganism in which the genes will be provided or the enzymes will be expressed.

RNA Polymerase Beta-Subunits

In some cases, polynucleotides encoding for RNA polymerase beta-subunits can be used. RNA polymerase beta-subunits (e.g., those with an EC:2.7.7.6) can be used to confer onto a microorganism resistance to some antibiotics, such as rifampin. In some cases, RNA polymerase beta-subunits can be expressed endogenously by a microorganism. Repression or knocking out of the genes encoding RNA polymerase beta-subunits (including but not limited to RNA polymerase beta-subunits encoded by such genes as rpoB or rpoB2) can lead to the loss of resistance to such antibiotics, such as rifampin. In these cases, repressing or knocking out of the genes encoding RNA polymerase beta-subunits can lead to cell death.

The microorganism can contain (either endogenously or heterologous) one or more polynucleotides encoding for RNA polymerase beta-subunits. One or more of the polynucleotides can be native to the microorganism. In some cases, one or more of the polynucleotides can be heterologous to the microorganism.

In some cases, the RNA polymerase beta-subunits can be encoded by a polynucleotide that is substantially similar to SEQ ID NO: 123 or 126. In some cases, the gRNA used can be substantially similar to SEQ ID NO: 124 or 125.

In some cases, the donor DNA can be substantially similar to SEQ ID NO: 126.

In some cases, the promoters and/or the introns of the RNA polymerase beta-subunits gene(s) can be altered using the advance genome editing tools described herein. This alteration may enhance the expression of the genes that are controlled by the promoters and/or introns. In some cases, the alternation may inhibit the expression of the genes that are controlled by the promoters and/or introns.

In some cases, the codons can be optimized based on the microorganism in which the genes will be provided or the enzymes will be expressed.

Vectors

Since Cas enzymes are not native to some microorganisms, expression vectors can be used to express Cas enzymes within most microorganisms and cells. Methylotrophs such as methanotrophs do not naturally express Cas enzymes. Therefore, in some cases, the Cas enzymes can be expressed using certain expression vectors. Vector constructs prepared for introduction into the host microorganisms described throughout may typically, but not always, comprise a replication system (i.e. vector) recognized by the host. In some cases, the vector includes the intended polynucleotide fragment encoding the desired polypeptide and, optionally, transcription and translational initiation regulatory sequences operably linked to the polypeptide-encoding segment. Expression vectors may include, for example, an origin of replication or autonomously replicating sequence (ARS), expression control sequences, a promoter, an enhancer and necessary processing information sites, such as ribosome-binding sites, RNA splice sites, polyadenylation sites, transcriptional terminator sequences, mRNA stabilizing sequences, polynucleotides homologous to host chromosomal DNA, and/or a multiple cloning site. Signal peptides may also be included where appropriate, preferably from secreted polypeptides of the same or related species, which allow the protein to cross and/or lodge in cell membranes or be secreted from the cell.

The vectors can be constructed using standard methods (see, e.g., Sambrook et al., Molecular Biology: A Laboratory Manual, Cold Spring Harbor, N.Y. 1989; and Ausubel, et al., Current Protocols in Molecular Biology, Greene Publishing, Co. N.Y, 1995).

Manipulation of polynucleotides that encode the enzymes disclosed throughout is typically carried out in recombinant vectors. Vectors which may be employed include bacterial plasmids, bacteriophage, artificial chromosomes, episomal vectors and gene expression vectors. Vectors may be selected to accommodate a polynucleotide encoding a protein of a desired size. Following production of a selected vector, a suitable host cell (e.g., the microorganisms described herein) is transfected or transformed with the vector. Each vector contains various functional components, which generally include a cloning site, an origin of replication and at least one selectable marker gene. A vector may additionally possess one or more of the following elements: an enhancer, promoter, a transcription termination sequence and/or other signal sequences. Such sequence elements may be optimized for the selected host species. Such sequence elements may be positioned in the vicinity of the cloning site, such that they are operatively linked to the gene encoding a preselected enzyme.

Vectors, including cloning and expression vectors, may contain polynucleotides that enable the vector to replicate in one or more selected microorganisms. For example, the sequence may be one that enables the vector to replicate independently of the host chromosomal DNA and may include origins of replication or autonomously replicating sequences. Such sequences are well known for a variety of bacteria, yeast and viruses. For example, the origin of replication from the plasmid pBR322 is suitable for most gram-negative bacteria, the origin of replication for 2 micron plasmid is suitable for yeast, and various viral origins of replication (e.g. SV40, adenovirus) are useful for cloning vectors.

A cloning or expression vector may contain a selection gene, also referred to as a selectable marker. This gene encodes a protein necessary for the survival or growth of transformed microorganisms in a selective culture medium. Microorganisms not transformed with the vector containing the selection gene will therefore not survive in the culture medium. Typical selection genes encode proteins that confer resistance to antibiotics and other toxins, e.g. ampicillin, neomycin, methotrexate, hygromycin, thiostrepton, apramycin or tetracycline, complement auxotrophic deficiencies, or supply critical nutrients not available in the growth media.

The replication of vectors may be performed in *E. coli*. An example of a *E. coli*-selectable marker is the β-lactamase gene, which confers resistance to the antibiotic ampicillin. These selectable markers can be obtained from *E. coli* plasmids, such as pBR322 or a pUC plasmid such as pUC18 or pUC19, or pUC119.

The vectors of the present invention can comprise one or more switches, such as an inducible or repressible switch, e.g., an arabinose or lanthanum switch. The vectors can also comprise one or more different/same promoters.

Promoters

Vectors may contain a promoter that is recognized by the host microorganism. The promoter may be operably linked to a coding sequence of interest. Such a promoter may be inducible or constitutive. Polynucleotides are operably linked when the polynucleotides are in a relationship permitting them to function in their intended manner.

Different promoters can be used to drive the expression of the genes. For example, if temporary gene expression (i.e., non-constitutively expressed) is desired, expression can be driven by inducible promoters.

In some cases, the desired gene is expressed temporarily. In other words, the desired gene is not constitutively expressed. The expression of the desired gene can be driven by inducible or repressible promoters. Examples of inducible or repressible promoters include, but are not limited to, those promoters inducible or repressible by: (a) sugars such as arabinose and lactose (or non-metabolizable analogs, e.g., isopropyl β-D-1-thiogalactopyranoside (IPTG)); (b) metals such as rare earth metals (e.g., lanthanum or cerium), copper, and calcium; (c) temperature; (d) nitrogen-source; (e) oxygen; (f) cell state (growth or stationary); (g) metabolites such as phosphate; (h) CRISPRi; (i) jun; (j) fos; (k) metallothionein, and/or (l) heat shock. These promoters can be used in a methanotroph system. An example of an inducible promoter that can be used within methanotrophs is a pBAD promoter.

Inducible or repressible promoters that can be particularly useful are sugar and rare earth metal switches. For example, promoters that are sensitive to the sugar arabinose can be used as an inducible switch. In some cases, arabinose switches can be used to drive expression of one or more genes. For example, in the presence arabinose, a desired vector or expression of a gene set can be "turned-on." The arabinose switch can turn on the expression of a desired gene.

Other particularly useful switches can be rare earth metal switches, such as lanthanum switches. In some cases, the lanthanum switch can be a repressible switch that can be used to repress expression of one or more genes, until the repressor is removed, after which the genes are "turned-on". For example, in the presence the metal lanthanum, the desired gene set or vector can be "turned-off." The lanthanum switch can turned off (and expression of the genes induced) by either removing the lanthanum from the media or diluting the lanthanum in the media to levels where its repressible effects are reduced, minimized, or eliminated.

Constitutively expressed promoters can also be used in the vector systems herein. For example, the expression of one or more desired genes can be controlled by constitutively active promoters. Examples of such promoters include but are not limited to pMxaF and p.Bba.J23111.

Promoters suitable for use with prokaryotic hosts may include, for example, the α-lactamase and lactose promoter systems, alkaline phosphatase, the tryptophan (trp) promoter system, the erythromycin promoter, apramycin promoter, hygromycin promoter, methylenomycin promoter and hybrid promoters such as the tac promoter. Promoters for use in bacterial systems will also generally contain a Shine-Dalgarno sequence operably linked to the coding sequence.

Generally, a strong promoter may be employed to provide for high level transcription and expression of the desired product. For example, promoters that can be used include but are not limited to a pMxaF promoter. In some cases, a mutation can increase the strength of the promoter and therefore result in elevated levels of expression.

In some cases however, a weaker promoter is desired. For example, this is the case where too much expression of a certain gene results in a detrimental effect (e.g., the killing of cells). A weak promoter can be used, for example, a pBAD promoter. However, in some cases, a weaker promoter can be made by mutation. For example, the pMxaF promoters can be mutated to be weaker.

One or more promoters of a transcription unit can be an inducible promoter. For example, a green fluorescent protein (GFP) can be expressed from a constitutive promoter while an inducible promoter is used to drive transcription of a gene coding for one or more enzymes as disclosed herein and/or the amplifiable selectable marker.

Some vectors may contain prokaryotic sequences that facilitate the propagation of the vector in bacteria. Thus, the vectors may have other components such as an origin of replication (e.g., a polynucleotide that enables the vector to replicate in one or more selected microorganisms), antibiotic resistance genes for selection in bacteria, and/or an amber stop codon which can permit translation to read through the codon. Additional selectable gene(s) may also be incorporated. Generally, in cloning vectors, the origin of replication is one that enables the vector to replicate independently of the host chromosomal DNA, and includes origins of replication or autonomously replicating sequences. Such sequences can include the ColEl origin of replication in bacteria or other known sequences.

Genes

The genes described throughout all have a promoter driving their expression. The methods described herein, e.g., genome editing and expression inhibition using Cas, can be used to edit the polynucleotide of the promoters or used to inhibit the effectiveness of the promoters. Inhibition can be done by blocking the transcription machinery (e.g., transcription factors) from binding to the promoter or by altering the promoter in such a way that the transcription machinery no longer recognizing the promoter sequence.

The vectors described throughout can also comprise a polynucleotide encoding for one or more of the genes within the 2,3-butanediol (2,3-BDO), 1,4-butanediol (1,4-BDO), isobutyraldehyde, or isobutanol pathway. The vectors described throughout can also comprise a polynucleotide encoding for an RNA polymerase beta-subunit. These vectors can also contain one or more regulatory elements (inducible and/or repressible promoters) that control the expression of the genes within the vectors. In some cases, the switches that can be used include, but are not limited to, inducible or repressible switches, e.g., an arabinose or lanthanum switches. These genes can be heterologous to the microorganism in which the vector is contacted with (and eventually transformed with).

The genes used in the vectors can be any genes described throughout the application. For example, the genes of the 2,3-BDO, 1,4-BDO, isobutanol, and/or isobutyraldehyde pathways. These enzymes can be encoded by a polynucleotide that is at least 60%, 65%, 70%, 75%, 80%, 85%, 90%, 91%, 92%, 93%, 94%, 95%, 96%, 97%, 98%, 99%, 99.9%, 99.99%, 99.999%, or 99.9999% identical to any one of SEQ ID NOs: 1 to 77. In some cases, the RNA polymerase beta-subunit genes can be used in the vectors. This enzyme can be encoded by a polynucleotide that is at least 60%, 65%, 70%, 75%, 80%, 85%, 90%, 91%, 92%, 93%, 94%, 95%, 96%, 97%, 98%, 99%, 99.9%, 99.99%, 99.999%, or 99.9999% identical to SEQ ID NOs: 123 or 126.

The genes that are inserted into a microorganism can be heterologous to the microorganism itself. For example, if the microorganism is a methanotroph, the inserted genes can, for example, be from yeast, a bacterium, or a different species of methanotroph. Further, the genes can be endogenously part of the genome of the microorganism.

III. Techniques for Genetic Modification

The microorganisms disclosed herein may be genetically engineered by using classic microbiological techniques. These classical techniques can be in addition to the advanced genome editing techniques. Some of such classical techniques are generally disclosed, for example, in Sambrook et al., 1989, Molecular Cloning: A Laboratory Manual, Cold Spring Harbor Labs Press.

The genetically modified microorganisms disclosed herein may include a polynucleotide that has been inserted, deleted or modified (i.e., mutated; e.g., by insertion, deletion, substitution, and/or inversion of nucleotides), in such a manner that such modifications provide the desired effect of expression (e.g., over-expression or decreased expression) of one or more enzymes as provided herein within the microorganism. Genetic modifications which result in an increase in gene expression or function can be referred to as amplification, overproduction, overexpression, activation, enhancement, addition, or up-regulation of a gene. Addition of a gene to increase expression can include maintaining the gene(s) on replicating plasmids or integrating the cloned gene(s) into the genome of the production microorganism. Furthermore, increasing the expression of desired genes can include operatively linking the cloned gene(s) to native or heterologous transcriptional control elements. Additionally, increasing expression of a desired gene can also include modifying the promoter region of the gene. Genetic modifications which result in a decrease in gene expression or function can be referred to as reduction, repression, underproduction, deactivation, deletion, or down-regulation of a gene. In some cases, the genetic modification which results in a decrease in gene expression or function can be complete elimination of gene expression (knockout) or partial elimination of gene expression (knockdown—e.g., via RNAi).

Where desired, the expression of one or more of the enzymes provided herein is under the control of a regulatory sequence that controls directly or indirectly the enzyme expression in a time-dependent fashion during the fermentation. Inducible promoters can be used to achieve this. As discussed throughout, the methods described herein can be used to alter the polynucleotide of the promoters.

In some cases, a microorganism is transformed or transfected with a genetic vehicle, such as an expression vector comprising a heterologous polynucleotide encoding for the enzymes as provided herein. In some cases, the heterologous polynucleotide encoding for the enzymes throughout can be altered using the techniques described throughout, before or after, the heterologous enzyme is placed within the microorganism.

To facilitate insertion and expression of different genes coding for the enzymes as disclosed herein from the constructs and expression vectors, the constructs may be designed with at least one cloning site for insertion of any gene coding for any enzyme disclosed herein. The cloning site may be a multiple cloning site, e.g., containing multiple restriction sites.

Transfection

Standard transfection techniques can be used to insert genes into a microorganism. As used herein, the term "transfection" or "transformation" can refer to the insertion of an exogenous nucleic acid or polynucleotide into a host cell. The exogenous nucleic acid or polynucleotide may be maintained as a non-integrated vector, for example, a plasmid, or alternatively, may be integrated into the host cell genome. The term transfecting or transfection is intended to encompass all conventional techniques for introducing nucleic acid or polynucleotide into microorganisms. Examples of transfection techniques include, but are not limited to, calcium phosphate precipitation, DEAE-dextran-mediated transfection, lipofection, electroporation, microinjection, rubidium chloride or polycation mediated transfection, protoplast fusion, and sonication. The transfection method that provides optimal transfection frequency and expression of the construct in the particular host cell line and type is favored. For stable transfectants, the constructs are integrated so as to be stably maintained within the host chromosome. In some cases, the preferred transfection is a stable transfection.

Transformation

Expression vectors or other nucleic acids may be introduced to selected microorganisms by any of a number of suitable methods. For example, vector constructs may be introduced to appropriate cells by any of a number of transformation methods for plasmid vectors. Standard calcium-chloride-mediated bacterial transformation is still commonly used to introduce naked DNA to bacteria (see, e.g., Sambrook et al., 1989, Molecular Cloning, A Laboratory Manual, Cold Spring Harbor Laboratory Press, Cold Spring Harbor, N.Y.), but electroporation and conjugation may also be used (see, e.g., Ausubel et al., 1988, Current Protocols in Molecular Biology, John Wiley & Sons, Inc., NY, N.Y.).

For the introduction of vector constructs to yeast or other fungal cells, chemical transformation methods may be used (e.g., Rose et al., 1990, Methods in Yeast Genetics, Cold Spring Harbor Laboratory Press, Cold Spring Harbor, N.Y.). Transformed cells may be isolated on selective media appropriate to the selectable marker used. Alternatively, or in addition, plates or filters lifted from plates may be scanned for GFP fluorescence to identify transformed clones.

For the introduction of vectors comprising differentially expressed sequences to certain types of cells, the method used may depend on the form of the vector. Plasmid vectors may be introduced by any of a number of transfection methods, including, for example, lipid-mediated transfection ("lipofection"), DEAE-dextran-mediated transfection, electroporation or calcium phosphate precipitation (see, e.g., Ausubel et al., 1988, Current Protocols in Molecular Biology, John Wiley & Sons, Inc., NY, N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. Many companies offer kits and ways for this type of transfection.

The host cell may be capable of expressing the construct encoding the desired protein, processing the protein and transporting a secreted protein to the cell surface for secretion. Processing includes co- and post-translational modification such as leader peptide cleavage, GPI attachment, glycosylation, ubiquitination, and disulfide bond formation.

Microorganisms can be transformed or transfected with the above-described expression vectors or polynucleotides coding for one or more enzymes as disclosed herein and cultured in nutrient media modified as appropriate for the specific microorganism, inducing promoters, selecting transformants, or amplifying the genes encoding the desired sequences. In some cases, electroporation methods can be used to deliver an expression vector.

Expression of a vector (and the gene contained in the vector) can be verified by an expression assay, for example, qPCR or by measuring levels of RNA. Expression level can be indicative also of copy number. For example, if expression levels are extremely high, this can indicate that more than one copy of a gene was integrated in a genome. Alternatively, high expression can indicate that a gene was integrated in a highly transcribed area, for example, near a highly expressed promoter. Expression can also be verified by measuring protein levels, such as through Western blotting.

CRISPR Cas

The methods disclosed throughout can involve pinpoint nucleotide replacement, pinpoint insertion of one or more nucleotides (e.g., addition of genes or parts of genes) or the pinpoint deletion of one or more nucleotide (e.g., deletion of genes or parts of genes). Methods described herein can use a CRISPR/cas system. For example, double-strand breaks (DSBs) can be generated using a CRISPR/cas system, e.g., a type II CRISPR/cas system. A Cas enzyme used in the methods disclosed herein can be Cas9, which catalyzes DNA cleavage. Enzymatic action by Cas9 from *Streptococcus pyogenes* or any closely related Cas9 can generate double stranded breaks at target site sequences which hybridize to 20 nucleotides of a guide sequence and have a protospacer-adjacent motif (PAM) following the 20 nucleotides of the target sequence.

A vector can also encode a Cas enzyme. Cas enzymes that can be used include class 1 and class 2. Non-limiting examples of Cas enzymes include Cas1, Cas1B, Cas2, Cas3, Cas4, Cas5, Cas5d, Cas5t, Cas5h, Cas5a, Cas6, Cas7, Cas8, Cas9 (also known as Csn1 or Csx12), Cas10, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Csd1, Csd2, Cst1, Cst2, Csh1, Csh2, Csa1, Csa2, Csa3, Csa4, Csa5, C2c1, C2c2, C2c3, Cpf1, CARF, DinG, homologues thereof, or modified versions thereof. An unmodified Cas enzyme can have DNA cleavage activity. A Cas enzyme can direct cleavage of one or both strands at a target sequence, such as within a target sequence and/or within a complement of a target sequence. For example, a Cas enzyme can direct cleavage of one or both strands within 1, 2, 3, 4, 5, 6, 7, 8, 9, 10, 15, 20, 25, 30, 35, 40, 45, 50, 60, 70, 80, 90, 100, 125, 150, 175, 200, 300, 400, 500, or more base pairs from the first or last nucleotide of a target sequence. A vector that encodes a Cas enzyme that is mutated with respect to a corresponding wild-type enzyme such that the mutated Cas enzyme lacks the ability to cleave one or both strands of a target polynucleotide containing a target sequence can be used. Additionally, a modified Cas enzyme that lacks the ability to cleave but has the ability to block binding of the transcriptional machinery can be used.

A vector that encodes a Cas enzyme comprising one or more nuclear localization sequences (NLSs) can be used. For example, there can be 1, 2, 3, 4, 5, 6, 7, 8, 9, 10 NLSs used. A Cas enzyme can comprise the NLSs at or near the ammo-terminus (e.g., 1, 2, 3, 4, 5, 6, 7, 8, 9, 10 NLSs), or at or near the carboxy-terminus (e.g., 1, 2, 3, 4, 5, 6, 7, 8, 9, 10 NLSs), or any combination of these (e.g., one or more NLS at the ammo-terminus and one or more NLS at the carboxy terminus). When more than one NLS is present, each can be selected independently of others, such that a single NLS can be present in more than one copy and/or in combination with one or more other NLSs present in one or more copies.

Cas enzyme used in the methods can comprise at most 6 NLSs. An NLS is considered near the N- or C-terminus when the nearest amino acid to the NLS is within 50 amino acids along a polypeptide chain from the N- or C-terminus, e.g., within 1, 2, 3, 4, 5, 10, 15, 20, 25, 30, 40, or 50 amino acids.

Guide RNA

As used herein, the term "guide RNA" (gRNA) and its grammatical equivalents can refer to an RNA which can be specific for a target DNA and can form a complex with Cas enzyme. An RNA/Cas complex can assist in "guiding" Cas enzyme to a target DNA.

A method disclosed herein also can comprise introducing into a microorganism at least one guide RNA or other nucleic acid, e.g., DNA encoding at least one guide RNA. A guide RNA can interact with a RNA-guided endonuclease to direct the endonuclease to a specific target site, at which site the 5' end of the guide RNA base pairs with a specific protospacer sequence in a chromosomal sequence.

A guide RNA can comprise two RNAs, e.g., CRISPR RNA (crRNA) and transactivating crRNA (tracrRNA). A guide RNA can sometimes comprise a single-chain RNA, or single guide RNA (sgRNA) formed by fusion of a portion (e.g., a functional portion) of crRNA and tracrRNA. A guide RNA can also be a dualRNA comprising a crRNA and a tracrRNA. Furthermore, a crRNA can hybridize with a target DNA.

As discussed above, a guide RNA can be an expression product. For example, a DNA that encodes a guide RNA can be a vector comprising a sequence coding for the guide RNA. A guide RNA can be transferred into a microorganism by transfecting the microorganism with an isolated guide RNA or plasmid DNA comprising a sequence encoding for the guide RNA and a promoter. A guide RNA can also be transferred into a microorganism in other ways, such as using virus-mediated gene delivery.

A guide RNA can be isolated. For example, a guide RNA can be transfected in the form of an isolated RNA into a microorganism. A guide RNA can be prepared by in vitro transcription using any in vitro transcription system. A guide RNA can be transferred to a microorganism in the form of isolated RNA rather than in the form of plasmid comprising encoding sequence for a guide RNA.

A guide RNA can comprise three regions: a first region at the 5' end that can be complementary to a target site in a chromosomal sequence; a second internal region that can form a stem loop structure; and a third 3' region that can be single-stranded. A first region of each guide RNA can also be different such that each guide RNA guides a fusion protein to a specific target site. Further, second and third regions of each guide RNA can be identical in all guide RNAs.

A first region of a guide RNA can be complementary to sequence at a target site in a chromosomal sequence such that the first region of the guide RNA can base pair with the target site. In some cases, a first region of a guide RNA can comprise from 10 nucleotides to 25 nucleotides (i.e., from 10 nts to 25 nts; or 10 nts to 25 nts; or from 10 nts to 25 nts; or from 10 nts to 25 nts) or more. For example, a region of base pairing between a first region of a guide RNA and a target site in a chromosomal sequence can be 10, 11, 12, 13, 14, 15, 16, 17, 18, 19, 20, 22, 23, 24, 25, or more nucleotides in length. Sometimes, a first region of a guide RNA can be 19, 20, or 21 nucleotides in length.

A guide RNA can also comprises a second region that forms a secondary structure. For example, a secondary structure formed by a guide RNA can comprise a stem (or hairpin) and a loop. A length of a loop and a stem can vary. For example, a loop can range from 3 to 10 nucleotides in length, and a stem can range from 6 to 20 base pairs in length. A stem can comprise one or more bulges of 1 to 10 nucleotides. The overall length of a second region can range from 16 to 60 nucleotides in length. For example, a loop can be 4 nucleotides in length and a stem can be 12 base pairs.

A guide RNA can also comprise a third region at the 3' end that can be essentially single-stranded. For example, a third region is sometimes not complementarity to any chromosomal sequence in a cell of interest and is sometimes not complementarity to the rest of a guide RNA. Further, the length of a third region can vary. A third region can be more than 4 nucleotides in length. For example, the length of a third region can range from 5 to 60 nucleotides in length.

A guide RNA can be introduced into a microorganism as an RNA molecule. For example, a RNA molecule can be transcribed in vitro and/or can be chemically synthesized. An RNA can be transcribed from a synthetic DNA molecule, e.g., a gBlocks® gene fragment. A guide RNA can then be introduced into a microorganism as an RNA molecule. A guide RNA can also be introduced into a microorganism in the form of a non-RNA nucleic acid molecule, e.g., DNA molecule. For example, a DNA encoding a guide RNA can be operably linked to promoter control sequence for expression of the guide RNA in a microorganism of interest. A RNA coding sequence can be operably linked to a promoter sequence that is recognized by an RNA polymerase. Plasmid vectors that can be used to express guide RNA include, but are not limited to, px330 vectors and px333 vectors. In some cases, a plasmid vector (e.g., px333 vector) can comprise two guide RNA-encoding DNA sequences.

A DNA sequence encoding a guide RNA can also be part of a vector. Further, a vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. A DNA molecule encoding a guide RNA can also be linear. A DNA molecule encoding a guide RNA can also be circular.

When DNA sequences encoding an RNA-guided endonuclease and a guide RNA are introduced into a cell, each DNA sequence can be part of a separate molecule (e.g., one vector containing an RNA-guided endonuclease coding sequence and a second vector containing a guide RNA coding sequence) or both can be part of a same molecule (e.g., one vector containing coding (and regulatory) sequence for both an RNA-guided endonuclease and a guide RNA).

Donor DNA

As used herein, the term "donor DNA" and its grammatical equivalents can refer to a polynucleotide that provides a template for "repair" during the insertion of one or more nucleotides during genome editing. For example, the Cas9 enzyme can provide specific double stranded DNA breaks using a guide RNA. Should one or more nucleotides be desired to be inserted into this double stranded break, the donor DNA can be used. The donor DNA can be inserted into the double stranded break site. Further, a single strand of DNA can be provided at the break site and a microorganism's repair mechanisms can be used to complete the full insertion of a double stranded DNA.

Timing of Transformation

The timing of the expression of the specific components used in genome editing can be important in its efficacy. For example, for some microorganisms, transformation of plasmids expressing a Cas protein, guide RNA, and/or donor DNA can be simultaneously introduced into the microorganism and effectively be used to insert or delete one or more nucleotides.

However, for certain microorganisms that are capable of converting a $C_1$ carbon into a product, e.g., methanotrophs, the order in which a Cas protein, guide RNA, and/or donor DNA are transformed into the microorganism makes a significant difference in the effectiveness of genome editing as well as survival of the microorganism. For example, the transformation of Cas proteins prior to the transformation of the guide RNA and/or donor DNA results in an increased amount of cell death and decreased editing efficiency. To increase editing efficiency and to reduce unwanted cell death, the microorganisms can be transformed with a guide RNA and/or donor DNA prior to the transformation of a Cas protein.

In some cases, the guide RNA, donor DNA, and/or Cas enzyme, are found on separate plasmids/vectors. In some cases, the guide RNA and donor DNA are on a single plasmid/vector, while the Cas enzyme is expressed from a separate plasmid/vector. In some cases, the guide RNA is expressed on a single plasmid/vector, while the donor DNA and Cas enzyme are expressed on a separate plasmid/vector.

In some cases, the donor DNA is expressed on a single plasmid/vector, while the guide RNA and Cas enzyme are expressed on a separate plasmid/vector.

In some cases, the guide RNA and Cas enzyme can be controlled by different promoters. For example, in some cases, the guide RNA can be controlled by a constitutively expressed promoter while the expression of the Cas enzyme is controlled by an inducible promoter. In some cases, should a donor DNA be required, it can be expressed under the control of either a constitutively expressed promoter or an inducible promoter. This, in some cases, can allow for transformation of a microorganism with guide RNA and Cas enzyme (and optionally donor DNA) at the same time.

Site-Specific Insertion

Insertion of the one or more nucleotides (e.g., genes) can be site-specific. For example, one or more nucleotides (e.g., genes) can be inserted adjacent to a promoter.

Modification of a targeted locus of a microorganism can be produced by introducing DNA into microorganisms, where the DNA has homology to the target locus. DNA can include a marker gene, allowing for selection of cells comprising the integrated construct. Homologous DNA in a target vector can recombine with DNA at a target locus. A marker gene can be flanked on both sides by homologous DNA sequences, a 3' recombination arm, and a 5' recombination arm.

A variety of enzymes can catalyze insertion of foreign DNA into a microorganism genome. For example, site-specific recombinases can be clustered into two protein families with distinct biochemical properties, namely tyrosine recombinases (in which DNA is covalently attached to a tyrosine residue) and serine recombinases (where covalent attachment occurs at a serine residue). In some cases, recombinases can comprise Cre, fC31 integrase (a serine recombinase derived from *Streptomyces* phage fC31), or bacteriophage derived site-specific recombinases (including Flp, lambda integrase, bacteriophage HK022 recombinase, bacteriophage R4 integrase and phage TP901-1 integrase).

The CRISPR/Cas system can be used to perform site specific insertion. For example, a nick on an insertion site in the genome can be made by CRISPR/Cas to facilitate the insertion of a transgene at the insertion site.

The techniques which can be used to allow a DNA or RNA construct entry into a host microorganism in the methods described herein include, but are not limited to, calcium phosphate/DNA coprecipitation, microinjection of DNA into a nucleus, electroporation, bacterial protoplast fusion with intact cells, transfection, lipofection, infection, particle bombardment, sperm mediated gene transfer, or any other technique.

Certain aspects disclosed herein can utilize vectors (including the ones described above). Any plasmids and vectors can be used as long as they are replicable and viable in a selected host microorganism. Vectors known in the art and those commercially available (and variants or derivatives thereof) can be engineered to include one or more recombination sites for use in the methods herein. Vectors that can be used include, but are not limited to, expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), pXT1, pSG5, pPbac, pMbac, p.MClneo, and pOG44 (Stratagene, Inc.), and pYES2, pAC360, pBlueBa-cHis A, B, and C, pVL1392, pBlueBac111, pCDM8, pcDNA1, pZeoSV, pcDNA3, pREP4, pCEP4, and pEBVHis (Invitrogen, Corp.), and variants or derivatives thereof.

These vectors can be used to express a gene or portion of a gene of interest. A gene or a portion of a gene can be inserted by using known methods, such as restriction enzyme-based techniques.

IV. Methods of Altering Nucleic Acids

The nucleic acids contained within the microorganism disclosed throughout can be altered in specific ways. Depending on the type of modification desired, guide RNAs can be made and targeted to specific sequences. For example, the nucleic acids described throughout can be within the microorganism described herein. Then if specific modifications are desired, the modifications can be made within the microorganism without going through an entire process of genetically engineering the microorganism from the beginning.

In some cases, wild-type, unmodified microorganisms can be altered by the methods described. For example, wild-type methylotrophs, such as methanotrophs, e.g. *Methylococcus capsulatus*, can be genetically altered. In some cases, previously genetically modified microorganisms can be altered by the methods described. For example, the genetically modified microorganism described herein, such as those that produce 2,3-BDO, 1,4-BDO, isobutanol and/or isobutyraldehyde, can be further genetically modified using the methods described throughout. The nucleic acids within the microorganism (both heterologous or native) can be introduced with point mutations, addition of one or more nucleic acids, and/or deletion of one or more nucleic acids.

General Methods

Generally described throughout are methods of genetic engineering. In one example, described herein is a method of genetic engineering comprising: (a) contacting a microorganism that is capable of converting a $C_1$ carbon to a multicarbon product with a polynucleotide encoding for a Cas enzyme and a guide ribonucleic acid (gRNA); and (b) growing the microorganism until a genetic modification occurs.

In some cases, the microorganism is a microorganism as described throughout, such as a methylotroph. For example, the methylotroph can be a methanotroph, such as from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis*, or Methyloacidophilum. In some cases, the methanotroph can be from the genus *Methylococcus*, such as a *Methylococcus capsulatus*.

In some cases, the $C_1$ carbon can be any $C_1$ carbon disclosed throughout. For example, in some cases the $C_1$ carbon is carbon monoxide (CO), carbon dioxide ($CO_2$), methane ($CH_4$), or any combination thereof. In some cases, the $C_1$ carbon is $CH_4$.

The Cas enzymes that can be used for any of the methods described throughout include but are not limited to Cas1, Cas1B, Cas2, Cas3, Cas4, Cas5, Cas5d, Cas5t, Cas5h, Cas5a, Cas6, Cas7, Cas8, Cas9 (also known as Csn1 or Csx12), Cas10, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Csd1, Csd2, Cst1, Cst2, Csh1, Csh2, Csa1, Csa2, Csa3, Csa4, Csa5, C2c1, C2c2, C2c3, Cpf1, CARF, DinG, homologues thereof, or modified versions thereof. In some cases, the Cas enzyme is a Cas9 enzyme.

In some cases, the gRNA can be at least partially or fully homologous to any one of the genes or promoters described throughout. In some instances, the gRNA is at least partially homologous or fully homologous to a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the term "at least partially homologous" can refer to having at least two or more nucleotides identical in a sequence. In most cases, the term at least partially homologous refers to a polynucleotide that is identical in at least a 10 nucleotide stretch. Thus, at least 10 or more nucleotides from the gRNA can bind to the polynucleotide that is being pinpointed and/or altered.

In some cases, the gRNA is directed to a promoter, intron, or coding sequence of gene within the 2,3-BDO pathway. The gene within the 2,3-BDO can be an acetoin reductase, alpha-acetolactate decarboxylase, and/or acetolactate synthase gene.

In other cases, the gRNA is directed to a promoter, intron, or coding sequence of a gene within the 1,4-BDO pathway. The gene can be within the 1,4-BDO pathway can be a pyruvate dehydrogenase (aceEF), citrate synthase (gltA), aconitate hydratase 1 (acnA), isocitrate dehydrogenase (icdA), citrate synthase (gltA), succinyl-CoA synthetase (SucC), CoA-dependent succinate semialdehyde dehydrogenase (SucD), 4-hyrobutyrate dehydrogenase (4hbD), 4-hydroxybutyryl-CoA transferase (Cat2), aldehyde dehydrogenase (Ald), alcohol dehydrogenase (Adh), and/or α-ketoglutarate decarboxylase (kgd) gene.

In some cases, the gRNA is directed to a promoter, intron, or coding sequence of a gene within the isobutyraldehyde pathway. The gene within the isobutyraldehyde pathway can be an acetolactate synthase (AlsS), ketol-acid reductoisomerase (IlvC), dihydroxy-acid dehydratase (IlvD), and/or 2-keto acid decarboxylase (KDC) gene.

In other cases, the gRNA is directed to a gene within the isobutanol pathway. The gene within the isobutanol pathway can be an AlsS, IlvC, IlvD, KDC, and/or ADH gene.

In some cases, the gRNA is transformed prior to a polynucleotide encoding for a Cas enzyme.

In some cases, the microorganism is also contacted with a donor polynucleotide. In some cases, the donor polynucleotide is contacted with the microorganism prior to being contacted with a polynucleotide encoding for a Cas enzyme. In some cases, the microorganism is contacted concurrently with a donor polynucleotide and a guide RNA. In some cases, the donor polynucleotide and guide RNA are on a single plasmid.

If a donor polynucleotide is used, the donor polynucleotide can be less than 10,000 bases. For example, the donor polynucleotide can be less than 5,000 bases. In some cases, the donor polynucleotide is less than 4,000 bases. In some cases, the donor polynucleotide is less than 3,000 bases. In some cases, the donor polynucleotide is less than 2,000 bases. In some cases, the donor polynucleotide is less than 1,000 bases. In some cases, the donor polynucleotide is less than 950 bases. In some cases, the donor polynucleotide is less than 900 bases. In some cases, the donor polynucleotide is less than 850 bases. In some cases, the donor polynucleotide is less than 800 bases. In some cases, the donor polynucleotide is less than 750 bases. In some cases, the donor polynucleotide is less than 700 bases. In some cases, the donor polynucleotide is less than 650 bases. In some cases, the donor polynucleotide is less than 600 bases. In some cases, the donor polynucleotide is less than 550 bases. In some cases, the donor polynucleotide is less than 500 bases. In some cases, the donor polynucleotide is less than 450 bases. In some cases, the donor polynucleotide is less than 400 bases. In some cases, the donor polynucleotide is less than 350 bases. In some cases, the donor polynucleotide is less than 300 bases. In some cases, the donor polynucleotide is less than 250 bases. In some cases, the donor polynucleotide is less than 200 bases. In some cases, the donor polynucleotide is less than 150 bases. In some cases, the donor polynucleotide is less than 100 bases. In some cases, the donor polynucleotide is less than 95 bases. In some cases, the donor polynucleotide is less than 90 bases. In some cases, the donor polynucleotide is less than 85 bases. In some cases, the donor polynucleotide is less than 80 bases. In some cases, the donor polynucleotide is less than 75 bases. In some cases, the donor polynucleotide is less than 70 bases. In some cases, the donor polynucleotide is less than 65 bases. In some cases, the donor polynucleotide is less than 60 bases. In some cases, the donor polynucleotide is less than 55 bases. In some cases, the donor polynucleotide is less than 50 bases. In some cases, the donor polynucleotide is less than 45 bases. In some cases, the donor polynucleotide is less than 40 bases. In some cases, the donor polynucleotide is less than 35 bases. In some cases, the donor polynucleotide is less than 30 bases. In some cases, the donor polynucleotide is less than 25 bases. In some cases, the donor polynucleotide is less than 20 bases. In some cases, the donor polynucleotide is less than 15 bases. In some cases, the donor polynucleotide is less than 10 bases. In some cases, the donor polynucleotide is less than 5 bases.

If a donor polynucleotide is used, the donor polynucleotide can be from 10,000 bases to 1 base. For example, the donor polynucleotide can be from 5,000 to 5 bases. In some cases, the donor polynucleotide can be from 2,500 to 10 bases. In some cases, the donor polynucleotide can be from 2,000 to 15 bases. In some cases, the donor polynucleotide can be from 1,500 to 25 bases. In some cases, the donor polynucleotide can be from 1,000 to 100 bases. In some cases, the donor polynucleotide can be from 750 to 125 bases. In some cases, the donor polynucleotide can be from 500 to 250 bases. In some cases, the donor polynucleotide can be from 1,000 bases to 1 base. In some cases, the donor polynucleotide can be from 900 to 5 bases. In some cases, the donor polynucleotide can be from 750 to 10 bases. In some cases, the donor polynucleotide can be from 650 to 5 bases. In some cases, the donor polynucleotide can be from 700 to 10 bases. In some cases, the donor polynucleotide can be from 600 to 10 bases. In some cases, the donor polynucleotide can be from 500 to 5 bases.

In some cases, the polynucleotide encoding for a Cas enzyme is within a plasmid.

In some cases, the plasmids used do not comprise a strong promoter. For example, the plasmid can comprise a mutated promoter. In some cases, the mutation can lead to a decrease in activity. In some cases, the promoter is a pMxaF promoter.

In some cases, the microorganism that is being used does not efficiently take up nucleic compared to an *E. coli* bacteria. Transformation efficiency can refer to the number of viable transformants obtained based on a predetermined amount of a compound to be transformed, which is often measured as colony forming units (CFU) per μg compound used. For example, transfection/transformation efficiency of highly competent *E. coli* cells can reach approximately $2\times10^{10}$-$4\times10^{10}$ cfu/μg of nucleic acid used for the transformations. In some cases, the microorganisms used throughout have very low transformation efficiency. In some cases, the transformation efficiency of the microorganisms used herein is lower than $2\times10^{10}$ cfu/μg. For example, the transformation efficiency of the microorganism used herein can be 0 cfu/μg. In some cases, the transformation efficiency can be 0 to $1\times10^2$ cfu/μg; $1\times10^2$ cfu/μg to $1\times10^3$ cfu/μg; $1\times10^3$ cfu/μg to $1\times10^4$ cfu/μg; $1\times10^4$ cfu/μg to $1\times10^5$ cfu/μg; $1\times10^5$ cfu/μg to $1\times10^6$ cfu/μg; $1\times10^6$ cfu/μg to $1\times10^7$ cfu/μg; $1\times10^7$ cfu/μg to $1\times10^8$ cfu/μg; $1\times10^8$ cfu/μg to $1\times10^9$ cfu/μg; $1\times10^9$ cfu/μg to $1\times10^{10}$ cfu/μg; or $1\times10^{10}$ cfu/μg to $1.9999\times10^{10}$ cfu/μg. In some cases, the transformation efficiency can be 0 cfu/μg to less than 1 cfu/μg; 1 cfu/μg to 5 cfu/μg; 5 cfu/μg to 10 cfu/μg; 10 cfu/μg to 20 cfu/μg; 20 cfu/μg to 30 cfu/μg; 30 cfu/μg to 40 cfu/μg; 40 cfu/μg to 50 cfu/μg; 50 cfu/μg to 100 cfu/μg; 100 cfu/μg to 150 cfu/μg; 150 cfu/μg to 200 cfu/μg; 200 cfu/μg to 250 cfu/μg; 250 cfu/μg to 500 cfu/μg; 500 cfu/μg to 1000 cfu/μg; 1000 cfu/μg to 1500 cfu/μg; 1500 cfu/μg to 2000 cfu/μg; or 2000 cfu/μg to 5000 cfu/μg.

In some cases, the microorganism is made electroporation competent prior to transformation. In some cases, some chemical is made to make the microorganism electroporation competent prior to transformation. In some cases, a microorganism can be made to take up nucleic acids more efficiently compared to a non-modified microorganism.

Point Mutations

Described herein is a method of replacing a single nucleotide within the genome of a microorganism comprising: (a) contacting the microorganism with a polynucleotide encoding for i) a Cas enzyme and ii) a gRNA; and (b) growing the microorganism until a single nucleotide is replaced within the genome of the microorganism.

As described above, the microorganism used can be a microorganism that is capable of converting a $C_1$ carbon to a multicarbon product, for example, a methylotroph or any other microorganism described throughout the disclosure.

Further, as described throughout, the $C_1$ carbon can be carbon monoxide (CO), carbon dioxide ($CO_2$), methane ($CH_4$), or any combination thereof.

Additionally, as described through, the Cas enzyme can be any described throughout, including but not limited to Cas9.

As described throughout, the gRNA can target particular pathway genes. For example, as described throughout, the gRNA can be at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the gRNA is transformed prior to a polynucleotide encoding for a Cas enzyme.

In some cases, the polynucleotide encoding for a Cas enzyme is within a plasmid.

In some cases, the plasmids used do not comprise a strong promoter. For example, the plasmid can comprise a mutated promoter. In some cases, the mutation can lead to a decrease in activity. In some cases, the promoter is a pMxaF promoter.

In some cases, when the replacement method is used, the replacement results in a different nucleotide. For example, should a nucleotide within a specific genetic sequence be desired, this method can change the desired nucleotide, e.g., from A to T, C, or G; from T to A, C, or G; from C to A, T, or G; or from G to A, T, or C.

In some cases, the replacement occurs at a single nucleotide within a promoter, intron, or coding sequence of an rpoB gene or a gene within the 2,3-butanediol (2,3-BDO), 1,4-butanediol (1,4-BDO), isobutyraldehyde, or isobutanol pathway. The replacement can in some cases result in a change of expression of one or more genes. The replacement in some cases can also result in a change of activity of one or more enzymes.

Adding Nucleotides

Described herein is a method of adding one or more nucleotides to the genome of a microorganism comprising: (a) contacting the microorganism with a polynucleotide encoding for i) a Cas enzyme and ii) a gRNA; and (b) growing the microorganism until one or more nucleotides is added to the genome of the microorganism.

As described above, the microorganism used can be a microorganism that is capable of converting a $C_1$ carbon to a multi-carbon product, for example, a methylotroph or any other microorganism described throughout the disclosure.

Further, as described throughout, the $C_1$ carbon can be carbon monoxide (CO), carbon dioxide ($CO_2$), methane ($CH_4$), or any combination thereof.

Additionally, as described through, the Cas enzyme can be any described throughout, including but not limited to Cas9.

As described throughout, the gRNA can target particular pathway genes to insert one or more nucleotides. For example, as described throughout, the gRNA can be at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the gRNA is transformed prior to a polynucleotide encoding for a Cas enzyme.

In some cases, the polynucleotide encoding for a Cas enzyme is within a plasmid.

In some cases, the plasmids used do not comprise a strong promoter. For example, the plasmid can comprise a mutated promoter. In some cases, the mutation can lead to a decrease in activity. In some cases, the promoter is a pMxaF promoter.

In some cases, the microorganism is also contacted with a donor polynucleotide. In some cases, the donor polynucleotide is contacted with the microorganism prior to being contacted with a polynucleotide encoding for a Cas enzyme. In some cases, the microorganism is contacted concurrently with a donor polynucleotide and a guide RNA. In some cases, the donor polynucleotide and guide RNA are on a single plasmid.

If a donor polynucleotide is used, the donor polynucleotide can be less than 10,000 bases. For example, the donor polynucleotide can be less than 5,000 bases. In some cases, the donor polynucleotide is less than 4,000 bases. In some cases, the donor polynucleotide is less than 3,000 bases. In some cases, the donor polynucleotide is less than 2,000 bases. In some cases, the donor polynucleotide is less than 1,000 bases. In some cases, the donor polynucleotide is less than 950 bases. In some cases, the donor polynucleotide is less than 900 bases. In some cases, the donor polynucleotide is less than 850 bases. In some cases, the donor polynucleotide is less than 800 bases. In some cases, the donor polynucleotide is less than 750 bases. In some cases, the donor polynucleotide is less than 700 bases. In some cases, the donor polynucleotide is less than 650 bases. In some cases, the donor polynucleotide is less than 600 bases. In some cases, the donor polynucleotide is less than 550 bases. In some cases, the donor polynucleotide is less than 500 bases. In some cases, the donor polynucleotide is less than 450 bases. In some cases, the donor polynucleotide is less than 400 bases. In some cases, the donor polynucleotide is less than 350 bases. In some cases, the donor polynucleotide is less than 300 bases. In some cases, the donor polynucleotide is less than 250 bases. In some cases, the donor polynucleotide is less than 200 bases. In some cases, the donor polynucleotide is less than 150 bases. In some cases, the donor polynucleotide is less than 100 bases. In some cases, the donor polynucleotide is less than 95 bases. In some cases, the donor polynucleotide is less than 90 bases. In some cases, the donor polynucleotide is less than 85 bases. In some cases, the donor polynucleotide is less than 80 bases. In some cases, the donor polynucleotide is less than 75 bases. In some cases, the donor polynucleotide is less than 70 bases. In some cases, the donor polynucleotide is less than 65 bases. In some cases, the donor polynucleotide is less than 60 bases. In some cases, the donor polynucleotide is less than 55 bases. In some cases, the donor polynucleotide is less than 50 bases. In some cases, the donor polynucleotide is less than 45 bases. In some cases, the donor polynucleotide is less than 40 bases. In some cases, the donor polynucleotide is less than 35 bases. In some cases, the donor polynucleotide is less than 30 bases. In some cases, the donor polynucleotide is less than 25 bases. In some cases, the donor polynucleotide is less than 20 bases. In some cases, the donor polynucleotide is less than 15 bases. In some cases, the donor polynucleotide is less than 10 bases. In some cases, the donor polynucleotide is less than 5 bases.

If a donor polynucleotide is used, the donor polynucleotide can be from 10,000 bases to 1 base. For example, the donor polynucleotide can be from 5,000 to 5 bases. In some cases, the donor polynucleotide can be from 2,500 to 10 bases. In some cases, the donor polynucleotide can be from 2,000 to 15 bases. In some cases, the donor polynucleotide can be from 1,500 to 25 bases. In some cases, the donor polynucleotide can be from 1,000 to 100 bases. In some cases, the donor polynucleotide can be from 750 to 125 bases. In some cases, the donor polynucleotide can be from 500 to 250 bases. In some cases, the donor polynucleotide can be from 1,000 bases to 1 base. In some cases, the donor polynucleotide can be from 900 to 5 bases. In some cases, the donor polynucleotide can be from 750 to 10 bases. In some cases, the donor polynucleotide can be from 650 to 5 bases. In some cases, the donor polynucleotide can be from 700 to 10 bases. In some cases, the donor polynucleotide can be from 600 to 10 bases. In some cases, the donor polynucleotide can be from 500 to 5 bases.

The method described herein can result in a polynucleotide where two or more nucleotides are added. In some cases, the number of nucleotides added can be up to 10 kb. In some cases, however, the efficiency of gene editing efficiency can be increased by inserting less than 1000 base pairs. In some cases, the efficiency of gene editing can be significantly increased by inserting 500 nucleotides or less. In some cases, the efficiency of gene editing can be even more significantly increased by inserting 100 nucleotides or less.

The amount of nucleotides that can be inserted using the techniques described herein can potentially be endless. In some cases, the number of nucleotides inserted can be from 1 to 5, 4 to 10, 9 to 15, 14 to 20, 19 to 25, 24 to 30, 29 to 35, 34 to 40, 39 to 45, 44 to 50, 49 to 55, 54 to 60, 59 to 65, 64 to 70, 69 to 75, 74 to 80, 79 to 85, 84 to 90, 89 to 95, or 94 to 100. In some cases, the number of nucleotides that can be inserted can be under 5000 kb, for example, from 99 to 500, 499 to 1000, 999 to 1500, 1499 to 2000, 1999 to 2500, 2499 to 3000, 2999 to 3500, 3499 to 4000, 3999 to 4500, or 4499 to 4999.

As described throughout, the gRNA can target particular pathway genes. For example, as described throughout, the gRNA can be at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway. Targeting these sequences can add additional nucleotides within the promoter, intron, or coding sequence. This addition can affect the expression of their respective genes. This addition can also affect the activity of the gene product, e.g., an enzyme of the pathway.

Deleting Nucleotides

Described herein is a method of removing one or more nucleotides from the genome of a genetically modified microorganism comprising: (a) contacting the microorganism with a polynucleotide encoding for i) a Cas enzyme and ii) a gRNA; and (b) growing the microorganism until one or more nucleotides within the genome of the microorganism is removed.

As described above, the microorganism used can be a microorganism that is capable of converting a $C_1$ carbon to a multicarbon product, for example, a methylotroph or any other microorganism described throughout the disclosure.

Further, as described throughout, the $C_1$ carbon can be carbon monoxide (CO), carbon dioxide ($CO_2$), methane ($CH_4$), or any combination thereof.

Additionally, the Cas enzyme can be any described throughout, including but not limited to Cas9.

In some cases, the polynucleotide encoding for a Cas enzyme is within a plasmid.

In some cases, the plasmids used do not comprise a strong promoter. For example, the plasmid can comprise a mutated promoter. In some cases, the mutation can lead to a decrease in activity. In some cases, the promoter is a pMxaF promoter.

In some cases, the gRNA is transformed prior to a polynucleotide encoding for a Cas enzyme.

As described throughout, the gRNA can target particular pathway genes to delete one or more nucleotides. For example, as described throughout, the gRNA can be at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway.

The method described herein can result in a polynucleotide where one or more nucleotides are deleted. The amount of nucleotides that can be deleted using the techniques described herein can potentially be endless. In some cases, the number of nucleotides deleted can be from 1 to 5, 4 to 10, 9 to 15, 14 to 20, 19 to 25, 24 to 30, 29 to 35, 34 to 40, 39 to 45, 44 to 50, 49 to 55, 54 to 60, 59 to 65, 64 to 70, 69 to 75, 74 to 80, 79 to 85, 84 to 90, 89 to 95, or 94 to 100. In some cases, the number of nucleotides that can be deleted can be under 5000 kb, for example, from 99 to 500, 499 to 1000, 999 to 1500, 1499 to 2000, 1999 to 2500, 2499 to 3000, 2999 to 3500, 3499 to 4000, 3999 to 4500, or 4499 to 4999. In some cases, the number of nucleotides that are deleted can be up to 10 kb or more.

As described throughout, the gRNA can target particular pathway genes. For example, as described throughout, the gRNA can be at least partially complementary to a polynucleotide that is within a promoter, intron, or coding sequence of an rpoB gene or a gene within the 2,3-butanediol (2,3-BDO), 1,4-butanediol (1,4-BDO), isobutyraldehyde, or isobutanol pathway. Targeting these sequences can delete nucleotides within the promoter, intron, or coding sequence. This deletion can affect the expression of their respective genes. This deletion can also affect the activity of the gene product, e.g., an enzyme of the pathway.

IV. Methods of Inhibiting Gene Expression

Modified Cas Enzyme

The Cas enzymes can be genetically altered (by the methods described throughout or any other method) so that it is catalytically inactive. For example, one or more nucleotides encoding an amino acid sequence that is a part of the catalytic domain of the Cas enzyme can be altered. In other words, one or more nucleotides that encode for the catalytic domain of the Cas enzyme can be deleted, added, or substituted. The resulting sequence can encode for a Cas enzyme that is catalytically inhibited and/or inactive.

The catalytically inactive enzyme can be used to inhibit expression of one or more genes. For example, a specific gRNA can be used to target the promoter, intron, and/or coding sequence of a particular gene. The specific gRNA and inactive Cas enzyme can be expressed within a microorganism. Once this happens, gene expression can be reduced or inhibited.

The binding of the catalytically inactive Cas enzyme can result in steric hindrance of the transcription mechanism. For example, the inactive Cas enzyme that is bound to the gRNA can interrupt transcript initiation or elongation by RNA polymerase.

In some cases, the binding of this blocking complex can be permanent. In some cases the binding of this blocking complex can be temporary. Further, the inactive Cas enzyme can be expressed within a microorganism and be under the control of an inducible or repressible promoter. Additionally, in some cases the gRNA can be expressed within a vector and also be controlled by an inducible and/or repressible promoter. This way, the induction or repression of the desired gene can be specifically controlled at any time by the addition or removal of the inducing/repressing agent.

Targeting Specific Genes

The expression of any number of genes can be inhibited by the methods described throughout. For example, an rpoB gene or any of the genes described within the 2,3-BDO, 1,4-BDO, isobutanol, and/or isobutyraldehyde pathways can be targeted by the gRNA and thus by the inactive Cas enzyme. Any of the gRNA described throughout can be used herein. The gRNA can be substantially similar to the genes described throughout.

Inhibiting Gene Expression

Described herein is a method of inhibiting the expression of a gene within a microorganism comprising contacting the microorganism with a polynucleotide encoding for i) a modified Cas enzyme and ii) a gRNA, where the modified Cas enzyme does not cleave nucleic acids. Also described herein is a method of inhibiting the expression of a gene within a microorganism comprising contacting the microorganism with i) a gRNA and ii) a polynucleotide encoding for a modified Cas enzyme, where the modified Cas enzyme does not cleave nucleic acids.

In some cases, the microorganism used can be a microorganism that is capable of converting a $C_1$ carbon to a multicarbon product. For example, the microorganism can be a microorganism as described throughout, such as a methylotroph. For example, the methylotroph can be a methanotroph, such as from the genera *Methylobacter, Methylomicrobium, Methylomonas, Methylocaldum, Methylococcus*, Methylosoma, Methylosarcina, Methylothermus, Methylohalobius, Methylogaea, Methylovulum, Crenothrix, Clonothrix, Methylosphaera, Methylocapsa, *Methylocella, Methylosinus, Methylocystis*, or Methyloacidophilum. In some cases, the methanotroph can be from the genus *Methylococcus*, such as a *Methylococcus capsulatus*.

In some cases, the $C_1$ carbon can be any $C_1$ carbon disclosed throughout. For example, in some cases the $C_1$ carbon is carbon monoxide (CO), carbon dioxide ($CO_2$), methane ($CH_4$), or any combination thereof. In some cases, the $C_1$ carbon is $CH_4$.

The modified Cas enzymes that can be used for any of the methods described throughout include but are not limited to Cas1, Cas1B, Cas2, Cas3, Cas4, Cas5, Cas5d, Cas5t, Cas5h, Cas5a, Cas6, Cas7, Cas8, Cas9 (also known as Csn1 or Csx12), Cas10, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Csd1, Csd2, Cst1, Cst2, Csh1, Csh2, Csa1, Csa2, Csa3, Csa4, Csa5, C2c1, C2c2, C2c3, Cpf1, CARF, DinG, or homologues thereof. In some cases, the Cas enzyme is a modified Cas9 enzyme. As described above, the modification can be a modified that renders the Cas enzyme partially inactive. The partial inactivity can mean that the Cas enzyme has the ability to bind to its targeted sequence, but does not have the ability to cleave the nucleic acids. In some cases, the polynucleotide encoding for a Cas enzyme or a modified Cas enzyme is within a plasmid.

In some cases, the gRNA can be at least partially or fully homologous to any one of the genes or promoters described throughout. In some instances, the gRNA is at least partially homologous or fully homologous to a promoter, intron, or coding sequence of an rpoB gene or a gene within the 2,3-butanediol (2,3-BDO), 1,4-butanediol (1,4-BDO), isobutyraldehyde, or isobutanol pathway.

In some cases, the gRNA is directed to a promoter, intron, or coding sequence of gene within the 2,3-BDO pathway. The gene within the 2,3-BDO can be an acetoin reductase, alpha-acetolactate decarboxylase, and/or acetolactate synthase gene.

In other cases, the gRNA is directed to a promoter, intron, or coding sequence of a gene within the 1,4-BDO pathway. The gene can be within the 1,4-BDO pathway can be a pyruvate dehydrogenase (aceEF), citrate synthase (gltA), aconitate hydratase 1 (acnA), isocitrate dehydrogenase (icdA), citrate synthase (gltA), succinyl-CoA synthetase (SucC), CoA-dependent succinate semialdehyde dehydrogenase (SucD), 4-hyrobutyrate dehydrogenase (4hbD), 4-hydroxybutyryl-CoA transferase (Cat2), aldehyde dehydrogenase (Ald), alcohol dehydrogenase (Adh), and/or $\alpha$-ketoglutarate decarboxylase (kgd) gene.

In some cases, the gRNA is directed to a promoter, intron, or coding sequence of a gene within the isobutyraldehyde pathway. The gene within the isobutyraldehyde pathway can be an acetolactate synthase (AlsS); ketol-acid reductoisomerase (IlvC); dihydroxy-acid dehydratase (IlvD); and/or 2-keto acid decarboxylase (KDC) gene.

In other cases, the gRNA is directed to a gene within the isobutanol pathway. The gene within the isobutanol pathway can be an AlsS, IlvC, IlvD, KDC, and/or ADH gene.

In some cases, the plasmids used do not comprise a strong promoter. For example, the plasmid can comprise a mutated promoter. In some cases, the mutation can lead to a decrease in activity. In some cases, the promoter is a pMxaF promoter.

In some cases, the gRNA is transformed prior to a polynucleotide encoding for a Cas enzyme.

In some cases, the microorganism that is being used does not efficiently take up nucleic acid compared to an *E. coli* bacteria. Transformation efficiency can refer to the number of viable transformants obtained based on a predetermined amount of a compound to be transformed, which is often measured as colony forming units (CFU) per μg compound used. For example, transfection/transformation efficiency of highly competent *E. coli* cells can reach approximately $2\times10^{10}$-$4\times10^{10}$ cfu/μg of nucleic acid used for the transformations. In some cases, the microorganisms used throughout have very low transformations efficiency. In some cases, the transformation efficiency of the microorganisms used herein is lower than $2\times10^{10}$ cfu/μg. For example, the transformation efficiency of the microorganism used herein can be 0 cfu/μg. In some cases, the transformation efficiency can be 0 to $1\times10^2$ cfu/μg; $1\times10^2$ cfu/μg to $1\times10^3$ cfu/μg; $1\times10^3$ cfu/μg to $1\times10^4$ cfu/μg; $1\times10^4$ cfu/μg to $1\times10^5$ cfu/μg; $1\times10^5$ cfu/μg to $1\times10^6$ cfu/μg; $1\times10^6$ cfu/μg to $1\times10^7$ cfu/μg; $1\times10^7$ cfu/μg to $1\times10^8$ cfu/μg: $1\times10^8$ cfu/μg to $1\times10^9$ cfu/μg; $1\times10^9$ cfu/μg to $1\times10^{10}$ cfu/μg; or $1\times10^{10}$ cfu/μg to $1.9999\times10^{10}$ cfu/μg. In some cases, the transformation efficiency can be 0 cfu/μg to less than 1 cfu/μg; 1 cfu/μg to 5 cfu/μg; 5 cfu/μg to 10 cfu/μg; 10 cfu/μg to 20 cfu/μg; 20 cfu/μg to 30 cfu/μg; 30 cfu/μg to 40 cfu/μg; 40 cfu/μg to 50 cfu/μg; 50 cfu/μg to 100 cfu/μg; 100 cfu/μg to 150 cfu/μg; 150 cfu/μg to 200 cfu/μg; 200 cfu/μg to 250 cfu/μg; 250 cfu/μg to 500 cfu/μg; 500 cfu/μg to 1000 cfu/μg; 1000 cfu/μg to 1500 cfu/μg; 1500 cfu/μg to 2000 cfu/μg; or 2000 cfu/μg to 5000 cfu/μg.

In some cases, the microorganism is made electroporation competent prior to transformation. In some cases, some chemical is made to make the microorganism electroporation competent prior to transformation.

In some cases, the inhibition of gene expression is greater than 10%, 20%, 30%, 40%, 50%, 60%, 70%, 80%, or 90%, compared to a wild-type microorganism of the same species. In some cases, the inhibition of gene expression is greater than 5%, 15%, 25%, 35%, 45%, 55%, 65%, 75%, 85%, or 95% compared to a wild-type microorganism of the same species. In some cases, the inhibition of gene expression is greater than 10% compared to a wild-type microorganism of the same species. In some cases, the inhibition of gene expression is greater than 50% compared to a wild-type microorganism of the same species. In some cases, the inhibition of gene expression is 100% compared to a wild-type microorganism of the same species.

EXAMPLES

Example 1: Single Plasmid

The *Streptococcus pyogenes* Cas9 gene was codon optimized for expression in *Methylococcus capsulatus*. The codon optimized Cas9 gene was expressed using a pMxaF promoter. A single guide RNA (gRNA) targeting multiple sites along a gene of interest were expressed driven by a $P_{mmo2}$ or J23115 promoter. Double stranded DNA having a 1.5 kb homologous region were created. Two gRNA constructs were tested initially.

Initial tests proved to be ineffective at gene editing. As seen in FIG. 1, no colonies were seen when Cas9, gRNA, and double stranded donor DNA were transfected into a *Methylococcus capsulatus*. Later tests showed that pMxaF driving the expression of Cas9 is toxic to *Methylococcus capsulatus*.

Four (4) different promoters were used to drive Cas9 expression: pMxaF_Cas9; pMxaF*_Cas9; pBAD_Cas9; PJ23115_gRNA. pMxaF*_Cas9 was found to be the most efficient and least toxic.

Example 2: Two Plasmid System

Figure 2:
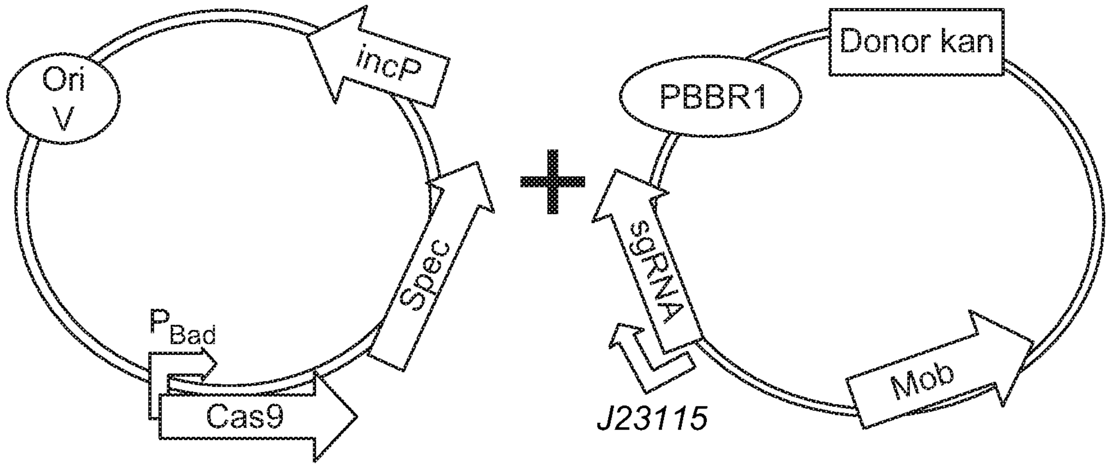
FIG. 2 depicts a two plasmid approach for advanced genome editing (AGE). In one plasmid, Cas9 is expressed with a promoter, such as a weak promoter. In the second plasmid, a gRNA and a donor dsDNA are expressed.

In order to mitigate the toxic effects of Cas9, a two plasmid system was designed. See FIG. 2. In one plasmid, the Cas9 was driven by either pBAD or a mutant pMxaF (a "weak" promoter), whereas the sgRNA was driven by a J23115 promoter.

It was found that pBAD or mutant pMxaF produces enough Cas9 expression to cleave the dsDNA without much off-target effects. However, it was still found that in the presence of gRNA, very few colonies were observed. Of those few colonies, no correct gene editing was observed.

Example 3: Rifamycin Testing

Figure 3:
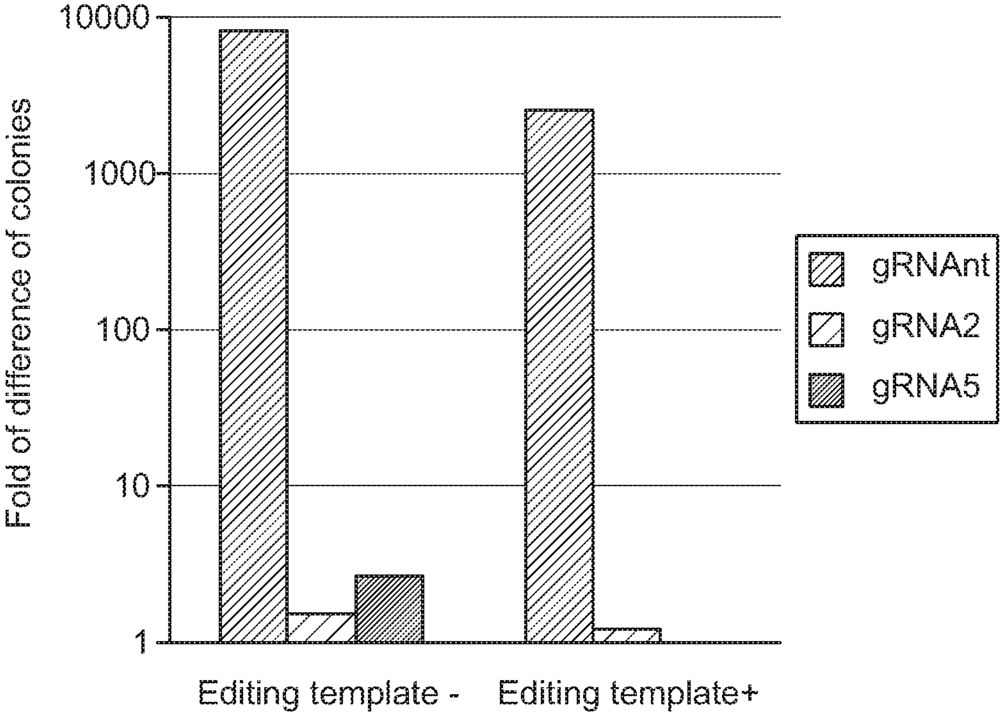
FIG. 3 depicts the number of colony forming units (CFU) for gene editing of the gene rpoB. As shown, the targeting of the rpoB gene resulted in four orders of magnitude drop of CFUs.
Figure 4:
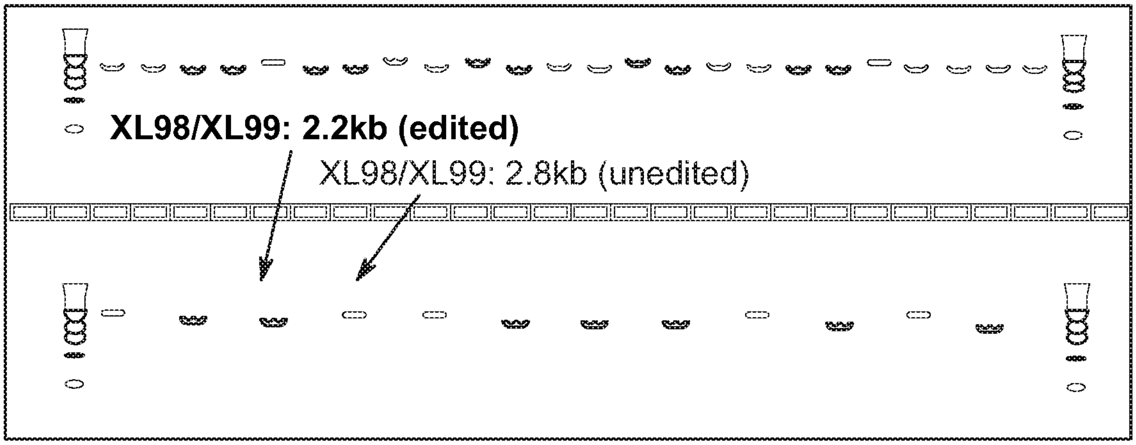
FIG. 4 depicts a colony polymerase chain reaction (cPCR) verification of a ppdK deletion of about 600 bases. As shown in the gel, approximately 72% of the clones were successfully edited.
Figure 5:
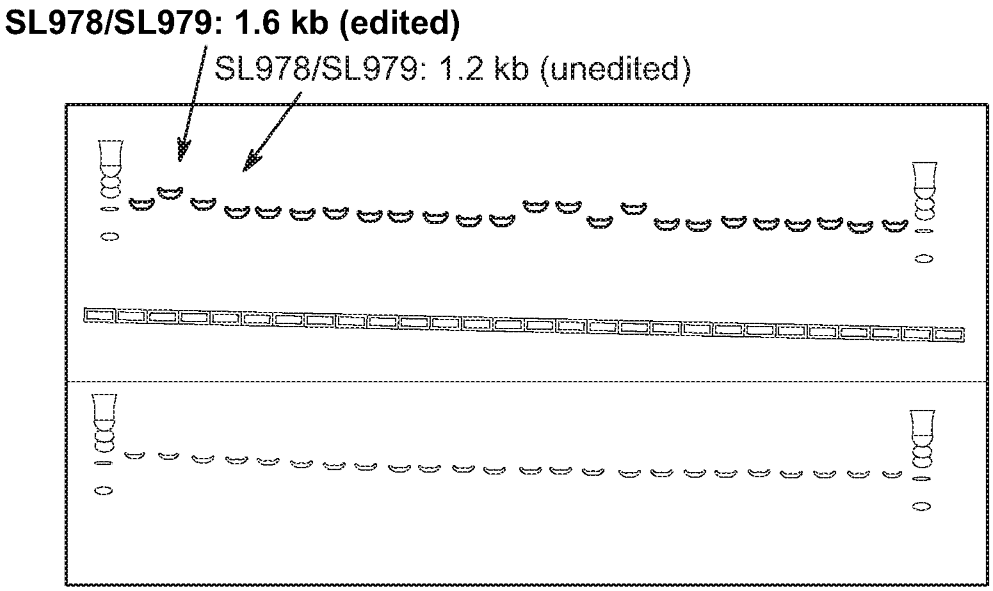
FIG. 5 depicts a cPCR verification of a ppdK addition of about 400 bases. As shown in the gel, several clones were successfully edited.
Figure 6:
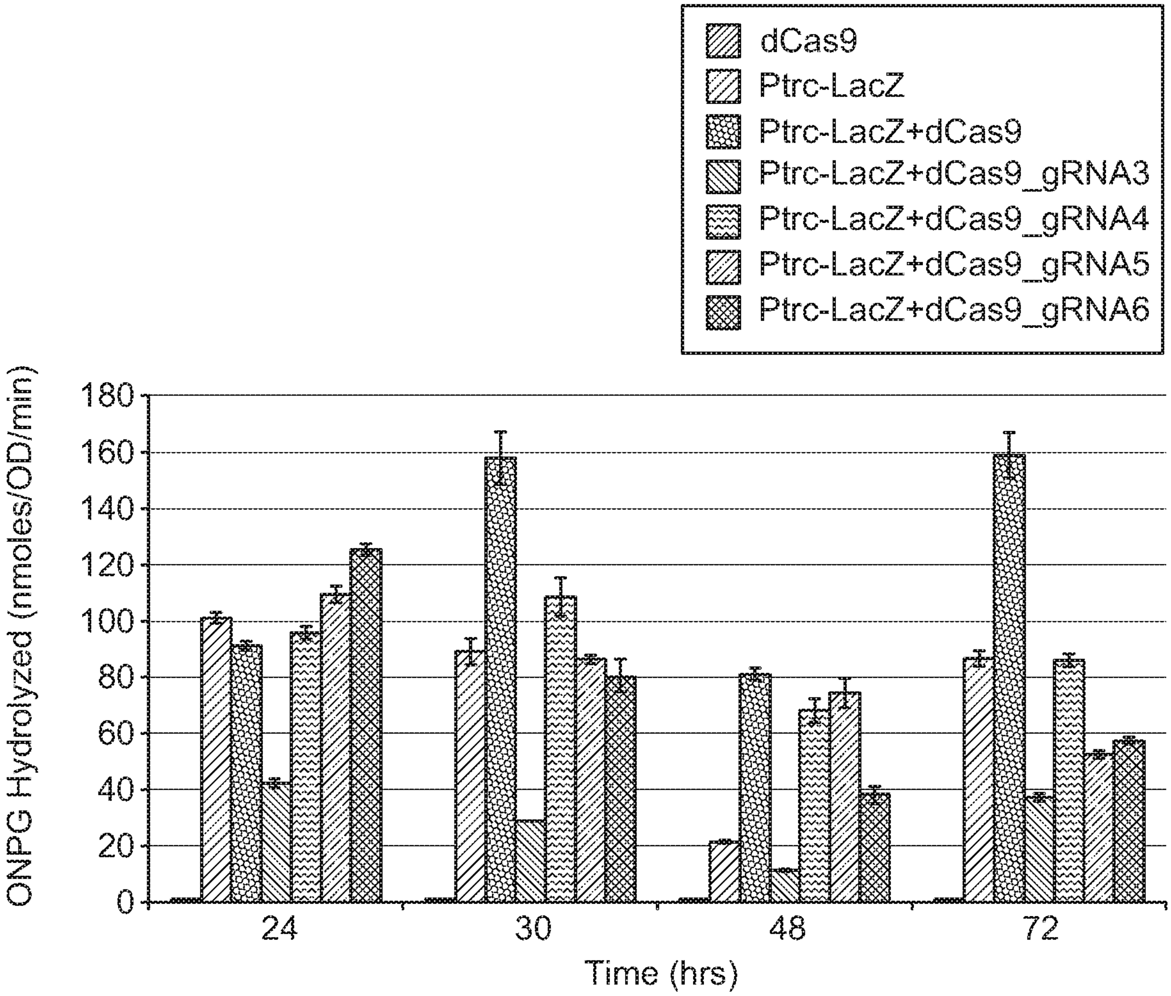
FIG. 6 shows that the expression of LacZ was successfully inhibited by the introduction of dCas9 in combination of a LacZ specific gRNA after 24, 30, 48, and 72 hours. The inhibition of LacZ in some strains was up to 8-fold (30 hours−Ptrc=LacZ+dCas9_gRNA3).

In order to quickly and efficiently troubleshoot the issues with genome editing within *Methylococcus capsulatus*, gene editing targeting the rpoB was used. In *Methylococcus capsulatus* the rpoB gene confers resistance to the antibiotic rifamycin. Therefore, in the presence of rifamycin, *Methylococcus capsulatus* having an active rpoB gene will form many colonies, while the *Methylococcus capsulatus* that were edited will be killed. A 1 kb long rpoB dsDNA was designed and used as the editing template in this experiment. As shown in FIG. 3, the gRNA targeting rpoB was effective and resulted in four orders of magnitude drop of colony forming units (CFU). However, verification revealed that the efficiency of gene editing was only approximately 0.5 to 1%.

Even though the use of a mutant pMxaF gave low background, editing efficiency was still low. In order to improve the efficiency of genome editing, the number of unedited clones needed to be reduced. Therefore, additional testing focused on "killing" efficiency.

Example 4: Promoters and Transformation Order

It was found that promoter strength of Cas9/gRNA affects the activity of CRISPR-Cas9 system. A stronger promoter that drives gRNA expression works better than a weaker promoter. On the other hand, Cas9 expression by a strong promoter is lethal to the microorganism.

The best "killing" rate was observed when the gRNA was present first then Cas9 encoding plasmid was subsequently transformed. However, even though the kill rate went up, increased editing efficiency did not improve.

A new approach was taken. The gRNA and donor DNA, contained on the same plasmid, were first transformed into a *Methylococcus capsulatus*. After this plasmid containing both the gRNA and donor DNA was inserted, a plasmid expression Cas9 was then transformed. Editing efficiency was achieved at about 70%, using rpoB as a target.

Other systems were tested, including a Red promoter driving Cas9 expression. However, this promoter did not result in high editing efficiency. Additionally, Cas9 was first transformed and then gRNA and donor DNA was later transformed. This procedure resulted in very low editing. It was found that high rates of transformation and recombination was required for advance genome editing.

Example 5: Cas9 Expression in Methanotrophs

The *Streptococcus pyogenes* Cas9 gene was codon optimized for expression in *Methylococcus capsulatus*. The codon optimized Cas9 gene was expressed using a variant pMxaF promoter referred to as pMxaF*. The pMxaF*-Cas9 DNA cassette was then cloned into an OriV-based plasmid. The final construct was named pSL95. The pMxaF* and Cas9 sequences used are displayed in Table 1.

TABLE 1

| SEQ ID NO. | NAME | SEQUENCE |
|---|---|---|
| 78 | pMxaF* | GAGGTTCAGGCGAAACCGCAGACTCAAGGGCGCTTGCTCCCGGGAA<br>AGATCGTATTAGTTTGCCTCGATCGGCGGTCCTTGTGACAGGGAGAT<br>ATTCCCGACGGATCCGGGGCATTCGAGCGGAACCGCCCGCCGTGGG<br>AGTTTTTCCAGCGAGCATTCGAGAGTTTTTCAAGGCGGCTTCGAGGG<br>GTTATTCCGTAACGCCGCCGACATGATCTGTCCCGGAATCTCCGCCG<br>CTGTTCGTAGAGCGCCGATGCAGGGTCGGCATCAATCATTCTTGGAG<br>GAGACAC |
| 79 | Cas9 | ATGGACAAGAAGTATTCGATCGGCCTGGACATCGGCACCAACAGCG<br>TCGGCTGGGCGGTCATCACGGATGAGTACAAGGTGCCGTCGAAGAA<br>GTTCAAGGTGCTGGGCAATACCGACCGCCATAGCATCAAGAAGAAT<br>CTCATCGGCGCACTGCTGTTCGACTCCGGCGAAACCGCCGAAGCGAC<br>CCGCCTCAAGCGCACGGCCCGGCGGCGCTATACGCGCCGGAAGAAC<br>CGCATCTGCTACCTCCAGGAAATCTTCTCCAACGAGATGGCCAAGGTG<br>GATGACTCCTTCTTCCATCGCCTGGAAGAATCCTTCCTGGTCGAAGAA<br>GATAAGAAACATGAGCGCCACCCCATCTTCGGCAATATCGTGGACGA<br>GGTGGCGTATCACGAGAAATACCCGACCATCTATCACCTGCGGAAAA<br>AGCTGGTGGACTCGACGGACAAAGCCGACCTGCGCCTCATCTATCTGG<br>CCCTGGCCCACATGATCAAGTTCCGGGGCCATTTCCTGATCGAAGGCG<br>ACCTGAACCCCGATAACAGCGACGTGGACAAGCTCTTCATCCAGCTCG<br>TCCAGACCTATAACCAGCTGTTCGAGGAGAACCCCATCAACGCCTCGG<br>GCGTGGACGCCAAGGCCATCCTGAGCGCACGGCTCTCCAAGTCGCGCC<br>GCCTGGAAAACCTGATCGCGCAGCTGCCGGGCGAAAAGAAAAACGGC<br>CTGTTCGGCAACCTGATCGCCCTGTCCCTCGGCCTCACCCCGAACTTCA<br>AGTCCAACTTCGACCTGGCCGAGGACGCGAAGCTCCAGCTGTCGAAAG<br>ACACCTACGATGACGACCTGGACAACCTCCTGGCGCAGATCGGCGACC<br>AGTACGCCGACCTCTTCCTCGCGGCCAAGAATCTGTCGGACGCCATCCT<br>GCTGTCGGATATCCTGCGGGTGAATACGGAGATCACGAAGGCCCCCCT<br>CTCGGCCTCGATGATCAAGCGCTACGACGAGCACCATCAGGACCTGAC<br>GCTGCTCAAGGCCCTCGTCCGGCAGCAGCTGCCGGAGAAGTATAAAGA<br>GATCTTCTTCGACCAGTCCAAGAACGGCTACGCGGGCTACATCGACGG<br>CGGCGCGTCGCAGGAGGAGTTCTATAAATTCATCAAGCCGATCCTGGA<br>GAAAATGGACGGCACCGAAGAACTCCTCGTCAAGCTGAACCGGGAGGA<br>TCTGCTCCGCAAGCAGCGCACCTTCGACAATGGCTCCATCCCGCACCAG<br>ATCCATCTCGGCGAGCTGCACGCCATCCTGCGCCGCCAGGAGGACTTCT<br>ACCCCTTCCTCAAAGACAACCGGGAGAAAATCGAGAAGATCCTGACGTT<br>CCGCATCCCCTACTACGTGGGCCCCCTCGCCCGCGGCAACTCGCGGTTCG<br>CGTGGATGACCCGGAAGAGCGAGGAGACGATCACCCCGTGGAATTTCGA<br>GGAGGTCGTCGATAAAGGCGCGTCGGCGCAGTCGTTCATCGAGCGCATG<br>ACCAACTTCGATAAAAATCTGCCGAACGAAAAAGTCCTGCCCAAGCATA<br>GCCTGCTGTACGAGTACTTCACGGTCTACAACGAGCTGACGAAAGTGAA<br>ATATGTCACGGAGGGCATGCGCAAACCGGCCTTCCTGTCCGGCGAGCAG<br>AAAAAGGCCATCGTGGATCTGCTGTTCAAGACGAACCGGAAGGTCACCG<br>TGAAACAGCTGAAGGAAGATTACTTCAAGAAAATCGAGTGCTTCGATTC<br>CGTCGAAATCAGCGGCGTGGAGGACCGCTTCAATGCCTCGCTGGGCACC<br>TATCACGATCTCCTCAAGATCATCAAGGACAAGGACTTCCTGGACAACG<br>AAGAGAACGAGGACATCCTGGAAGACATCGTCCTCACCCTGACCCTGTT<br>CGAGGACCGCGAAATGATCGAAGAGCGCCTGAAGACCTACGCCCACCTG<br>TTCGACGACAAGGTCATGAAGCAGCTCAAGCGCCGCCGGTACACCGGCT<br>GGGGCCGCCTGTCCCGGAAGCTGATCAACGGCATCCGCGATAAGCAGAG<br>CGGCAAGACGATCCTGGACTTCCTCAAGAGCGACGGCTTCGCCAATCGGA<br>ATTTCATGCAGCTCATCCACGACGATAGCCTGACCTTCAAAGAGGATATC<br>CAGAAGGCGCAGGTGTCCGGCCAGGGCGACAGCCTGCACGAACATATCG<br>CCAACCTGGCGGGCTCCCCCGCGATCAAGAAAGGCATCCTCCAGACGGTC<br>AAAGTCGTGGACGAGCTGGTCAAGGTGATGGGCCGCCACAAACCGGAGA<br>ATATCGTCATCGAGATGGCACGCGAGAACCAGACCACGCAGAAGGGCCA<br>GAAGAACAGCCGGGAACGCATGAAACGGATCGAAGAGGGCATCAAGGA<br>ACTGGGCTCGCAGATCCTGAAGGAGCACCCCGTCGAAAACACGCAGCTC<br>CAGAACGAGAAGCTGTATCTGTACTATCTCCAGAACGGCCGGGACATGTA<br>TGTCGATCAGGAACTGGATATCAACCGCCTCTCCGATTACGATGTGGACC<br>ACATCGTGCCGCAGAGCTTCCTGAAAGACGACTCGATCGACAACAAGGTC<br>CTGACCCGGTCGGACAAGAACCGCGGCAAGTCGGATAACGTGCCGTCGG<br>AAGAAGTCGTGAAAAAGATGAAGAACTACTGGCGGCAGCTCCTGAACGC<br>GAAGCTCATCACGCAGCGCAAGTTCGACAATCTGACCAAGGCCGAGCGC<br>GGCGGCCTCTCGGAACTCGACAAGGCGGGCTTCATCAAACGGCAGCTCG<br>TCGAGACGCGCCAGATCACCAAACACGTGGCCCAGATCCTGGACAGCCG<br>GATGAACACCAAATACGACGAAAACGACAAGCTGATCCGCGAAGTCAAG<br>GTCATCACGCTGAAGAGCAAGCTGGTGTCGGATTTCCGCAAGGATTTCCA<br>GTTCTACAAGGTGCGCGAGATCAACAATTACCATCACGCGCACGATGCCT<br>ATCTCAATGCGGTCGTGGGCACCGCCCTGATCAAAAAGTACCCGAAACTG<br>GAGTCCGAGTTCGTCTACGGCGACTATAAGGTCTATGATGTCCGCAAGAT<br>GATCGCCAAATCGGAGCAGGAGATCGGCAAGGCGACCGCGAAATATTTC<br>TTCTACTCGAACATCATGAATTTCTTCAAGACCGAGATCACGCTGGCGAA |

TABLE 1-continued

| SEQ ID NO. | NAME | SEQUENCE |
|---|---|---|
| | | CGGCGAAATCCGCAAGCGGCCCCTGATCGAAACCAATGGCGAGACCGGC GAGATCGTGTGGGACAAAGGCCGGGATTTCGCCACCGTCCGCAAGGTCCT CTCGATGCCGCAGGTGAACATCGTCAAGAAGACGGAGGTCCAGACCGGC GGCTTCAGCAAAGAAAGCATCCTCCCCAAGCGGAATAGCGACAAACTGA TCGCCCGGAAGAAGGACTGGGACCCGAAGAAGTATGGCGGCTTCGATAG CCCCACCGTCGCCTATTCCGTCCTGGTGGTGGCGAAGGTGGAGAAAGGCA AAAGCAAGAAACTGAAGAGCGTGAAGGAGCTGCTGGGCATCACCATCAT GGAACGCAGCAGCTTCGAGAAGAACCCGATCGACTTCCTGGAAGCCAAA GGCTATAAGGAAGTGAAGAAGGACCTCATCATCAAACTCCCGAAGTATT CGCTGTTCGAGCTGGAAAATGGCCGCAAACGGATGCTCGCCTCCGCGGG CGAACTCCAGAAGGGCAACGAACTGGCGCTGCCGTCCAAATACGTCAAC TTCCTCTATCTGGCCAGCCATTACGAAAAGCTGAAGGGCTCGCCCGAAGA TAACGAGCAGAAACAGCTGTTCGTCGAGCAGCACAAGCACTACCTCGAC GAGATCATCGAGCAGATCAGCGAGTTCTCCAAGCGGGTGATCCTCGCGG ACGCCAACCTGGACAAGGTGCTGTCGGCGTACAACAAACATCGGGATAA GCCGATCCGCGAGCAGGCCGAAAATATCATCCACCTGTTCACCCTGACGA ACCTCGGCGCCCCCGCCGCCTTCAAGTATTTCGATACCACCATCGACCGGA AGCGCTATACCTCCACCAAAGAGGTCCTGGATGCCACCCTCATCCACCAG TCCATCACGGGCCTGTACGAGACCCGCATCGACCTGTCGCAGCTGGGCGG CGACTAA |

Example 6: Synthetic gRNA Expression

Synthetic gRNA were made which contained a 20 bp target region and a 83 bp Cas9 handle and terminator region. This synthetic gRNA was made to be driven by a constitutively expressed J23111 promoter. This J23111 promoter-gRNA sequence was cloned into a pBBR1-based plasmid (pSL90). Other J series promoters such as J23115 were also tested resulting in high editing efficiency (>50%). Additionally, a donor sequence was cloned in the same pBBR1-based plasmid containing the gRNA. The J23111 and Cas9 sequences used are shown in Table 2.

TABLE 2

| SEQ ID NO. | NAME | SEQUENCE |
|---|---|---|
| 80 | J23111 | TTGACGGCTAGCTCAGTCCTAGGTATAGTGCTAGC |
| 81 | Cas9 handle and terminator region | GTTTTAGAGCTAGAAATAGCAAGTTAAAATAAGGCTAGT CCGTTATCAACTTGAAAAAGTGGCACCGAGTCGGTGCTT TTTTT |

Example 7: Preparation for Genome Editing

A two-step two-plasmid system was employed in order to achieve high editing efficiency via CRISPR-Cas9 genome editing in *Methylococcus capsulatus*.

A "base" strain was created by transforming a pBBR1_gRNA_donor plasmid into *Methylococcus capsulatus* through electroporation. The base strains were frozen as a stock for future editing.

To perform gene editing, the base strain was pre-cultured by thawing out frozen stock vial of the base strain. The pre-cultures were grown to saturation (Optical Density (OD) at 600 nm of approximately 1-1.5). Once saturation was reached, a 1:100 dilution was made. The diluted cells were allowed to grow to an appropriate cell density (OD of 0.4-0.8). The cells were then prepared for electroporation.

The cells were washed three times in a solution comprising 2.5% sucrose and concentrated. The concentrated cells were then re-suspend in the solution comprising 2.5% sucrose to achieve an OD between 40-90. 300 ng of genetic materials to be electroporated, for example pSL95 (from example 1), were used for electroporation per 50 ul electrocompetent cells. The cells were cultured in IM5 media supplemented with 2.5% sucrose for at least 4 hours up to overnight. Then cells were plated on agar plates containing spectinomycin and kanamycin. The plates were placed in incubators containing 95% methane and 5% $CO_2$ until the appearance of colonies.

Editing efficiency was measured by confirming the proper nucleotide sequence using PCR and sequencing. First, a pair of primers were designed so that they anneal to the outside of donor region. PCR reactions were performed on several colonies (e.g., 8-12 colonies (colony PCR)), using the aforementioned primers for the amplification reaction. DNA sequencing of the amplified DNA products was used to determine the number of isolates that display correct editing (editing efficiency).

Example 8: Incorporating Point Mutations Using AGE

Point mutations were incorporating using AGE within the ppdK locus.

Two gRNAs were designed to knock out ppdK function through introducing stop codons and frame shift mutations. The gRNA and donor sequences are listed in Table 3A.

TABLE 3A

| Plasmid | gRNA1 | Targeting Sequence | Full sgRNA sequence | Donor sequence | Editing efficiency |
|---|---|---|---|---|---|
| pSL148 | gRNA1 | GCTCGAAG CCCATTAC CACG (SEQ ID NO. 82) | TTGACGGCTAGCTCAGTCC TAGGTATAGTGCTAGCGCT CGAAGCCCATTACCACGGT TTTAGAGCTAGAAATAGCA AGTTAAAATAAGGCTAGTC CGTTATCAACTTGAAAAAG TGGCACCGAGTCGGTGCTT TTTTT (SEQ ID NO. 83) | GTTCGACGCCGAATTCGAAGCC ATCAAGCACCAGGCCGGGGTCG CCGCCGACATCGGCCTGAGCGC CGTCCATCTCGCCGACATCGGCG AACGTTTCCTCGCCGTCGTACGC CGCCATACCGGCAAGCCTTTCCC CGAGGACGTCTACGAGCAGCTC GAGATCGCGATCCGGGCGGTAT TCGACTCCTGGATGGGAAACGC (SEQ ID NO. 84) | 83% |
| pSL150 | gRNA2 | TCAACCAC GATACACT CCAG (SEQ ID NO. 85) | TTGACGGCTAGCTCAGTCC TAGGTATAGTGCTAGCTCA ACCACGATACACTCCAGGT TTTAGAGCTAGAAATAGCA AGTTAAAATAAGGCTAGTC CGTTATCAACTTGAAAAAG TGGCACCGAGTCGGTGCTT TTTTT (SEQ ID NO. 86) | GTGACCGAGCCTATCTGGAATTG CTCAAGGCCCTGGCCCAGTTGCG CCTGCTGGAACGGCTGAATGCTC GAAAAATGGGCCGGAACCGGCT CTGATCCTGCAGTGACAAGCGG CGAACGCGACAGTTCGAGGAGA CCATCATGACGATGAAAAAGCG TGTCTACGCCTTCTCCGAAGGCG ACGGCAAGAACAAACGCCT (SEQ ID NO. 87) | 100% |

Additional targets were chosen for point mutations. For example, the genes rpoB, MCA2598, and MDH were targeted for point mutation editing. Editing efficiency for these genes ranged from 88% to 96%. The gRNA and donor sequences are listed in Table 3B.

TABLE 3B

| Plasmid | Gene Target | Targeting Sequence | Full sgRNA sequence | Donor sequence | Editing efficiency |
|---|---|---|---|---|---|
| pSL128 | rpoB | GGACCAGA ACAATCCG TTGT (SEQ ID NO. 88) | TTGACGGC TAGCTCAG TCCTAGGT ATAGTGCT AGCGGACC AGAACAAT CCGTTGTG TTTTAGAG CTAGAAAT AGCAAGTT AAAATAAG GCTAGTCC GTTATCAA CTTGAAAA AGTGGCAC CGAGTCGG TGCTTTTTT T (SEQ ID NO. 89) | TACCATGCGCATCGATCTGACCGAGACGCAGCTGGATGCCCTG GTGGAAATCTACCGGATGATGCGGCCGGGCGAACCGCCGACC AAGGAGGCCGCCCAGACCCTGTTCGAAAATCTGTTTTTCTCGG CCGAACGCTATGATCTGTCGGCTGTCGGCCGGATGAAGTTCAA CCGGCGCCTGGGGCGGACCGATCCTACCGGCCCCGGCGTGCT GGAAAACGATGACATCATCGCGGTGCTGAAGGAACTGATCAA CATCCGTAACGGGGGGGGCACGGTCGACGACATCGACCATCT GGGTAACCGCCGCGTCCGGTCCGTGGGGGAGATGGTGGAGA ATCAGTTCAGGCTCGGGCTGGTCCGGGTCGAACGGGCCGTGA AGGAGCGTCTGTCGCTGCCCGACGCCGATGGTCTGATGCCACA GGAGATCATCAACGCCAAACCGGTGGCCGCTTCCATCAAGGA ATTCTTCGGTTCGAGCCAGCTTTCGCGGTTCATGGACCAGAAT AACCCATTATCTGAGGTCACTCACAAGCGCCGTGTCTCGGCTCT GGGGCCGGGGGGGCTGGCGCGTGAGCGCGCCGGCTTCGAAG TGCGCGACGTGCATACCACCCACTACGGCCGTGTCTGTCCGAT CGAAACGCCCGAAGGTCCGAACATCGGCCTGATCAACTCGCTC GCGGTCTACTCGCGCACCAACGAATACGGCTTTCTGGAGACGC CGTATCGAAAGGTGATCGACGGCCGGGTGACCGATCAGATCG AGTACCTGTCGGCTATCGAGGAGGGCCAGTACTACATTGCTCA GGCCAGCGCCTCGGTCGATGAAAACGGCATGCTCAAGGATGA ACTGGTGTCGTGTCGCCACAAGGATGAATTCACCCTGGCGTCG CGGGAAAACATCAACTACATGGATGTGTCGTCCAAACAGATCG TGTCGGTCGCGGCCTCGCTGATCCCCTTCCTCGAACACGATGA TGCCAACCGCGCCCTGATGGGCTCGAACATGCAGCGGCAGGC CGTCCCGACGCTGCGTACGGAGAA (SEQ ID NO. 90) | 96% |
| gap gRNA5 | MCA25 98 | CGTCGTGC ATGAGTGC ACCG (SEQ ID NO. 91) | TTGACGGC TAGCTCAG TCCTAGGT ATAGTGCT AGCCGTCG TGCATGAG TGCACCGG TTTTAGAG CTAGAAAT AGCAAGTT AAAATAAG GCTAGTCC GTTATCAA CTTGAAAA | CCGGGACGGAACGCTTGCCAGGCCATCTGGATGTGGCGGGGA CCGGCGCCGTCGACGAACACGATCTCGAGGTCGTCGGCCACC GCCAGATAGAGCATGTTGCGAATGGGGACGAACAGTGGGTCG GGGCGCCGGCGGCCGAGCAGTACCCGGCTGAGGTTGTAGGTT GCGGCGCCGAGCAGGCGTGCCTCGCGTCGGAGTTCGCGCGAA CGATGGAAGGTTTCCTGCATGTGGATGGCGTCGCTTGCTGGGT CCCGGTTTAAGCTATCAGCCTTGGTGCGCGAAGGGCAAGAACT GGACGCTCGGCGCGGCGCTTTGCTATATTGGCCACGCTTTGTA TTGACAGATTCCCCGGAGAATGCCCGATTCTCCCTCGCCGAAG GCCCGCAGGCGTCCGGCCGGGACGGCCTCGACTGCTCTCCCCA CCCCACTCCGCCGGTCGCCAAGGGTGCGAGGGCTCTCGCGCAT GACCCCATCCTCACTTTATTTCAGCATTTCTGGAGCAGGGCAAT GACGATTAAGATTGCAATCAATGGATATGGGCGCATCGGCCG CAACATCCTGCGGGCGATTTACGAAACCGGGCGCAAGGATGT | 88% |

TABLE 3B-continued

| Plasmid | Gene Target | Targeting Sequence | Full sgRNA sequence | Donor sequence | Editing efficiency |
|---|---|---|---|---|---|
| | | | AGTGGCAC<br>CGAGTCGG<br>TGCTTTTT<br>T (SEQ ID<br>NO. 92) | GGAGATCGTCGCCATCAATGACCTGGGGGATGCCCAGATCAA<br>CGCCCATCTCACCCGCCATGACACCGTGCACGGGCCGTTCCGG<br>GGGACCGTGGAGGTCGGCGAGGGCGAAATCATCGTCAACGG<br>CGACCGCATCAGGGTTTTTCCGAGAAGGATCCTTCCAAGCTG<br>CCCTGGGGGGCTTTGGGCGTGGACGTCGTGCATGAGTGATAG<br>CACCTGTTCCGCACCAAGGCCAAATGCCAGCCGCATCTCGATG<br>CCGGCGCCAAGAAGGTGATCATTTCGGCCCCGGCCGACAAGA<br>ACGAGTGCGACGCGACCATCGTCTACGGGGTCAATGAGCATA<br>CGCTGAAAGCCGCCCACACCGTCATCTCGAATGCATCCTGCAC<br>CACCAACTGCCTGGCGCCGCTGGTCAAGCCGCTGCTGGGAAA<br>AATCGGGATCGTGTCCGGCCTCATGACCACCGTGCATTCCTAC<br>ACCAACGACCAGGTGCTCACCGACGTTTATCACAAGGATCTGT<br>ACCGGGCACGGGCGGCGGCGCTGAACATGATCCCGACCAAGA<br>CCGGCGCGGCGCAGGCCGTGGGGCTGGTGCTGCCGGAGCTG<br>GACGGCAAACTGTCCGGTTTCGCCATCCGGGTGCCGACCGCCA<br>ATGTATCGGTCGTGGACCTGACCTTCATCGCGGCCCGGGAAAC<br>CGACAAGGACGAGATCAACGCCATCCTCAAGGC (SEQ ID NO.<br>93) | |
| plK11 | MDH | CCCATCAC<br>CTATCAGC<br>ACAA<br>(SEQ ID<br>NO. 94) | TTGACGGC<br>TAGCTCAG<br>TCCTAGGT<br>ATAGTGCT<br>AGCCCCAT<br>CACCTATC<br>AGCACAAG<br>TTTTAGAG<br>CTAGAAAT<br>AGCAAGTT<br>AAAATAAG<br>GCTAGTCC<br>GTTATCAA<br>CTTGAAAA<br>AGTGGCAC<br>CGAGTCGG<br>TGCTTTTT<br>T (SEQ ID<br>NO. 95) | AAGATCGATGACACCGTCAACTGGGTGAAAAAGGTCGATCTG<br>AAGACCGGCCTGCCGATCCGCGATCCGGAGTACAGCACCCGC<br>ATGGACCACAATGCCAAAGGCATCTGTCCCTCGGCCATGGGCT<br>ATCACAACCAGGGCATCGAGTCCTACGATCCGGACAAGAAGCT<br>GTTCTTCATGGGCGTGAACCACATCTGCATGGACTGGGAGCCG<br>TTCATGCTGCCCTACCGCGCCGGCCAGTTCTTTGTGGGGGCGA<br>CCCTCAACATGTATCCGGGACCCAAGGGGATGCTGGGTCAGG<br>TCAAGGCGATGAACGCGGTCACCGGCAAGATGGAATGGGAA<br>GTGCCGGAGAAGTTTGCGGTCTGGGGTGGCACCTTGGCGACC<br>GCCGGCGACCTCGTGTTCTACGGTACCCTCGACGGCTTCATCA<br>AGGCCCGCGACACCCGTACCGGCGAGCTGAAGTGGCAGTTCC<br>AGTTGCCCTCCGGCGTGATCGGCCATCCCATCACGTACCAACA<br>TAACGGCAAGCAATACATTGCCATCTACTCCGGCGTCGGCGGC<br>TGGCCAGGAGTAGGGCTGGTATTCGACCTGAAGGACCCGACC<br>GCAGGTCTGGGAGCTGTGGGTGCGTTCAGGGAACTGGCGCAT<br>TACACCCAGATGGGTGGATCGGTGTTCGTGTTCTCGCTTTGAG<br>TCGAAGGGGTGGAGGCGCTCCTGGGGGAGCGCCCCTATCCCA<br>TGCTGTCGAAAGGATGAATCATGCGAATGAACCGTATTGCAGC<br>CGCGGGGTTGGCCGCCTCCCTCGCGGTCGTGGGATGCGTGCA<br>GGCAGCGACGAGCGTCGAACCGCTCAAGGTCTGCTCCGCGGA<br>AAACGAGATGCCGTATTCGGACAAGGCCGGAGAGGGTTTCGA<br>AAATAAGTTGGCTGAGCTCCTTGGAAAGGGATTGGGACGGCC<br>AGTCGAGAACGTGTGGTGGACCGATGCCCGCTATTTCGTCCGG<br>GATTATCTGGACAGGGGTTTGTGCGATGTGGTCATCGGCGTCG<br>ATACCGGCGACCCGCGGATGCTCACCAGCAGTCCTTATTACCG<br>GTCCGGCTACGTATTCGTCTACCGCAAGGACACGGGACTGAGC<br>ATCCAAGATTGGAACAGCGCGGCACTGAAGACCGTGAAGCGG<br>ATC (SEQ ID NO. 96) | 88% |

Example 9: Deletion of Portions of Genes

Portions of genes were deleted using AGE within specific genes such as the ppdK locus.

gRNA2 was designed to knock out ppdK function through gene deletion. Table 4A contains the gRNA and donor sequences used for creating the ppdK deletions.

TABLE 4A

| Plasmid | gRNA1 | Targeting Sequence | Full sgRNA sequence | Donor sequence | Editing efficiency |
|---|---|---|---|---|---|
| pSL178 | gRNA2 | TCAACCAC<br>GATACACT<br>CCAG (SEQ<br>ID NO. 97) | TTGACGGCTAGCTCAGTCC<br>TAGGTATAGTGCTAGCTCA<br>ACCACGATACACTCCAGGT<br>TTTAGAGCTAGAAATAGCA<br>AGTTAAAATAAGGCTAGTC<br>CGTTATCAACTTGAAAAAG<br>TGGCACCGAGTCGGTGCTT<br>TTTTT (SEQ ID NO. 98) | GTGTTCCCTGGAACACGCCATCA<br>ATTTCGATCTCGTGCTCAACACC<br>GACCATCTGCCAGCCGGTAACG<br>CTCTGCCGACCGTACTCATGGCG<br>GTACGGCAGTTCGGCTTCGAAAT<br>CTTCGATCTCGGTCAGCGGGAA<br>GCCTCGTGAGCCCGGCGGTGGG<br>ACAGACCGCATCCCGTCTGCTAA<br>CGGTCGAGATCGTCGACGTCTG<br>CCGGGAGATATTTTCCGGGCGTT<br>GTAGCCGGGTGGTCGCGCCAGC | 72% |

TABLE 4A-continued

| Plasmid | gRNA1 | Targeting Sequence | Full sgRNA sequence | Donor sequence | Editing efficiency |
|---|---|---|---|---|---|
| | | | | GGCAGACGGTGAGGTCGGCGTT CTGCCCCGTCATACGCCGTTCCT GACCCGGCTCCGGCCCGGCGAG ATAAGGC (SEQ ID NO. 99) | |

Additional targets were chosen for deletions within the ppdK gene. The deletion size of this second locus was 200 base pairs. Editing efficiency for the second locus was 88%. The gRNA and donor sequences are listed in Table 4B.

TABLE 4B

| Plasmid | Gene target | Targeting Sequence | Full sgRNA sequence | Donor sequence | Editing efficiency |
|---|---|---|---|---|---|
| pSL179 | ppdK | TCAACCAC GATACACT CCAG (SEQ ID NO. 100) | TTGACGGC TAGCTCAG TCCTAGGT ATAGTGCT AGCTCAAC CACGATAC ACTCCAGG TTTTAGAG CTAGAAAT AGCAAGTT AAAATAAG GCTAGTCC GTTATCAA CTTGAAAA AGTGGCAC CGAGTCGG TGCTTTTT T (SEQ ID NO. 101) | GTGTTCCCTGGAACACGCCATCAATTTCGATCTCGTGCTCAACACC GACCATCTGCCAGCCGGTAACGCTCTGCCGACCGTACTCATGGCGG TACGGCAGTTCGGCTTCGAAATCTTCGATCTCGGTCAGCGGGAAGC CTCGTGAGCCCGGCGGTGGGACAGACCGCATCCCGTCTGCTAACG GTCGAGATCGTCGACGTCTGCCGGGAGATATTTTCCGGGCGTTGT AGCCGGGTGGTCGCGCCAGCGGCAGACGGTGAGGTCGGCGTTCT GCCCCGTCATACGCCGTTCCTGACCCGGCTCCGGCCCGGCGAGATA AGGCTCAGGACCGAGGCAGGCGAAGACCAGTATTTCTACCTCTCC GGGGGCTACATGGAGGTGCAGCGCTGGGAGGTCAGCATCCTGGC CGACCAGGTGCTCCGCTCCCAAGAGATCGACCGGGAAGCGGCCCT GGCGGCCAAGCGCAACGCAGAGCGGATGCTCCGCGAGAACCGGA TTCCCGGCGAGCGTGACCGAGCCTATCTGGAATTGCTCAAGGCCCT GGCCCAGTTGCGCCTGCTGGAACGGCTGAATGCTCGAAAAATGGG CCGGAACCGGCTCTGATCCTGCAGTGACAAGCGGCGAACGCGACA GTTCGAGGAGACCATCATGACGATGAAAAAGCGTGTCTACGCCTT CTCCGAAGGCGACGGCAAGAACAAACGCCTGCTCGGCGGCAAGG GCGCCAACCTCTGCGAAATGACGCAGATCGGGCTCAACGTGCCGC CGGGTTTCGTTATTACCACGGAAGCCTGCCTCGAATACCTGGCAGA CAAGAAGCTGCCGGCCGGCTTGATGGACGAAGTCCGGGAGCACAT GGCCCGGCTCGAACGGGCTACCGGCAAGCGCTTCGGCGATCCCGC CAATCCACTCTTGGTTTCGGTGCGTTCCGGTTCGGCCCTGTCCATGC CGGGCATGATGGATACCATTCTCAACCTCGGCCTCAACCACGATAC ACTCTTTCCTCGCCGTCGTACGCCGCCATACCGGCAAGCCTTTCCCC GAGGACGTCTACGAGCAGCTCGAGATCGCGATCCGGGCGGTATTC GACTCCTGGATGGGAAAGCGCGCGGTGGATTACCGCCGCGAATTC CACATCACGCCCGACCAGGCCAACGGCACGGCGGTGAACGTGGTG ACCATGGTGTTCGGCAACATGGGCGACGACTCCGCCACCGGTGTC GGCTTCACCCGCAATCCGGGTACCGGTGAGAACGAGATGTTCGGC GAGTATCTGGTCAACGCCCAGGGTGAGGATGTGGTAGCCGGAATC CGCACGCCCAAGCCCGTGCACGAGATGGCAACCGAAATGCCGGCG CTTTACGCCCAACTGGTGGAACTGCGCGACAAGCTCGAAGCCCATT ACCACGAGGTGCAGGACTTCGAGTACACCATCGAGAAGGGGGTCT TGTACTGTCTGCAGACGCGCAACGGCAAGATGAACGCCCAGGCGA TGGTGCGCACCTCGGTCGAGATGTGCCGGGAAGGACTGATCACGC GGGATCAGGCCCTCTTGCGGGTCAACCCCGCCCATCTGGAACAGTT ACTCCATCCCTGCCTCGACACCTCGCACAACCCCACGCCGCTGGCG CAGGGGCTGCCTGCCTCGCCCGGCGCCGCCAGCGGCCGTTGCGTG TTCGATGCGGATCAGGCCGAACTGTTGGGACGGGCCGGTGAAAA GGTCATCCTGGTGCGTGAGGAGACCAAGCCGGAAGACATCCACGG CTTCTTCGCGGCCCAGGGAATCCTCACCAGTCGCGGCGGCAAGAC CTCGCATGCCGCCGTGGTCGCCCGCGGCATGGGCAAGGCCTGCGT GGCCGGGGCCGAAGGCATCAGGGTGGACAGCCGGGCGCGGCTG GCAACGGTGGGAGAGGTCACGTTGCACGAAGGTGACATCATCACC ATCGACGGCAGCACCGGCCGTGTCTATCTCGGCGCGATCCCGACG ATCGCGCCGACCTTCTCCGAACACCTCAGGACACTGCTGTC (SEQ ID NO. 102) | 88% |

Example 10: Insertion of Nucleotides

Nucleotides were inserted using AGE within the ppdK locus.

gRNA2 was designed to integrate gamma protein gene (417 bp) at ppdK locus. Table 5A indicates the gRNA and donor sequences used for creating the gamma protein gene integration.

TABLE 5A

| Plasmid | gRNA1 | Targeting Sequence | Full sgRNA sequence | Donor sequence | Editing efficiency |
|---|---|---|---|---|---|
| pSL162 | gRNA2 | TCAACCAC<br>GATACACT<br>CCAG (SEQ<br>ID NO.<br>103) | TTGACGGCTAGCTCAGTCC<br>TAGGTATAGTGCTAGCTCA<br>ACCACGATACACTCCAGGT<br>TTTAGAGCTAGAAATAGCA<br>AGTTAAAATAAGGCTAGTC<br>CGTTATCAACTTGAAAAAG<br>TGGCACCGAGTCGGTGCTT<br>TTTTT (SEQ ID NO.<br>104) | GTGACCGAGCCTATCTGGAATTG<br>CTCAAGGCCCTGGCCCAGTTGCG<br>CCTGCTGGAACGGCTGAATGCTC<br>GAAAAATGGGCCGGAACCGGCT<br>CTGATCCTGCAGTGACAAGCGG<br>CGAACGCGACAGTTCGAGGAGA<br>CCATCATGACGATGAAAAAGCG<br>TGTCTACGCCTTCTCCGAAGGCG<br>ACGGCAAGAACAAACGCCT<br>(SEQ ID NO. 105) | 11% |

Additional targets were chosen for insertions within specific genes. The size of the fragments were relatively small, i.e., 34 and 39 bps. Editing efficiency for the second locus was 83% for both of these genes. The gRNA and donor sequences are listed in Table 5B.

TABLE 5B

| Plasmid | Gene target | Targeting Sequence sequence | Full sgRNA | Donor sequence | Editing efficiency |
|---|---|---|---|---|---|
| pSL154 | ppdK<br>(attB<br>site) | TCAACCAC<br>GATACACT<br>CCAG (SEQ<br>ID NO.<br>106) | TTGACGGC<br>TAGCTCAG<br>TCCTAGGT<br>ATAGTGCT<br>AGCTCAAC<br>CACGATAC<br>ACTCCAGG<br>TTTTAGAG<br>CTAGAAAT<br>AGCAAGTT<br>AAAATAAG<br>GCTAGTCC<br>GTTATCAA<br>CTTGAAAA<br>AGTGGCAC<br>CGAGTCGG<br>TGCTTTTT<br>T (SEQ ID<br>NO. 107) | GTGACCGAGCCTATCTGGAATTGCTCAAGGCCCTGGCCCAGTTGCG<br>CCTGCTGGAACGGCTGAATGCTCGAAAAATGGGCCGGAACCGGCT<br>CTGATCCTGCAGTGACAAGCGGCGAACGCGACAGTTCGAGGAGAC<br>CATCATGACGATGAAAAAGCGTGTCTACGCCTTCTCCGAAGGCGAC<br>GGCAAGAACAAACGCCTGCTCGGCGGCAAGGGCGCCAACCTCTGC<br>GAAATGACGCAGATCGGGCTCAACGTGCCGCCGGGTTTCGTTATT<br>ACCACGGAAGCCTGCCTCGAATACCTGGCAGACAAGAAGCTGCCG<br>GCCGGCTTGATGGACGAAGTCCGGGAGCACATGGCCCGGCTCGAA<br>CGGGCTACCGGCAAGCGCTTCGGCGATCCCGCCAATCCACTCTTGG<br>TTTCGGTGCGTTCCGGTTCGGCCCTGTCCATGCCGGGCATGATGGA<br>TACCATTCTCAACCTCGGCCTCAACCACGATACACTCTAAGTGCCAG<br>GGCGTGCCCTTGGGCTCCCCGGGCGCGGGGTTGATCCGGCAGACC<br>GGCAACGAGCGCTTCGGTCACGATGCCTACCGGCGGTTCATCCAG<br>TTGTTCGGCAAGGTTGCCCTCGGTGTTCCCGACGAGCTGTTCGACG<br>CCGAATTCGAAGCCATCAAGCACCAGGCCGGGGTCGCCGCCGACA<br>TCGGCCTGAGCGCCGTCCATCTCGCCGACATCGGCGAACGTTTCCT<br>CGCCGTCGTACGCCGCCATACCGGCAAGCCTTTCCCCGAGGACGTC<br>TACGAGCAGCTCGAGATCGCGATCCGGGCGGTATTCGACTCCTGG<br>ATGGGAAAGCGCGCGGTGGATTACCGCCGCGAATTCCACATCACG<br>CCCGACCAGGCCAACGGCACGGCGGTGAACGTGGTGACCATGGT<br>GTTCGGCAACATGGGCGACGACTCCGCCACCGGTGTCGGCTTCAC<br>CCGCAATCCGGGTACCGGTGAGAACGAGATGTTCGGCGAGTATCT<br>GGTCAACGCCCAGGGTGAGGATGTGGTAGCCGGAATCCGCACGCC<br>CAAGCCCGTGCACGAGATGGCAACCGAAATGC (SEQ ID NO. 108) | 83% |
| pSL175 | aacC<br>(attP)<br>site) | TACTACGG<br>AGCAAGTT<br>CCCG (SEQ<br>ID NO.<br>109) | TTGACGGC<br>TAGCTCAG<br>TCCTAGGT<br>ATAGTGCT<br>AGCTACTA<br>CGGAGCAA<br>GTTCCCGG<br>TTTTAGAG<br>CTAGAAAT<br>AGCAAGTT<br>AAAATAAG<br>GCTAGTCC<br>GTTATCAA<br>CTTGAAAA<br>AGTGGCAC<br>CGAGTCGG<br>TGCTTTTT<br>T (SEQ ID<br>NO. 110) | GCCAGGACAGAAATGCCTCGACTTCGCTGCTGCCCAAGGTTGCCG<br>GGTGACGCACACCGTGGAAACGGATGAAGGCACGAACCCAGTTG<br>ACATAAGCCTGTTCGGTTCGTAAACTGTAATGCAAGTAGCGTATGC<br>GCTCACGCAACTGGTCCAGAACCTTGACCGAACGCAGCGGTGGTA<br>ACGGCGCAGTGGCGGTTTTCATGGCTTGTTATGACTGTTTTTTTGTA<br>CAGTCTATGCCTCGGGCATCCAAGCAGCAAGCGCGTTACGCCGTG<br>GGTCGATGTTTGATGTTATGGAGCAGCAACGATGTTACGCAGCAG<br>CAACGATGTTACGCAGCAGGGCAGTCGCCCTAAAACAAAGTTAGG<br>TGGCTCAAGTATGGGCATCATTCGCACATGTAGGCTCGGCCCTGAC<br>CAAGTCAAATCCATGCGGGCTGCTCTTGATCTMCGGTCGTGAGT<br>TCGGAGACGTAGCCACCTACTCCCAACATCAGCCGGACTCCGATTA<br>GCTCCCCCAACTGAGAGAACTCAAAGGTTACCCCAGTTGGGGCGG<br>GTAACTTGCTCCGTAGTAAGACATTCATCGCGCTTGCTGCCTTCGA<br>CCAAGAAGCGGTTGTTGGCGCTCTCGCGGCTTACGTTCTGCCCAGG<br>TTTGAGCAGCCGCGTAGTGAGATCTATATCTATGATCTCGCAGTCT<br>CCGGCGAGCACCGGAGGCAGGGCATTGCCACCGCGCTCATCAATC<br>TCCTCAAGCATGAGGCCAACGCGCTTGGTGCTTATGTGATCTACGT<br>GCAAGCAGATTACGGTGACGATCCCGCAGTGGCTCTCTATACAAA<br>GTTGGGCATACGGGAAGAAGTGATGCACTTTGATATCGACCCAAG<br>TACCGCCACCTAACAATTCGTTCAAGCCGAGATCGGCTTCATAACTT<br>CGTATAGCATACATTATACGAAGTTATTGGCAGAGCATTACGCTGA<br>CTTGACCAGAGGCTGCATTTCCACCGCTGATTGCGATTCGGAAGGT<br>GCAGGCCGGAGGGTCCGGACCGCCGCTCCACCCGTTGTTTTC<br>(SEQ ID NO. 111) | 83% |

Larger insertional targets were chosen. Targets with DNA insertion size of 684 bp and 1083 bp were chosen. Editing efficiency was lower for larger insertional size fragments, i.e., under 100% efficiency. The gRNA and donor sequences are listed in Table 5C.

TABLE 5C

| Plasmid | Gene target | Targeting Sequence | Full sgRNA sequence | Donor sequence | Editing efficiency |
|---|---|---|---|---|---|
| pSL163 | ppdK (mcherry) | TCAACCAC<br>GATACACT<br>CCAG (SEQ<br>ID NO.<br>112) | TTGACGGC<br>TAGCTCAG<br>TCCTAGGT<br>ATAGTGCT<br>AGCTCAAC<br>CACGATAC<br>ACTCCAGG<br>TTTTAGAG<br>CTAGAAAT<br>AGCAAGTT<br>AAAATAAG<br>GCTAGTCC<br>GTTATCAA<br>CTTGAAAA<br>AGTGGCAC<br>CGAGTCGG<br>TGCTTTTTT<br>T (SEQ ID<br>NO. 113) | GTGACCGAGCCTATCTGGAATTGCTCAAGGCCCTGGCCCAGTTGCG<br>CCTGCTGGAACGGCTGAATGCTCGAAAAATGGGCCGGAACCGGCT<br>CTGATCCTGCAGTGACAAGCGGCGAACGCGACAGTTCGAGGAGAC<br>CATCATGACGATGAAAAAGCGTGTCTACGCCTTCTCCGAAGGCGAC<br>GGCAAGAACAAACGCCTGCTCGGCGGCAAGGGCGCCAACCTCTGC<br>GAAATGACGCAGATCGGGCTCAACGTGCCGCCGGGTTTCGTTATT<br>ACCACGGAAGCCTGCCTCGAATACCTGGCAGACAAGAAGCTGCCG<br>GCCGGCTTGATGGACGAAGTCCGGGAGCACATGGCCCGGCTCGAA<br>CGGGCTACCGGCAAGCGCTTCGGCGATCCCGCCAATCCACTCTTGG<br>TTTCGGTGCGTTCCGGTTCGGCCCTGTCCATGCCGGGCATGATGGA<br>TACCATTCTCAACCTCGGCCTCAACCACGATACACTCTAATTGACGG<br>CTAGCTCAGTCCTAGGTATAGTGCTAGCAAAAAGCTCAACGAGAG<br>GAAGTTCCATGGCCATCATCAAGGAGTTCATGCGCTTCAAGGTGCA<br>CATGGAGGGCTCCGTGAACGGCCACGAGTTCGAGATCGAGGGCG<br>AGGGCGAGGGCCGCCCCTACGAGGGCACCCAGACCGCCAAGCTG<br>AAGGTGACCAAGGGTGGCCCCCTGCCCTTCGCCTGGGACATCCTGT<br>CCCCTCAGTTCATGTACGGCTCCAAGGCCTACGTGAAGCACCCCGC<br>CGACATCCCCGACTACTTGAAGCTGTCCTTCCCCGAGGGCTTCAAG<br>TGGGAGCGCGTGATGAACTTCGAGGACGGCGGCGTGGTGACCGT<br>GACCCAGGACTCCTCCCTCCAGGACGGCGAGTTCATCTACAAGGTG<br>AAGCTGCGCGGCACCAACTTCCCCTCCGACGGCCCCGTAATGCAGA<br>AGAAGACCATGGGCTGGGAGGCCTCCTCCGAGCGGATGTACCCCG<br>AGGACGGCGCCCTGAAGGGCGAGATCAAGCAGAGGCTGAAGCTG<br>AAGGACGGCGGCCACTACGACGCTGAGGTCAAGACCACCTACAAG<br>GCCAAGAAGCCCGTGCAGCTGCCCGGCGCCTACAACGTCAACATC<br>AAGTTGGACATCACCTCCCACAACGAGGACTACACCATCGTGGAAC<br>AGTACGAACGCGCCGAGGGCCGCCACTCCACCGGCGGCATGGAC<br>GAGCTGTACAAGTAAGGGTTGATCCGGCAGACCGGCAACGAGCG<br>CTTCGGTCACGATGCCTACCGGCGGTTCATCCAGTTGTTCGGCAAG<br>GTTGCCCTCGGTGTTCCCGACGAGCTGTTCGACGCCGAATTCGAAG<br>CCATCAAGCACCAGGCCGGGGTCGCCGCCGACATCGGCCTGAGCG<br>CCGTCCATCTCGCCGACATCGGCGAACGTTTCCTCGCCGTCGTACG<br>CCGCCATACCGGCAAGCCTTTCCCCGAGGACGTCTACGAGCAGCTC<br>GAGATCGCGATCCGGGCGGTATTCGACTCCTGGATGGGAAAGCGC<br>GCGGTGGATTACCGCCGCGAATTCCACATCACGCCCGACCAGGCC<br>AACGGCACGGCGGTGAACGTGGTGACCATGGTGTTCGGCAACATG<br>GGCGACGACTCCGCCACCGGTGTCGGCTTCACCCGCAATCCGGGT<br>ACCGGTGAGAACGAGATGTTCGGCGAGTATCTGGTCAACGCCCAG<br>GGTGAGGATGTGGTAGCCGGAATCCGCACGCCCAAGCCCGTGCAC<br>GAGATGGCAACCGAAATGC (SEQ ID NO. 114) | 6% |
| pSL165 | ppdK (adh) | TCAACCAC<br>GATACACT<br>CCAG (SEQ<br>ID NO.<br>115) | TTGACGGC<br>TAGCTCAG<br>TCCTAGGT<br>ATAGTGCT<br>AGCTCAAC<br>CACGATAC<br>ACTCCAGG<br>TTTTAGAG<br>CTAGAAAT<br>AGCAAGTT<br>AAAATAAG<br>GCTAGTCC<br>GTTATCAA<br>CTTGAAAA<br>AGTGGCAC<br>CGAGTCGG<br>TGCTTTTTT<br>T (SEQ ID<br>NO. 116) | GTGACCGAGCCTATCTGGAATTGCTCAAGGCCCTGGCCCAGTTGCG<br>CCTGCTGGAACGGCTGAATGCTCGAAAAATGGGCCGGAACCGGCT<br>CTGATCCTGCAGTGACAAGCGGCGAACGCGACAGTTCGAGGAGAC<br>CATCATGACGATGAAAAAGCGTGTCTACGCCTTCTCCGAAGGCGAC<br>GGCAAGAACAAACGCCTGCTCGGCGGCAAGGGCGCCAACCTCTGC<br>GAAATGACGCAGATCGGGCTCAACGTGCCGCCGGGTTTCGTTATT<br>ACCACGGAAGCCTGCCTCGAATACCTGGCAGACAAGAAGCTGCCG<br>GCCGGCTTGATGGACGAAGTCCGGGAGCACATGGCCCGGCTCGAA<br>CGGGCTACCGGCAAGCGCTTCGGCGATCCCGCCAATCCACTCTTGG<br>TTTCGGTGCGTTCCGGTTCGGCCCTGTCCATGCCGGGCATGATGGA<br>TACCATTCTCAACCTCGGCCTCAACCACGATACACTCTAATTGACGG<br>CTAGCTCAGTCCTAGGTATAGTGCTAGCAAAAAGCTCAACGAGAG<br>GAAGTTCCATGAGCTATCCCGAGAAGTTCGAGGGGATCGCCATCC<br>AGAGCCACGAGGACTGGAAGAACCCGAAAAAGACCAAGTATGAT<br>CCGAAGCCCTTCTACGATCACGACATCGACATCAAGATCGAGGCCT<br>GCGGCGTCTGCGGCAGCGATATCCATTGTGCGGCTGGCCACTGGG<br>GCAACATGAAGATGCCGTTGGTCGTCGGCCACGAGATCGTGGGCA<br>AGGTCGTGAAGTTAGGCCCGAAAAGCAACAGCGGCTTGAAGGTG<br>GGCCAGCGCGTGGGTGTGGGTGCGCAGGTCTTCAGCTGTCTGGAG<br>TGCGACCGTTGCAAGAACGACAACGAACCGTACTGCACCAAGTTC<br>GTCACCACCTACTCGCAGCCCTACGAGGACGGCTACGTCTCGCAGG<br>GCGGTTACGCCAACTATGTCCGAGTCCACGAACACTTCGTGGTGCC<br>CATCCCGGAAAATATCCCCAGCCATCTGGCGGCTCCCCTGCTGTGC<br>GGTGGCTTGACCGTCTACAGCCCCCTCGTCCGCAATGGCTGCGGTC<br>CCGGCAAGAAGGTGGGTATCGTGGGCCTCGGCGGTATAGGCTCTA<br>TGGGCACGCTGATCTCGAAAGCGATGGGCGCAGAAACGTACGTGA<br>TCTCGCGTTCCTCGCGCAAGCGCGAGGATGCGATGAAGATGGGTG<br>CGGACCACTACATCGCCACGCTGGAGGAGGGTGACTGGGGTGAG | 5% |

TABLE 5C-continued

| Plasmid | Gene target | Targeting Sequence | Full sgRNA sequence | Donor sequence | Editing efficiency |
|---|---|---|---|---|---|
| | | | | AAGTACTTCGACACGTTCGACCTCATCGTGGTGTGCGCGAGTTCCC TGACGGACATCGACTTCAATATCATGCCCAAGGCGATGAAGGTCG GAGGGCGCATCGTCTCCATCTCGATCCCGGAGCAGCACGAAATGC TGTCGCTGAAGCCCTACGGCCTGAAAGCCGTCTCCATTAGCTACTC GGCGCTCGGTAGTATCAAGGAGCTCAACCAGCTGTTGAAGTTGGT TTCCGAAAAGGACATCAAGATCTGGGTGGAAACGCTCCCGGTGGG CGAAGCCGGTGTGCACGAGGCCTTTGAGCGGATGGAGAAGGGGG ATGTCCGTTATCGGTTTACACTCGTCGGCTACGATAAAGAGTTCTC GGATTAAGGGTTGATCCGGCAGACCGGCAACGAGCGCTTCGGTCA CGATGCCTACCGGCGGTTCATCCAGTTGTTCGGCAAGGTTGCCCTC GGTGTTCCCGACGAGCTGTTCGACGCCGAATTCGAAGCCATCAAG CACCAGGCCGGGGTCGCCGCCGACATCGGCCTGAGCGCCGTCCAT CTCGCCGACATCGGCGAACGTTTCCTCGCCGTCGTACGCCGCCATA CCGGCAAGCCTTTCCCCGAGGACGTCTACGAGCAGCTCGAGATCG CGATCCGGGCGGTATTCGACTCCTGGATGGGAAAGCGCGCGGTG GATTACCGCCGCGAATTCCACATCACGCCCGACCAGGCCAACGGC ACGGCGGTGAACGTGGTGACCATGGTGTTCGGCAACATGGGCGAC GACTCCGCCACCGGTGTCGGCTTCACCCGCAATCCGGGTACCGGTG AGAACGAGATGTTCGGCGAGTATCTGGTCAACGCCCAGGGTGAGG ATGTGGTAGCCGGAATCCGCACGCCCAAGCCCGTGCACGAGATGG CAACCGAAATGC (SEQ ID NO. 117) | |

Example 11: Inhibition of Gene Expression Using AGEi-dCas9

Catalytically inactive Cas9 protein (dCas9) can form a complex with sgRNA and can bind to a target region to create a steric block interrupting transcript initiation or elongation by RNA polymerase. This can, if done correctly and in certain organisms, result in repression of a target gene, which is referred to as AGEi.

AGEi was performed in *Methylococcus capsulatus* using a two-plasmid based lacZ reporter assay (from Invitrogen lacZ assay kit): 1) OriV origin based plasmid carries pBAD_dCas9 and gRNA. 2) pBBR1 based plasmids carries Ptrc_lacZ. Five gRNA were designed to target different regions of lacZ. One gRNA that targets the promoter region of the reporter repressed lacZ expression consistently over a 72 hour time point. The relevant information related to the sequences is presented in Table 6A, Table 6B, and Table 6C below.

TABLE 6A

| SEQ ID NO. | NAME | SEQUENCE |
|---|---|---|
| 118 | dCas9 | ATGGACAAGAAGTATTCGATCGGCCTGGCCATCGGCACCAACAGCGTCGGCTGGGCGGTCATCACGGATGAGTAC AAGGTGCCGTCGAAGAAGTTCAAGGTGCTGGGCAATACCGACCGCCATAGCATCAAGAAGAATCTCATCGGCGCA CTGCTGTTCGACTCCGGCGAAACCGCCGAAGCGACCCGCCTCAAGCGCACGGCCCGGCGGCGCTATACGCGCCGG AAGAACCGCATCTGCTACCTCCAGGAAATCTTCTCCAACGAGATGGCCAAGGTGGATGACTCCTTCTTCCATCGCCT GGAAGAATCCTTCCTGGTCGAAGAAGATAAGAAACATGAGCGCCACCCCATCTTCGGCAATATCGTGGACGAGGT GGCGTATCACGAGAAATACCCGACCATCTATCACCTGCGGAAAAAGCTGGTGGACTCGACGGACAAAGCCGACCT GCGCCTCATCTATCTGGCCCTGGCCCACATGATCAAGTTCCGGGGCCATTTCCTGATCGAAGGCGACCTGAACCCC GATAACAGCGACGTGGACAAGCTCTTCATCCAGCTCGTCCAGACCTATAACCAGCTGTTCGAGGAGAACCCCATCA ACGCCTCGGGCGTGGACGCCAAGGCCATCCTGAGCGCACGGCTCTCCAAGTCGCGCCGCCTGGAAAACCTGATCG CGCAGCTGCCGGGCGAAAAGAAAAACGGCCTGTTCGGCAACCTGATCGCCCTGTCCCTCGGCCTCACCCCGAACTT CAAGTCCAACTTCGACCTGGCCGAGGACGCGAAGCTCCAGCTGTCGAAAGACACCTACGATGACGACCTGGACAA CCTCCTGGCGCAGATCGGCGACCAGTACGCCGACCTCTTCCTCGCGGCCAAGAATCTGTCGGACGCCATCCTGCTG TCGGATATCCTGCGGGTGAATACGGAGATCACGAAGGCCCCCCTCTCGGCCTCGATGATCAAGCGCTACGACGAG CACCATCAGGACCTGACGCTGCTCAAGGCCCTCGTCCGGCAGCAGCTGCCGGAGAAGTATAAAGAGATCTTCTTCG ACCAGTCCAAGAACGGCTACGCGGGCTACATCGACGGCGGCGCGTCGCAGGAGGAGTTCTATAAATTCATCAAGC CGATCCTGGAGAAAATGGACGGCACCGAAGAACTCCTCGTCAAGCTGAACCGGGAGGATCTGCTCCGCAAGCAGC GCACCTTCGACAATGGCTCCATCCCGCACCAGATCCATCTCGGCGAGCTGCACGCCATCCTGCGCCGCCAGGAGGA CTTCTACCCCTTCCTCAAAGACAACCGGGAGAAAATCGAGAAGATCCTGACGTTCCGCATCCCCTACTACGTGGGCC CCCTCGCCCGCGGCAACTCGCGGTTCGCGTGGATGACCCGGAAGAGCGAGGAGACGATCACCCCGTGGAATTTCG AGGAGGTCGTCGATAAAGGCGCGTCGGCGCAGTCGTTCATCGAGCGCATGACCAACTTCGATAAAAATCTGCCGA ACGAAAAAGTCCTGCCCAAGCATAGCCTGCTGTACGAGTACTTCACGGTCTACAACGAGCTGACGAAAGTGAAATA TGTCACGGAGGGCATGCGCAAACCGGCCTTCCTGTCCGGCGAGCAGAAAAAGGCCATCGTGGATCTGCTGTTCAA GACGAACCGGAAGGTCACCGTGAAACAGCTGAAGGAAGATTACTTCAAGAAAATCGAGTGCTTCGATTCCGTCGA AATCAGCGGCGTGGAGGACCGCTTCAATGCCTCGCTGGGCACCTATCACGATCTCCTCAAGATCATCAAGGACAAG GACTTCCTGGACAACGAAGAGAACGAGGACATCCTGGAAGACATCGTCCTCACCCTGACCCTGTTCGAGGACCGC GAAATGATCGAAGAGCGCCTGAAGACCTACGCCCACCTGTTCGACGACAAGGTCATGAAGCAGCTCAAGCGCCGC CGGTACACCGGCTGGGGCCGCCTGTCCCGGAAGCTGATCAACGGCATCCGCGATAAGCAGAGCGGCAAGACGATC CTGGACTTCCTCAAGAGCGACGGCTTCGCCAATCGGAATTTCATGCAGCTCATCCACGACGATAGCCTGACCTTCAA AGAGGATATCCAGAAGGCGCAGGTGTCCGGCCAGGGCGACAGCCTGCACGAACATATCGCCAACCTGGCGGGCT CCCCCGCGATCAAGAAAGGCATCCTCCAGACGGTCAAAGTCGTGGACGAGCTGGTCAAGGTGATGGGCCGCCACA AACCGGAGAATATCGTCATCGAGATGGCACGCGAGAACCAGACCACGCAGAAGGGCCAGAAGAACAGCCGGGAA CGCATGAAACGGATCGAAGAGGGCATCAAGGAACTGGGCTCGCAGATCCTGAAGGAGCACCCCGTCGAAAACAC GCAGCTCCAGAACGAGAAGCTGTATCTGTACTATCTCCAGAACGGCCGGGACATGTATGTCGATCAGGAACTGGAT ATCAACCGCCTCTCCGATTACGATGTGGACGCCATCGTGCCGCAGAGCTTCCTGAAAGACGACTCGATCGACAACA |

TABLE 6A-continued

| SEQ ID NO. | NAME | SEQUENCE |
|---|---|---|
| | | AGGTCCTGACCCGGTCGGACAAGAACCGCGGCAAGTCGGATAACGTGCCGTCGGAAGAAGTCGTGAAAAAGATG |
| | | AAGAACTACTGGCGGCAGCTCCTGAACGCGAAGCTCATCACGCAGCGCAAGTTCGACAATCTGACCAAGGCCGAG |
| | | CGCGGCGGCCTCTCGGAACTCGACAAGGCGGGCTTCATCAAACGGCAGCTCGTCGAGACGCGCCAGATCACCAAA |
| | | CACGTGGCCCAGATCCTGGACAGCCGGATGAACACCAAATACGACGAAAACGACAAGCTGATCCGCGAAGTCAAG |
| | | GTCATCACGCTGAAGAGCAAGCTGGTGTCGGATTTCCGCAAGGATTTCCAGTTCTACAAGGTGCGCGAGATCAACA |
| | | ATTACCATCACGCGCACGATGCCTATCTCAATGCGGTCGTGGGCACCGCCCTGATCAAAAAGTACCCGAAACTGGA |
| | | GTCCGAGTTCGTCTACGGCGACTATAAGGTCTATGATGTCCGCAAGATGATCGCCAAATCGGAGCAGGAGATCGG |
| | | CAAGGCGACCGCGAAATATTTCTTCTACTCGAACATCATGAATTTCTTCAAGACCGAGATCACGCTGGCGAACGGC |
| | | GAAATCCGCAAGCGGCCCCTGATCGAAACCAATGGCGAGACCGGCGAGATCGTGTGGGACAAAGGCCGGGATTT |
| | | CGCCACCGTCCGCAAGGTCCTCTCGATGCCGCAGGTGAACATCGTCAAGAAGACGGAGGTCCAGACCGGCGGCTT |
| | | CAGCAAAGAAAGCATCCTCCCCAAGCGGAATAGCGACAAACTGATCGCCCGGAAGAAGGACTGGGACCCGAAGA |
| | | AGTATGGCGGCTTCGATAGCCCCACCGTCGCCTATTCCGTCCTGGTGGTGGCGAAGGTGGAGAAAGGCAAAAGCA |
| | | AGAAACTGAAGAGCGTGAAGGAGCTGCTGGGCATCACCATCATGGAACGCAGCAGCTTCGAGAAGAACCCGATC |
| | | GACTTCCTGGAAGCCAAAGGCTATAAGGAAGTGAAGAAGGACCTCATCATCAAACTCCCGAAGTATTCGCTGTTCG |
| | | AGCTGGAAAATGGCCGCAAACGGATGCTCGCCTCCGCGGGCGAACTCCAGAAGGGCAACGAACTGGCGCTGCCG |
| | | TCCAAATACGTCAACTTCCTCTATCTGGCCAGCCATTACGAAAAGCTGAAGGGCTCGCCCGAAGATAACGAGCAGA |
| | | AACAGCTGTTCGTCGAGCAGCACAAGCACTACCTCGACGAGATCATCGAGCAGATCAGCGAGTTCTCCAAGCGGG |
| | | TGATCCTCGCGGACGCCAACCTGGACAAGGTGCTGTCGGCGTACAACAAACATCGGGATAAGCCGATCCGCGAGC |
| | | AGGCCGAAAATATCATCCACCTGTTCACCCTGACGAACCTCGGCGCCCCCGCCGCCTTCAAGTATTTCGATACCACC |
| | | ATCGACCGGAAGCGCTATACCTCCACCAAAGAGGTCCTGGATGCCACCCTCATCCACCAGTCCATCACGGGCCTGT |
| | | ACGAGACCCGCATCGACCTGTCGCAGCTGGGCGGCGACTAA (SEQ ID NO. 118) |

TABLE 6B

| Plasmid | gRNA name | Targeting Sequence | Full sgRNA sequence |
|---|---|---|---|
| oriv_ dCas9_ gRNA3 | gRNA3 | ATAATGTG TGGAATTG TGAG (SEQ ID NO. 119) | TTTATAGCTAGCTCAGCCCTTGGTACAATGCTAGCATAATGTGTGGAATTGTGAGGTTTTAGAGCTAG AAATAGCAAGTTAAAATAAGGCTAGTCCGTTATCAACTTGAAAAAGTGGCACCGAGTCGGTGCTTTT TTT (SEQ ID NO. 120) |

TABLE 6C

| Plasmid | Promoter | LacZ sequence |
|---|---|---|
| Ptrc_ | TTGACAAT | ATGACCATGATTACGGATTCACTGGCCGTCGTTTTACAACGTCGTGACTGGGAAAACCCTGGCGTTACCCAACTT |
| laxZ | TAATCATCC | AATCGCCTTGCAGCACATCCCCCTTTCGCCAGCTGGCGTAATAGCGAAGAGGCCCGCACCGATCGCCCTTCCCAA |
| | GGCTCGTA | CAGTTGCGCAGCCTGAATGGCGAATGGCGCTTTGCCTGGTTTCCGGCACCAGAAGCGGTGCCGGAAAGCTGGCT |
| | TAATGTGT | GGAGTGCGATCTTCCTGAGGCCGATACTGTCGTCGTCCCCTCAAACTGGCAGATGCACGGTTACGATGCGCCCAT |
| | GGAATTGT | CTACACCAACGTGACCTATCCCATTACGGTCAATCCGCCGTTTGTTCCCACGGAGAATCCGACGGGTTGTTACTC |
| | GAGCGGAT | GCTCACATTTAATGTTGATGAAAGCTGGCTACAGGAAGGCCAGACGCGAATTATTTTTGATGGCGTTAACTCGGC |
| | AACAATTA | GTTTCATCTGTGGTGCAACGGGCGCTGGGTCGGTTACGGCCAGGACAGTCGTTTGCCGTCTGAATTTGACCTGA |
| | ACGAGAGG | GCGCATTTTTACGCGCCGGAGAAAACCGCCTCGCGGTGATGGTGCTGCGCTGGAGTGACGGCAGTTATCTGGAA |
| | AAGTTCC | GATCAGGATATGTGGCGGATGAGCGGCATTTTCCGTGACGTCTCGTTGCTGCATAAACCGACTACACAAATCAG |
| | (SEQ ID | CGATTTCCATGTTGCCACTCGCTTTAATGATGATTTCAGCCGCGCTGTACTGGAGGCTGAAGTTCAGATGTGCGG |
| | NO. 121) | CGAGTTGCGTGACTACCTACGGGTAACAGTTTCTTTATGGCAGGGTGAAACGCAGGTCGCCAGCGGCACCGCGC |
| | | CTTTCGGCGGTGAAATTATCGATGAGCGTGGTGGTTATGCCGATCGCGTCACACTACGTCTGAACGTCGAAAAC |
| | | CCGAAACTGTGGAGCGCCGAAATCCCGAATCTCTATCGTGCGGTGGTTGAACTGCACACCGCCGACGGCACGCT |
| | | GATTGAAGCAGAAGCCTGCGATGTCGGTTTCCGCGAGGTGCGGATTGAAAATGGTCTGCTGCTGCTGAACGGC |
| | | AAGCCGTTGCTGATTCGAGGCGTTAACCGTCACGAGCATCATCCTCTGCATGGTCAGGTCATGGATGAGCAGAC |
| | | GATGGTGCAGGATATCCTGCTGATGAAGCAGAACAACTTTAACGCCGTGCGCTGTTCGCATTATCCGAACCATCC |
| | | GCTGTGGTACACGCTGTGCGACCGCTACGGCCTGTATGTGGTGGATGAAGCCAATATTGAAACCCACGGCATGG |
| | | TGCCAATGAATCGTCTGACCGATGATCCGCGCTGGCTACCGGCGATGAGCGAACGCGTAACGCGAATGGTGCA |
| | | GCGCGATCGTAATCACCCGAGTGTGATCATCTGGTCGCTGGGGAATGAATCAGGCCACGGCGCTAATCACGACG |
| | | CGCTGTATCGCTGGATCAAATCTGTCGATCCTTCCCGCCCGGTGCAGTATGAAGGCGGCGGAGCCGACACCACG |
| | | GCCACCGATATTATTTGCCCGATGTACGCCCGCGTGGATGAAGACCAGCCCTTCCCGGCTGTGCCGAAATGGTCC |
| | | ATCAAAAAATGGCTTTCGCTACCTGGAGAGACGCGCCCGCTGATCCTTTGCGAATACGCCCACGCGATGGGTAA |
| | | CAGTCTTGGCGGTTTCGCTAAATACTGGCAGGCGTTTCGTCAGTATCCCCGTTTACAGGGCGGCTTCGTCTGGGA |
| | | CTGGGTGGATCAGTCGCTGATTAAATATGATGAAAACGGCAACCCGTGGTCGGCTTACGGCGGTGATTTTGGCG |
| | | ATACGCCGAACGATCGCCAGTTCTGTATGAACGGTCTGGTCTTTGCCGACCGCACGCCGCATCCAGCGCTGACG |
| | | GAAGCAAAACACCAGCAGCAGTTTTTCCAGTTCCGTTTATCCGGGCAAACCATCGAAGTGACCAGCGAATACCT |
| | | GTTCCGTCATAGCGATAACGAGCTCCTGCACTGGATGGTGGCGCTGGATGGTAAGCCGCTGGCAAGCGGTGAA |
| | | GTGCCTCTGGATGTCGCTCCACAAGGTAAACAGTTGATTGAACTGCCTGAACTACCGCAGCCGGAGAGCGCCGG |
| | | GCAACTCTGGCTCACAGTACGCGTAGTGCAACCGAACGCGACCGCATGGTCAGAAGCCGGGCACATCAGCGCCT |
| | | GGCAGCAGTGGCGTCTGGCGGAAAACCTCAGTGTGACGCTCCCCGCCGCGTCCCACGCCATCCCGCATCTGACC |
| | | ACCAGCGAAATGGATTTTTGCATCGAGCTGGGTAATAAGCGTTGGCAATTTAACCGCCAGTCAGGCTTTCTTTCA |
| | | CAGATGTGGATTGGCGATAAAAAACAACTGCTGACGCCGCTGCGCGATCAGTTCACCCGTGCACCGCTGGATAA |

TABLE 6C-continued

| Plasmid | Promoter | LacZ sequence |
|---|---|---|
| | | CGACATTGGCGTAAGTGAAGCGACCCGCATTGACCCTAACGCCTGGGTCGAACGCTGGAAGGCGGCGGGCCAT TACCAGGCCGAAGCAGCGTTGTTGCAGTGCACGGCAGATACACTTGCTGATGCGGTGCTGATTACGACCGCTCA CGCGTGGCAGCATCAGGGGAAAACCTTATTTATCAGCCGGAAAACCTACCGGATTGATGGTAGTGGTCAAATGG CGATTACCGTTGATGTTGAAGTGGCGAGCGATACACCGCATCCGGCGCGGATTGGCCTGAACTGCCAGCTGGCG CAGGTAGCAGAGCGGGTAAACTGGCTCGGATTAGGGCCGCAAGAAAACTATCCCGACCGCCTTACTGCCGCCTG TTTTGACCGCTGGGATCTGCCATTGTCAGACATGTATACCCCGTACGTCTTCCCGAGCGAAAACGGTCTGCGCTG CGGGACGCGCGAATTGAATTATGGCCCACACCAGTGGCGCGGCGACTTCCAGTTCAACATCAGCCGCTACAGTC AACAGCAACTGATGGAAACCAGCCATCGCCATCTGCTGCACGCGGAAGAAGGCACATGGCTGAATATCGACGG TTTCCATATGGGGATTGGTGGCGACGACTCCTGGAGCCCGTCAGTATCGGCGGAATTCCAGCTGAGCGCCGGTC GCTACCATTACCAGTTGGTCTGGTGTCAAAAATAA (SEQ ID NO. 122) |

What is claimed is:

1. A method of genetic engineering comprising transforming a methylotroph with a polynucleotide encoding a Cas9 protein operably linked to a weak promoter comprising the sequence of SEQ ID NO: 78, wherein the methylotroph comprises a previously introduced polynucleotide encoding a guide ribonucleic acid (gRNA).

2. The method of claim 1, wherein the methylotroph is a methanotroph.

3. The method of claim 2, wherein the methanotroph is from a genus selected from *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis*, or Methyloacidophilum.

4. The method of claim 2, wherein the methanotroph is from the genus *Methylococcus.*

5. The method of claim 2, wherein the methanotroph is a *Methylococcus capsulatus.*

6. The method of claim 1, further comprising contacting the methylotroph with a donor polynucleotide, wherein the donor polynucleotide and the polynucleotide encoding the gRNA are contained on a single plasmid, and wherein the methylotroph is contacted with the donor polynucleotide prior to being contacted with the polynucleotide encoding the Cas9 protein.

7. The method of claim 6, wherein the donor polynucleotide comprises fewer than 1000 bases.

8. The method of claim 6, wherein the donor polynucleotide encodes a point mutation, a deletion, or an insertion at a target locus in the genome of the methylotroph.

* * * * *